United States Patent
Zuk, Jr.

(10) Patent No.: US 8,361,320 B2
(45) Date of Patent: *Jan. 29, 2013

(54) BIOLOGICAL FLUID FILTRATION APPARATUS

(75) Inventor: Peter Zuk, Jr., Harvard, MA (US)

(73) Assignee: Hemerus Medical, LLC, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/842,579

(22) Filed: Jul. 23, 2010

(65) Prior Publication Data

US 2010/0282681 A1 Nov. 11, 2010

Related U.S. Application Data

(63) Continuation of application No. 10/934,881, filed on Sep. 3, 2004.

(60) Provisional application No. 60/500,970, filed on Sep. 5, 2003, provisional application No. 60/524,014, filed on Nov. 20, 2003.

(51) Int. Cl.
- *B01D 35/28* (2006.01)
- *B01D 37/00* (2006.01)
- *B01D 61/00* (2006.01)
- *B01D 35/00* (2006.01)

(52) U.S. Cl. ........ 210/645; 210/335; 210/343; 210/436; 210/472; 210/651; 210/767; 210/806

(58) Field of Classification Search .................. 210/335, 210/645, 321.6, 321.72, 321.75, 321.84, 210/340, 343, 456, 323.1, 436, 472, 605, 210/651, 767, 806; 604/406

See application file for complete search history.

(56) References Cited

U.S. PATENT DOCUMENTS

| | | | |
|---|---|---|---|
| 4,304,670 A | 12/1981 | Watanabe et al. | |
| 4,925,572 A | 5/1990 | Pall | |
| 4,963,260 A | 10/1990 | Naoi et al. | |
| 5,045,207 A | 9/1991 | Fecondini et al. | |
| 5,439,587 A | 8/1995 | Stankowski et al. | |
| 5,766,468 A | 6/1998 | Brown et al. | |
| 5,779,902 A | 7/1998 | Zuk, Jr. | |
| 6,010,633 A | 1/2000 | Zuk, Jr. et al. | |
| 6,231,770 B1 | 5/2001 | Bormann et al. | |
| 6,660,171 B2 | 12/2003 | Zuk, Jr. | |
| 7,270,757 B1 | 9/2007 | Zuk, Jr. | |
| 7,854,845 B2 * | 12/2010 | Zuk, Jr. | 210/645 |

* cited by examiner

*Primary Examiner* — Nam Nguyen
*Assistant Examiner* — Madeline Gonzalez
(74) *Attorney, Agent, or Firm* — Marshall & Melhorn, LLC

(57) ABSTRACT

Biological fluid filtration systems including biological fluid filtration devices capable of filtering blood or blood products, including the removal of leukocytes from the blood or blood product. Each system includes a means to automatically drain the biological fluid upstream of the biological fluid filtration media disposed in the biological fluid filtration device. Both single sided and double sided biological fluid filtration devices are disclosed, including double sided biological fluid filtration devices with a solid partition wall with a first independent fluid flow path on one side of the partition wall, and a second independent fluid flow path on the other side of the partition wall. Draining means include vent filtration devices, diaphragm draining devices, and biological fluid filtration devices that include an integral diaphragm. The biological fluid filtration devices include low hold-up volume filter underdrains that purge in excess of 95% of the initial air in the device before liquid begins to flow from the outlet, thereby allowing the devices to be used in bed side applications. Variable surface area biological fluid filtration devices are disclosed that further reduce hold-up volume.

24 Claims, 45 Drawing Sheets

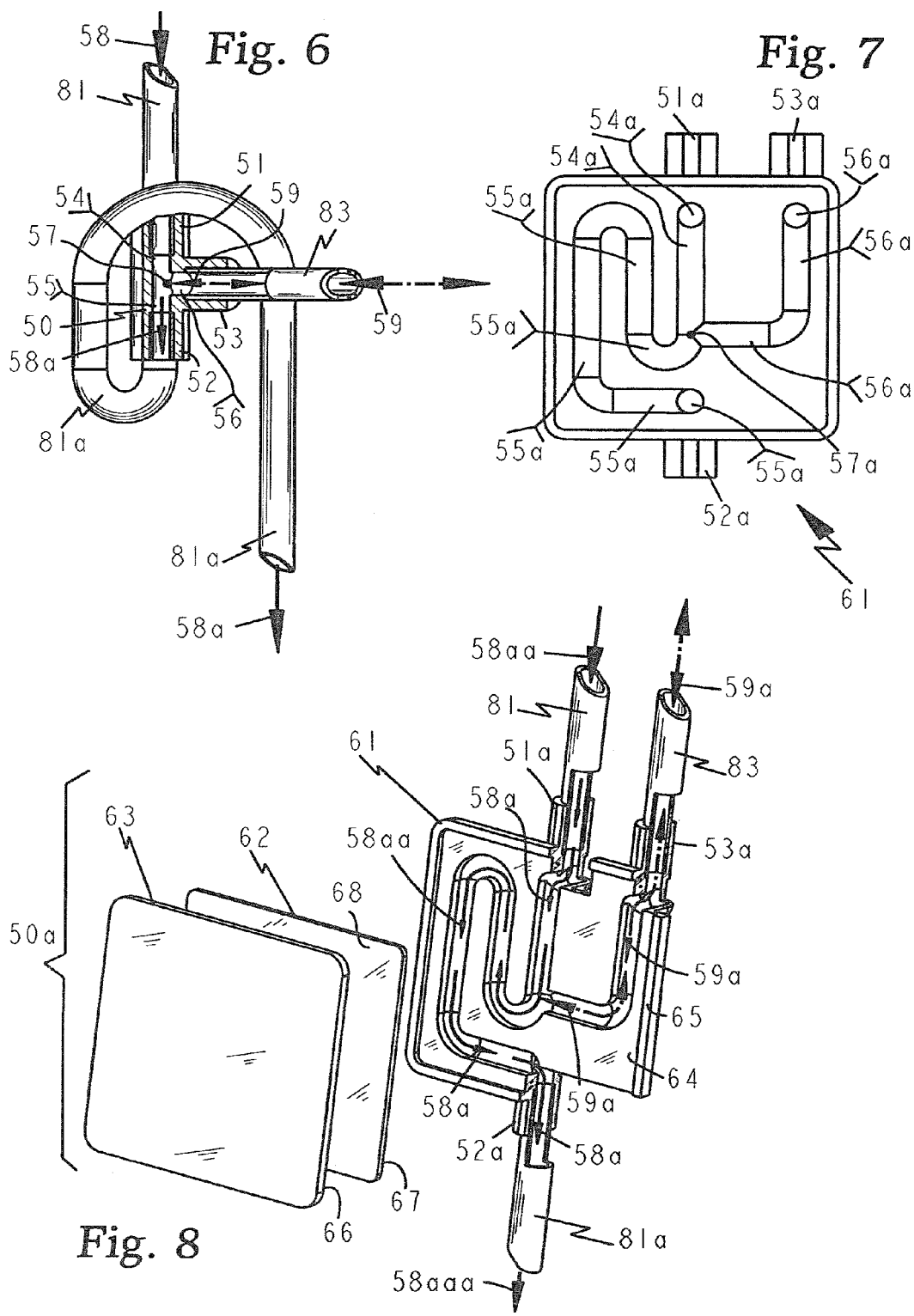

Fig. 25
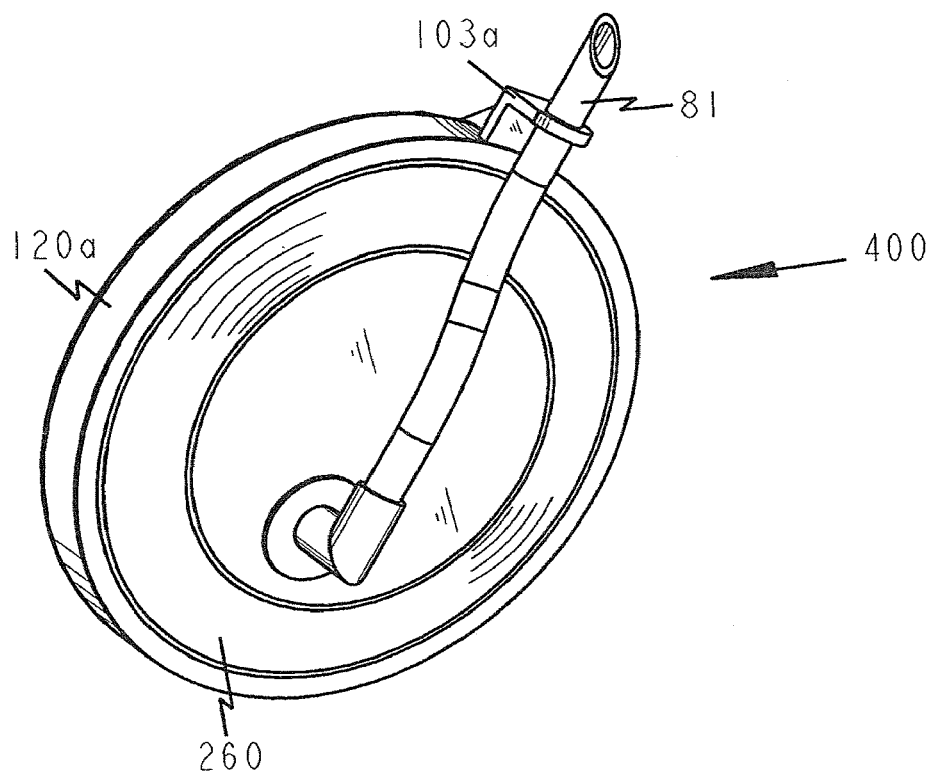
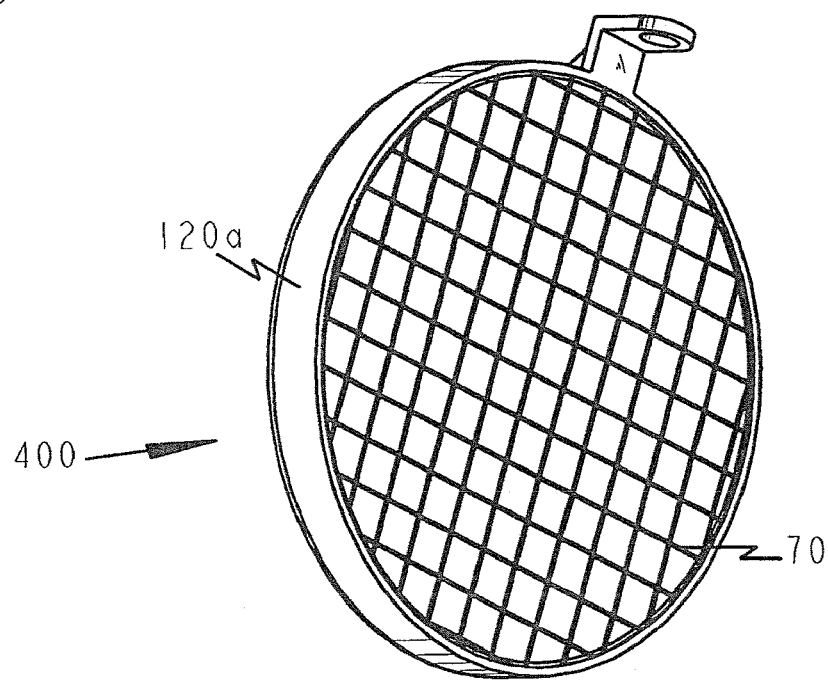
Fig. 26

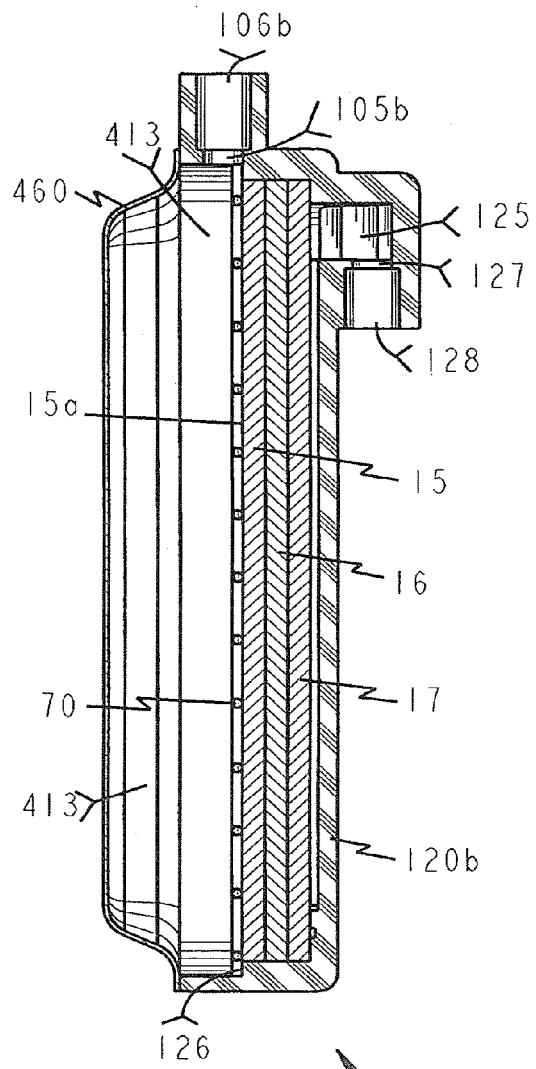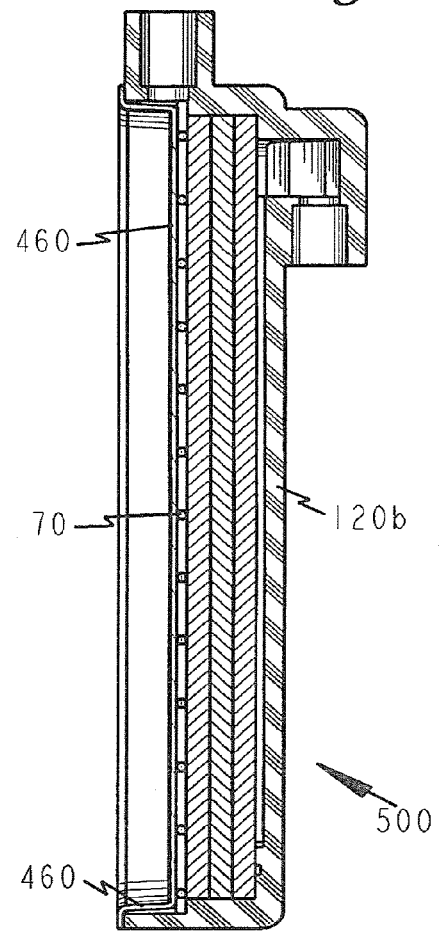
Fig. 27
Fig. 28

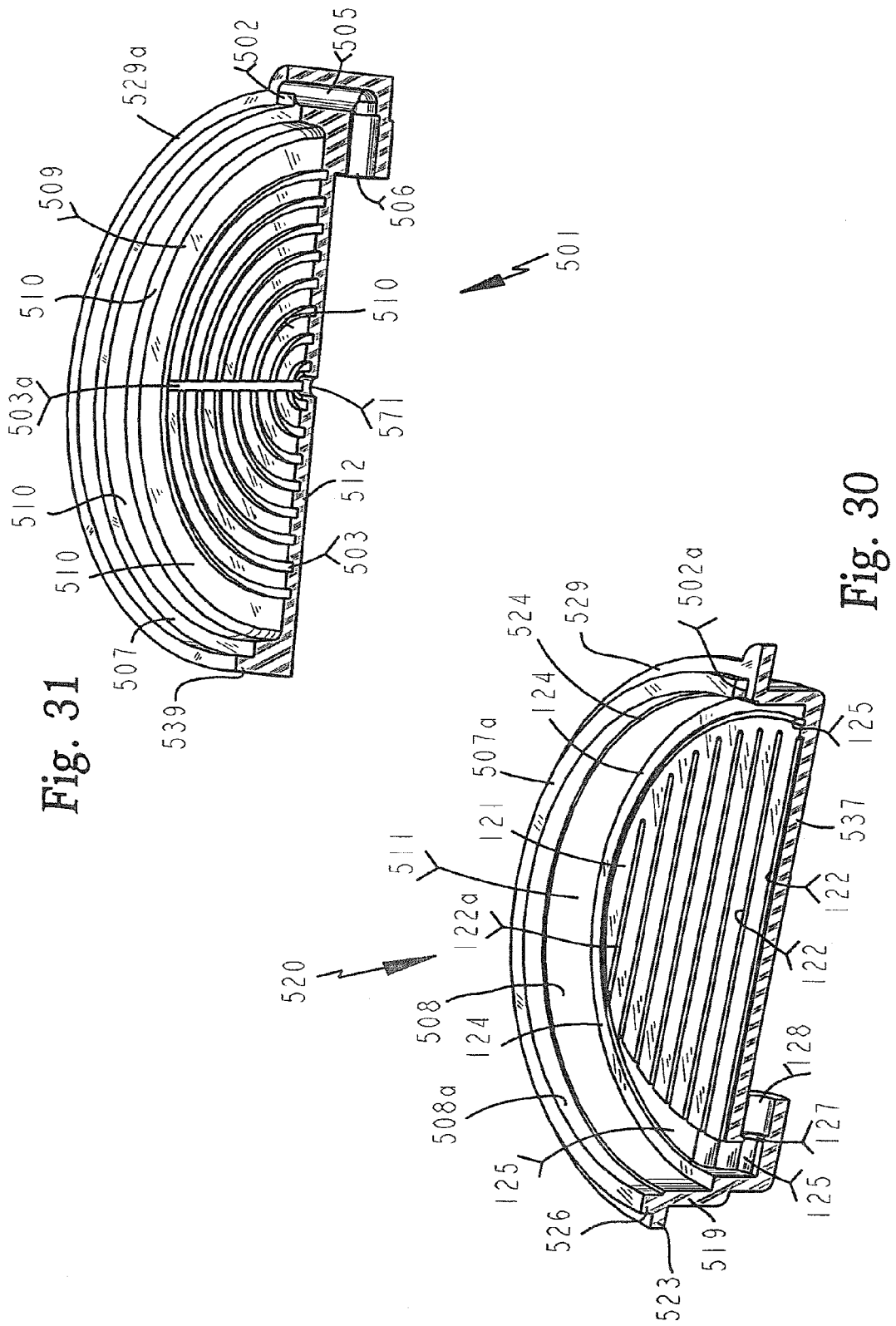

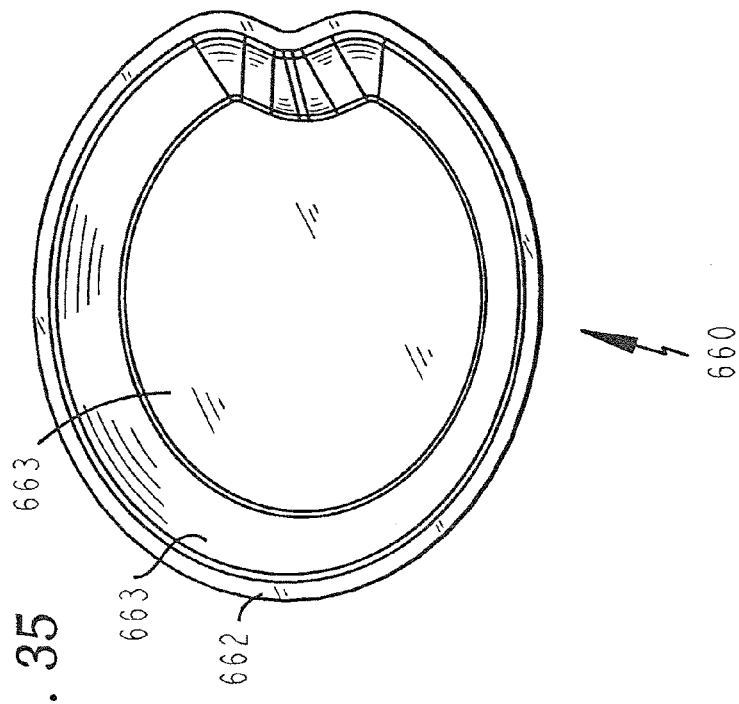
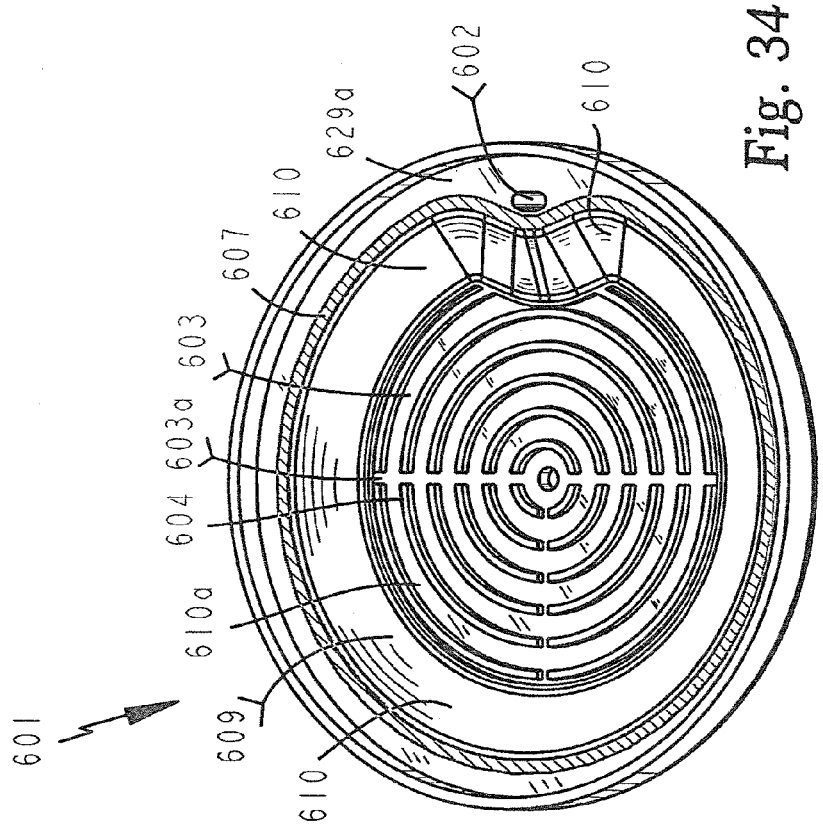

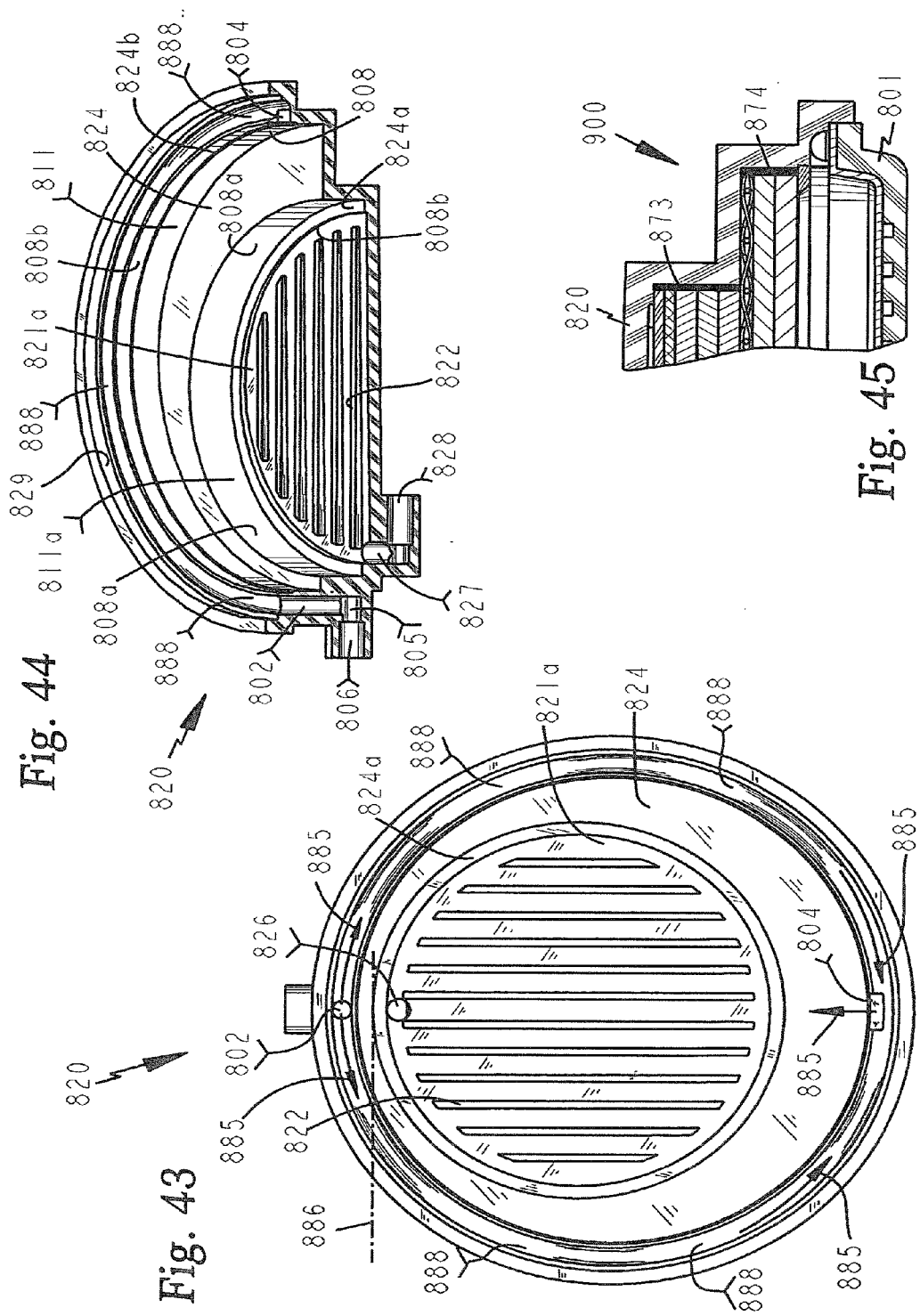

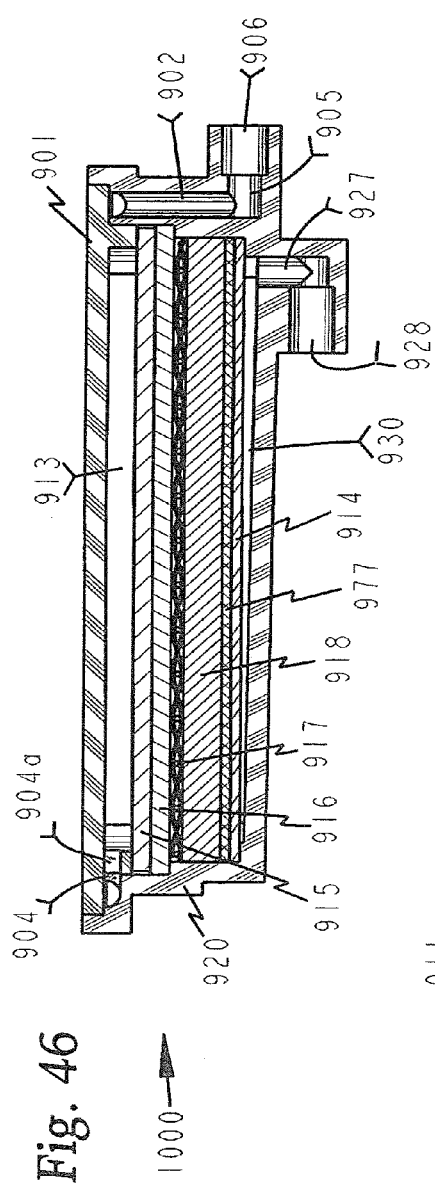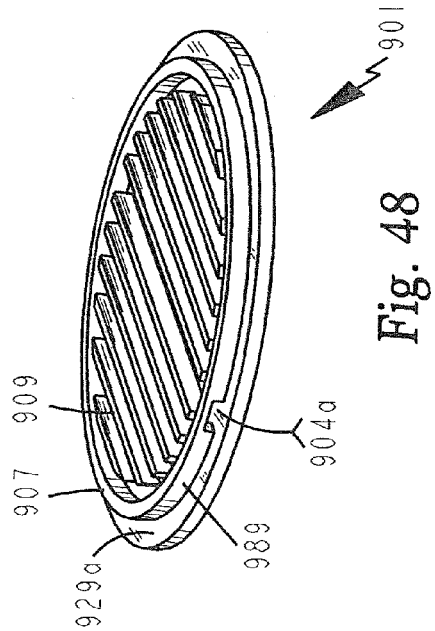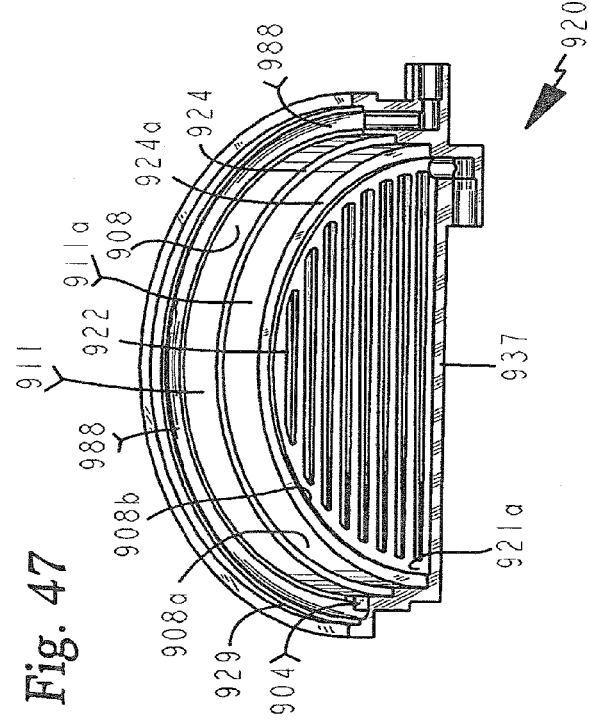
Fig. 46
Fig. 48
Fig. 47

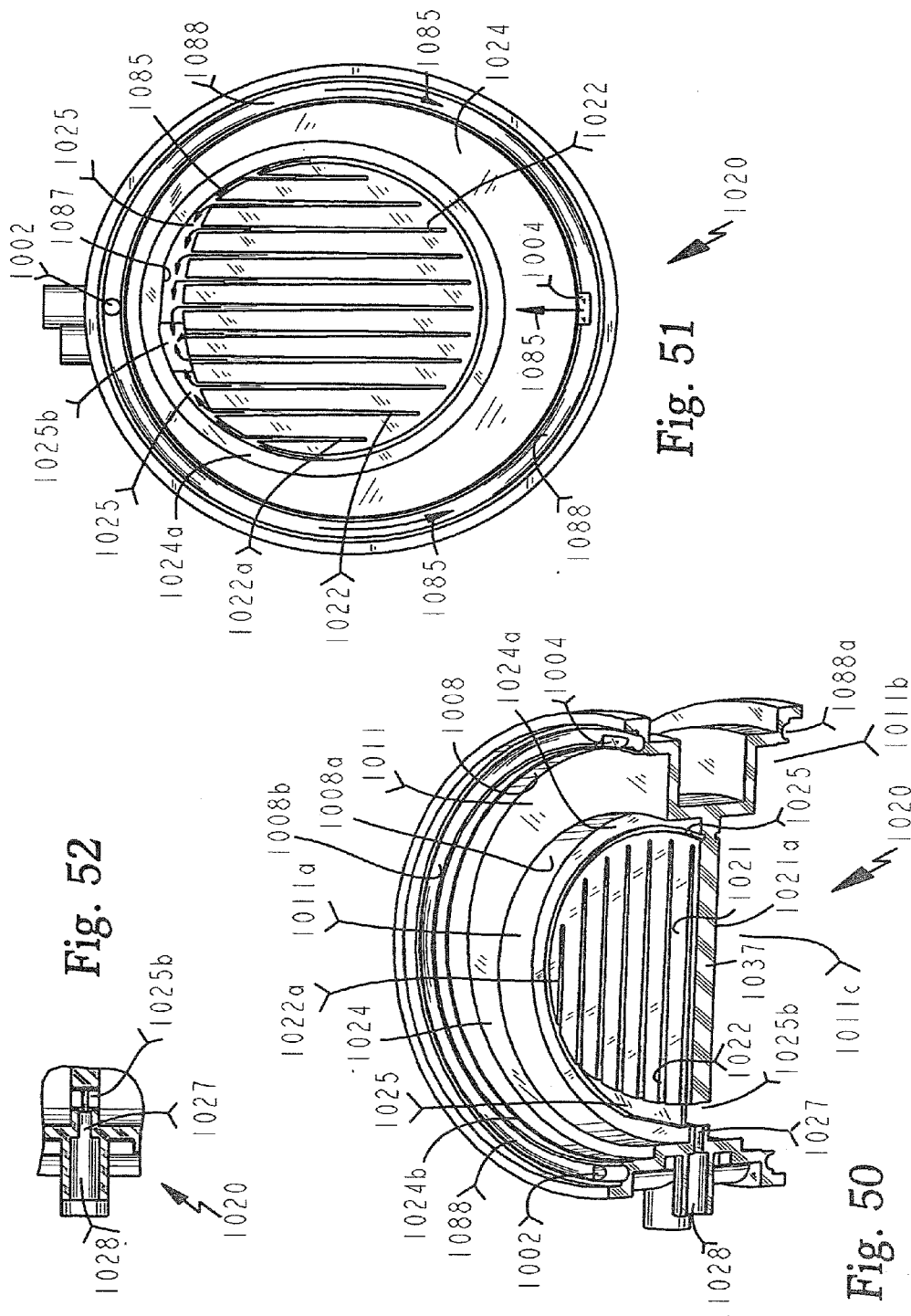

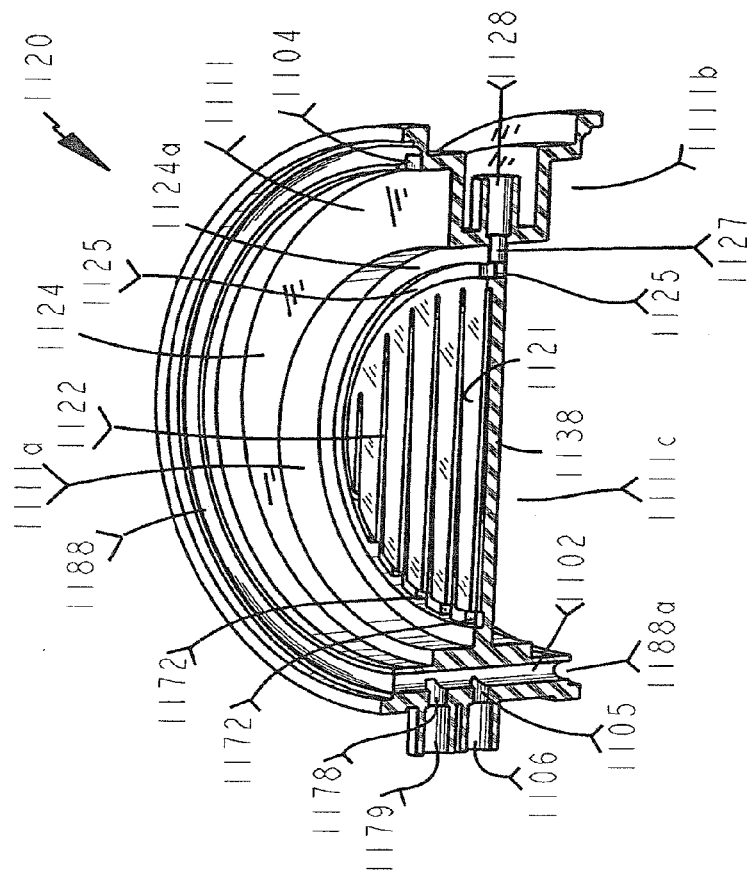
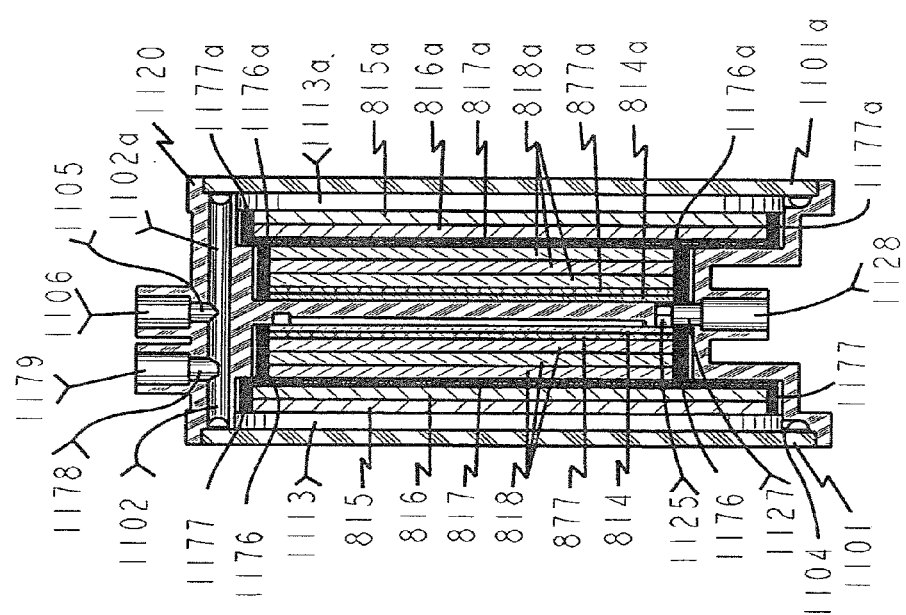
Fig. 56
Fig. 55

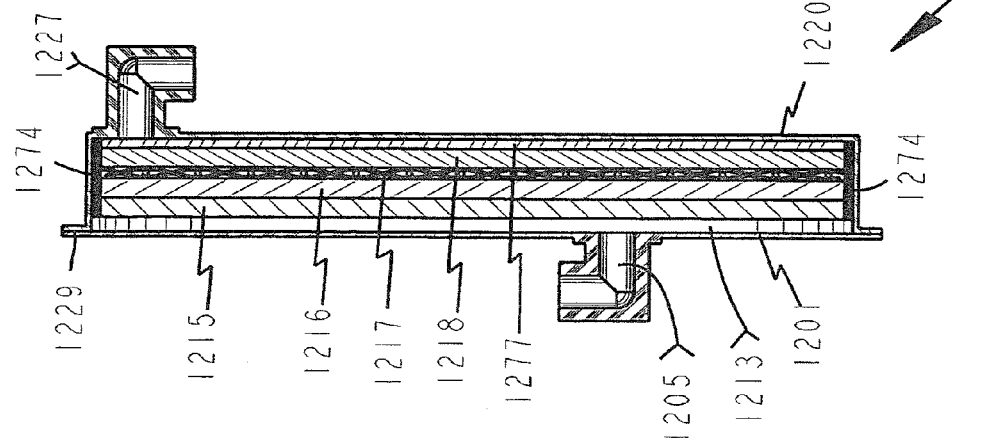
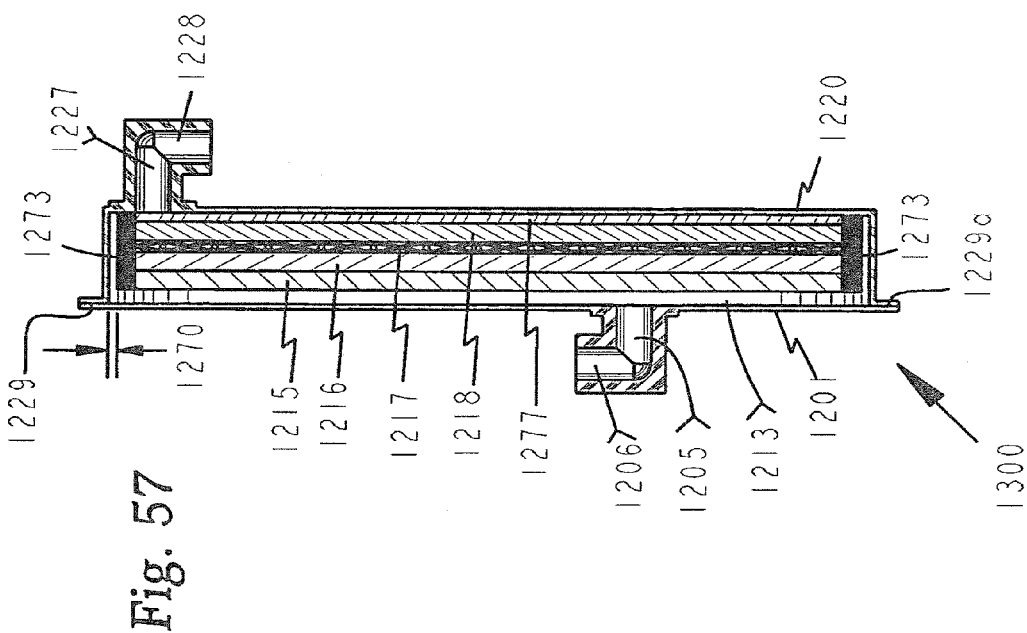

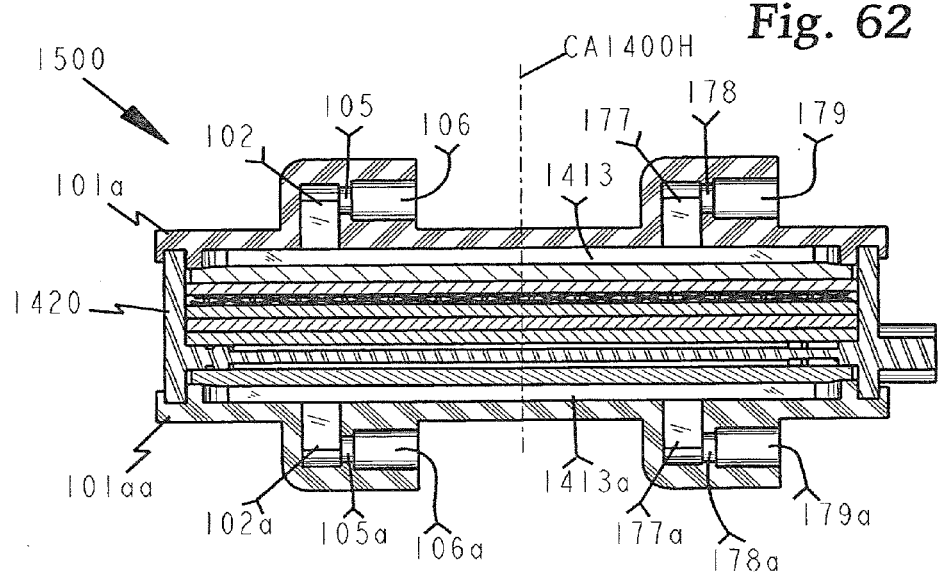
Fig. 62
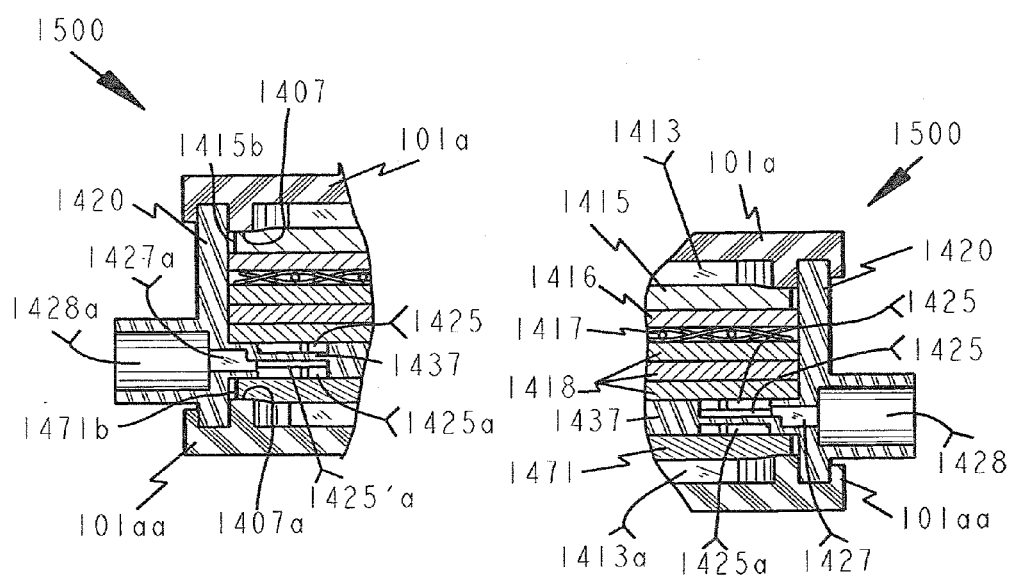
Fig. 63
Fig. 64

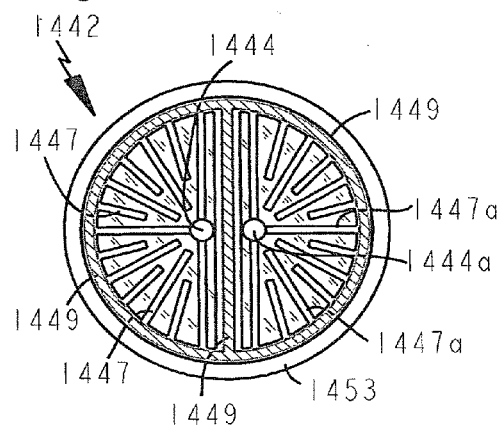
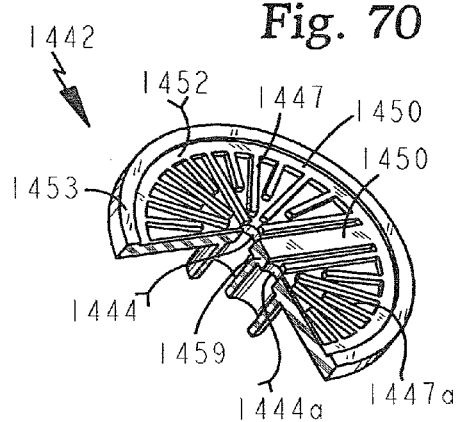
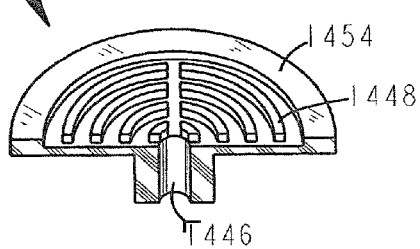
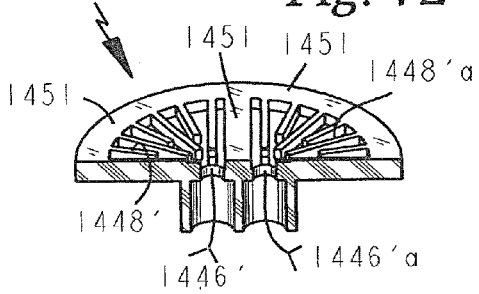
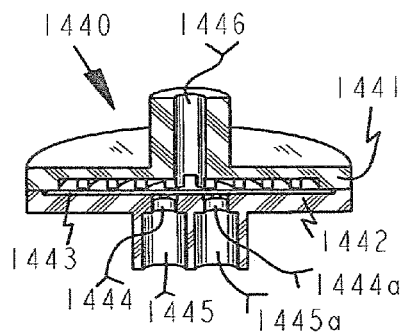
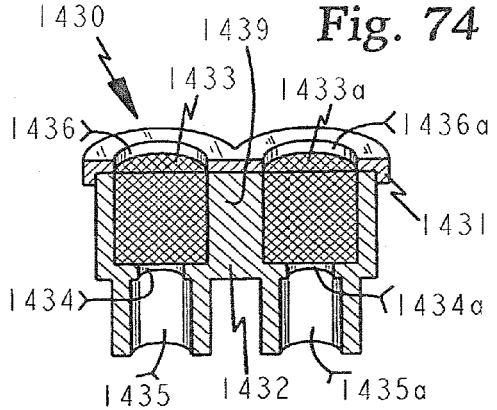

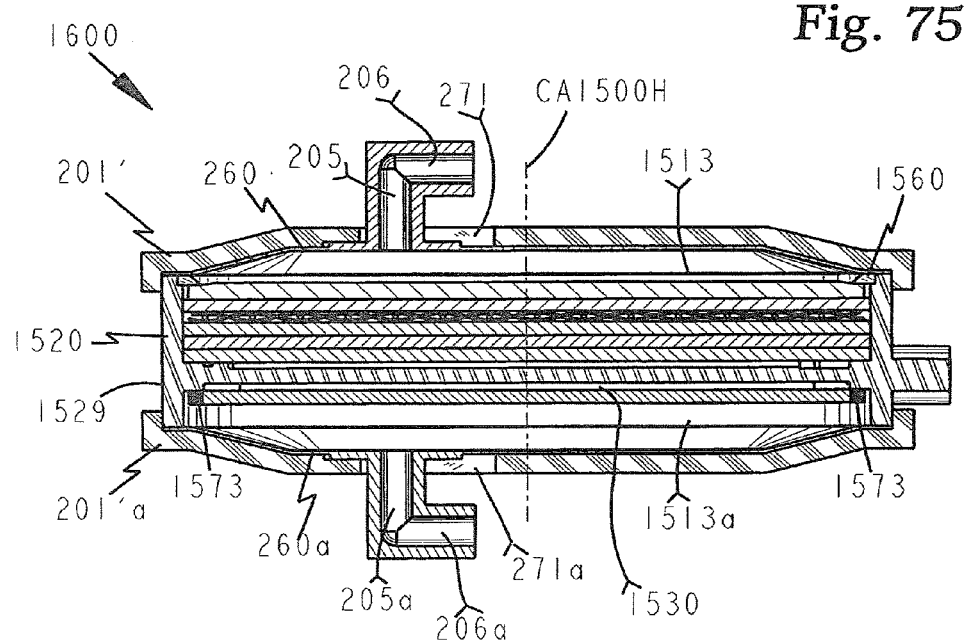
Fig. 75
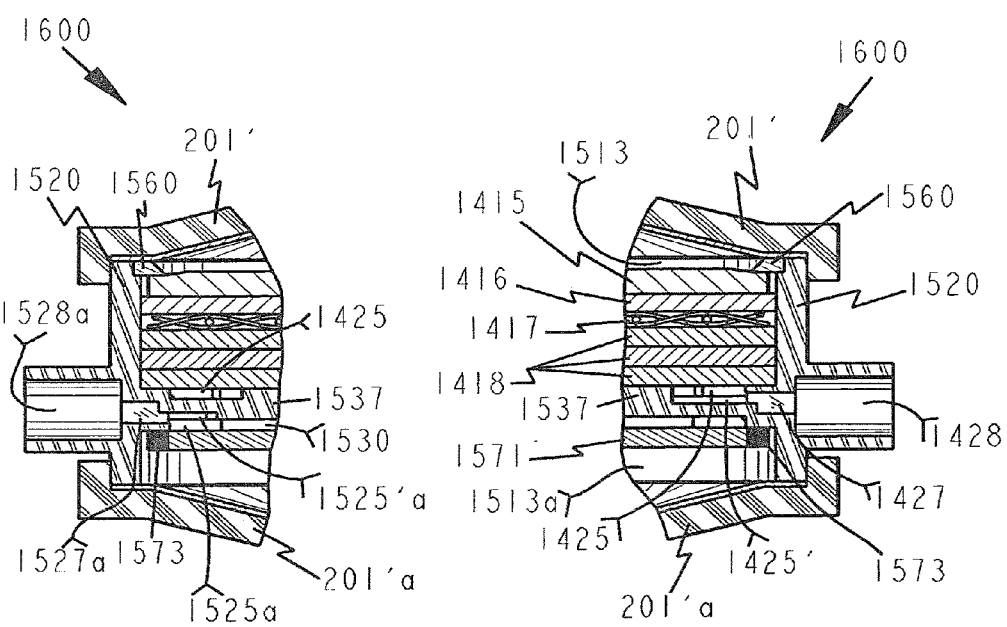
Fig. 76
Fig. 77

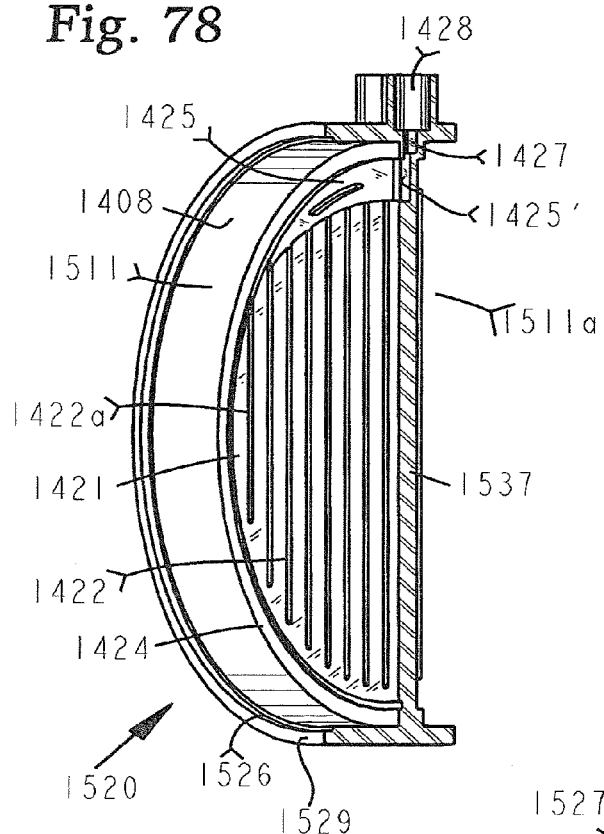
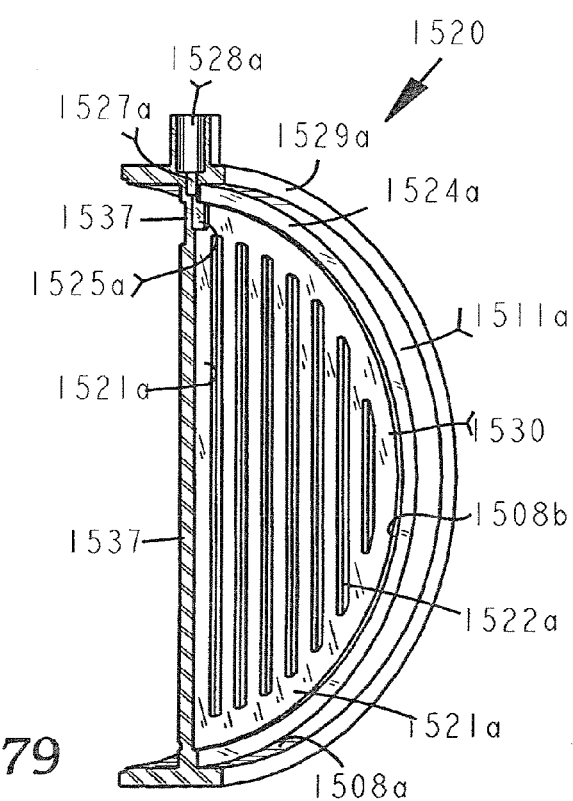

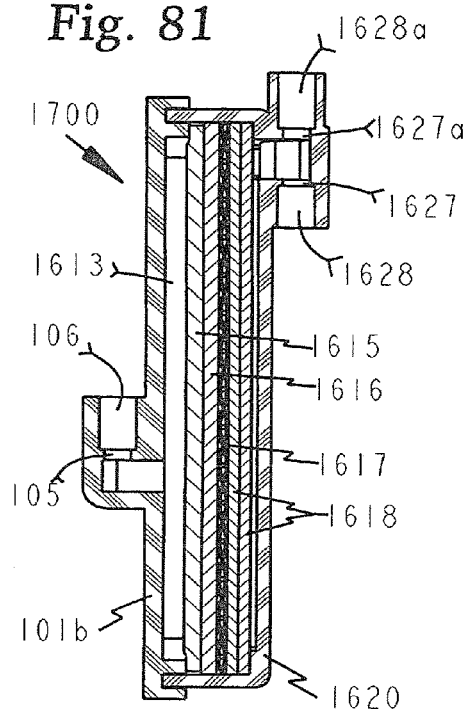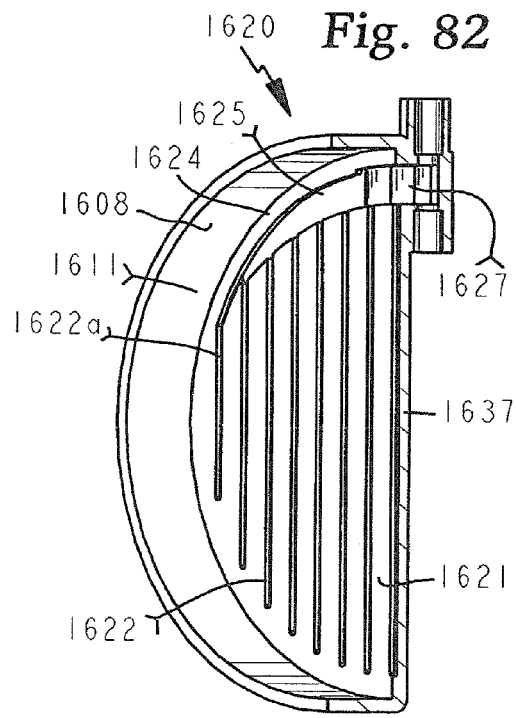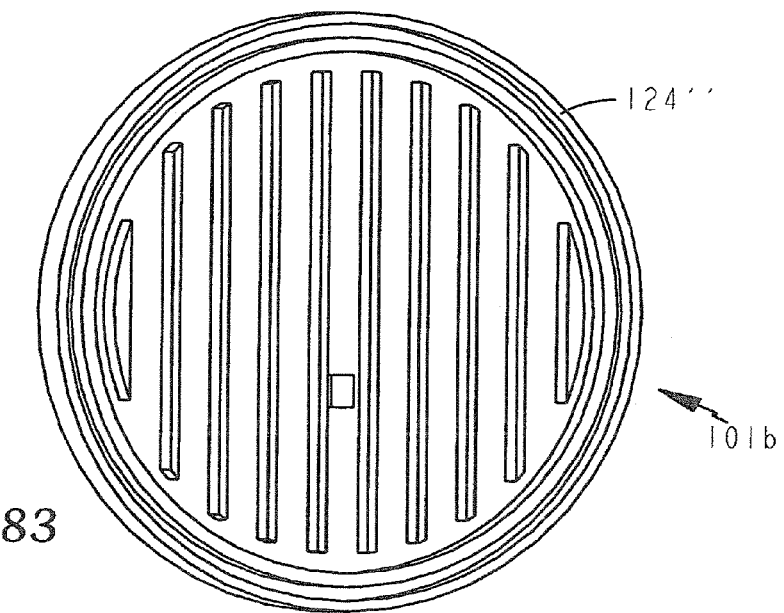

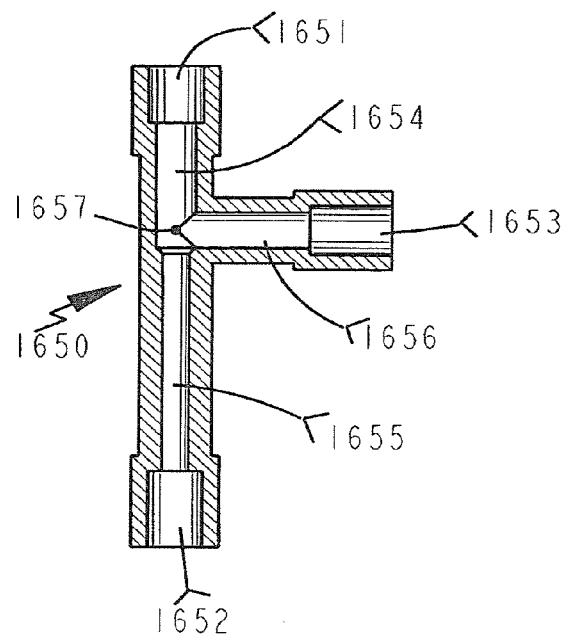
Fig. 89
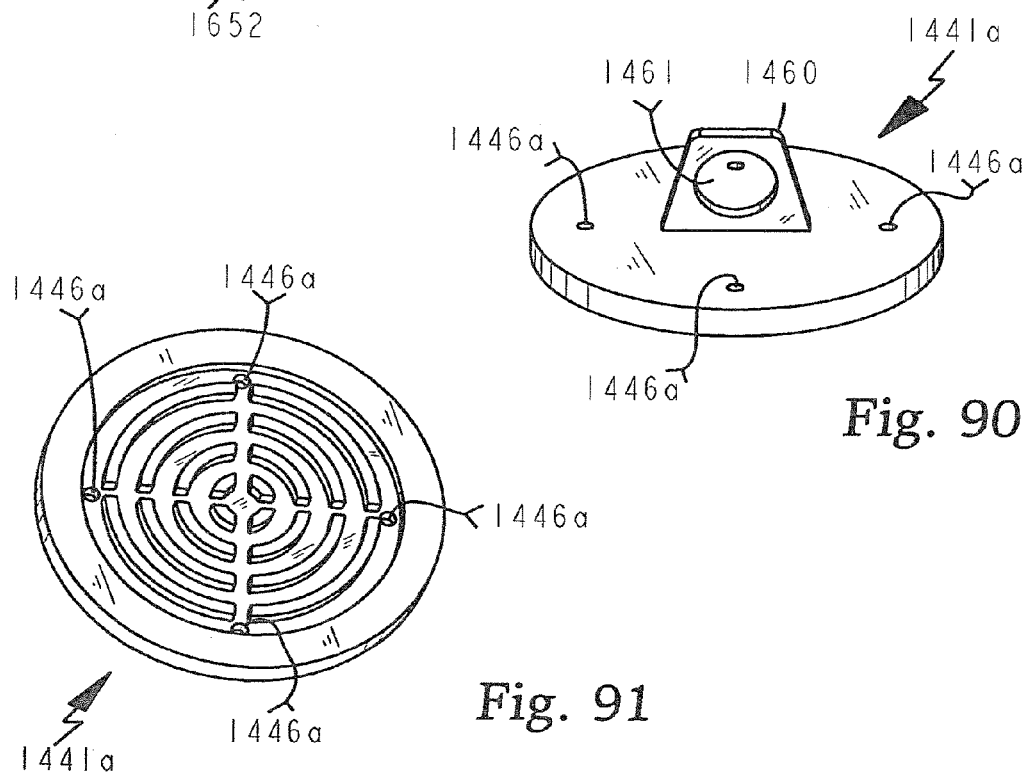
Fig. 90
Fig. 91

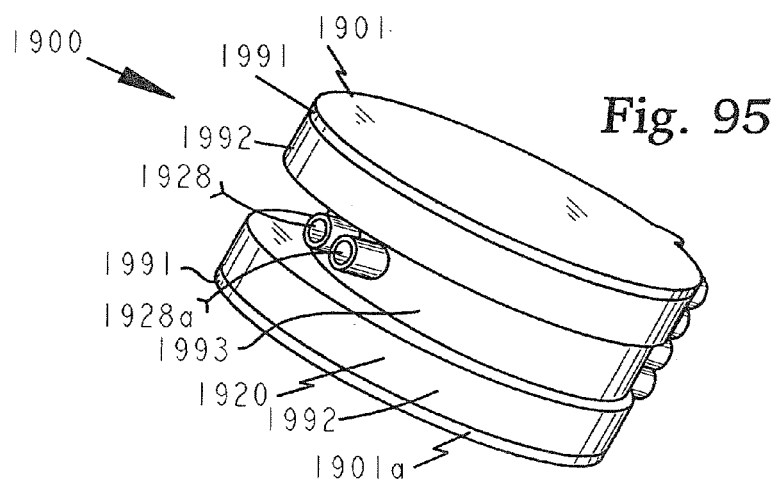
Fig. 95
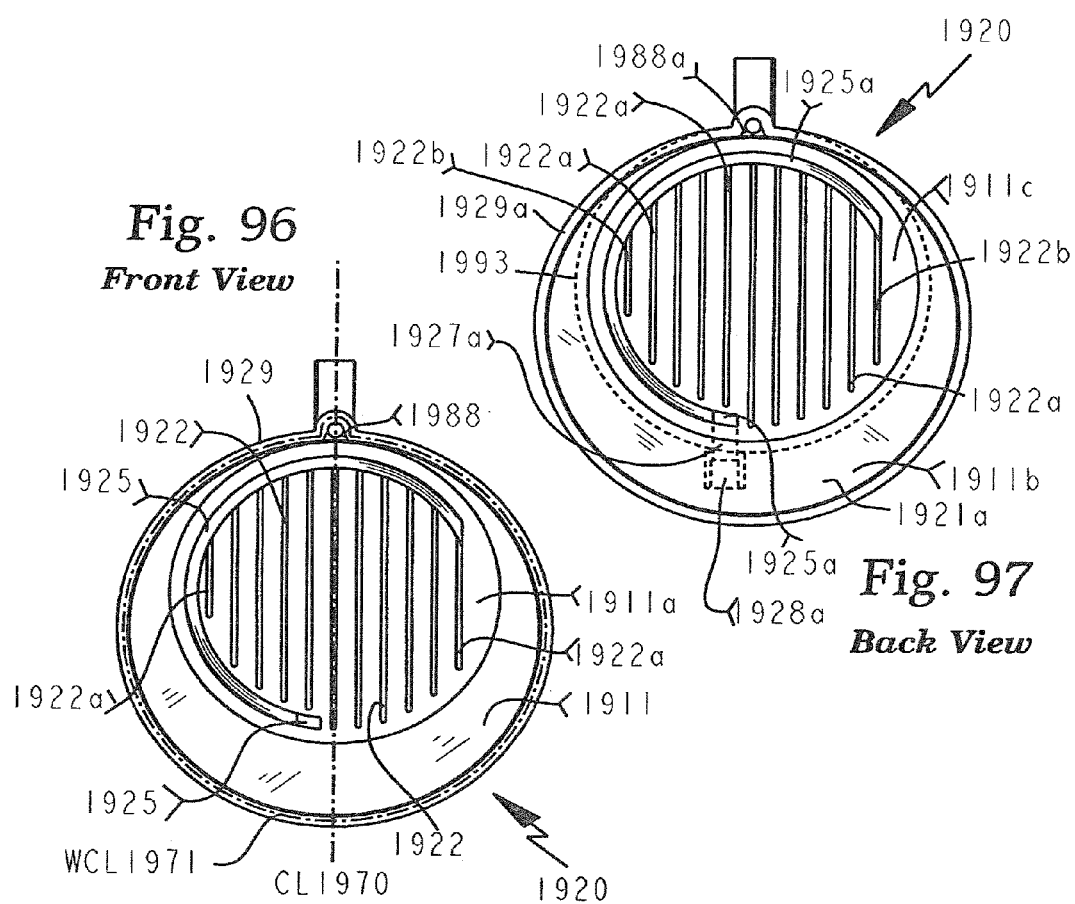
Fig. 96
Front View
Fig. 97
Back View

BIOLOGICAL FLUID FILTRATION APPARATUS

CROSS REFERENCE TO RELATED APPLICATIONS

The present application is a continuation of application Ser. No. 10/934,881, filed Sep. 3, 2004, for A Biological Fluid Filter Apparatus. Application Ser. No. 10/934,881, pursuant to 35 U.S.C. §119(e)(1), claimed priority from Provisional Application Ser. No. 60/500,970, filed Sep. 5, 2003, and of Provisional Application Ser. No. 60/524,014, filed Nov. 20, 2003. Application Ser. No. 10/934,881 is pending as of the filing date of the present application.

BACKGROUND OF THE INVENTION

This invention relates to the filtration field, and more particularly, to an improved low hold up biological fluid filtration system, including a low hold up biological fluid filter device capable of filtering biological fluids, including the removal of components or chemicals from blood or blood products, and including the removal of leukocytes from packed red cells, and prions from blood or blood products.

There are currently available filtration devices for filtering blood or blood products. The currently available devices use multiple layers of filtration media of different pore size, but of the same diameter. Some devices use a vent filter to drain the upstream side of the filtration device after filtration is complete to minimize hold up volume. These vent filters either have to be isolated from the fluid being filtered during the filtration cycle by a clamp or valve which has to be manually opened once filtration is complete to drain the device, or in an automatic system multiple layers of different pore size vent filter media must be used to prevent fouling the vent filter during the filtration cycle. Some of these devices require a negative pressure on the outlet of the device to eliminate air from the downstream side of the device. In all of the devices a quantity of biological fluid will flow from the outlet of the device before all of the air has been purged from the device. For a device to be usable in bed side applications (i.e. for direct transfusion to a patient), the amount of biological fluid that flows from the outlet of the device before all of the air has been purged from the device must be minimized. Furthermore, currently available filtration devices are designed to filter one type of blood or blood product per device.

It is therefore an object of the present invention to provide a biological fluid filtration system including a biological fluid filtration device that runs automatically, minimizes hold up volume, does not require a negative pressure at the outlet to eliminate air from the down stream side of the biological fluid filtration device, and in several embodiments use smaller surface area downstream filter elements to reduce hold up volume of the device. It is also an object of the present invention to minimize the amount of biological fluid that flows from the outlet of the biological fluid filtration device before all of the air has been purged from the device, so that the biological fluid filtration device will be usable in bed side applications. It is a further object of the present invention to eliminate the need for vent filters to drain the upstream chamber of the biological fluid filtration device after the filtration cycle has been completed. Another object of the present invention is to be able to filter two different types of blood or blood product using a single biological fluid filtration device that includes two independent fluid flow paths, without fluid flow communication between the two fluid flow paths. For example leukocytes could be removed from packed red cells through one fluid flow path, and leukocytes could be removed from a platelet concentrate through the other fluid flow path. It is also an object of the present invention to provide a single vent filtration device that can vent the two fluid flow paths of a biological fluid filtration device that includes two independent fluid flow paths.

DEFINITIONS

A Biological Fluid Filtration Device (hereinafter referred to as BFFD) as used herein means a filtration device comprising a housing containing an inlet and an outlet, with a fluid flow path defined between the inlet and the outlet, with a biological fluid filtration media interposed between the inlet and the outlet and across the fluid flow path, and sealed to the housing to prevent the flow of biological fluid between the housing and the biological fluid filtration media. The biological fluid filtration device being capable of filtering biological fluids, including blood or blood products to remove leukocytes, prions, other blood components, cells, and chemical agents which may be used to treat the biological fluid, from the biological fluid. A biological fluid filtration device that contains a single inlet and a single outlet with one biological fluid filtration media interposed between the inlet and the outlet may be referred to as a single sided biological fluid filtration device. The term Biological Fluid Filtration Device may also refer to a filtration device comprising a housing containing two inlets and two outlets, with a first fluid flow path defined between the first inlet and the first outlet, with a first biological fluid filtration media interposed between the first inlet and the first outlet and across the first fluid flow path, and sealed to the housing to prevent the flow of biological fluid between the housing and the first biological fluid filtration media; and with a second independent fluid flow path defined between the second inlet and the second outlet, with a second biological fluid filtration media interposed between the second inlet and the second outlet and across the second fluid flow path, and sealed to the housing to prevent the flow of biological fluid between the housing and the second biological fluid filtration media. The biological fluid filtration device that contains two independent fluid flow paths being capable of simultaneously filtering two different types biological fluids, including blood or blood products to remove leukocytes, prions, other blood components, cells, and chemical agents which may be used to treat the biological fluid, from the biological fluid. A biological fluid filtration device that contains a single inlet and a single outlet with two biological fluid filtration media interposed between the inlet and the outlet, with a first fluid flow path flowing from the inlet, through the first biological fluid filtration media to the outlet, and with a second fluid flow path flowing from the inlet, through the second biological fluid filtration media to the outlet, may be referred to as a double sided biological fluid filtration device. Likewise, a biological fluid filtration device that contains two inlets and two outlets, with a first fluid flow path flowing from the first inlet, through the first biological fluid filtration media to the first outlet, and with a second fluid flow path flowing from the second inlet, through the second biological fluid filtration media to the second outlet, may also be referred to as a double sided biological fluid filtration device.

Biological Fluid Filtration Media (hereinafter referred to as BFFM) as used herein means a porous filtration media capable of filtering biological fluids, including blood or blood products to remove leukocytes, prions, other blood components, cells, and chemical agents which may be used to treat the biological fluid, from the biological fluid. The biological fluid filtration media (BFFM) comprises at least one filter element, with each filter element containing one or more layers of porous filter material of the same type. The biological fluid filtration media may contain more than one filter element, with each filter element containing a different type of filter material.

Vent Filtration Media as used herein means the filtration media used in a vent filter device. The media may be microporous filter material made from a material such as Teflon or PVDF, preferably with a pore size of $0.2\mu$ or smaller, or the media may be a depth media, such as cotton, spun bound polyester, or a molded depth media such as Porex.

Housing as used herein means the enclosure into which the filtration media is sealed. The housing of a BFFD contains an inlet and an outlet, with a fluid flow path defined between the inlet and the outlet, with a BFFM interposed between the inlet and the outlet and across the fluid flow path, and sealed to the housing to prevent the flow of biological fluid between the housing and the BFFM. The housing of a BFFD may contain two inlets and two outlets, with a first fluid flow path defined between the first inlet and the first outlet, with a first BFFM interposed between the first inlet and the first outlet and across the first fluid flow path, and sealed to the housing to prevent the flow of biological fluid between the housing and the first BFFM; and with a second fluid flow path defined between the second inlet and the second outlet, with a second BFFM interposed between the second inlet and the second outlet and across the second fluid flow path, and sealed to the housing to prevent the flow of biological fluid between the housing and the second BFFM. The housing may be made from a rigid material such as stainless steel or aluminum, or from any rigid molded plastic material such as Acrylic, Polycarbonate, Polypropylene, Polyethylene, or from any flexible plastic film material such as PVC, Polypropylene, Polyethylene, or from a combination of rigid and flexible materials. The housing of a vent filtration device contains a vent port in fluid flow communication with atmosphere, and a system port in fluid flow communication with the biological fluid filtration system, with a fluid flow path defined between the vent port and the system port, with a vent filtration media interposed between the vent port and the system port and across the fluid flow path, and sealed to the housing to prevent the flow of biological fluid or gas between the vent filtration media and the housing. Alternately the housing of a vent filtration device may contain a vent port in fluid flow communication with atmosphere, and a first system port in fluid flow communication with the biological fluid filtration system, with a first fluid flow path defined between the vent port and the first system port, with a vent filtration media interposed between the vent port and the first system port and across the first fluid flow path, and sealed to the housing to prevent the flow of biological fluid or gas between the vent filtration media and the housing; and a second system port in fluid flow communication with the biological fluid filtration system, with a second fluid flow path defined between the vent port and the second system port, with a vent filtration media interposed between the vent port and the second system port and across the second fluid flow path, and sealed to the housing to prevent the flow of biological fluid or gas between the vent filtration media and the housing.

Three Tube Connector as used herein means a tubing connector containing three tube sockets. One end of a first length of tubing is connected to the first tube socket, one end of a second length of tubing is connected to the second tube socket, and one end of a third length of tubing is connected to the third tube socket. The three tube connector contains a common node that is in fluid flow communication with the three lengths of tubing. A tubing Tee is one form of a three tube connector. A tubing Y is another form of a three tube connector.

Biological Fluid as used herein means any type of biological liquid, including blood or blood product, and including leukocyte containing suspensions or a prion containing suspensions.

Leukocyte Containing Suspension as used herein means a liquid in which leukocytes are suspended. Examples of leukocyte-containing suspensions include whole blood; red cell products, such as concentrated red cells, washed red cells, leukocyte-removed cells, thawed red cell concentrate and thawed red cell suspension; plasma products, such as platelet-poor plasma, platelet-enriched plasma, fresh lyophilized plasma, fresh liquid plasma and cryoprecipitate; and other leukocyte-containing blood products, such as concentrated platelet cells, buffy coat and buffy coat-removed blood. The leukocyte-containing suspension to be filtered by the devices and systems described in the present invention is not limited to the above examples.

Prion Containing Suspension as used herein means a liquid in which prions are suspended.

Diaphragm Draining Device (hereinafter referred to as DDD) as used herein means a device having a housing with an inlet in fluid flow communication with atmosphere, with an outlet in fluid flow communication with a second device to be drained, and with a diaphragm interposed between the inlet and the outlet, with the housing containing a volume of gas between the diaphragm and the outlet in its normal state.

SUMMARY OF THE INVENTION

The foregoing problems of the prior art are solved, and the objects of the present invention are achieved, by use of a biological fluid filtration device (BFFD) and system constructed in accordance with the principles of the present invention. The biological fluid filtration system of the present invention is capable of filtering biological fluids, including blood or blood products to remove leukocytes, prions, other blood components, cells, and chemical agents which may be used to treat the biological fluid, from the biological fluid.

The biological fluid filtration system includes a feed container, normally a collapsible blood bag and a receiving container, normally a collapsible blood bag with a BFFD interposed between the two blood bags. The BFFD includes a housing having an inlet and an outlet with a fluid flow path defined between the inlet and the outlet. A biological fluid filtration media (BFFM) is interposed between the inlet and the outlet, and across the fluid flow path. The BFFM may contain one filter element or multiple filter elements of different types. The housing also includes a chamber located between the inlet and the upstream surface of the BFFM. In several embodiments the housing also includes an outlet channel interposed between the downstream side of the BFFM and the outlet, with the outlet channel being in direct fluid flow relation with the outlet port, and with at least the portion of the outlet channel adjoining the outlet having a cross sectional flow area greater than the cross sectional flow area of the outlet.

In another embodiment of the BFFD an outlet chamber or plenum is interposed between the downstream side of the BFFM and the outlet.

Several embodiments of the biological fluid filtration system include a three tube connector inserted into the length of tubing between the feed container and the inlet of the BFFD, so that a first length of tubing connects the feed container to a first port on the three tube connector, and a second length of tubing connects the inlet of the BFFD to a second port on the three tube connector, and a third length of tubing connects a vent filtration device to the third port of the three tube connector. The vent filtration device contains a vent port in fluid flow communication with atmosphere. The three tube connector contains a common node. A first flow path is defined between the feed container and the common node. A second flow path is defined between the common node and the inlet of the BFFD. A third flow path is defined between the common node and the vent port. The distance between the top of the biological liquid in the feed container and the common node must be greater than the distance between the common node and the inlet of the BFFD until the BFFM in the BFFD has been wetted with biological liquid. A portion of the second fluid flow path is disposed above the common node a sufficient distance to create a positive pressure at the common node whenever biological liquid flows through the first and second fluid flow paths, thereby preventing air from entering the system whenever biological liquid flows through the first fluid flow path and through the second fluid flow path without the need to manually close the third fluid flow path. Alternately the three tube connector can contain a flow restriction in the second flow path in which case a portion of the second fluid flow path does not have to be disposed above the common node. In either case the vent filtration device could be replaced with a diaphragm draining device defined above, and described below.

Alternately, the BFFD may contain a second inlet upstream of the BFFM. A vent filtration device containing a vent filter element is connected to the second inlet via a length of tubing. The vent filtration device contains a vent port in fluid flow communication with atmosphere, and a fluid flow path is defined between the vent port and the upstream chamber of the BFFD, with the vent filter element interposed between the vent port and the second inlet of the BFFD, and across the fluid flow path.

Several embodiments of the BFFD include a diaphragm disposed upstream of the BFFM. In the normal state of the diaphragm an upstream chamber is defined between the upstream surface of the BFFM and the inner surface of the diaphragm, with the inlet in fluid flow communication with the upstream chamber. When the filtration cycle is complete and the feed blood bag is emptied, the negative pressure created by the column of filtered biological fluid in the outlet tubing causes the diaphragm to collapse onto the upstream surface of the BFFM, thereby forcing the unfiltered biological fluid in the upstream chamber through the BFFM into the outlet, thereby minimizing hold up volume.

To further reduce hold up volume several embodiments of the BFFD contain variable surface area filter elements, with one or more filter elements of a first surface area, followed by one or more filter elements of a second smaller surface area. Interposed between the larger surface area filter elements and the smaller surface area filter elements is a flow distribution filter element with a pore size greater than that of the others.

Several embodiments of the BFFD contain a single inlet and a single outlet with two sets of BFFM, each set having variable surface area.

Several embodiments of the BFFD contain a housing with a solid partition wall that divides the housing into two independent BFFD's, with two independent flow paths. The BFFD is capable of filtering two different types of biological fluid simultaneously. For example, a unit of packed red blood cells can be filtered through the first fluid flow path on one side of the solid partition wall, while a unit of blood platelets can be filtered through the second fluid flow path on the other side of the solid partition wall. Each fluid flow path may contain a different type of BFFM. The BFFM could also be used to filter two independent units of the same type of biological fluid.

An embodiment of a biological fluid filtration system that uses a BFFD with a solid partition wall, also contains a vent filtration device that can vent the two BFFD's on either side of the solid partition wall simultaneously.

In any of the embodiments the BFFM may include a first filter element composed of one or more layers of porous filter material of a first pore size, followed by a second filter element composed of one or more layers of porous filter material of a second pore size smaller than that of the first pore size, followed by a third filter element composed of one or more layers of porous filter material of a third pore size larger than that of the second pore size, followed by a fourth filter element composed of one or more layers of porous filter material of a fourth pore size smaller than the pore size of the second filter element. The first filter element may include means to remove gels from blood or blood product, the second filter element may include means to remove microaggregates from blood or blood products, the fourth filter element may include means to remove leukocytes from blood or blood products, while the third filter element acts as a flow distribution layer.

In any of the embodiments a vent filtration device may be added to a port on the receiving container normally a collapsible blood bag to purge air from the receiving blood bag after filtration is complete. Also in any of the embodiments a means can be added to drain the biological fluid in the tubing downstream of the BFFD into the receiving blood bag after the filtration cycle is complete, and then mix the biological fluid in the receiving blood bag, and then express a quantity of mixed biological fluid back into the tubing downstream of the BFFD.

BRIEF DESCRIPTION OF THE DRAWINGS

The invention may be best understood by reference to the detailed description of the preferred embodiments herein when read in conjunction with the drawings in which:

FIG. 6 is an isometric view with portions thereof removed of the three tube connector and the tubing connected to the three tube connector, shown in FIG. 1;

FIG. 7 is a top view of the body of a second embodiment of a three tube connector containing a built in loop;

FIG. 8 is an exploded isometric view with portions thereof removed of a second embodiment of a three tube connector using the body shown in FIG. 7;

FIG. 25 is an isometric view of the BFFD shown in FIG. 23;

FIG. 26 is an isometric view of the BFFD shown in FIG. 23 without the diaphragm;

FIG. 27 is a cross-sectional view of a fifth embodiment of a BFFD constructed in accordance with the principles of the present invention, usable for the filtration of biological fluids, containing a diaphragm, with the inlet located at the top of the housing. The fifth embodiment does not contain a rigid housing inlet half;

FIG. 28 is a cross-sectional view of the BFFD shown in FIG. 27 with the diaphragm shown in the collapsed state after the filtration cycle is complete;

FIG. 30 is an isometric view with portions thereof removed of the housing outlet half of the BFFD shown in FIG. 29;

FIG. 31 is an isometric view with portions thereof removed of the housing inlet half of the BFFD shown in FIG. 29;

FIG. 34 is an isometric view of the housing inlet half of the BFFD shown in FIG. 33;

FIG. 35 is an isometric view of the diaphragm of the BFFD shown in FIG. 33;

FIG. 43 is a top view of the housing outlet half of the BFFD shown in FIG. 40;

FIG. 44 is an isometric view with portions thereof removed of the housing outlet half of the BFFD shown in FIG. 40;

FIG. 45 is a partial cross-sectional view of the BFFD shown in FIG. 40 with a different sealing means being used to seal the filter elements to the housing;

FIG. 46 is a cross-sectional view of a tenth embodiment of a BFFD constructed in accordance with the principles of the present invention, usable for the filtration of biological fluids. The tenth embodiment contains a gel removing filter element, followed by a microaggregate removing filter element, followed by a flow distribution filter element, followed by a leukocyte removing filter element, followed by a second flow distribution filter element, followed by a particle trapping filter element;

FIG. 47 is an isometric view with portions thereof removed of the housing outlet half of the BFFD shown in FIG. 46;

FIG. 48 is an isometric view of the housing inlet half of the BFFD shown in FIG. 46;

FIG. 50 is a isometric view with portions thereof removed of the housing outlet half of the BFFD shown in FIG. 49;

FIG. 51 is a top view of the housing outlet half of the BFFD shown in FIG. 49;

FIG. 52 is a partial cross-sectional view of the outlet portion of the housing outlet half shown in FIG. 50;

FIG. 55 is a cross-sectional view of a twelfth embodiment of a BFFD constructed in accordance with the principles of the present invention, usable for the filtration of biological fluids. The BFFD shown in FIG. 55 is double sided and uses variable surface area like the BFFD shown in FIG. 40. The BFFD shown in FIG. 55 also contains a vent inlet;

FIG. 56 is an isometric view with portions thereof removed of the housing outlet half of the BFFD shown in FIG. 55;

FIG. 57 is a cross-sectional view of a thirteenth embodiment of a BFFD constructed in accordance with the principles of the present invention, usable for the filtration of biological fluids. The BFFD shown in FIG. 55 uses a flexible housing;

FIG. 58 is a cross-sectional view of the BFFD shown in FIG. 57 using a different method to seal the BFFM to the flexible housing;

FIG. 62 is a cross-sectional view of the fifteenth embodiment of a BFFD constructed in accordance with the principles of the present invention, usable for the filtration of biological fluids;

FIG. 63 is a partial cross-sectional view of the BFFD shown in FIG. 62, rotated 180° about the central axis of the BFFD, showing the bottom outlet of the BFFD;

FIG. 64 is a partial cross-sectional view of the BFFD shown in FIG. 62, showing the top outlet of the BFFD;

FIG. 69 is a top view of the housing body used in the vent filtration device shown in FIG. 73;

FIG. 70 is an isometric view with portions thereof removed of the housing body shown in FIG. 69;

FIG. 71 is an isometric view with portions thereof removed of the housing cap used in the vent filtration device shown in FIG. 73;

FIG. 72 is an isometric view with portions thereof removed of an alternate housing cap that can be used in the vent filtration device shown in FIG. 73;

FIG. 73 is an isometric view with portions thereof removed of the vent filtration device used in the biological fluid filtration system shown in FIG. 61;

FIG. 74 is an isometric view with portions thereof removed of an alternate vent filtration device that can be used in the biological fluid filtration system shown in FIG. 61;

FIG. 75 is a cross-sectional view of the sixteenth embodiment of a BFFD constructed in accordance with the principles of the present invention, usable for the filtration of biological fluids;

FIG. 76 is a partial cross-sectional view of the BFFD shown in FIG. 75, rotated 180° about the central axis of the BFFD, showing the bottom outlet of the BFFD;

FIG. 77 is a partial cross-sectional view of the BFFD shown in FIG. 75, showing the top outlet of the BFFD;

FIG. 78 is an isometric view with portions thereof removed of the front of the housing outlet half of the BFFD shown in FIG. 75;

FIG. 79 is an isometric view with portions thereof removed of the back of the housing outlet half of the BFFD shown in FIG. 75;

FIG. 81 is a cross-sectional view of the eighteenth embodiment of a BFFD constructed in accordance with the principles of the present invention, usable for the filtration of biological fluids;

FIG. 82 is an isometric view with portions thereof removed of the housing outlet half of the BFFD shown in FIG. 81;

FIG. 83 is an isometric vie of the housing inlet half of the BFFD shown in FIG. 81;

FIG. 89 is a cross-sectional view of the three tube connector containing a restriction shown in FIG. 80;

FIG. 90 is an isometric view of the top of the housing cap used in the vent filtration device shown in FIG. 80;

FIG. 91 is an isometric view of the bottom of the housing cap used in the vent filtration device shown in FIG. 80;

FIG. 95 is an isometric view of the seventeenth embodiment of a BFFD constructed in accordance with the principles of the present invention, usable for the filtration of biological fluids;

FIG. 96 is a front view of the housing outlet half of the BFFD shown in FIG. 94;

FIG. 97 is a back view of the housing outlet half of the BFFD shown in FIG. 94.

DETAILED DESCRIPTION OF THE FIRST EMBODIMENT

Figure 1:
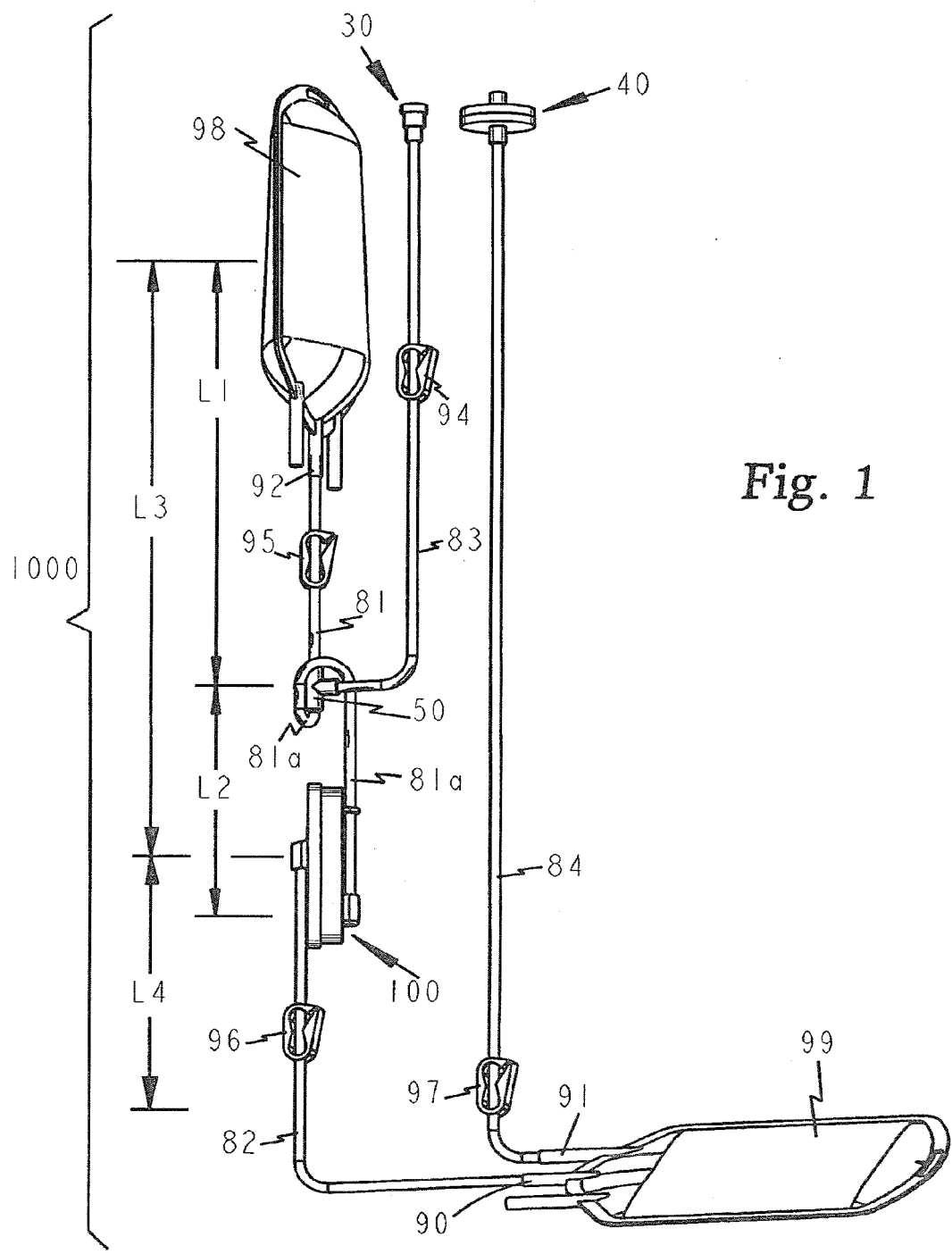
FIG. 1 is an isometric view of a first embodiment of a biological fluid filtration system constructed in accordance with the principles of the present invention, usable for the filtration of biological fluids, containing a feed blood bag, a receiving blood bag, with the first embodiment of a BFFD interposed between the feed blood bag and the receiving blood bag, and with a three tube connector interposed between the feed blood bag and the BFFD. A first vent filtration device is connected to the three tube connector, and a second vent filtration device is connected to the receiving blood bag.

Although various embodiments of the biological fluid filtration system and the biological fluid filtration device (BFFD) constructed in accordance with the principles of the present invention are disclosed herein, each embodiment minimizes the holdup of biological fluid in the biological fluid filtration device (BFFD) after filtration is complete by incorporating filter support structures that minimize liquid holdup downstream of the biological fluid filtration media (BFFM) used in the biological fluid filtration device (BFFD), and by incorporating a means to automatically drain the liquid upstream of the biological fluid filtration media (BFFM) once filtration is complete; and each embodiment minimizes the amount of air that is purged from the BFFD after biological fluid starts to flow from the outlet of the BFFD.

One embodiment of the biological fluid filtration system constructed in accordance with the principles of the present invention, is shown in FIG. 1 through FIG. 6, FIG. 10, and FIG. 11. Biological fluid filtration system 1000 shown in FIG. 1 contains feed blood 98 and receiving blood bag 99. Interposed between feed blood bag 98 and receiving blood bag 99 is a biological fluid filtration device (BFFD) 100. Three tube connector 50 is interposed between feed blood bag 98 and BFFD 100. First length of tubing 81 connects the outlet of feed blood bag 98 to first tube socket 51 of three tube connector 50. Second length of tubing 81a connects second tube socket 52 of three tube connector 50 to the inlet tube socket 6 of BFFD 100. Third length of tubing 83 connects third tube socket 53 of three tube connector 50 to tube socket 35 of vent filtration device 30. A fourth length of tubing 82 connects outlet tube socket 28 of BFFD 100 to the inlet of receiving blood bag 99. A fifth length of tubing 84 connects a vent port on receiving blood bag 99 to tube socket 45 of vent filtration device 40. Tubing 81 may contain tube clamp 95, tubing 82 may contain tube clamp 96, tubing 84 may contain tube clamp 97, and tubing 83 may contain tube clamp 94.

Referring to FIG. 2 through FIG. 5, BFFD 100 contains a rigid housing that includes housing inlet half 1 and housing outlet half 20. Housing seal surface 29a of housing inlet half 1 is bonded to housing seal surface 29 of housing outlet half 20. The bond is preferably an ultrasonic weld but may be a heat bond, a glue bond, a solvent bond, or any other type of leak tight bond.

Figure 2:
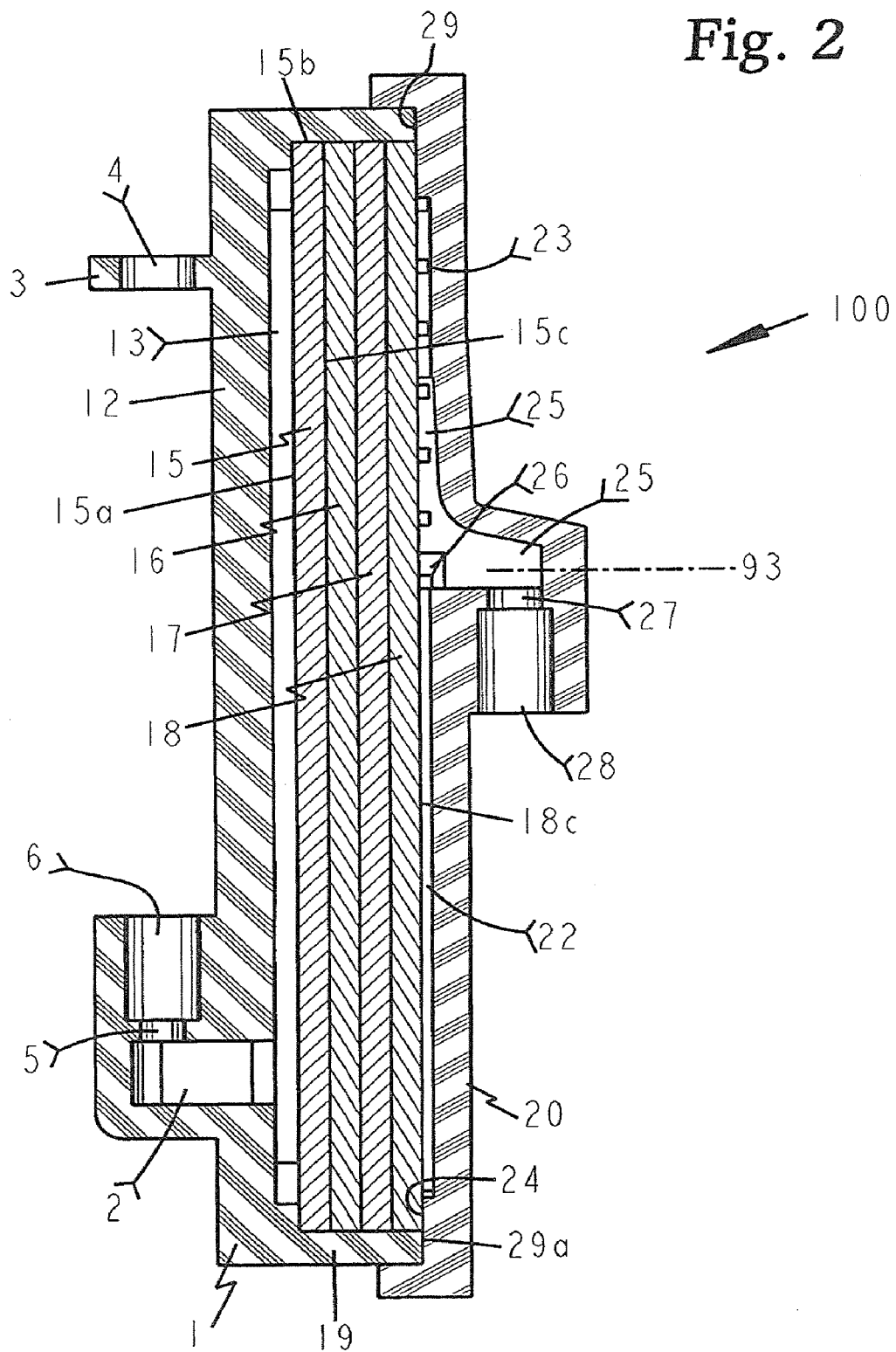
FIG. 2 is a cross-sectional view of the first embodiment of a BFFD constructed in accordance with the principles of the present invention, usable for the filtration of biological fluids.
Figure 5:
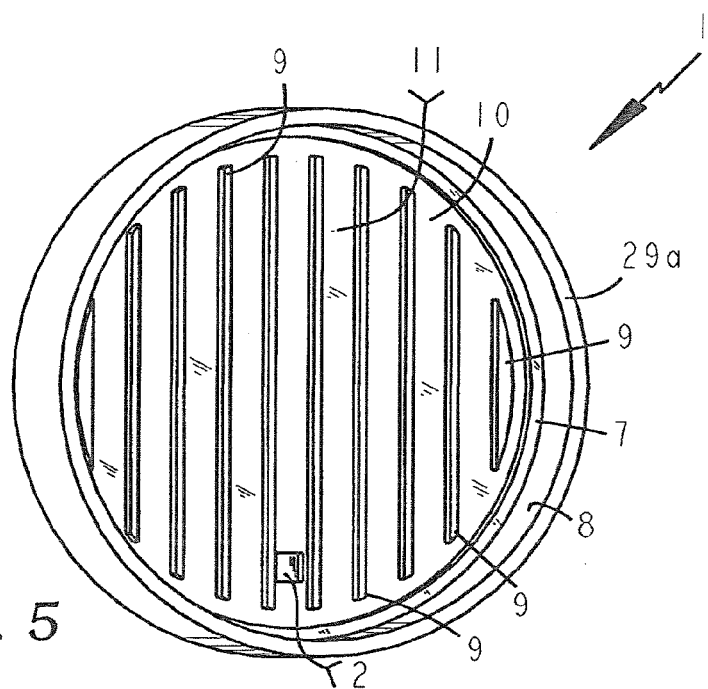
FIG. 5 is an isometric view of the housing inlet half of the BFFD shown in FIG. 2.

Referring to FIG. 2 and FIG. 5 housing inlet half 1 contains filter well 11 bounded by inner side wall 8 and by a plane that goes through filter seal surface 7. Upstream chamber 13 is bounded by inner wall 10 of housing inlet half 1 and by upstream surface 15a of filter element 15. Upstream chamber 13 contains filter support ribs 9. Inlet 5 is in fluid flow communication with upstream chamber 13, via inlet slot 2. The outlet end of tubing 81a is inserted into and bonded to inlet tube socket 6. Inlet 5 and inlet slot 2 are shown located near the bottom of upstream chamber 13 and on the vertical center line of housing inlet half 1, they could however, be located anywhere between the top and the bottom of upstream chamber 13, and could also be located to the right or to the left of the vertical center line.

Figure 3:
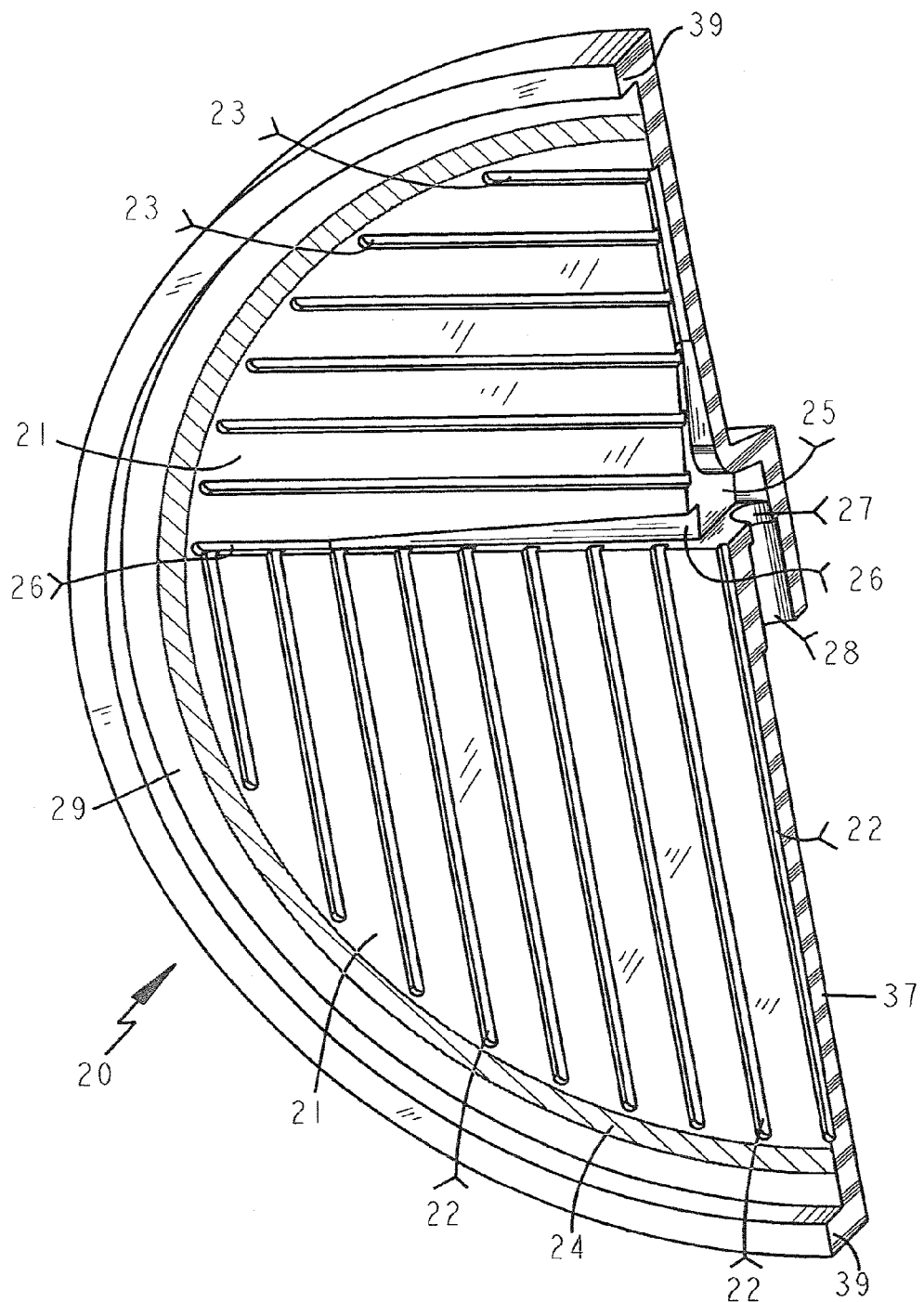
FIG. 3 is an isometric view with portions thereof removed of the housing outlet half of the BFFD shown in FIG. 2.
Figure 4:
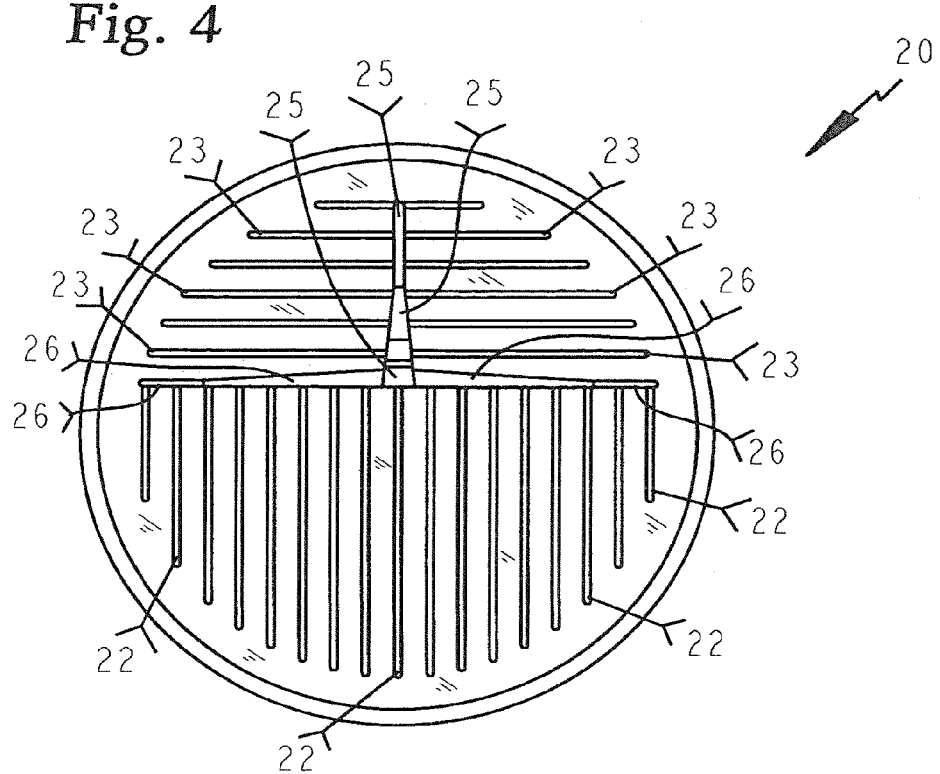
FIG. 4 is a top view of the housing outlet half of the BFFD shown in FIG. 2.

Referring to FIG. 2, FIG. 3, and FIG. 4 housing outlet half 20 contains vertical outlet channel 25 and outlet 27. Vertical outlet channel 25 is in direct fluid flow communication with outlet 27, and the portion of vertical outlet channel 25 that adjoins outlet 27 has a cross-sectional flow area that is greater than the cross-sectional flow area of outlet 27. Housing outlet half 20 also contains horizontal collection channel 26, a plurality of vertical channels 22, and a plurality of horizontal channels 23. One end of each of the vertical and horizontal channels is in fluid flow communication with vertical outlet channel 25. The vertical channels being in fluid flow communication with the vertical outlet channel via the horizontal collection channel. The vertical outlet channel, the horizontal collection channel, the vertical channels, and the horizontal channels combined create a filter under drain structure. The channels are cut into wall 37 of housing outlet half 20 so that the inner surface of all of the channels lies below inner wall 21 of housing outlet half 20 as shown in FIG. 3. The cross sectional area of the vertical outlet channel, the horizontal collection channel, the vertical channels, and the horizontal channels is defined by the inner surface of each channel and by the downstream surface of the BFFM. As shown in FIG. 2, FIG. 3, and FIG. 4, the distance between vertical channels 22 is much greater than the width of vertical channels 22, and of the depth of vertical channels 22. The distance between the horizontal channels 23 is much greater than the width of the horizontal channels 23, and of the depth of horizontal channels 23. For example, the center line distance between the vertical channels and center line distance between the horizontal channels may be equal to 0.150 in., with the width of the vertical channels and the width of the horizontal channels equal to 0.032 in., and with the depth of the vertical channels and the depth of the horizontal channels equal to 0.025 in. As shown in FIG. 2, FIG. 3, and FIG. 4, the depth and width of the horizontal collection channel (i.e. the cross-sectional area of the horizontal collection channel) is sufficiently greater than that of the other horizontal channels to accommodate the flow of biological fluid from the vertical channels, through the horizontal collection channel, into outlet channel 25, without creating an excessive pressure drop across the horizontal collection channel. Housing outlet half 20 also contains filter seal surface 24 and housing seal surface 29 both of which are a part of inner wall 21.

Referring to FIG. 2 and FIG. 3, a biological fluid filtration media (BFFM) that contains at least one filter element is interposed between inlet 5 and outlet 27, and is sealed to the housing to prevent the flow of unfiltered biological fluid from flowing between the housing and the BFFM to prevent bypass of unfiltered biological fluid around the BFFM. The BFFM shown in FIG. 2 contains filter elements 15, 16, 17, and 18. The filter elements may all be of the same type or may be different types filter elements. Each filter element contains an upstream surface designated as upstream surface 15a for filter element 15, a downstream surface designated as downstream surface 15c for filter element 15, and a perimeter surface designated as perimeter surface 15b for filter element 15. The downstream surface of the BFFM shown as downstream surface 18c of filter element 18 is in contact with inner wall 21 of housing outlet half 20. Because the downstream surface of the BFFM contacts inner wall 21 of housing outlet half 20, BFFD 100 does not contain an open chamber or plenum downstream of the BFFM. The air or liquid that is forced through the BFFM must pass through the horizontal and vertical channels and the horizontal collection channel and the outlet channel before flowing into outlet 27 of BFFD 100. The at least one filter element may be sealed to the housing with an interference fit between perimeter surface of the filter element and inner side wall 8 of housing inlet half 1, or the at least one filter element may be sealed to the housing with a compression seal by compressing the outer periphery of the at least one filter element between filter seal surface 7 of housing inlet half 1 and filter seal surface 24 of housing outlet half 20, or the at least one filter element may be sealed to the housing a heat seal, an ultrasonic weld, a glue seal, a solvent seal, a radio frequency weld, or any other type of leak tight seal. A combination of sealing methods may also be used to seal the at least one filter element to the housing. For example, as shown in FIG. 2, the BFFM may be sealed to the housing a combination of an interference fit between perimeter surface of the at least one filter element and inner side wall 8 of housing inlet half 1, and a compression seal between the outer periphery of the at least one filter element between filter seal surface 7 of housing inlet half 1 and filter seal surface 24 of housing outlet half 20.

Referring to FIG. 2, a first fluid flow path is defined between inlet 5 of BFFD 100 and outlet 27 of BFFD 100 with the at least one filter element of the BFFM interposed between inlet 5 and outlet 27, and across the fluid flow path. With the BFFM sealed to the housing to prevent bypass of un-filtered biological fluid (i.e. liquid) around the BFFM. The first fluid flow path flows from inlet 5, through inlet slot 2, into upstream chamber 13, through the at least one filter element of the BFFM, into the vertical channels 22, and into horizontal collection channel 26, and into the horizontal channels 23, into vertical outlet channel 25, and then into outlet 27.

Housing inlet half 1 may contain tube guide 3 to keep BFFD 100 hanging plumb when BFFD 100 is suspended from tubing 81a as shown in FIG. 1.

Figure 11:
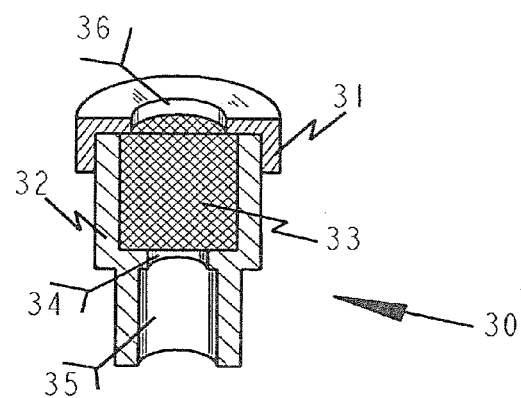
FIG. 11 is an isometric view with portions thereof removed of a second embodiment of a vent filtration device.

Referring to FIG. 11 vent filtration device 30 contains a housing comprised of housing cap 31 and housing body 32. The housing contains a vent port 36 and a system port 34, with a first vent fluid flow path defined between vent port 36 and system port 34, with vent filtration media 33 interposed between the vent port and the system port and across the first vent fluid flow path. With the vent filtration media sealed to the housing to prevent bypass of un-filtered gas (i.e. air) around the vent filtration media. The vent filtration media 33 is shown as a depth filter media, such as a wad of cotton, a non-woven depth filter material, a spun bound filter material, a molded porous filter material or any other type of depth filter material. The vent filtration media may be hydrophobic or hydrophilic. Preferably vent filtration device 30 is located above the liquid level in feed blood bag 98 as shown in FIG. 1.

Figure 10:
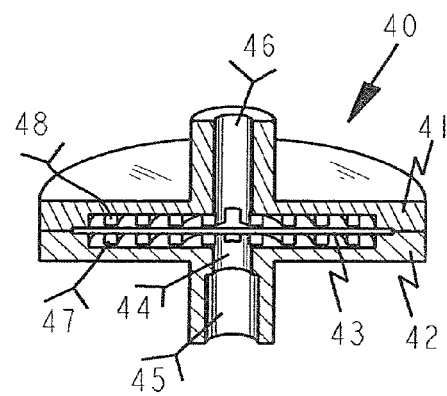
FIG. 10 is an isometric view with portions thereof removed of a first embodiment of a vent filtration device.

Vent filtration device 40 shown in FIG. 10 may be interchanged with vent filtration device 30 shown in FIG. 11. Vent filtration device 40 contains a housing comprised of housing cap 41 and housing body 42. The housing contains a vent port 46 and a system port 44, with a second vent fluid flow path defined between vent port 46 and system port 44, with vent filtration media 43 interposed between the vent port and the system port and across the second vent fluid flow path. With the vent filtration media sealed to the housing to prevent bypass of un-filtered gas (i.e. air) around the vent filtration media. The vent filtration media 43 is shown as a microporous filter media such as a 0.2 μm microporous filter material, but may be any type of depth filter media, such as a non-woven depth filter material, a spun bound filter material, a molded porous filter material or any other type of depth filter material. The vent filtration media may be hydrophobic or hydrophilic. Preferably vent filtration device 40 is located above the liquid level in feed blood bag 98 as shown in FIG. 1.

Referring to FIG. 6 three tube connector 50 contains first tube socket 51, second tube socket 52, and third tube socket 53. One end of tubing 81 is connected to first tube socket 51, one end of tubing 81a is connected to second tube socket 52, and one end of tubing 83 is connected to third tube socket 53. Three tube connector 50 contains first channel 54, second channel 55, and third channel 56. First channel 54 may be referred to as inlet 54, second channel 55 may be referred to as outlet 55, and third channel 56 may be referred to as side port 56. Common node 57 (shown as a dot) places each of the three channels in fluid flow communication with the other two channels.

Referring to FIG. 1, FIG. 2, FIG. 6, and FIG. 11, a second fluid flow path 58 is defined between feed blood bag 98 and common node 57 of three tube connector 50, with the flow in the second fluid flow path flowing from feed blood bag 98 through tubing 81, into first channel 54 of three tube connector 50, to the common node. A third fluid flow path 58a is defined between common node 57 of three tube connector 50 and inlet 5 of BFFD 100, with the flow in the third fluid flow path flowing from common node 57 through tubing 81a, to inlet 5 of BFFD 100. A portion of the third fluid flow path is disposed above the common node. A fourth fluid flow path 59 is defined between the common node and atmosphere, with the flow of the fourth fluid flow path flowing from atmosphere, through vent port 36 of vent filtration device 30, through vent filtration media 33 of vent filtration device 30, through system port 34 of vent filtration device 30, through tubing 83, through third channel 56 of three tube connector 50, to the common node of three tube connector 50.

Referring to FIG. 1 and FIG. 10, biological fluid filtration system 1000 may contain tubing 84 and vent filtration device 40. One end of tubing 84 is connected to tube socket 45 of vent filtration device 40 and the other end of tubing 84 is connected to vent port 91 of receiving blood bag 99. A fifth fluid flow path is defined from atmosphere to vent port 91 of receiving blood bag 99. The fifth fluid flow path flows from vent port 46 of vent filtration device 40, through vent filtration media 43 of vent filtration device 40, through system port 44 of vent filtration device 40 through tubing 84, into vent port 91 of receiving blood bag 99, when tube clamp 97 is open. Preferably vent filtration device 40 is located above the liquid level in feed blood bag 98 as shown in FIG. 1.

Referring to FIG. 1, FIG. 6, and FIG. 11, biological fluid filtration system 1000 functions as follows. The user will purchase the system with all components as shown in FIG. 1, less feed blood bag 98. The user will connect tubing 81 to outlet 92 of feed blood bag 98 in a manner known in the art. Feed blood bag 98, vent filtration device 30, and vent filtration device 40 may be hung from a blood bag pole known in the art, and receiving blood bag 99 may be placed on a table top or the like, so that the various components of the system will be positioned as shown in FIG. 1. Tube clamp 95 should be closed before connecting tubing 81 to feed blood bag 98. Before opening tube clamp 95 to start the flow of biological fluid (i.e. liquid) through the system, tube clamps 94 and 96 should be open, and tube clamp 97 should be closed. Referring to FIG. 1, FIG. 2, and FIG. 6, the distance L1 between the top of the liquid in feed blood bag 98 and common node 57 of three tube connector 50 must be greater than the distance L2 between common node 57 of three tube connector 50 and inlet 5 of BFFD 100.

The same fluid flow path designations that were used above will be used in the following analysis. Referring to FIG. 1, FIG. 2, FIG. 6, and FIG. 11, when tube clamp 95 is opened biological fluid (i.e. liquid) will flow through the second fluid flow path 58, from feed blood bag 98, through tubing 81, through first channel 54 of three tube connector 50 to common node 57 of three tube connector 50. As biological fluid flows from the feed blood bag towards the common node a portion of the air in tubing 81 will be vented through vent filtration device 30, and the remainder of the air in tubing 81 will be forced into inlet 5 of BFFD 100. Once biological fluid reaches the common node it will flow through the third fluid flow path 58a from the common node, through second channel 55 of three tube connector 50, through tubing 81a, into inlet 5 of BFFD 100. If distance L1 from the top of the biological fluid in feed blood bag 98 to common node 57 of three tube connector 50 is greater than distance L2 from the common node to inlet 5 of BFFD 100, and if a portion of the third fluid flow path 58a is located above the common node as shown in FIG. 1, then the pressure at the common node will be positive, and a quantity of biological fluid will flow into tubing 83. The height of biological fluid in tubing 83 will be proportional to the value of the positive pressure at the common node, which is proportional to the ratio of L1 to L2. Therefore air will be prevented from flowing into the system from vent port 36 of vent filtration device 30 for all time when biological fluid flows through the second fluid flow path 58, and for all time when biological fluid flows through the second fluid flow path 58 and through the third fluid flow path 58a with tube clamp 94 in the open position.

Referring to FIG. 1 through FIG. 5, BFFD 100 functions as follows. Biological fluid (i.e. liquid) flowing from tubing 81a, will flow through the first fluid flow path by flowing into inlet 5 of BFFD 100, and then through inlet slot 2 of BFFD 100, into upstream chamber 13 of BFFD 100. Upstream chamber 13 will rapidly fill with biological fluid from the bottom up. As upstream chamber 13 fills from the bottom up, the initial air in upstream chamber 13 will be displaced by the biological fluid filling upstream chamber 13. The displaced air will be forced through the BFFM, into vertical channels 22, and into horizontal channels 23, and into horizontal collection channel 26, and into vertical outlet channel 25, and then into outlet 27 all of BFFD 100. The biological fluid in upstream chamber 13 will be pressurized, with the pressure at the bottom of upstream chamber 13 being proportional to the distance from the top of the biological fluid in feed blood bag 98 to the bottom of upstream chamber 13, and with the pressure at the top of upstream chamber 13 being proportional to the distance from the top of the biological fluid in feed blood bag 98 to the top of upstream chamber 13. Hence the pressure at the top of upstream chamber 13 will be less than the pressure at the bottom of upstream chamber 13. The positive pressure in upstream chamber 13 will cause the biological fluid to flow through the BFFM over the entire surface area of the BFFM and to displace the air within the pores of the BFFM with biological fluid, thereby wetting BFFM from the upstream side 15a of the BFFM to the downstream side 18c of the BFFM. As the BFFM wets the air that was initially in the pores of BFFM will be displaced by biological fluid and flow into vertical channels 22 and into horizontal channels 23, and into horizontal collection channel 26, and into vertical outlet channel 25, and then into outlet 27 all of BFFD 100, into tubing 82, into receiving blood bag 99. Because the pressure at the bottom of upstream chamber 13 is greater than the pressure at the top of upstream chamber 13, the flow rate of biological fluid through the BFFM will be greater at the bottom of the BFFM than at the top of the BFFM. Therefore, BFFM will first become completely wetted from the upstream surface 15a of BFFM to downstream surface 18c of BFFM at the bottom of the BFFM. If the width of vertical channels 22 is sufficiently small, and the depth of vertical channels is sufficiently shallow, so that the cross-sectional flow area of the vertical channels is sufficiently small, and if the distance between vertical channels is sufficiently large, as described above, the path of least resistance for continued biological fluid flow through the BFFM will be through the capillaries of the BFFM in both the horizontal and vertical directions and not through the vertical channels, because if the cross-sectional flow area of the vertical channels is sufficiently small, the displaced air flowing into and through the vertical channels will create a sufficiently high positive pressure in the vertical channels to prevent biological fluid from entering the vertical channels. The downstream surface 18c of the BFFM will therefore wet from the bottom up and the displaced air that was within the BFFM will continue to flow into the vertical channels, and into the horizontal collection channel, and into the horizontal channels, and into the outlet channel, and then into the outlet. When the downstream surface of the BFFM has become wetted to the level of horizontal collection channel 26, air flow through the vertical channels will stop because the downstream surface of the BFFM adjoining the vertical channels will be wetted. Therefore the pressure in the vertical channels will decrease allowing biological fluid to enter the vertical channels from the bottom up, thereby displacing the air that was in the vertical channels. At the same time the wetted level of the downstream surface of the BFFM will continue to wet in the vertical direction, wetting the downstream surface of the BFFM adjoining horizontal collection channel 26, and wetting the downstream surface of the BFFM adjoining the bottom of vertical outlet channel 25. Because neither the cross-sectional flow area of horizontal collection channel 26, or the cross-sectional flow area of vertical outlet channel 25 is sufficiently small to create a sufficient positive pressure in them due to the air flow through them, biological fluid will flow into horizontal collection channel 26 and into vertical outlet channel 25 as BFFM continues to wet in the vertical direction above the bottom of horizontal collection channel 26. The biological fluid flowing into vertical channels 22 and into horizontal collection channel 26 and into the bottom of vertical outlet channel 25 will flow into outlet 27 of BFFD 100 and then into tubing 82 toward receiving blood bag 99. As biological fluid starts to flow into outlet 27, BFFM will continue to wet vertically, wetting first close to the outer perimeter of BFFM, and then toward the vertical outlet channel 25. Hence the initial flow of biological fluid into tubing 82 will consist of alternate segments of biological fluid and air. As will be seen in the experimental data below, a BFFD constructed in accordance with the principles of the present invention, as shown in FIG. 2 through FIG. 5, will purge approximately 94% of the initial air in BFFD 100 before biological fluid begins to flow into outlet 27. To maximize the amount of air that is purged from BFFD 100 before biological fluid starts to flow into outlet 27, horizontal collection channel 26 should be located as high above the horizontal center line of BFFD 100 (and therefore above the horizontal centerline of the housing) as possible.

Referring to FIG. 1, when biological fluid starts to flow into tubing 82, the pressure P downstream of the BFFM and upstream of outlet 27 (i.e. downstream of the BFFM, but within BFFD 100) will be determined by the following formula:

$$P = L3 - \Delta p - L4$$

$\Delta p$ is the pressure drop across the BFFM due to biological fluid flow through the BFFM.

L3 is the distance between outlet 27 of BFFD 100 and the top of the biological fluid in feed blood bag 98.

L4 is the height of biological fluid minus any air segments downstream of outlet 27, in tubing 82.

Therefore the pressure P within BFFD 100 and downstream of the BFFM will be greater than or equal to zero until $L4 = L3 - \Delta p$. If the bottom of horizontal collection channel 26 is positioned a sufficient distance above the horizontal center line of BFFD 100, all of the air that was initially inside of BFFD 100 will be purged from BFFD 100 before the pressure P within BFFD 100 downstream of the BFFM becomes negative. If however, the bottom of horizontal collection channel 26 is positioned below the horizontal center line of BFFD 100, all of the air that was initially inside of BFFD 100 will not be purged from BFFD 100 before the pressure P within BFFD 100 downstream of the BFFM becomes negative. As described above the pressure within upstream chamber 13 of BFFD 100 will be positive as long as biological fluid is flowing into upstream chamber 13. The purging of air from within BFFD 100 is totally independent of whether or not the pressure within BFFD 100 downstream of the BFFM becomes negative. As will be seen in the experimental data below, all of the air will be purged from within BFFD 100 even if the pressure within BFFD 100 downstream of the BFFM never becomes negative, as long as feed blood bag 98 is positioned a sufficient distance above outlet 27 of BFFD 100.

If the flow rate through the BFFM is sufficiently small after the BFFM has become completely wetted, the distance L1 from the top of the biological fluid in feed blood bag 98 to common node 57 of three tube connector 50 may become less than distance L2 from the common node to inlet 5 of BFFD 100, without allowing air to enter into the system from tubing 83, because the reduced flow rate through the BFFM will cause biological fluid to back up into tubing 83.

Referring to FIG. 1, FIG. 2, FIG. 6, and FIG. 11, once all of the air has been purged from within BFFD 100, biological fluid will continue to flow through the first fluid flow path from the inlet of BFFD 100 to the outlet of BFFD 100, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in the second fluid flow path between the outlet of feed blood bag 98 and common node 57 of three tube connector 50. With the second fluid flow path shut off as just described, air will now flow through the fourth fluid flow path from vent port 36 of vent filtration device 30, through vent filtration media 33, through system port 34, into tubing 83, thereby draining the biological fluid in the fourth fluid flow path from system port 34 to common node 57 of three tube connector 50, and draining the biological fluid in the third fluid flow path from common node 57 to inlet 5 of BFFD 100, and then draining the biological fluid in upstream chamber 13 of BFFD 100. To complete the draining of biological fluid as just described, receiving blood bag 99 must be positioned a sufficient distance below outlet 27 of BFFD 100 to create a sufficiently negative pressure downstream of the BFFM and upstream of outlet 27 after all of the air has been purged from within BFFD 100 and tubing 82 is filled with biological fluid, to create a sufficient pressure differential between upstream surface 15a and downstream surface 18c of the BFFM to drain upstream chamber 13 to the bottom of upstream chamber 13, because, as the biological fluid level in upstream chamber 13 approaches the bottom of upstream chamber 13, the pressure on the bottom of the biological fluid in upstream 13 will approach zero. When the filtration cycle is complete, biological fluid will remain within the BFFM, and in the filter under drain structure of housing outlet half 20, and in tubing 82.

Referring to FIG. 1, when the filtration cycle is complete as just described, the user will close tube clamp 96, and then cut and seal tubing 82 above tube clamp 96, and then discard BFFD 100 and the remaining components attached to it in a safe manner. Tubing 82 may contain marks to divide it into segments. In this case tubing 82 would also be sealed at each segment so that the biological fluid remaining in each segment could be used for cross matching purposes Tube clamp 97 may now be opened, and the air in receiving blood bag 99 may be purged from receiving blood bag 99 by squeezing receiving blood bag 99 thereby forcing the air in receiving blood bag 99 through the fifth fluid flow path from vent port 91 of receiving blood bag 99 to atmosphere. Tubing 84 can then be sealed and cut near receiving blood bag 99, and then tubing 84 and vent filtration device 40 may be discarded in a safe manner. Alternately a quantity of biological fluid from receiving blood bag 99 may be squeezed into tubing 84 to be used for testing purposes, after the air is purged from the receiving blood bag. In this case tubing 84 may contain marks to divide it into segments. Tubing 84 would be sealed above the level of biological fluid in it, and at each segment mark, and then the portion of tubing 84 above the uppermost seal along with vent filtration device 40 would be cut away and discarded in a safe manner.

FIG. 7 and FIG. 8 show a second embodiment of the three tube connector. Three tube connector 50a contains body 61, gasket 62, and cover 63. Body 61 contains first channel 54a, second channel 55a, third channel 56a, common node 57a, first tube socket 51a, second tube socket 52a, and third tube socket 53a. A portion of second channel 55a is positioned above common node 57a. When the components of three tube connector 50a are assembled, surface 67 of gasket 62 is in contact with surface 64 of body 61, and surface 68 of gasket 62 is in contact with surface 66 of cover 63, with the outer periphery of cover 63 sealed to flange 65 of body 61, thereby compressing gasket 62 between body 61 and cover 63, thereby creating closed channels 54a, 55a, and 56a. When three tube connector 50a replaces three tube connector 50 in FIG. 1, tubing 81 is connected to first tube socket 51a, tubing 83 is connected to third tube socket 53a, and tubing 81a is connected to second tube socket 52a as shown in FIG. 8.

Referring to FIG. 6 and FIG. 8, flow path 58aa of three tube connector 50a replaces flow path 58 of three tube connector 50, flow path 58aaa of three tube connector 50a replaces flow path 58a of three tube connector 50, and flow path 59a of three tube connector 50a replaces flow path 59 of three tube connector 50. Since a portion of flow path 58aaa is positioned above the common node of three tube connector 50a, there is no need to have a loop in tubing 81a as shown in FIG. 1 (i.e. a straight length of tubing 81a from second tube socket 52a of three tube connector 50a to inlet tube socket 6 of BFFD 100 can be used). Referring to FIG. 1, FIG. 2, FIG. 6, and FIG. 8, three tube connector 50a without a loop in tubing 81a works the same as three tube connector 50 with a loop in tubing 81a, preventing air from entering the system during the filtration cycle, and draining tubing 83, tubing 81a, and upstream chamber 13 of BFFD 100 after the feed blood bag has emptied and flow stops through tubing 81, as described above.

Figure 9:
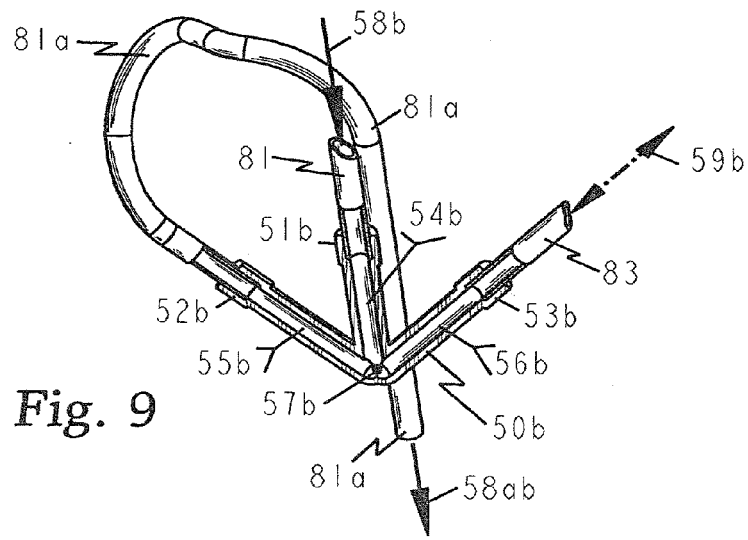
FIG. 9 is an isometric view with portions thereof removed of a third embodiment of a three tube connector and the tubing connected to it.

FIG. 9 shows a third embodiment of the three tube connector. V-shaped three tube connector 50b contains first channel 54b, second channel 55b, third channel 56b, common node 57b, first tube socket 51b, second tube socket 52b, and third tube socket 53b. When three tube connector 50b replaces three tube connector 50 in FIG. 1, tubing 81 is connected to first tube socket 51b, tubing 83 is connected to third tube socket 53b, and tubing 81a is connected to second tube socket 52b as shown in FIG. 9. Referring to FIG. 6 and FIG. 9, flow path 58b of three tube connector 50b replaces flow path 58 of three tube connector 50, flow path 58ab of three tube connector 50b replaces flow path 58a of three tube connector 50, and flow path 59b of three tube connector 50b replaces flow path 59 of three tube connector 50. Tubing 81a as shown in FIG. 9 contains a loop with the central axis of portion of tubing 81a that goes from the three tube connector to the BFFD being parallel to the central axis of tubing 81, thereby allowing the three tube connector to hang plumb. As long as V-shaped three tube connector 50b hangs plumb, it is not necessary to have a loop in tubing 81a, since second tube socket 52b is located above the common node. Referring to FIG. 1, FIG. 2, FIG. 6, and FIG. 9, three tube connector 50b with or without a loop in tubing 81a works the same as three tube connector 50 with a loop in tubing 81a, preventing air from entering the system during the filtration cycle, and draining tubing 83, tubing 81a, and upstream chamber 13 of BFFD 100 after the feed blood bag has emptied, as described above.

Other types of three tube connectors such as a tubing Y may also replace the tubing Tee three tube connector shown in FIG. 1 and FIG. 6. The only requirement for the three tube connector is that it place one end of the interior of three lengths of tubing 81, 81a, and 83, in fluid flow communication with each other.

Experimental Data of the First Embodiment

Experimental data was obtained by testing a machined BFFD constructed as shown in FIG. 2, FIG. 3, FIG. 4, and FIG. 5. The machined BFFD used a BFFM consisting of nine layers of 2.6 inch diameter by 0.030 inch thick fibrous filtration material. The BFFM was sealed to the housing an interference fit between the perimeter surface of the BFFM and the housing, and by compressing the outer periphery of the upstream surface of the BFFM and the outer periphery of the downstream surface of the BFFM between a filter seal surface on the housing inlet half and a filter seal surface on the housing outlet half, as shown in FIG. 2.

To determine how the air was purged from the BFFD the inlet of the BFFD was connected to an open top reservoir located above the BFFD with a ball valve located between the reservoir and the inlet of the BFFD, and the outlet of the BFFD was connected to a length of tubing with an open end. The distance L3 shown in FIG. 1 between the top of the fluid in the reservoir and the outlet of the BFFD was 21 inch. The test fluid was un-filtered tap water. A test hole was drilled and tapped through the housing outlet half through center line 93 shown in FIG. 2. One end of a water manometer was connected to the test hole to measure the pressure P (defined above) within the BFFD downstream of the BFFM and upstream of the outlet of the BFFD.

In the first test the reservoir was filled with un-filtered tap water so that L3 shown in FIG. 1 was 21 inches. The outlet tubing was held horizontal a the level of the outlet of the BFFD. The ball valve was opened allowing the un-filtered tap water to flow from the reservoir to the inlet of the BFFD. The BFFD filled, and wetted the BFFM and purged all of the air from within the BFFD just as described in the detailed description of the first embodiment above. The pressure P as measured by the manometer was zero until liquid started to flow downstream of the BFFM into the outlet tubing. At this point the pressure became positive and remained positive. The outlet end of the outlet tubing was then slowly lowered. As the outlet end of the outlet tubing was lowered, the pressure P decreased and became zero when the outlet end of the outlet tubing was 15½ inches below the outlet of the BFFD. From the equation P=L3−Δp−L4, defined above, substituting zero for P, we have Δp=L3−L4, or in the experiment just described, Δp=21−15.5=5.5 in. $H_2O$. Therefore, for the conditions just described, the pressure P downstream of the BFFM and upstream of the outlet of the BFFD will be greater than or equal to zero for all time until the length of a column of water, either a continuous water column, or the sum of the length of the water segments in a column consisting of alternate water-air segments, equals 15½ inches. This test was repeated several times yielding the same results.

To determine the quantity of air that is purged from the BFFD after liquid starts to flow from the outlet of the BFFD the inlet of the BFFD was connected to an open top reservoir located above the BFFD with a ball valve located between the reservoir and the inlet of the BFFD, and the outlet of the BFFD was connected to a length of tubing with an open end. The distance L3 shown in FIG. 1 between the top of the fluid in the reservoir and the outlet of the BFFD was 21 inch. The test fluid was un-filtered tap water. The test hole was sealed.

In the second test the reservoir was filled with un-filtered tap water so that L3 shown in FIG. 1 was 21 inches. The outlet tubing was held horizontal at the level of the outlet of the BFFD. The ball valve was opened allowing the un-filtered tap water to flow from the reservoir to the inlet of the BFFD. The BFFD filled, and wetted the BFFM and purged all of the air from within the BFFD just as described above in the detailed description of the first embodiment above. After all of the air was purged from the BFFD, the ball valve was closed to stop flow and the length of the column of alternate segments of air and liquid in the outlet tubing was measured. This was done several times, with the length of the column of alternate segments of air and liquid in the outlet tubing varying between 10 inches and 15 inches, with approximately half of the column consisting of air with the remainder being water. Hence, the column of liquid in the outlet tubing varied between 5 inches and 7.5 inches at the point when all of the air had been purged from the BFFD. For this device the first experiment shows that it takes a column of water 15.5 inches high in the outlet tubing to make the pressure P equal to zero, and the second experiment shows that the column of water is 5 inches to 7.5 inches high when all of the air has been purged from the BFFD. Therefore, all of the air is purged from the BFFD before the pressure P becomes negative, so that a negative pressure P is not used to purge air from the BFFD. Furthermore, the first experiment shows that all of the air in the BFFD will be purged from the BFFD for conditions where the pressure P remains positive throughout the filtration cycle (i.e. the outlet tubing was held at the level of centerline 93 shown in FIG. 2). Therefore purging the air from the downstream side of the BFFM within the housing does not depend on a negative pressure downstream of the BFFM. For the above conditions, if the outlet tubing is positioned below the outlet, than when the length of the liquid column in the outlet tube exceeds 15.5 inches the negative pressure downstream of the BFFM will increase the total pressure available to force liquid through the BFFM, and therefore decrease the filtration time, but will have no effect on weather or not air is purged from downstream of the BFFM within the housing.

To verify the performance of the three tube connector shown in FIG. 1 and FIG. 6, the following third test was performed. A tubing tee as shown in FIG. 1 and FIG. 6 was used for the three tube connector. Referring to FIG. 1, an open top reservoir was used in place of feed blood bag 98, and the outlet end of tubing 81a was open to atmosphere, with the open end positioned below the common node of the tubing tee and with a portion of tubing 81a positioned above the common node of the tubing tee as shown in FIG. 1. The vent filtration device 30 was positioned above the top of the liquid level in the open top reservoir as shown in FIG. 1. The liquid was un-filtered tap water. The BFFD and the receiving blood bag were not used. A ball valve was used in place of tube clamp 95. At the start of the experiment the distance between the open end of tubing 81a and the common node of the tubing tee was less than the distance between the common node of the tubing tee and the top of the liquid in the reservoir. When the ball valve was opened to start liquid flow, water flowed from the reservoir through tubing 81 and through tubing 81a to the outlet end of tubing 81a, with a quantity of water flowing into tubing 83, indicating that the pressure at the common node of the tubing tee was positive as explained above in the detailed description of the first embodiment. The open end of tubing 81a was then slowly lowered while observing the liquid level in tubing 83. As the open end of tubing 81a was lowered, the liquid level in tubing 83 receded toward the common node of the tubing tee. When the open end of tubing 81a was lowered to the point that the distance between the open end of tubing 81a and the common node of the tubing tee was equal to the distance between the common node of the tubing tee and the top of the liquid in the reservoir, all of the liquid had receded from tubing 83. When the open end of tubing 81a was lowered further so that distance between the open end of tubing 81a and the common node of the tubing tee was greater than the distance between the common node of the tubing tee and the top of the liquid in the reservoir, air began to flow into the tubing tee from tubing 83, and then flow into tubing 81a. The open end of tubing 81a was then raised so that the distance between the open end of tubing 81a and the common node of the tubing tee was equal to the distance between the common node of the tubing tee and the top of the liquid in the reservoir, at which point air stopped flowing into the tubing tee from tubing 83. When the open end of tubing 81a was raised further, water started to flow into tubing 83 indicating a positive pressure at the common node of the tubing tee. This experimental data confirms the detailed description of the three tube connector above.

The third test was repeated using the three tube connector shown in FIG. 7 and FIG. 8 to replace the tubing tee shown in FIG. 1 and FIG. 6. The results were the same as the results of the third test.

A fourth test was performed as follows: Referring to FIG. 1, FIG. 2, and FIG. 6, a tubing tee was used for the three tube connector with a portion of tubing 81a positioned above the common node of the tee as shown in FIG. 1. An open top reservoir was used in place of feed blood bag 98, and the outlet end of tubing 81a was connected to the inlet of the BFFD used in the first and second tests above, with the outlet end of tubing 82 open to atmosphere. A ball valve was used in place of tube clamp 95. The distance L1 from the bottom of the reservoir to the common node of the tubing tee was greater than the distance from the common node of the tubing tee to the inlet of the BFFD. Vent filtration device 30 was positioned above the top of the liquid in the reservoir as shown in FIG. 1. When the ball valve was opened to allow un-filtered tap water to flow from the reservoir, water flowed from the reservoir through tubing 81 and through tubing 81a into the inlet of the BFFD, with a quantity of water flowing into tubing 83, thereby preventing air from entering the tee from tubing 83. The BFFD filled, and wetted the BFFM and purged all of the air from within the BFFD just as described in the detailed description of the first embodiment above. Liquid flow continued from the reservoir, through the BFFD, into tubing 82 until the ball valve was closed to simulate feed blood bag 98 emptying and then collapsing. Once liquid flow was stopped in tubing 81, air entered tubing 83 through vent filtration device 30, thereby draining the liquid in tubing 83, and the liquid in tubing 81a, and the liquid in the tubing tee between tubing 83 and tubing 81a, and the liquid in upstream chamber 13 of the BFFD just as described in the detailed description of the first embodiment above.

Detailed Description of the Second Embodiment

A second embodiment of the biological fluid filtration system constructed in accordance with the principles of the present invention, is shown in FIG. 10 through FIG. 16. Biological fluid filtration system 2000 shown in FIG. 12 contains feed blood 98 and receiving blood bag 99. Interposed between feed blood bag 98 and receiving blood bag 99 is a biological fluid filtration device (BFFD) 200. First length of tubing 81 connects the outlet of feed blood bag 98 to the inlet tube socket 106 of BFFD 200. A second length of tubing 82 connects outlet tube socket 128 of BFFD 200 to the inlet of receiving blood bag 99. Third length of tubing 85 connects vent tube socket 179 of BFFD 200 to tube socket 45 of vent filtration device 40. A fourth length of tubing 84 connects a vent port on receiving blood bag 99 to tube socket 35 of vent filtration device 30. Tubing 81 may contain tube clamp 95, tubing 82 may contain tube clamp 96, tubing 84 may contain tube clamp 97, and tubing 85 may contain tube clamp 94.

Figure 13:
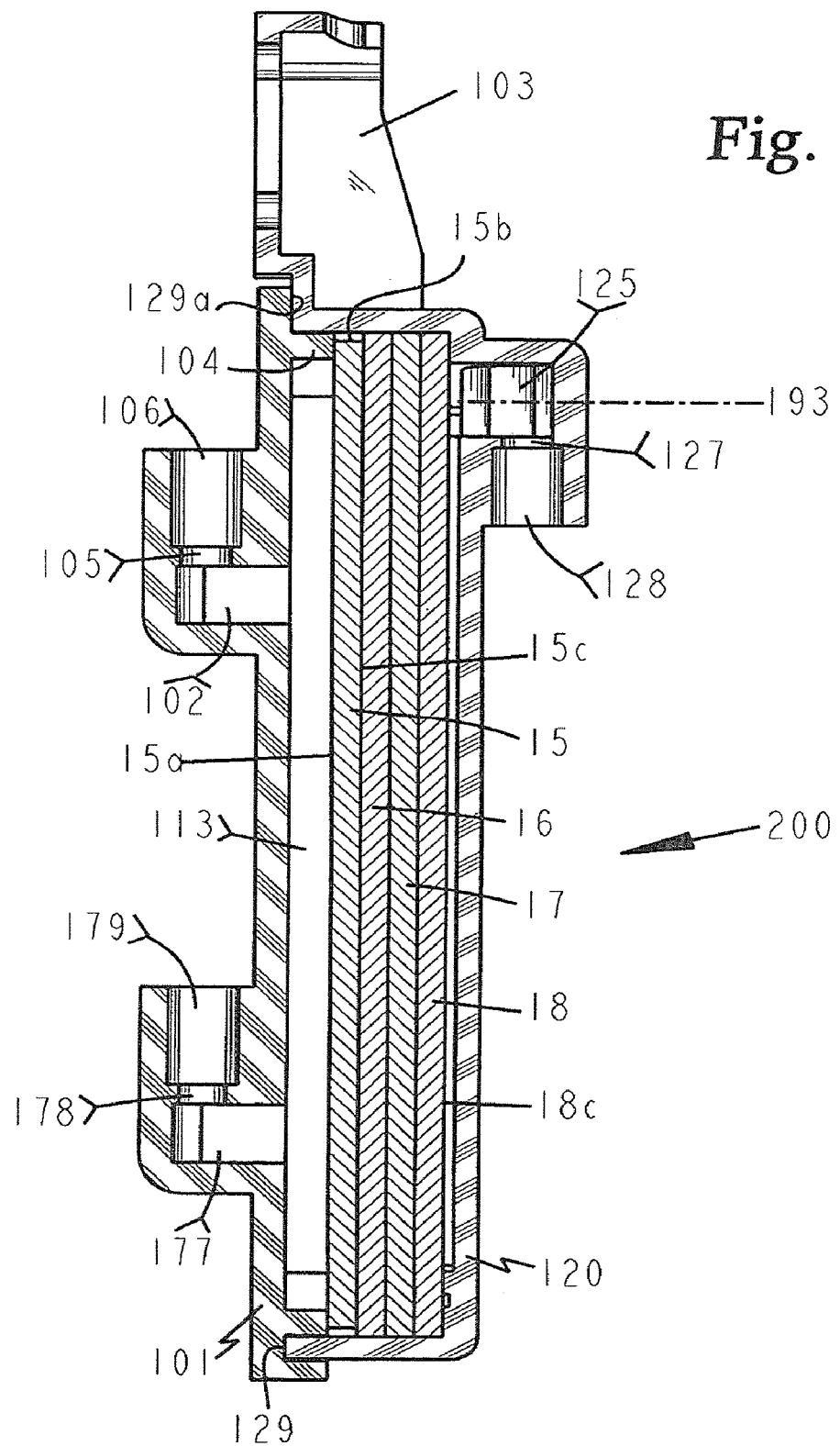
FIG. 13 is a cross-sectional view of the second embodiment of a BFFD constructed in accordance with the principles of the present invention, usable for the filtration of biological fluids.

Referring to FIG. 13, BFFD 200 contains a rigid housing that includes housing inlet half 101 and housing outlet half 120. Housing seal surface 129a of housing inlet half 101 is bonded to housing seal surface 129 of housing outlet half 120. The bond is preferably an ultrasonic weld but may be a heat bond, a glue bond, a solvent bond, or any other type of leak tight bond.

Figure 16:
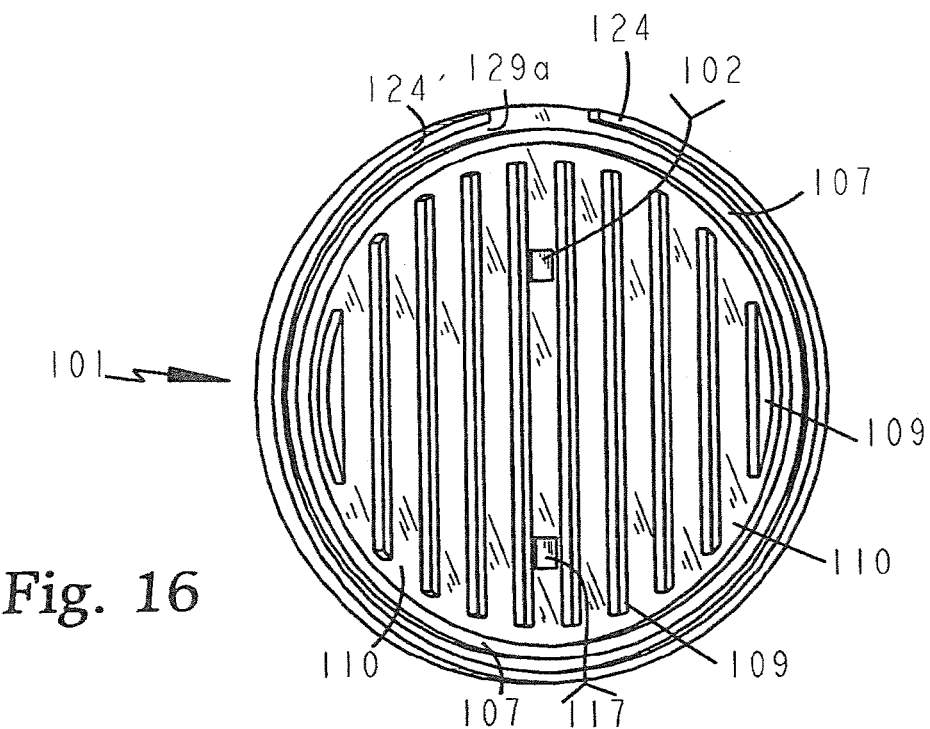
FIG. 16 is an isometric view of the housing inlet half of the BFFD shown in FIG. 13.

Referring to FIG. 13 and FIG. 16 housing inlet half 101 contains upstream chamber 113 that is bounded by inner wall 110 of housing inlet half 101 and by upstream surface 15a of filter element 15. Upstream chamber 113 contains filter support ribs 109. Inlet 105 is in fluid flow communication with upstream chamber 113, via inlet slot 102. The outlet end of tubing 81 is inserted into and bonded to inlet tube socket 106. Inlet 105 and inlet slot 102 are shown located near the top of upstream chamber 113 and on the vertical center line of housing inlet half 101, they could however, be located anywhere between the top and the bottom of upstream chamber 113, and could also be located to the right or to the left of the vertical center line. Housing inlet half 101 also contains vent inlet 178, and vent inlet slot 177. One end of tubing 85 is inserted into and bonded to vent tube socket 179. Vent inlet 178 and vent inlet slot 177 are shown located near the bottom of upstream chamber 113 and on the vertical center line of housing inlet half 101, they could however, be located anywhere between the top and the bottom of upstream chamber 113, and could also be located to the right or to the left of the vertical center line.

Figure 12:
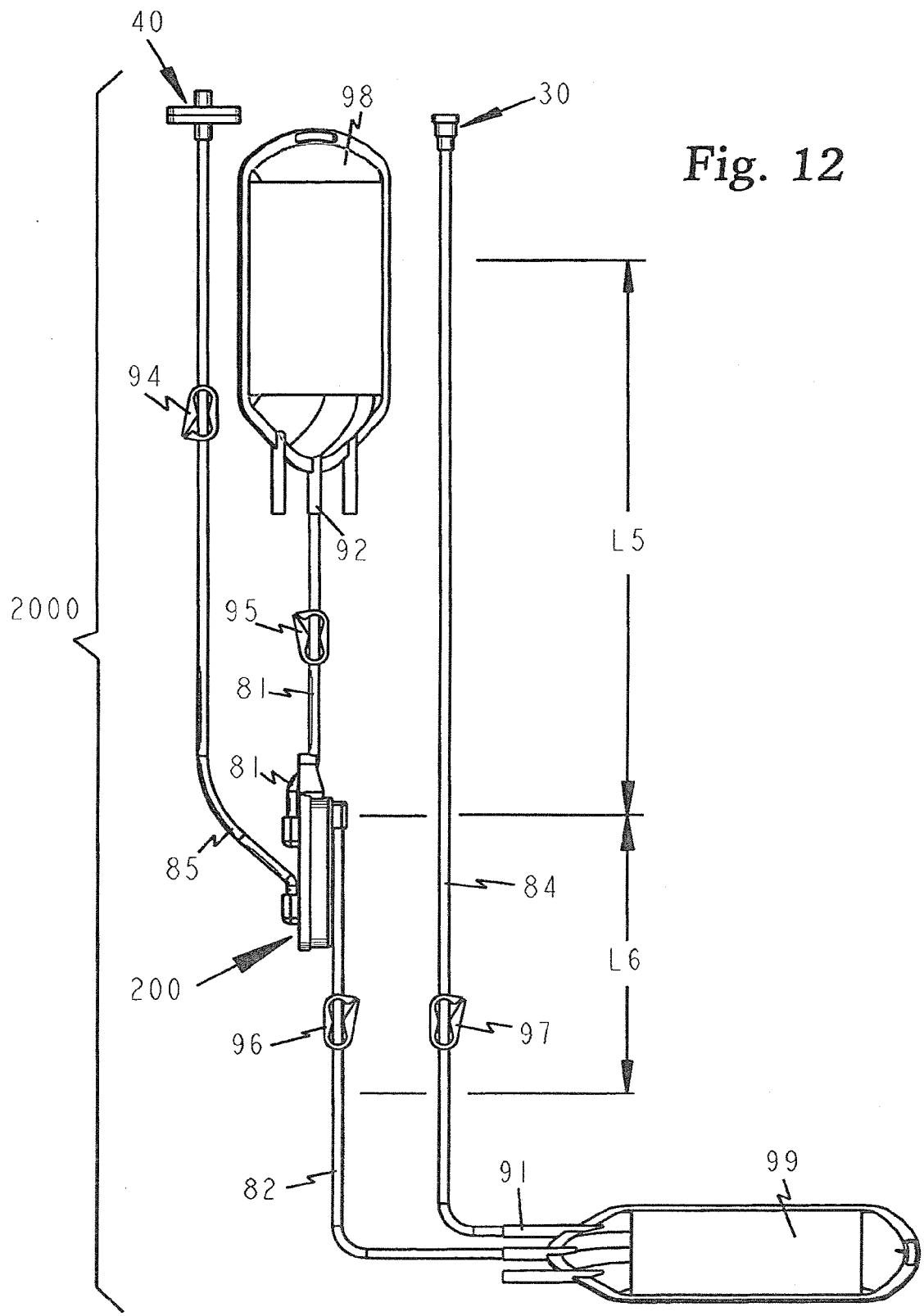
FIG. 12 is an isometric view of a second embodiment of a biological fluid filtration system constructed in accordance with the principles of the present invention, usable for the filtration of biological fluids, containing a feed blood bag, a receiving blood bag, with a second embodiment of a BFFD interposed between the feed blood bag and the receiving blood bag. A first vent filtration device is connected to a second inlet of the BFFD, and a second vent filtration device is connected to the receiving blood bag.
Figure 14:
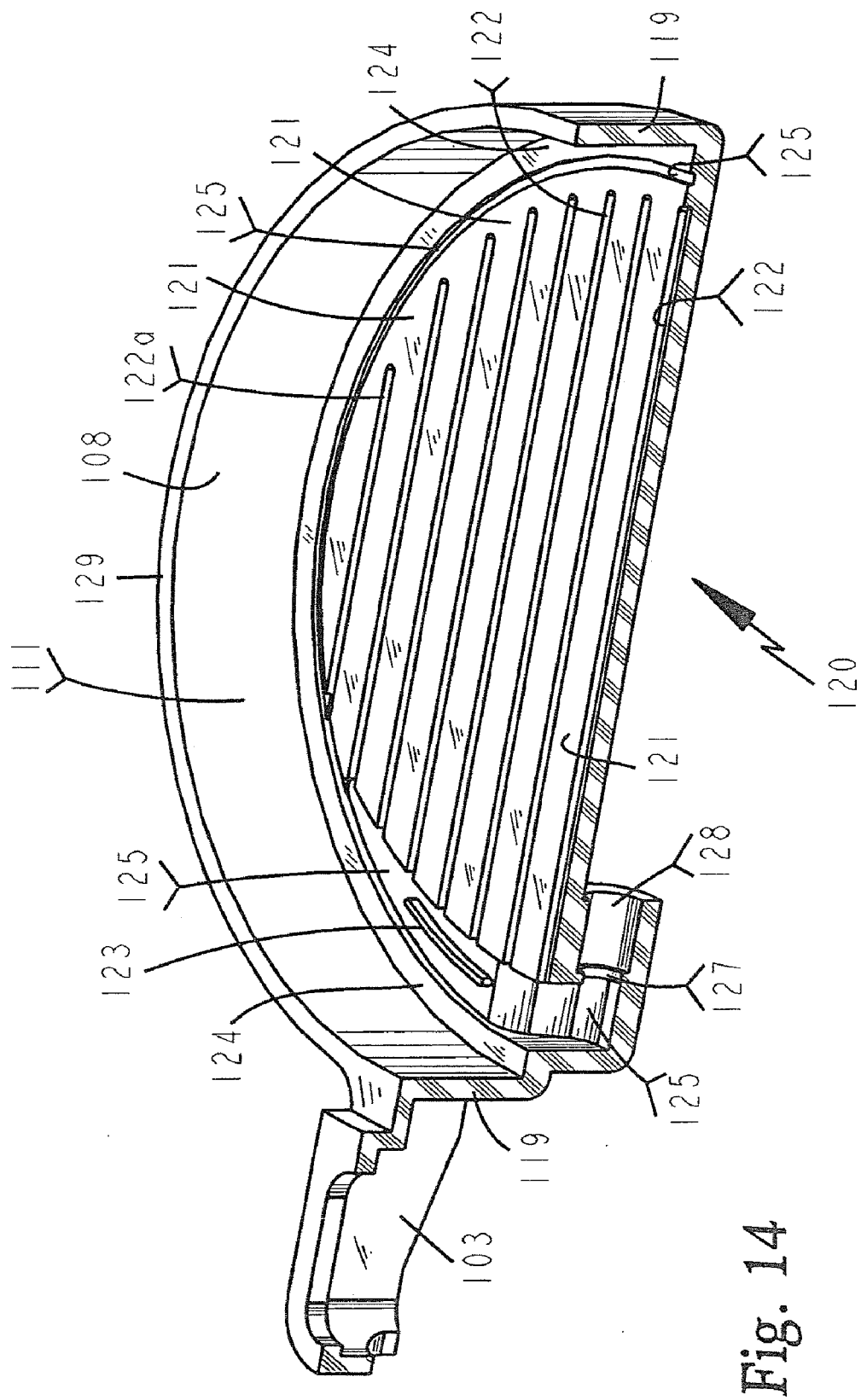
FIG. 14 is an isometric view with portions thereof removed of the housing outlet half of the BFFD shown in FIG. 13.
Figure 15:
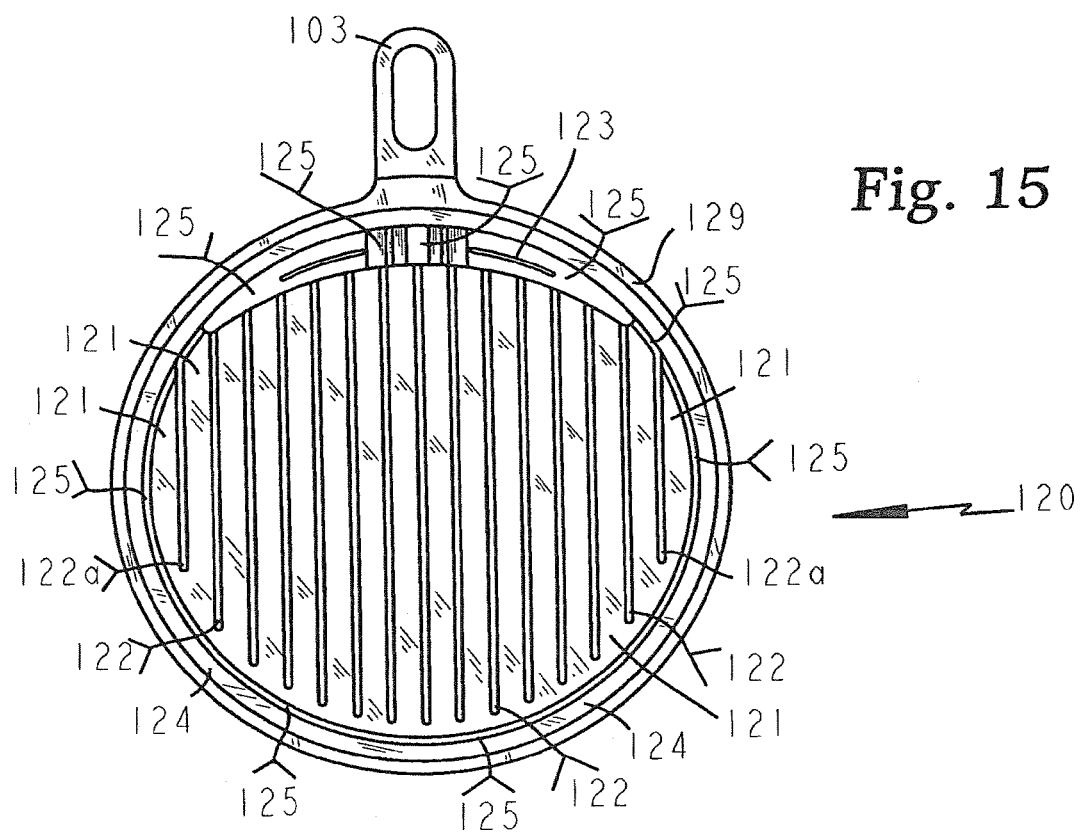
FIG. 15 is a top view of the housing outlet half of the BFFD shown in FIG. 13.

Referring to FIG. 13, FIG. 14, and FIG. 15 housing outlet half 120 contains filter well 111 bounded by inner side wall 108 and by a plane that goes through filter seal surface 124. Housing outlet half also contains circular outlet channel 125 and outlet 127. Circular outlet channel 125 is in direct fluid flow communication with outlet 127, and the portion of circular outlet channel 125 that adjoins outlet 127 has a cross-sectional flow area that is greater than the cross-sectional flow area of outlet 127. Housing outlet half 120 also contains a plurality of open top closed bottom vertical channels 122 and 122a. One end of each of the vertical channels 122 and 122a is in fluid flow communication with circular outlet channel 125. The upper part of circular outlet channel 125 increases in width to accommodate the flow of biological fluid from vertical channels 122 and 122a. The width of the remainder of circular outlet channel 125 (i.e. the lower part of circular outlet channel 125) is preferably equal to the width of the vertical channels. Preferably the upper part of circular outlet channel 125 is also deeper than the lower part of circular outlet channel 125 as shown in FIG. 13. However, the upper part of circular outlet channel 125 may increase in depth, or increase in width, or both, from its outer edges toward the center of circular outlet channel 125, so that its cross-sectional area will increase to accommodate the flow from all of the vertical channels without creating an excessive pressure drop through circular outlet channel 125. The two outermost vertical channels designated as vertical channels 122a adjoin circular outlet channel 125 where the width of circular outlet channel 125 is equal to the width of the vertical channels. The circular outlet channel and the vertical channels combined, create a filter under drain structure. The circular outlet channel and the vertical channels are cut into wall 137 of housing outlet half 120 so that the inner surface of all of the channels lies below inner wall 121 of housing outlet half 120 as shown in FIG. 14. The cross sectional area the outlet channel and of the vertical channels is defined by the inner surface of each channel and by the downstream surface of the BFFM. As shown in FIG. 14 and FIG. 15, the distance between vertical channels 122 and 122a is much greater than the width of vertical channels 122 and 122a; and the distance between vertical channels 122 and 122a is also much greater than the depth of vertical channels 122 and 122a. For example, the center line distance between the vertical channels may be equal to 0.150 in., with the width of the vertical channels equal to 0.032 in., and with the depth of the vertical channels equal to 0.025 in. Circular outlet channel 125 may contain filter support ribs 123. Housing outlet half 120 also contains fitter seal surface 124. Housing outlet half 120 may contain tube guide 103 to keep BFFD 200 hanging plumb when BFFD 200 is suspended from tubing 81 as shown in FIG. 12. Because housing outlet half 120 does not contain an open chamber or plenum downstream of the BFFM, hold up volume of biological fluid is minimized.

Referring to FIG. 13 through FIG. 16, a biological fluid filtration media (BFFM) that contains at least one filter element is interposed between inlet 105 and outlet 127, and is sealed to the housing to prevent the flow of unfiltered biological fluid from flowing between the housing and the BFFM to prevent bypass of unfiltered biological fluid around the BFFM. The BFFM shown in FIG. 13 contains filter elements 15, 16, 17, and 18. The filter elements may all be of the same type or may be different types filter elements. Each filter element contains an upstream surface designated as upstream surface 15a for filter element 15, a downstream surface designated as downstream surface 15c for filter element 15, and a perimeter surface designated as perimeter surface 15b for filter element 15. The downstream surface of the BFFM shown as downstream surface 18c of filter element 18 is in contact with inner wall 121 of housing outlet half 120. Because the downstream surface of the BFFM contacts inner wall 121 of housing outlet half 120, BFFD 200 does not contain an open chamber or plenum downstream of the BFFM. The air or liquid that is forced through the BFFM must pass through vertical channels and the circular outlet channel before flowing into outlet 127 of BFFD 200. The at least one filter element may be sealed to the housing with an interference fit between the perimeter surface of the filter element and inner side wall 108 of housing outlet half 120, or the at least one filter element may be sealed to the housing with a compression seal by compressing the outer periphery of the at least one filter element between filter seal surface 107 of housing inlet half 101 and filter seal surface 124 of housing outlet half 120, or the at least one filter element may be sealed to the housing a heat seal, an ultrasonic weld, a glue seal, a solvent seal, a radio frequency weld (i.e. R.F. weld), or any other type of leak tight seal. A combination of sealing methods may also be used to seal the at least one filter element to the housing. As shown in FIG. 13, filter element 15 has an outside diameter smaller than the inside diameter of inner side wall 108 of housing outlet half 120 preventing filter element 15 from being sealed to BFFD 200 with an interference fit between the perimeter surface 15b of filter element 15 and inner side wall 108 of housing outlet half 120. The outer periphery of filter element 15 is sealed to the housing by compressing the outer periphery of upstream surface 15a of filter element 15 with filter seal surface 107 of housing inlet half 101. Filter elements 16, 17, and 18 are shown sealed to the housing with an interference fit between the perimeter surface of each respective filter element and inner side wall 108 of housing outlet half 120. In addition the outer periphery of the BFFM comprised of filter elements 15, 16, 17, and 18, is compression sealed between filter seal surface 107 of housing inlet half 101, and filter seal surface 124 of housing outlet half 120.

Referring to FIG. 13 a first fluid flow path is defined between inlet 105 of BFFD 200 and outlet 127 of BFFD 200 with the at least one filter element of the BFFM interposed between inlet 105 and outlet 127, and across the fluid flow path (i.e. the BFFM is sealed to the housing to prevent the flow of un-filtered biological fluid between the BFFM and the housing thereby preventing bypass of un-filtered biological fluid around the BFFM). The first fluid flow path flows from inlet 105, through inlet slot 102, into upstream chamber 113, through the at least one filter element of the BFFM, into vertical channels 122, into circular outlet channel 125, and then into outlet 127.

Referring FIG. 12 vent filtration device 30 and vent filtration device 40 are the same vent filtration devices used in biological fluid filtration system 1000, and may be interchanged as was the case in biological fluid filtration system 1000.

Referring to FIG. 10 and FIG. 12 biological fluid filtration system 2000 may contain tubing 85 and vent filtration device 40. One end of tubing 85 is connected to tube socket 45 of vent filtration device 40 and the other end of tubing 85 is connected to vent tube socket 179 of BFFD 200. A second fluid flow path for biological fluid filtration system 2000 is defined from atmosphere to vent inlet 178 of BFFD 200. The second fluid flow path for biological fluid filtration system 2000 flows from vent port 46 of vent filtration device 40, through vent filtration media 43 of vent filtration device 40, through system port 44 of vent filtration device 40 through tubing 85, into vent inlet 178 of BFFD 200, when tube clamp 94 is open. Preferably vent filtration device 40 is located above the liquid level in feed blood bag 98 as shown in FIG. 12.

Referring to FIG. 11 and FIG. 12 biological fluid filtration system 2000 may contain tubing 84 and vent filtration device 30. One end of tubing 84 is connected to tube socket 35 of vent filtration device 30 and the other end of tubing 84 is connected to vent port 91 of receiving blood bag 99. A third fluid flow path for biological fluid filtration system 2000 is defined from atmosphere to vent port 91 of receiving blood bag 99. The third fluid flow path for biological fluid filtration system 2000 flows from vent port 36 of vent filtration device 30, through vent filtration media 33 of vent filtration device 30, through system port 34 of vent filtration device 30 through tubing 84, into vent port 91 of receiving blood bag 99, when tube clamp 97 is open. Preferably vent filtration device 30 is located above the liquid level in feed blood bag 98 as shown in FIG. 12.

Referring to FIG. 12, biological fluid filtration system 2000 functions as follows. The user will purchase the system with all components as shown in FIG. 12, less feed blood bag 98. The user will connect tubing 81 to outlet 92 of feed blood bag 98 in a manner known in the art. Feed blood bag 98, vent filtration device 30, and vent filtration device 40 may be hung from a blood bag pole known in the art, and receiving blood bag 99 may be placed on a table top or the like, so that the various components of the system will be positioned as shown in FIG. 12. Tube clamp 95 should be closed before connecting tubing 81 to feed blood bag 98. Before opening tube clamp 95 to start the flow of biological fluid through the system, tube clamps 94 and 96 should be open, and tube clamp 97 should be closed.

Referring to FIG. 12 through FIG. 16, BFFD 200 functions as follows. When tube clamp 95 is opened biological fluid (i.e. liquid) will flow from feed blood bag 98, through tubing 81, into inlet 105 of BFFD 200, and then through inlet slot 102 of BFFD 200, into upstream chamber 113 of BFFD 200. Upstream chamber 113 will rapidly fill with biological fluid from the bottom up. As upstream chamber 113 fills from the bottom up, the initial air in upstream chamber 113 will be displaced by the biological fluid filling upstream chamber 113. The displaced air will be forced through the BFFM, into vertical channels 122 and 122a, into circular outlet channel 125, and then into outlet 127 all of BFFD 200. The biological fluid in upstream chamber 113 will be pressurized, with the pressure at the bottom of upstream chamber 113 being proportional to the distance from the top of the biological fluid in feed blood bag 98 to the bottom of upstream chamber 113, and with the pressure at the top of upstream chamber 113 being proportional to the distance from the top of the biological fluid in feed blood bag 98 to the top of upstream chamber 113. Hence the pressure at the top of upstream chamber 113 will be less than the pressure at the bottom of upstream chamber 113. The positive pressure in upstream chamber 113 will cause the biological fluid to flow through the BFFM over the entire surface area of the BFFM and to displace the air within the pores of the BFFM with biological fluid, thereby wetting BFFM from the upstream side 15a of the BFFM to the downstream side 18c of the BFFM. As the BFFM wets the air that was initially in the pores of BFFM will be displaced by biological fluid and flow into vertical channels 122 and 122a, and into circular outlet channel 125, and than into outlet 127 all of BFFD 200, into tubing 82, and then into receiving blood bag 99. Because the pressure at the bottom of upstream chamber 113 is greater than the pressure at the top of upstream chamber 113, the flow rate of biological fluid through the BFFM will be greater at the bottom of the BFFM than at the top of the BFFM. Therefore, BFFM will first become completely wetted from the upstream surface 15a of BFFM to downstream surface 18c of BFFM at the bottom of the BFFM. If the width of vertical channels 122 and 122a is sufficiently small, and the depth of vertical channels 122 and 122a is sufficiently shallow, so that the cross-sectional flow area of vertical channels 122 and 122a is sufficiently small, and if the distance between vertical channels 122 is sufficiently large, as described above, the path of least resistance for continued biological fluid flow through the BFFM will be through the capillaries of the BFFM in both the horizontal and vertical directions and not through the vertical channels, because if the cross-sectional flow area of the vertical channels is sufficiently small, the displaced air flowing into and through the vertical channels will create a sufficiently high positive pressure in the vertical channels to prevent biological fluid from entering the vertical channels. The downstream surface 18c of the BFFM will therefore wet from the bottom up and the displaced air that was within the BFFM will continue to flow into the vertical channels, and into the circular outlet channel, and then into the outlet. When the downstream surface of the BFFM has become wetted to the level of the upper part of circular outlet channel 125 where circular outlet channel 125 begins to taper to a wider width, air flow through the lower part of circular outlet channel 125, and air flow through the two outermost vertical channels 122a will stop because the downstream surface of the BFFM adjoining the lower part of the circular outlet channel and the two outermost vertical channels will be wetted. Therefore the pressure in the lower part of the circular outlet channel and the pressure in the two outermost vertical channels will decrease allowing biological fluid to enter the lower part of the circular outlet channel and the two outermost vertical channels from the bottom up, thereby displacing the air that was in the lower part of the circular outlet channel and the two outermost vertical channels. At the same time the wetted level of the downstream surface of the BFFM will continue to wet in the vertical direction, wetting the downstream surface of the BFFM adjoining the upper part of circular outlet channel 125. Because the cross-sectional flow area of the upper part of circular outlet channel 125 is not sufficiently small to create a positive pressure in it due to the air flow through it, biological fluid will begin to into vertical channels 122 and into circular outlet channel 125 as BFFM continues to wet in the vertical direction above the lower part of the circular outlet channel. The biological fluid flowing into vertical channels 122 and 122a, and into the circular outlet channel 125 will flow into outlet 127 of BFFD 200 and then into tubing 82 toward receiving blood bag 99. As biological fluid starts to flow into outlet 127. BFFM will continue to wet vertically. Hence the initial flow of biological fluid through the upper part of circular outlet channel 125, and through outlet 127, will be a mixture of air and biological fluid so that the initial flow into tubing 82 will consist of alternate segments of biological fluid and air. As will be seen in the experimental data below, a BFFD constructed in accordance with the principles of the present invention, as shown in FIG. 12 through FIG. 16, will purge approximately 98% of the initial air in BFFD 200 before biological fluid begins to flow into outlet 127.

Referring to FIG. 12 and FIG. 13, when biological fluid starts to flow into tubing 82, the pressure P1 downstream of the BFFM and upstream of outlet 127 (i.e. downstream of the BFFM, but within BFFD 200) will be determined by the following formula:

$$P1=L5\Delta p-L6$$

Δp is the pressure drop across the BFFM due to biological fluid flow through the BFFM.

L5 is the distance between outlet 127 of BFFD 200 and the top of the biological fluid in feed blood bag 98.

L6 is the height of biological fluid minus any air segments downstream of outlet 127, in tubing 82.

Therefore the pressure P1 within BFFD 200 and downstream of the BFFM will be greater than or equal to zero until L6=L5−Δp. Because the upper part of circular outlet channel 125 is located a sufficient distance above the horizontal center line of BFFD 200, all of the air will be purged from within BFFD 200 before the pressure P1 becomes negative. As described above the pressure within upstream chamber 113 of BFFD 200 will be positive as long as biological fluid is flowing into upstream chamber 113. The purging of air from within BFFD 200 is only dependent upon the positive pressure upstream of the BFFM and is totally independent of whether or not the pressure within BFFD 200 downstream of the BFFM becomes negative. As will be seen in the experimental data below, all of the air will be purged from within BFFD 200 even if the pressure within BFFD 200 downstream of the BFFM never becomes negative, as long as feed blood bag 98 is positioned a sufficient distance above outlet 127 of BFFD 200.

Referring to FIG. 10, FIG. 12, and FIG. 13, a once all of the air has been purged from within BFFD 200, biological fluid will continue to flow through the first fluid flow path from the inlet of BFFD 200 to the outlet of BFFD 200, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. With flow through tubing 81 shut off as just described, air will now flow through the second fluid flow path from vent port 46 of vent filtration device 40, through vent filtration media 43, through system port 44, through tubing 85, through vent inlet 178, through vent inlet slot 177, and then into upstream chamber 113, all of BFFD 200, thereby draining the biological fluid in upstream chamber 113 of BFFD 200. To complete the draining of biological fluid as just described, receiving blood bag 99 must be positioned a sufficient distance below outlet 127 of BFFD 200 to create a sufficiently negative pressure P1 downstream of the BFFM and upstream of outlet 127 after all of the air has been purged from within BFFD 200 and tubing 82 is filled with biological fluid, to create a sufficient pressure differential between upstream surface 15*a* and downstream surface 18*c* of the BFFM to drain upstream chamber 113 to the bottom of upstream chamber 113, because as the biological fluid level in upstream chamber 113 approaches the bottom of upstream chamber 113, the pressure on the bottom of the biological fluid in upstream 113 will approach zero.

Referring to FIG. 12, FIG. 13, and FIG. 15, when the filtration cycle is complete as just described, the BFFM will remain wetted, vertical channels 122 and 122*a*, and circular outlet channel 125 will be filled with biological fluid, and tubing 82 will be filled with biological fluid. Because BFFD 200 does not contain a plenum downstream of the BFFM, the hold up volume of biological fluid within BFFD 200 will be minimized. The user will close tube clamp 96, and then cut and seal tubing 82 above tube clamp 96, and then discard BFFD 200 and the remaining components attached to it in a safe manner. Tubing 82 may contain segment marks, in which case tubing 82 would also be sealed at the segment marks. The biological fluid in the segments would be used for cross-matching purposes. Tube clamp 97 may nom/be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner. Alternately tubing 84 could also contain segment marks. In this case the biological fluid in receiving blood bag 99 would be mixed before opening tube clamp 97. Tube clamp 97 would then be opened, and the air in receiving blood bag 99 purged from receiving blood bag 99 by squeezing receiving blood bag 99 thereby forcing the air in receiving blood bag 99 through the third fluid flow path from vent port 91 of receiving blood bag 99 to atmosphere. Once the air is purged from receiving blood bag 99 a quantity of biological fluid would also be purged into tubing 84. Tubing 84 can then be sealed near receiving blood bag 99 and at the segment marks, and then the portion of tubing 84 above the seals and vent filtration device 30 may be discarded in a safe manner. The biological fluid in the segments could be used to test the filtered biological fluid.

Experimental Data of the Second Embodiment

Experimental data was obtained by testing a machined BFFD constructed as shown in FIG. 13, FIG. 14, FIG. 15, and FIG. 16. The machined BFFD used a BFFM consisting of nine layers of fibrous filtration material of 2.6 inch diameter, 0.030 inch thick. The BFFM was sealed to the housing an interference fit between the perimeter surface of the BFFM and the housing, and by compressing the outer periphery of the upstream surface of the BFFM and the outer periphery of the downstream surface of the BFFM between a filter seal surface on the housing inlet half and a filter seal surface on the housing outlet half, as shown in FIG. 13.

To determine how the air was purged from the BFFD the inlet of the BFFD was connected to an open top reservoir located above the BFFD with a ball valve located between the reservoir and the inlet of the BFFD, and the outlet of the BFFD was connected to a length of tubing with an open end. The distance L5 shown in FIG. 12 between the top of the fluid in the reservoir and the outlet of the BFFD was 21 inch. The test fluid was un-filtered tap water. A test hole was drilled and tapped through the housing outlet half through center line 193 shown in FIG. 13. One end of a water manometer was connected to the test hole to measure the pressure P1 (defined above) within the BFFD downstream of the BFFM and upstream of the outlet of the BFFD.

In the first test the reservoir was filled with un-filtered tap water so that L5 shown in FIG. 12 was 21 inches. The outlet tubing was held horizontal a the level of the outlet of the BFFD. The ball valve was opened allowing the un-filtered tap water to flow from the reservoir to the inlet of the BFFD. The BFFD filled, and wetted the BFFM and purged all of the air from within the BFFD just as described in the detailed description of the second embodiment above. The pressure P1 as measured by the manometer was zero until liquid started to flow downstream of the BFFM into the outlet tubing. At this point the pressure became positive and remained positive. The outlet end of the outlet tubing was then slowly lowered. As the outlet end of the outlet tubing was lowered, the pressure P1 decreased and became zero when the outlet end of the outlet tubing was 15½ inches below the outlet of the BFFD. From the equation P1=L5−Δp−L6, defined above, substituting zero for P1, we have Δp=L5−L6, or in the experiment just described, Δp=21−15.5=5.5 in. $H_2O$. Therefore, for the conditions just described, the pressure P1 downstream of the BFFM and upstream of the outlet of the BFFD will be greater than or equal to zero for all time until the length of a column of water, either a continuous water column, or the sum of the length of the water segments in a column consisting of alternate water-air segments, equals 15½ inches. This test was repeated several times yielding the same results.

To determine the quantity of air that is purged from the BFFD after liquid starts to flow from the outlet of the BFFD the inlet of the BFFD was connected to an open top reservoir located above the BFFD with a ball valve located between the reservoir and the inlet of the BFFD, and the outlet of the BFFD was connected to a length of tubing with an open end. The distance L5 shown in FIG. 12 between the top of the fluid in the reservoir and the outlet of the BFFD was 21 inch. The test fluid was un-filtered tap water. The test hole was sealed.

In the second test the reservoir was filled with un-filtered tap water so that L5 shown in FIG. 12 was 21 inches. The outlet tubing was held horizontal a the level of the outlet of the BFFD. The ball valve was opened allowing the un-filtered tap water to flow from the reservoir to the inlet of the BFFD. The BFFD filled, and wetted the BFFM and purged all of the air from within the BFFD just as described in the detailed description of the second embodiment above. After all of the air was purged from the BFFD, the ball valve was closed to stop flow and the length of the column of alternate segments of air and liquid in the outlet tubing was measured. This was done several times, with the length of the column of alternate segments of air and liquid in the outlet tubing varying between 4 inches and 5 inches, with approximately half of the column consisting of air with the remainder being water. Hence, the column of liquid in the outlet tubing varied between 2 inches and 2.5 inches at the point when all of the air had been purged from the BFFD. For this device the first experiment shows that it takes a column of water 15.5 inches high in the outlet tubing to make the pressure P1 equal to zero, and the second experiment shows that the column of water is 2 inches to 2.5 inches high when all of the air has been purged from the BFFD. Therefore, all of the air is purged from the BFFD before the pressure P1 becomes negative, so that a negative pressure P1 is not used to purge air from the BFFD. Furthermore, the first experiment shows that all of the air in the BFFD will be purged from the BFFD for conditions where the pressure P1 remains positive throughout the filtration cycle. The inside diameter of the tubing used was 0.3 cm. It takes a length L as shown in the following equation of this diameter tubing to equal an internal volume of 1 cc.

$L*((\Pi*0.3 \text{ cm}^2)/4)=1 \text{ cm}^3=1 \text{ ml}$

L=14.2 cm=5.6 in

Therefore, essentially all of the air is purged from a BFFD constructed according to FIG. 13, FIG. 14, FIG. 15, and FIG. 16, after only ½ of 1 ml of liquid has flowed from of the outlet of the BFFD.

Bed Side Applications of the Second Embodiment

Because essentially all of the air is purged from a BFFD constructed according to FIG. 13, FIG. 14, FIG. 15, and FIG. 16, after only ½ of 1 ml of liquid has flowed from of the outlet of the BFFD, this type of BFFD is ideally suited for bed side applications. Referring to FIG. 12, in a bed side application where blood or blood product is being transfused, receiving blood bag 99, tubing 84, vent filtration device 30, and tube clamp 97 would be eliminated, and the outlet end of tubing 82 would be connected to a drip chamber, with the outlet of the drip chamber connected to the patient. During priming the drip chamber is inverted and blood flows from the feed blood bag through tubing 81, through BFFD 200, through tubing 82 (as described above), and then into the drip chamber. When 3 to 4 ml of blood or blood product has been collected in the drip chamber, it is returned to its normal position, leaving a reservoir of fluid in the bottom of the drip chamber and an air space above the fluid. The transparent drip chamber allows observation of the drip rate through the air space, and prevents any air that may be purged from the BFFD after the drip chamber has been returned to its normal position from reaching the patient. This lagging air will displace an equivalent amount of fluid from the drip chamber. Because essentially all of the air in the BFFD will be purged before 3 to 4 ml of fluid is collected in the drip chamber as described above, a small drip chamber may be used without the concern that lagging air will drain the drip chamber and reach the patient, therefore minimizing wasted biological fluid. The hold up volume of vertical channels 122 and 122a, and of circular outlet channel 125 is less than the hold up volume of a plenum. Therefore, the hold up volume of BFFD 200 is further reduced because BFFD 200 does not contain a plenum downstream of the BFFM.

A BFFD containing the filter support structure of BFFD 100 could also be used in biological fluid filtration system 2000. Likewise a BFFD containing the filter support structure of BFFD 200 could also be used in biological fluid filtration system 1000.

Detailed Description of the Third Embodiment

A third embodiment of the BFFD constructed in accordance with the principles of the present invention, is shown in FIG. 17 through FIG. 21. BFFD 300 may be used in place of BFFD 100 in biological fluid filtration system 1000 shown in FIG. 1, and may also be used in place of BFFD 200 in biological fluid filtration system 2000 shown in FIG. 12.

Figure 17:
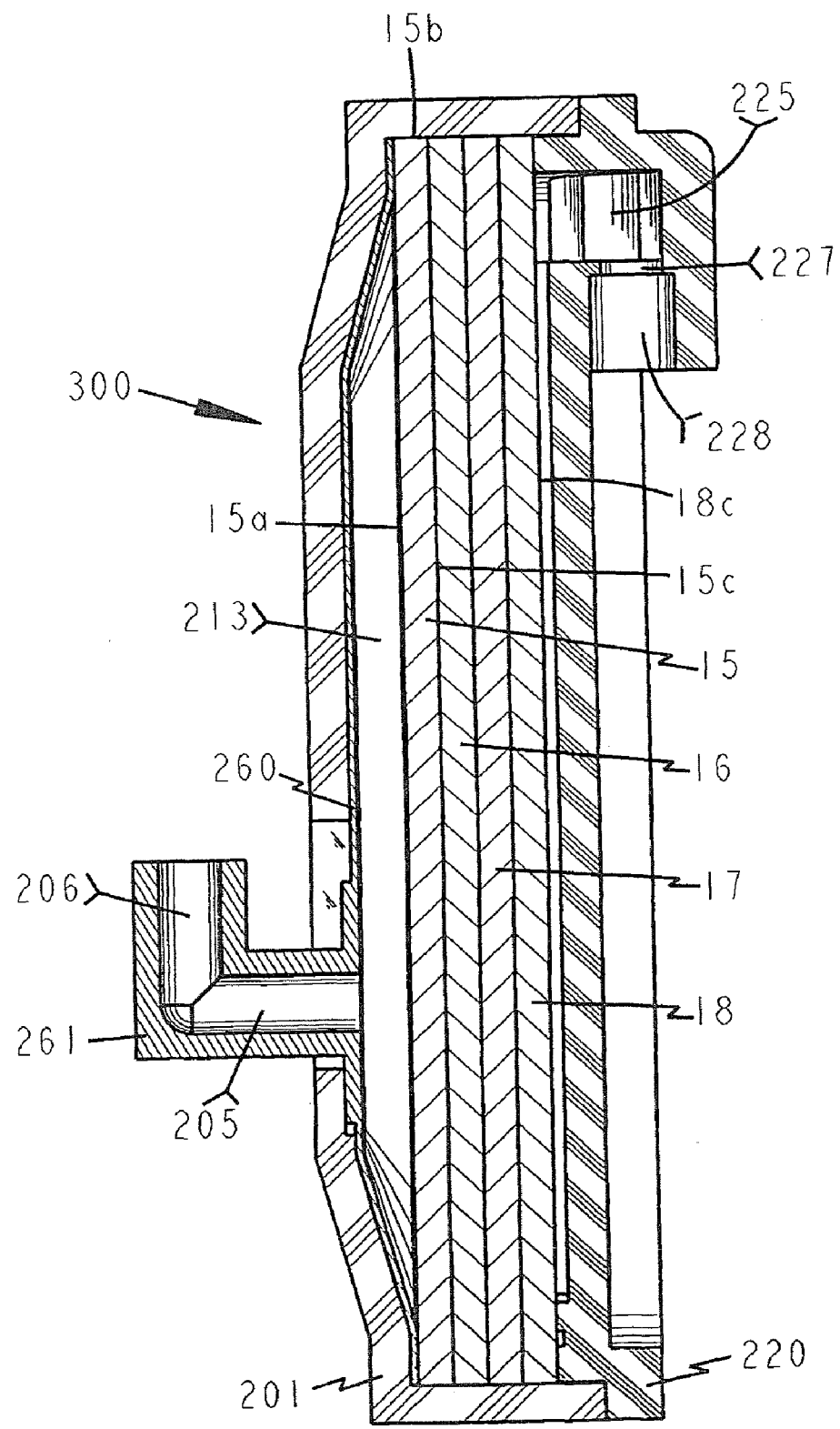
FIG. 17 is a cross-sectional view of a third embodiment of a BFFD constructed in accordance with the principles of the present invention, usable for the filtration of biological fluids, containing a diaphragm upstream of the BFFM. The third embodiment of the BFFD also contains a rigid housing inlet half.
Figure 18:
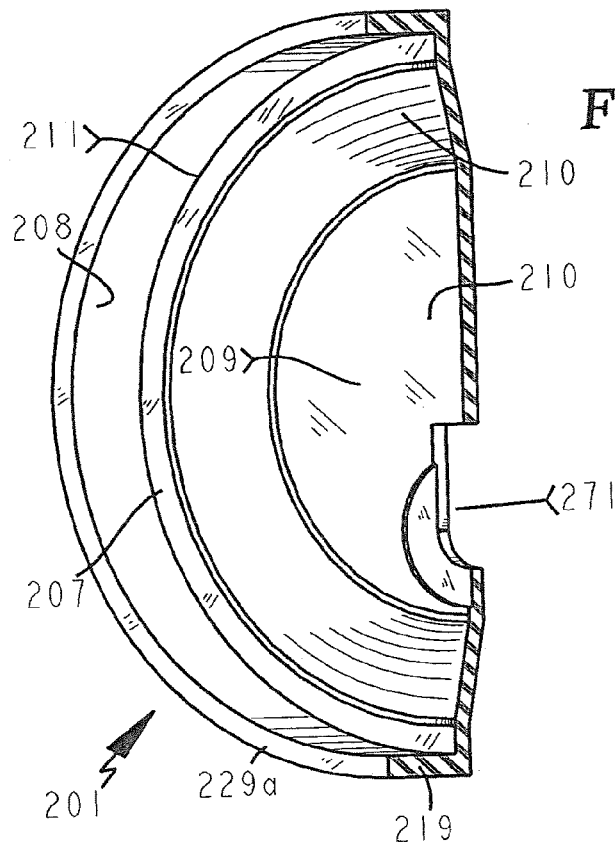
FIG. 18 is an isometric view with portions thereof removed of the housing inlet half of the BFFD shown in FIG. 17.
Figure 19:
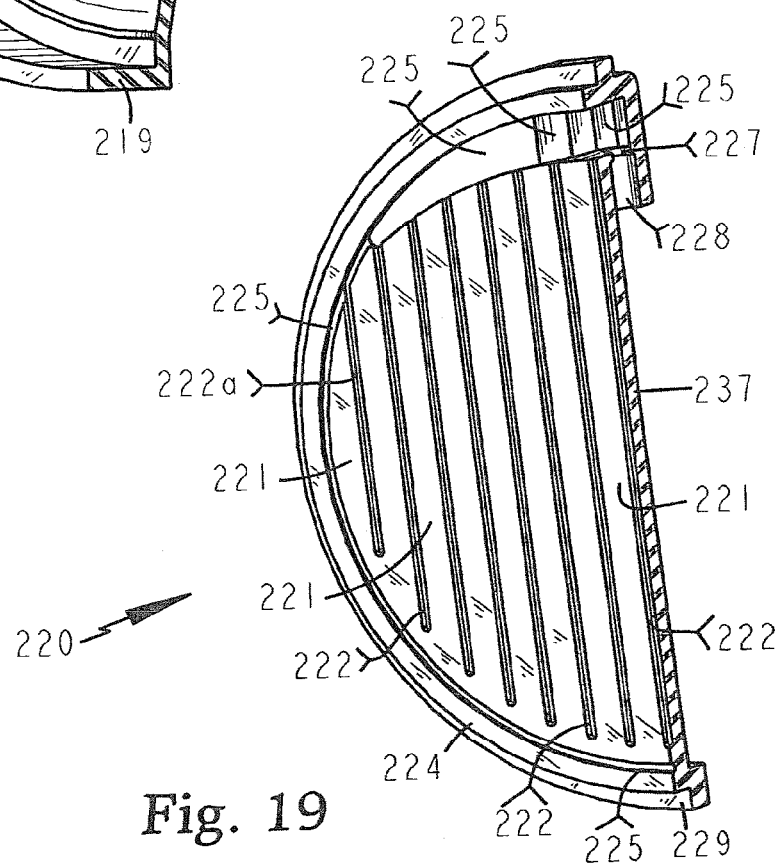
FIG. 19 is an isometric view with portions thereof removed of the housing outlet half of the BFFD shown in FIG. 17.
Figure 20:
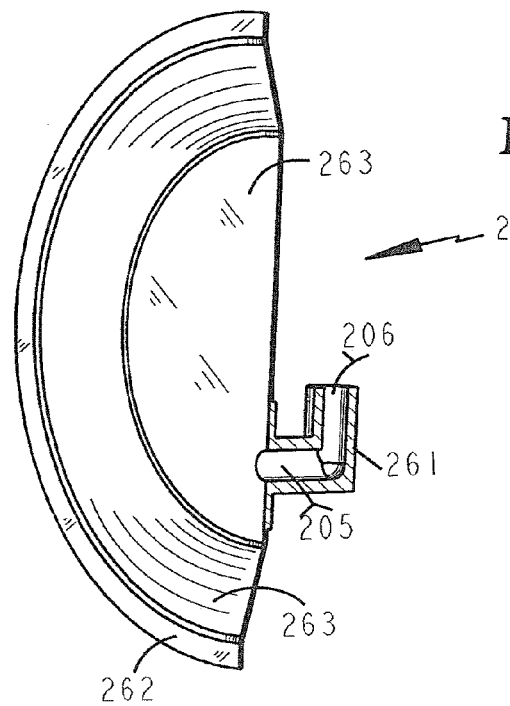
FIG. 20 is a bottom isometric view with portions thereof removed of the diaphragm used in the BFFD shown in FIG. 17.

Referring to FIG. 17, FIG. 18, and FIG. 19, BFFD 300 contains a rigid housing that includes housing inlet half 201 and housing outlet half 220. Housing seal surface 229a of housing inlet half 201 is bonded to housing seal surface 229 of housing outlet half 220. The bond is preferably an ultrasonic weld but may be a heat bond, a glue bond, a solvent bond, or any other type of leak tight bond.

Referring to FIG. 17, FIG. 18, FIG. 20, and FIG. 21, housing inlet half 201 contains filter well 211 bounded by inner side wall 208 and by a plane that goes through diaphragm seal surface 207. Housing inlet half 201 also contains diaphragm well 209 bounded by surface 210. Diaphragm well 209 contains hole 271. Flexible diaphragm 260 contains inner surface 263, outer surface 266, and flange 262. The outer surface of flange 262 is sealed to diaphragm seal surface of housing inlet half 201. The seal may be a heat seal, an ultrasonic seal, a glue seal, a solvent seal, or any other type of leak tight seal. Flexible diaphragm 260 may be molded from a flexible rubber material such as silicone rubber, or it may be molded or thermo formed from a material such as PVC, polyethylene, or polypropylene, but is not limited to these materials. Flexible diaphragm 260 is preferably shaped so that in its normal state outer surface 266 conforms to surface 210 of housing inlet half 201. Flexible diaphragm 260 also contains tube connector 261, that contains inlet tube socket 206, and inlet 205. Tube connector 261 loosely fits through hole 271 of housing inlet half 201. Upstream chamber 213 is bounded by inner surface 263 of flexible diaphragm 260 and by upstream surface 15a of filter element 15. Inlet 205 is in fluid flow communication with upstream chamber 213. When BFFD 300 is used in biological fluid filtration system 1000 shown in FIG. 1, the outlet end of tubing 81a is inserted into and bonded to inlet tube socket 206. When BFFD 300 is used in biological fluid filtration system 2000 shown in FIG. 12, the outlet and of tubing 81 is inserted into and bonded to inlet tube socket 206. Inlet 205 is shown located near the bottom of upstream chamber 213 and on the vertical center line of housing inlet half 201, it could however be located anywhere between the top and the bottom of upstream chamber 213, and could also be located to the right or to the left of the vertical center line of housing inlet half 201.

Referring to FIG. 17, and FIG. 19 housing outlet half 220 contains circular outlet channel 225 and outlet 227. Circular outlet channel 225 is in direct fluid flow communication with outlet 227, and the portion of circular outlet channel 225 that adjoins outlet 227 has a cross-sectional flow area that is greater than the cross-sectional flow area of outlet 227. Housing outlet half 220 also contains a plurality of open top closed bottom vertical channels 222 and 222a. One end of each of the vertical channels 222 and 222a is in fluid flow communication with circular outlet channel 225. The upper part of circular outlet channel 225 increases in width to accommodate the flow of biological fluid from vertical channels 222 and 222a. The width of the remainder of circular outlet channel 225 (i.e. the lower part of circular outlet channel 225) is preferably equal to the width of the vertical channels. The two outermost vertical channels designated as vertical channels 222a adjoin circular outlet channel 225 where the width of circular outlet channel 225 is equal to the width of the vertical channels. The outlet channel and the vertical channels that combined create a filter under drain structure, are cut into wall 237 of housing outlet half 220 so that the inner surface of all of the channels lies below inner wall 221 of housing outlet half 220 as shown in FIG. 19. The cross sectional area the outlet channel and of the vertical channels is defined by the inner surface of each channel and by the downstream surface of the BFFM. As shown in FIG. 19, the distance between vertical channels 222 and 222a is much greater than the width of vertical channels 222 and 222a, and the distance between vertical channels 222 and 222a is also much greater than the depth of vertical channels 222 and 222a. For example, the center line distance between the vertical channels may be equal to 0.150 in., with the width of the vertical channels equal to 0.032 in., and with the depth of the vertical channels equal to 0.025 in. Housing outlet half 220 also contains filter seal surface 224. Because housing outlet half 220 does not contain an open chamber or plenum downstream of the BFFM, hold up volume of biological fluid will be minimized.

Referring to FIG. 17, a biological fluid filtration media (BFFM) that contains at least one filter element is interposed between inlet 205 and outlet 227, and is sealed to the housing to prevent the flow of unfiltered biological fluid from flowing between the housing and the BFFM to prevent bypass of unfiltered biological fluid around the BFFM. The BFFM shown in FIG. 17 contains filter elements 15, 16, 17, and 18. The filter elements may all be of the same type or may be different types filter elements. Each filter element contains an upstream surface designated as upstream surface 15a for filter element 15, a downstream surface designated as downstream surface 15c for filter element 15, and a perimeter surface designated as perimeter surface 15b for filter element 15. The downstream surface of the BFFM shown as downstream surface 18c of filter element 18 is in contact with inner wall 221 of housing outlet half 220. Because the downstream surface of the BFFM contacts inner wall 221 of housing outlet half 220, BFFD 300 does not contain an open chamber or plenum downstream of the BFFM. The air or liquid that is forced through the BFFM must pass through the vertical channels and the circular outlet channel before flowing into outlet 227 of BFFD 300. The at least one filter element may be sealed to the housing with an interference fit between the perimeter surface of the at least one filter element and inner side wall 208 of housing inlet half 201, or the at least one filter element may be sealed to the housing with a compression seal by compressing the outer periphery of the at least one filter element between the inner surface of flange 262 of flexible diaphragm 260 and filter seal surface 224 of housing outlet half 220, or the at least one filter element may be sealed to the housing a heat seal, an ultrasonic weld, a glue seal, a solvent seal, a radio frequency weld, or any other type of leak tight seal. A combination of sealing methods may also be used to seal the at least one filter element to the housing.

Referring to FIG. 17 a first fluid flow path is defined between inlet 205 of BFFD 300 and outlet 227 of BFFD 300 with the at least one filter element of the BFFM interposed between inlet 205 and outlet 227, and across the fluid flow path. The first fluid flow path flows from inlet 205, into upstream chamber 213, through the at least one filter element of the BFFM, into vertical channels 222 and 222a, into circular outlet channel 225, and then into outlet 227.

Referring to FIG. 12 and FIG. 17, when BFFD 300 is used to replace BFFD 200 in biological fluid filtration system 2000, the system will function as follows. The user will purchase the system with all components as shown in FIG. 12, less feed blood bag 98. BFFD 300 will replace BFFD 200, tubing 85 and vent filtration device 40 will not be used. The user will connect tubing 81 to outlet 92 of feed blood bag 98 in a manner known in the art. Feed blood bag 98 and vent filtration device 30, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 should be open, and tube clamp 97 should be closed.

Referring to FIG. 12, FIG. 17, and FIG. 19, BFFD 300 functions as follows. When tube clamp 95 is opened biological fluid (i.e. liquid) will flow from feed blood bag 98, through tubing 81, into inlet 205 of BFFD 300 and then into upstream chamber 213 of BFFD 300. Upstream chamber 213 will rapidly fill with biological fluid from the bottom up. As upstream chamber 213 fills from the bottom up, the initial air in upstream chamber 213 will be displaced by the biological fluid filling upstream chamber 213. The displaced air will be forced through the BFFM, into vertical channels 222 and 222a, into circular outlet channel 225, and then into outlet 227 all of BFFD 300. The biological fluid in upstream chamber 213 will be pressurized, with the pressure at the bottom of upstream chamber 213 being proportional to the distance from the top of the biological fluid in feed blood bag 98 to the bottom of upstream chamber 213, and with the pressure at the top of upstream chamber 213 being proportional to the distance from the top of the biological fluid in feed blood bag 98 to the top of upstream chamber 213. Hence the pressure at the top of upstream chamber 213 will be less than the pressure at the bottom of upstream chamber 213. The positive pressure in upstream chamber 213 will cause the biological fluid to flow through the BFFM over the entire surface area of the BFFM and to displace the air within the pores of the BFFM with biological fluid, thereby wetting BFFM from the upstream side 15a of the BFFM to the downstream side 18c of the BFFM. As the BFFM wets the air that was initially in the pores of BFFM will be displaced by biological fluid and flow into vertical channels 222 and 222a, and into circular outlet channel 225, and then into outlet 227 all of BFFD 300, into tubing 82, and then into receiving blood bag 99. Because the pressure at the bottom of upstream chamber 213 is greater than the pressure at the top of upstream chamber 213, the flow rate of biological fluid through the BFFM will be greater at the bottom of the BFFM than at the top of the BFFM. Therefore, the BFFM will first become completely wetted from upstream surface 15a of the BFFM to downstream surface 18c of the BFFM, at the bottom of the BFFM. If the width of vertical channels 222 and 222a is sufficiently small, and the depth of vertical channels 222 and 222a is sufficiently shallow, so that the cross-sectional flow area of vertical channels 222 and 222a is sufficiently small, and if the distance between vertical channels 222 and 222a is sufficiently large, as described above, the path of least resistance for continued biological fluid flow through the BFFM will be through the capillaries of the BFFM in both the horizontal and vertical directions and not through the vertical channels, because if the cross-sectional flow area of the vertical channels is sufficiently small, the displaced air flowing into and through the vertical channels will create a sufficiently high positive pressure in the vertical channels to prevent biological fluid from entering the vertical channels. The downstream surface 18c of the BFFM will therefore wet from the bottom up and the displaced air that was within the BFFM will continue to flow into the vertical channels, and into the circular outlet channel, and then into the outlet. When the downstream surface of the BFFM has become wetted to the level of the upper part of circular outlet channel 225 where circular outlet channel 225 begins to taper to a wider width, air flow through the lower part of circular outlet channel 225, and air flow through the two outermost vertical channels 222a will stop because the downstream surface of the BFFM adjoining the lower part of the circular outlet channel and the two outermost vertical channels will be wetted. Therefore the pressure in the lower part of the circular outlet channel and the pressure in the two outermost vertical channels will decrease allowing biological fluid to enter the lower part of the circular outlet channel and the two outermost vertical channels from the bottom up, thereby displacing the air that was in the lower part of the circular outlet channel and the two outermost vertical channels. At the same time the wetted level of the downstream surface of the BFFM will continue to wet in the vertical direction, wetting the downstream surface of the BFFM adjoining the upper part of circular outlet channel 225. Because the cross-sectional flow area of the upper part of circular outlet channel 225 is not sufficiently small to create a positive pressure in it due to the air flow through it, biological fluid will flow into circular outlet channel 225 as BFFM continues to wet in the vertical direction above the lower part of the circular outlet. The biological fluid flowing into vertical channels 222 and 222a, and into circular outlet channel 225 will flow into outlet 227 of BFFD 300 and then into tubing 82 toward receiving blood bag 99. As biological fluid starts to flow into outlet 227, the BFFM will continue to wet vertically. Hence the initial flow of biological fluid through the upper part of circular outlet channel 225, and through outlet 227, will be a mixture of air and biological fluid so that the initial flow into tubing 82 will consist of alternate segments of biological fluid and air. From the experimental data of the second embodiment described above, a BFFD constructed in accordance with the principles of the present invention, as shown in FIG. 17 through FIG. 21, will purge approximately 98% of the initial air in BFFD 300 before biological fluid begins to flow into outlet 227.

Referring to FIG. 12 and FIG. 17, when biological fluid starts to flow into tubing 82, the pressure P2 downstream of the BFFM and upstream of outlet 227 (i.e. downstream of the BFFM, but within BFFD 300) will be determined by the following formula:

$$P2 = L5 - \Delta p - L6$$

$\Delta p$ is the pressure drop across the BFFM due to biological fluid flow through the BFFM.

L5 is the distance between outlet 227 of BFFD 300 and the top of the biological fluid in feed blood bag 98.

L6 is the height of biological fluid minus any air segments downstream of outlet 227, in tubing 82.

Therefore the pressure P2 within BFFD 300 and downstream of the BFFM will be greater than or equal to zero until $L6 = L5 - \Delta p$. Because the upper part of circular outlet channel 225 is located a sufficient distance above the horizontal center line of BFFD 300, all of the air will be purged from within BFFD 300 before the pressure P2 becomes negative. As described above the pressure within upstream chamber 213 of BFFD 300 will be positive as long as biological fluid is flowing into upstream chamber 213. The purging of air from within BFFD 300 is totally independent of whether or not the pressure within BFFD 300 downstream of the BFFM becomes negative as explained above.

Figure 22:
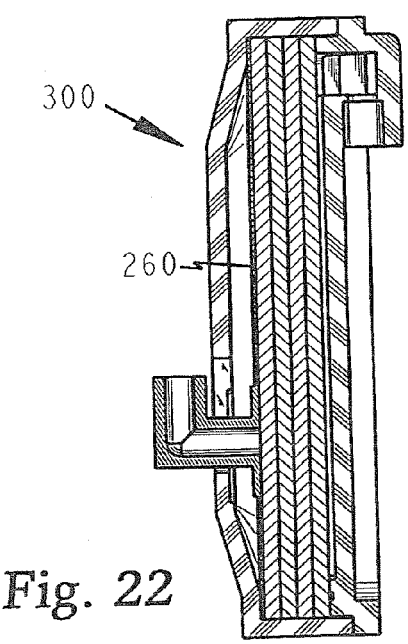
FIG. 22 is a cross-sectional view of the BFFD shown in FIG. 17 with the diaphragm shown in the collapsed state after the filtration cycle is complete.
Figure 21:
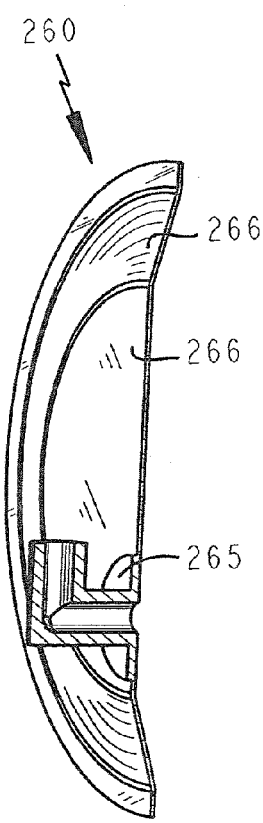
FIG. 21 is a top isometric view with portions thereof removed of the diaphragm used in the BFFD shown in FIG. 17.
Figure 23:
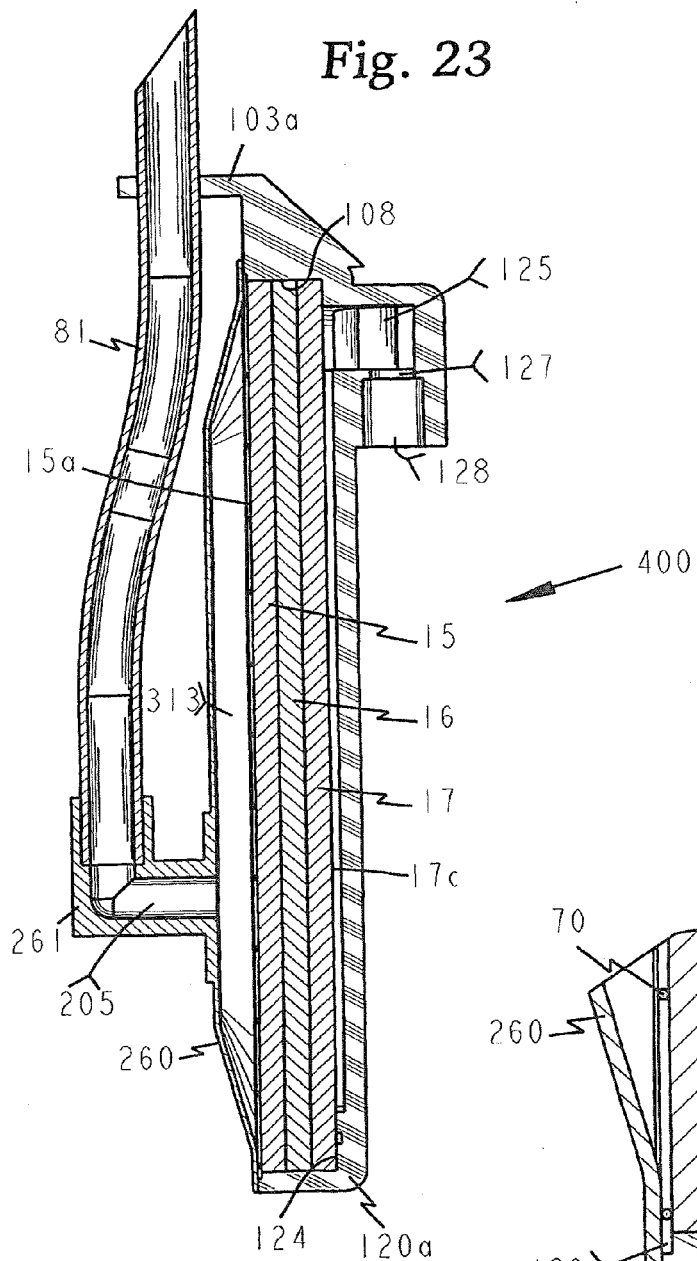
FIG. 23 is a cross-sectional view of a fourth embodiment of a BFFD constructed in accordance with the principles of the present invention, usable for the filtration of biological fluids, containing a diaphragm upstream of the BFFM. The fourth embodiment does not contain a rigid housing inlet half.
Figure 24:
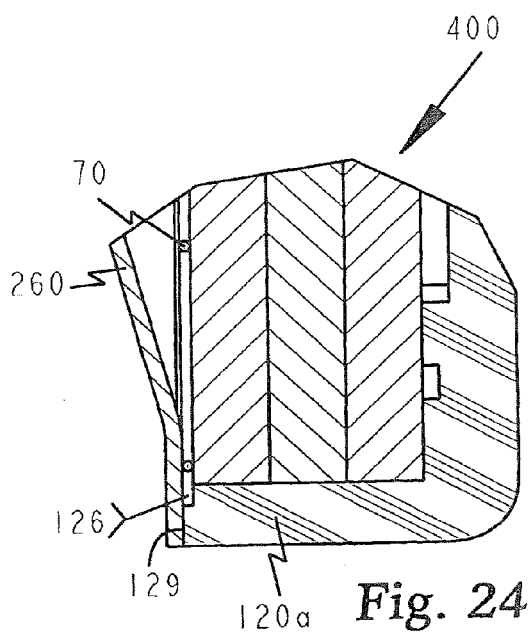
FIG. 24 is a partial cross-sectional view of the BFFD shown in FIG. 23 showing in greater detail the filter support screen.

Referring to FIG. 12, and FIG. 17 through FIG. 22, once all of the air has been purged from within BFFD 300, biological fluid will continue to flow through the first fluid flow path from the inlet of BFFD 300 to the outlet of BFFD 300, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 300, pressure P2 downstream of the BFFM and upstream of outlet 227 will be negative as described above. Once feed blood bag 98 collapses and biological fluid flow through the first fluid flow path stops the differential pressure across the BFFM will become zero, hence the pressure in upstream chamber 213 will become negative. The pressure on upstream surface 266 of flexible diaphragm 260 will be atmospheric because hole 271 of housing inlet half 201 is open to atmosphere. With atmospheric pressure on the outer surface 266 of flexible diaphragm 260, the negative pressure within upstream chamber 213 will cause flexible diaphragm 260 to collapse onto upstream surface 15a of the BFFM as shown in FIG. 22, thereby forcing the biological fluid in upstream chamber 213 through the BFFM, into the vertical channels and the circular outlet channel, into outlet 227, into tubing 82, and then into receiving blood bag 99.

Referring to FIG. 12, FIG. 17, and FIG. 19, when the filtration cycle is complete as just described, the BFFM will remain wetted, vertical channels 222 and 222a, and circular outlet channel 225 will be filled with biological fluid, and tubing 82 will be filled with biological fluid. Because BFFD 300 does not contain a plenum downstream of the BFFM, the hold up volume of biological fluid within BFFD 300 will be minimized. The user will close tube clamp 96, and then cut and seal tubing 82 above tube clamp 96, and then discard BFFD 300 and feed blood bag 98 in a safe manner. Tube clamp 97 may now be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner. If tubing 82 and 84 contain segment marks, then the procedure described in the second embodiment concerning the segment marks may be used.

BFFD 300 can be used to replace BFFD 100 in biological fluid filtration system 1000 shown in FIG. 1. If BFFD 300 is used in this manner, it will purge air and filter biological fluid as just described. Three tube connector 50 and vent filtration device 30 will function as described in the description of the first embodiment above. When the filtration cycle is complete, tubing 83, tubing 81a, and upstream chamber 213 of BFFD 300 will drain as described in the description of the first embodiment above, and flexible diaphragm 260 will remain in the un-collapsed state.

Detailed Description of the Fourth Embodiment

A fourth embodiment of the BFFD constructed in accordance with the principles of the present invention, is shown in FIG. 23 through FIG. 26. BFFD 400 may be used in place of BFFD 100 in biological fluid filtration system 1000 shown in FIG. 1, and may also be used in place of BFFD 200 in biological fluid filtration system 2000 shown in FIG. 12.

Referring to FIG. 14, FIG. 20, FIG. 21, FIG. 23, and FIG. 24, BFFD 400 contains a rigid housing outlet half 120a, and flexible diaphragm 260. BFFD 400 lacks a rigid housing inlet half. Housing outlet half 120a is the same as housing outlet half 120, with the following exceptions. Housing outlet half 120a contains counter bore 126, and tube guide 103a of housing outlet half 120a replaces tube guide 103 of housing outlet half 120. The inner surface of flange 262 of flexible diaphragm 260 is sealed to housing seal surface 129 of housing outlet half 120a. The seal may be a heat seal, an ultrasonic seal, a glue seal, a solvent seal, or any other type of leak tight seal. The BFFM shown in FIG. 23 contains filter elements 15, 16, and 17. The filter elements may all be of the same type or may be different types filter elements. The BFFM must contain at least one filter element. The at least one filter element may be sealed to the housing with an interference fit between the perimeter surface of the filter element and inner side wall 108 of housing outlet half 120a, or the at least one filter element may be sealed to the housing with a compression seal by compressing the outer periphery of the at least one filter element between the inner surface of flange 262 of flexible diaphragm 260 and filter seal surface 124 of housing outlet half 120a, or the at least one filter element may be sealed to the housing a heat seal, an ultrasonic weld, a glue seal, a solvent seal, a radio frequency weld, or any other type of leak tight seal. A combination of sealing methods may also be used to seal the at least one filter element to the housing. Upstream chamber 313 is defined between the inner surface 263 of flexible diaphragm 260, and upstream surface 15a of the BFFM. BFFD 400 may also contain filter support screen 70. Filter support screen 70 does not perform a filtration function but acts as a filter support and containment mechanism similar to filter support ribs 9 of housing inlet half 1 shown in FIG. 5. Therefore filter support screen 70 can have a very open structure as shown in FIG. 26. Preferably filter support screen 70 fits into counter bore 126 of housing inlet half 120a, and is bonded to the housing inlet half, or compressed between flange 262 of flexible diaphragm 260 and housing inlet half 120a. Tubing 81 may be bonded to tube guide 103a to relieve strain on flexible diaphragm 260 when BFFD 400 is suspended from tubing 81.

BFFD 400 works exactly as BFFD 300 when used in either biological fluid filtration system 1000, or in biological fluid filtration system 2000 as described above in the description of the third embodiment of the BFFD.

Detailed Description of the Fifth Embodiment

A fifth embodiment of the BFFD constructed in accordance with the principles of the present invention, is shown in FIG. 27 and FIG. 28. BFFD 500 contains rigid housing outlet half 120b and flexible diaphragm 460. Housing outlet half 120b is the same as housing outlet half 120a with the following exceptions. Housing outlet half 120b does not contain a tube guide, and housing outlet half 120b contains inlet 105b, and inlet tube socket 106b both located at the top of housing outlet half 120b. Flexible diaphragm 460 is the same as flexible diaphragm 260 with the exception that flexible diaphragm 460 does not contain a tube connector with an inlet. Upstream chamber 413 is bounded by the inner surface of flexible diaphragm 460 and by the upstream surface 15a of the BFFM. Inlet 105b is in fluid flow communication with upstream chamber 413 as shown in FIG. 27. BFFD 500 may contain filter support screen 70 bonded to housing outlet half 120b.

BFFD 500 may be used in place of BFFD 100 in biological fluid filtration system 1000 shown in FIG. 1, and may also be used in place of BFFD 200 in biological fluid filtration system 2000 shown in FIG. 12. BFFD 500 works exactly as BFFD 300 when used in either biological fluid filtration system 1000, or in biological fluid filtration system 2000 as described above in the description of the third embodiment of the BFFD. FIG. 28 shows flexible diaphragm 460 in the collapsed state after the filtration cycle has been completed.

Detailed Description of the Sixth Embodiment

Figure 29:
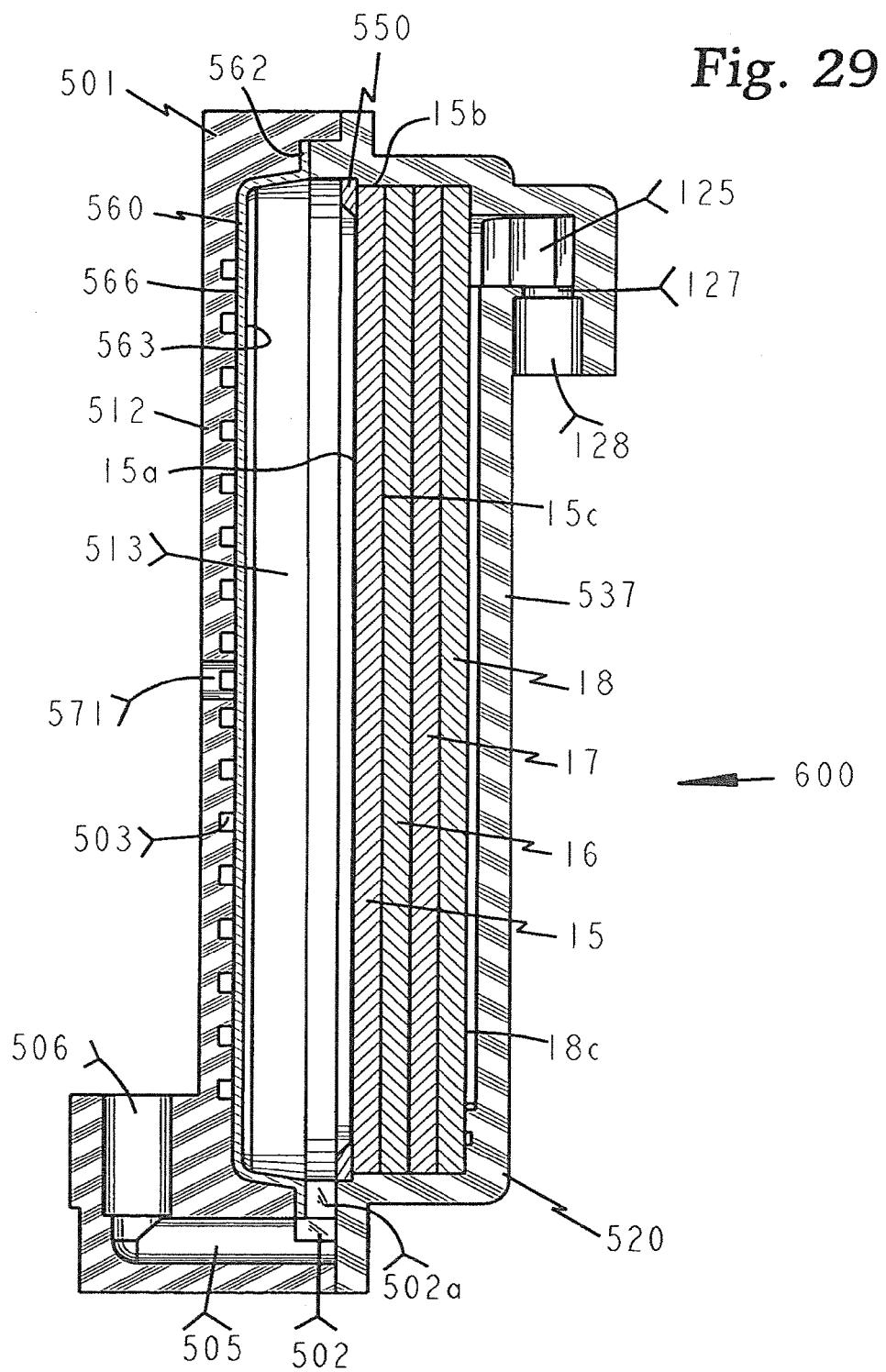
FIG. 29 is a cross-sectional view of a sixth embodiment of a BFFD constructed in accordance with the principles of the present invention, usable for the filtration of biological fluids, containing a diaphragm, with the inlet located entirely below the chamber upstream of the BFFM.

A sixth embodiment of the BFFD constructed in accordance with the principles of the present invention, is shown in FIG. 29 through FIG. 31. BFFD 600 contains a rigid housing that includes housing inlet half 501 and housing outlet half 520. Housing seal surface 529a of housing inlet half 501 is bonded to housing seal surface 529 of housing outlet half 520. The bond is preferably an ultrasonic weld but may be a heat bond, a glue bond, a solvent bond, or any other type of leak tight bond.

Referring to FIG. 29, and FIG. 31 housing inlet half 501 contains diaphragm well 509 bounded by surface 510. Hole 571 goes through wall 512 and is in fluid flow communication with circular vent channels 503 and radial vent channel 503a. Flexible diaphragm 560 contains inner surface 563, outer surface 566, and flange 562. The outer surface of flange 562 is sealed to diaphragm seal surface 507 of housing inlet half 501. The seal may be a heat seal, an ultrasonic seal, a glue seal, a solvent seal, or any other type of leak tight seal. Alternately flange 562 may be sealed to the housing by compressing flange 562 between diaphragm seal surface 507 of housing inlet half 501 and diaphragm seal surface 507a of housing outlet half 520. In which case diaphragm seal surface 507a should be an un-interrupted surface like filter seal surface 907 shown in FIG. 48, and second inlet slot 502a should be formed like slot 904a shown in FIG. 48. Flexible diaphragm 560 may be molded from a flexible rubber material such as silicone rubber, or it may be molded or thermo formed from a material such as PVC, polyethylene, or polypropylene, but is not limited to these materials. Flexible diaphragm 560 is preferably shaped so that in its normal state outer surface 566 conforms to surface 510 of housing inlet half 501. Housing inlet half 501 also contains inlet 505, first inlet slot 502, and inlet tube socket 506. Upstream chamber 513 is bounded by inner surface 563 of flexible diaphragm 560, and by surface 508a of housing outlet half 520, and by upstream surface 15a of filter element 15. Inlet 505 is in fluid flow communication with upstream chamber 513 through first inlet slot 502. When BFFD 600 is used in biological fluid filtration system 1000 shown in FIG. 1, the outlet end of tubing 81a is inserted into and bonded to inlet tube socket 506. Inlet 505 is located below the bottom of upstream chamber 513 and on the vertical center line of housing inlet half 501. When BFFD 600 is used in biological fluid filtration system 2000 shown in FIG. 12, the outlet end of tubing 81 is inserted into and bonded to inlet tube socket 506.

Referring to FIG. 29, and FIG. 30 housing outlet half 520 contains the same filter under drain structure that was used in the second embodiment described above and shown in FIG. 14, including vertical channels 122a, vertical channels 122, circular outlet channel 125 and outlet 127. Housing outlet half 520 contains filter well 511, bounded by a plane that goes through filter seal surface 124 and by inner side wall 508. The upper part of the inner side wall contains a counter bore bounded by inner side wall 508a and by surface 524. The bottom portion of ridge 526 contains second inlet slot 502a. Because housing outlet half 520 does not contain an open chamber or plenum downstream of the BFFM, the hold up volume of biological fluid will be minimized.

Referring to FIG. 29, a biological fluid filtration media (BFFM) that contains at least one filter element is interposed between inlet 505 and outlet 127, and is sealed to the housing to prevent the flow of unfiltered biological fluid from flowing between the housing and the BFFM to prevent bypass of unfiltered biological fluid around the BFFM. The BFFM shown in FIG. 29 contains filter elements 15, 16, 17, and 18. The filter elements may all be of the same type or may be different types filter elements. Each filter element contains an upstream surface designated as upstream surface 15a for filter element 15, a downstream surface designated as downstream surface 15c for filter element 15, and a perimeter surface designated as perimeter surface 15b for filter element 15. The downstream surface of the BFFM shown as downstream surface 18c of filter element 18 is in contact with inner wall 121 of housing outlet half 520. Because the downstream surface of the BFFM contacts inner wall 121 of housing outlet half 520, BFFD 600 does not contain an open chamber or plenum downstream of the BFFM. The air or liquid that is forced through the BFFM must pass through the vertical channels and the circular outlet channel before flowing into outlet 127 of BFFD 600. The at least one filter element may be sealed to the housing with an interference fit between the perimeter surface of the filter element and inner side wall 508 of housing outlet half 520, or the at least one filter element may be sealed to the housing with a compression seal by compressing the outer periphery of the at least one filter element between seal ring 550 and filter seal surface 124 of housing outlet half 520. Seal ring 550 is press fitted or bonded into the counter bore at the top of filter well 511 as shown in FIG. 29. The at least one filter element may also be sealed to the housing a heat seal, an ultrasonic weld, a glue seal, a solvent seal, a radio frequency weld, or any other type of leak tight seal. A combination of sealing methods may also be used to seal the at least one filter element to the housing.

Referring to FIG. 29 a first fluid flow path is defined between inlet 505 of BFFD 600 and outlet 127 of BFFD 600 with the at least one filter element of the BFFM interposed between inlet 505 and outlet 127, and across the fluid flow path. The first fluid flow path flows from inlet 505, through first inlet slot 502, through second inlet slot 502a, into upstream chamber 513, through the at least one filter element of the BFFM, into vertical channels 122 and 122a, into circular outlet channel 125, and then into outlet 127.

Referring to FIG. 12 and FIG. 29, when BFFD 600 is used to replace BFFD 200 in biological fluid filtration system 2000, the system will function as follows. The user will purchase the system with all components as shown in FIG. 12, less feed blood bag 98. BFFD 600 will replace BFFD 200, and tubing 85 and vent filtration device 40 will not be used. The user will connect tubing 81 to outlet 92 of feed blood bag 98 in a manner known in the art. Feed blood bag 98 and vent filtration device 30, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 should be open, and tube clamp 97 should be closed.

Referring to FIG. 12, and FIG. 29, BFFD 600 functions as follows. When tube clamp 95 is opened biological fluid (i.e. liquid) will flow from feed blood bag 98, through tubing 81, through inlet 505, through first inlet slot 502, through second inlet slot 502a and then into upstream chamber 513 of BFFD 600. Upstream chamber 513 will rapidly fill with biological fluid from the bottom up. The BFFM will wet and air will be purged from BFFD 600 as described for the third embodiment above, because BFFD 600 uses the same filter under drain structure that was used in BFFD 300 of the third embodiment.

Figure 32:
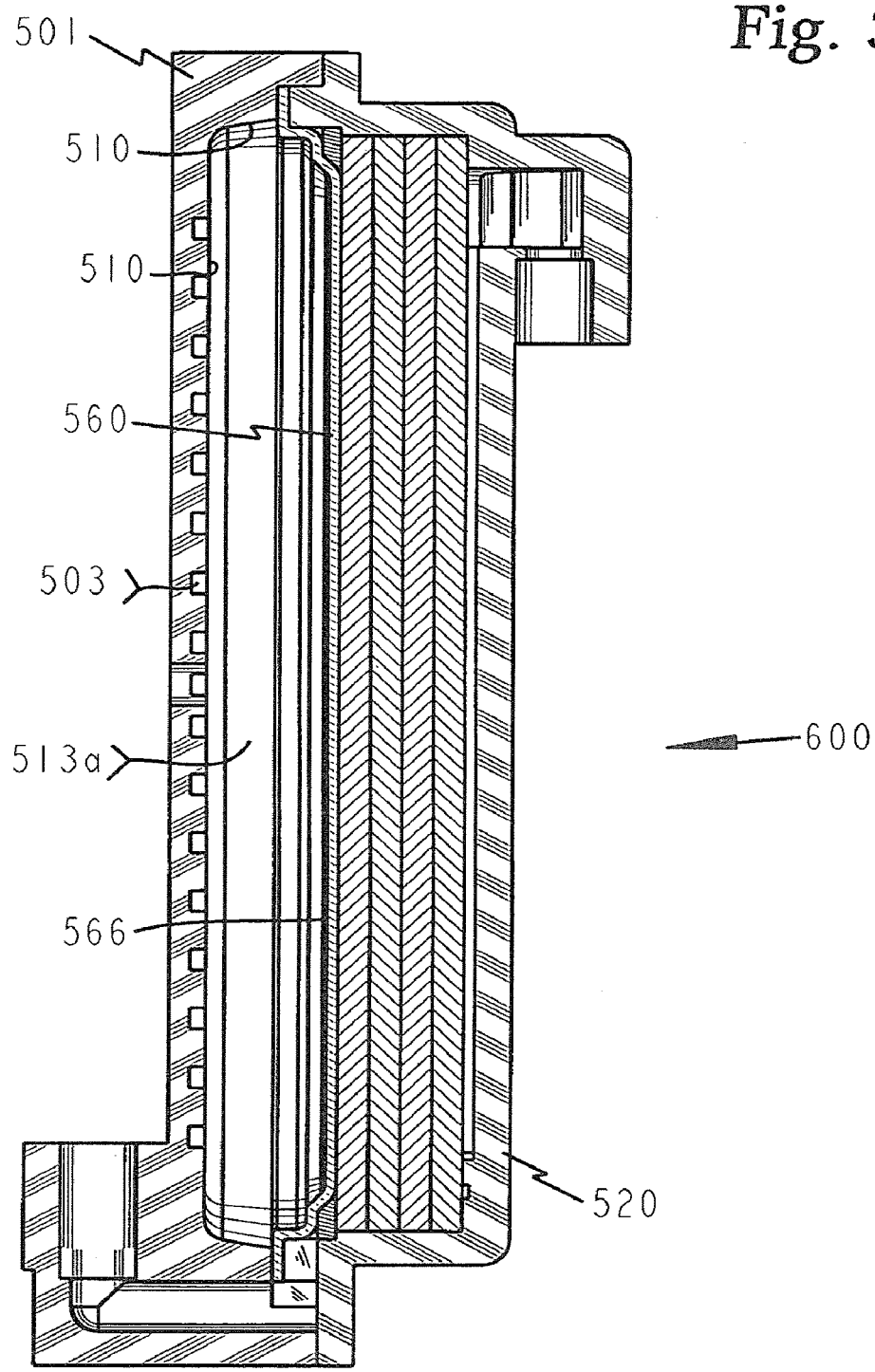
FIG. 32 is a cross-sectional view of the BFFD shown in FIG. 29 with the diaphragm shown in the collapsed state after filtration is complete.

Referring to FIG. 12, FIG. 29 and FIG. 31, once all of the air has been purged from within BFFD 600, biological fluid will continue to flow through the first fluid flow path from the inlet of BFFD 600 to the outlet of BFFD 600, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than the outlet of BFFD 600, pressure downstream of the BFFM and upstream of outlet 127 will be negative as described above. Once feed blood bag 98 collapses and biological fluid flow through the first fluid flow path stops the differential pressure across the BFFM will become zero, hence the pressure in upstream chamber 513 will become negative. The pressure on upstream surface 566 of flexible diaphragm 560 will be atmospheric because hole 571 of housing inlet half 501 is open to atmosphere, and in fluid flow communication with radial vent channel 503a and circular vent channels 503 of housing inlet half 501. With atmospheric pressure on the outer surface 566 of flexible diaphragm 560, the negative pressure within upstream chamber 513 will cause flexible diaphragm 560 to collapse onto upstream surface 15a of the BFFM as shown in FIG. 32, thereby forcing the biological fluid in upstream chamber 513 through the BFFM, into the vertical channels and the circular outlet channel, into outlet 127, into tubing 82, and then into receiving blood bag 99.

Referring to FIG. 12, FIG. 29, and FIG. 30, when the filtration cycle is complete as just described, the BFFM will remain wetted, vertical channels 122, vertical channels 122a and circular outlet channel 125 will be filled with biological fluid, and tubing 82 will be filled with biological fluid. Because BFFD 600 does not contain a plenum downstream of the BFFM, the hold up volume of biological fluid within BFFD 600 will be minimized. The user will close tube clamp 96, and then cut and seal tubing 82 above tube clamp 96, and then discard BFFD 600 and feed blood bag 98 in a safe manner. Tube clamp 97 may now be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner.

BFFD 600 can be used to replace BFFD 100 in biological fluid filtration system 1000 shown in FIG. 1. If BFFD 600 is used in this manner, it will purge air and filter biological fluid as described in the third embodiment. Three tube connector 50 and vent filtration device 30 will function as described in the description of the first embodiment above. When the filtration cycle is complete, tubing 83, tubing 81a, and upstream chamber 513 of BFFD 600 will drain as described in the description of the first embodiment above, and flexible diaphragm 560 will remain in the un-collapsed state.

Detailed Description of the Seventh Embodiment

Figure 33:
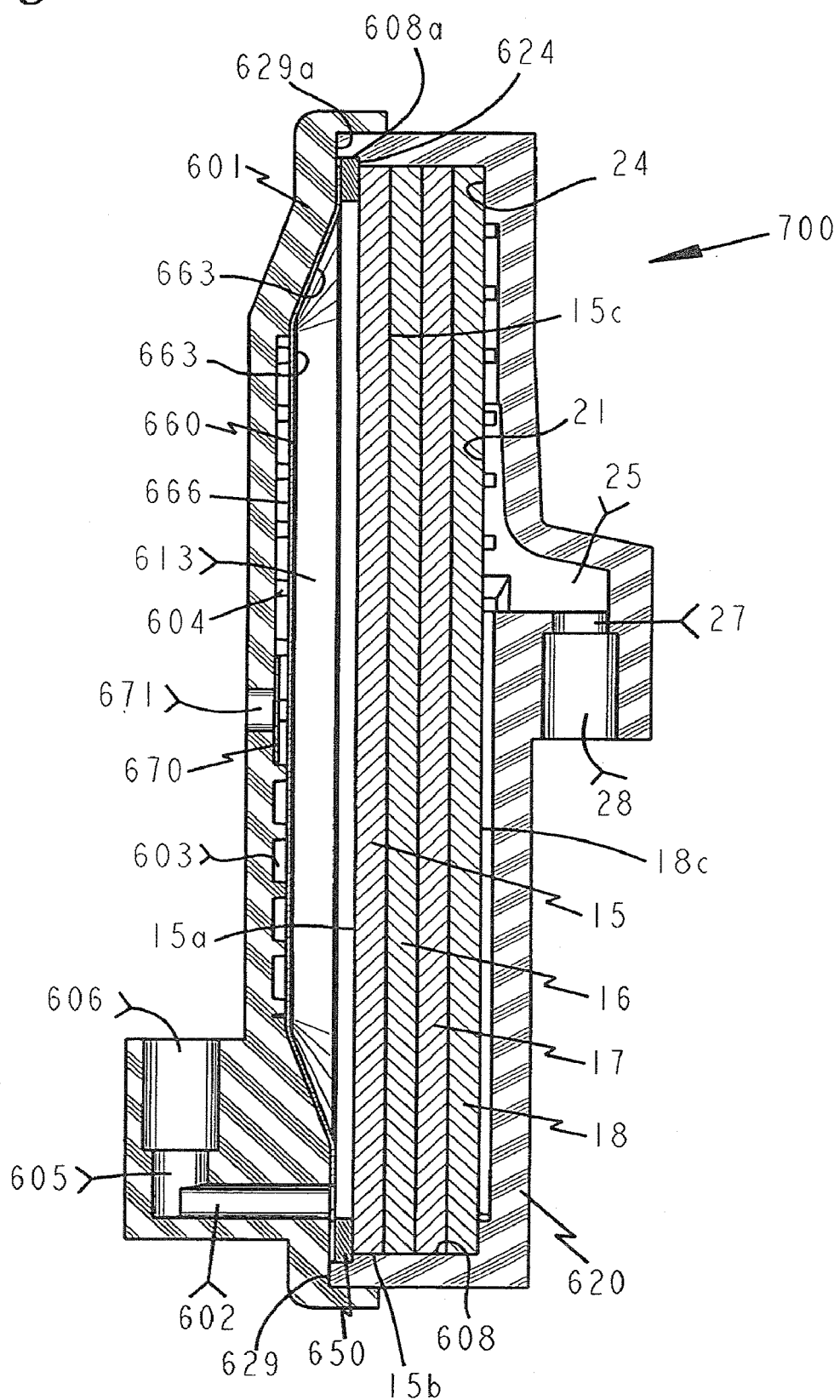
FIG. 33 is a cross-sectional view of a seventh embodiment of a BFFD constructed in accordance with the principles of the present invention, usable for the filtration of biological fluids, containing a diaphragm, with the inlet located at the bottom of the chamber upstream of the BFFM.

A seventh embodiment of the BFFD constructed in accordance with the principles of the present invention, is shown in FIG. 33 through FIG. 35. BFFD 700 contains a rigid housing that includes housing inlet half 601 and housing outlet half 620. Housing seal surface 629a of housing inlet half 601 is bonded to housing seal surface 629 of housing outlet half 620. The bond is preferably an ultrasonic weld but may be a heat bond, a glue bond, a solvent bond, or any other type of leak tight bond.

Referring to FIG. 33, and FIG. 34 housing inlet half 601 contains diaphragm well 609 bounded by surface 610 and a plane that goes through the top surface of ribs 604. Hole 671 goes through wall 612 and is in fluid flow communication with circular vent channels 603 and radial vent channel 603a. Vent filter element 670 may be sealed to surface 610a so that hole 671 is located within the seal as shown in FIG. 33. Vent filter element 670 is preferably a sterilizing grade filter that may be either hydrophobic, or hydrophilic. Vent filter element 670 adds a redundant layer of protection to BFFD 700. Flexible diaphragm 660 contains inner surface 663, outer surface 666, and flange 662. The outer surface of flange 662 is sealed to diaphragm seal surface 607 of housing inlet half 601. The seal may be a heat seal, an ultrasonic seal, a glue seal, a solvent seal, or any other type of leak tight seal. Flexible diaphragm 660 may be molded from a flexible rubber material such as silicone rubber, or it may be molded or thermo formed from a material such as PVC, polyethylene, or polypropylene, but is not limited to these materials. Housing inlet half 601 also contains inlet 605, inlet slot 602, and inlet tube socket 606. Upstream chamber 613 is bounded by inner surface 663 of flexible diaphragm 660, and by upstream surface 15a of filter element 15, and by the inner surface of seal ring 650. Inlet 605 is in fluid flow communication with upstream chamber 613 through inlet slot 602. Inlet slot 602 is located at the bottom of upstream chamber 613 and on the vertical center line of housing inlet half 601. The bottom portion of diaphragm well 609 protrudes inward towards the center of the diaphragm well so that inlet slot 602 is located outside of diaphragm seal surface 607 as shown in FIG. 34. Flexible diaphragm 660 is preferably shaped so that in its normal state outer surface 666 conforms to surface 610 of housing inlet half 601 as shown in FIG. 34 and FIG. 35.

Referring to FIG. 33 housing outlet half 620 contains the same filter under drain structure that was used in the first embodiment, and shown in FIG. 3, including vertical channels 22, horizontal channels 23, horizontal collection channel 26, outlet channel 25 and outlet 27. Housing outlet half 520 contains filter well 611 bounded by filter seal surface 24 and by inner side wall 608. The upper part of the inner side wall contains a counter bore bounded by inner side wall 608a and by surface 624.

Referring to FIG. 33, a biological fluid filtration media (BFFM) that contains at least one filter element is interposed between inlet 605 and outlet 27, and is sealed to the housing to prevent the flow of unfiltered biological fluid from flowing between the housing and the BFFM to prevent bypass of unfiltered biological fluid around the BFFM. The BFFM shown in FIG. 33 contains filter elements 15, 16, 17, and 18. The filter elements may all be of the same type or may be different types filter elements. Each filter element contains an upstream surface designated as upstream surface 15a for filter element 15, a downstream surface designated as downstream surface 15c for filter element 15, and a perimeter surface designated as perimeter surface 15b for filter element 15. The downstream surface of the BFFM shown as downstream surface 18c of filter element 18 is in contact with inner wall 21 of housing outlet half 620. Because the downstream surface of the BFFM contacts inner wall 21 of housing outlet half 620, BFFD 700 does not contain an open chamber or plenum downstream of the BFFM. The air or liquid that is forced through the BFFM must pass through the vertical channels 22, horizontal channels 23, horizontal collection channel 26, and outlet channel 25 before flowing into outlet 27 of BFFD 700. The at least one filter element may be sealed to the housing with an interference fit between the perimeter surface of the filter element and inner side wall 608 of housing outlet half 620, or the at least one filter element may be sealed to the housing with a compression seal by compressing the outer periphery of the at least one filter element between seal ring 650 and filter seal surface 24 of housing outlet half 620. Seal ring 650 is in the form of a hollow cylinder as shown in FIG. 33. Seal ring 650 is press fitted or bonded into the counter bore at the top of the filter well as shown in FIG. 33. The at least one filter element may also be sealed to the housing a heat seal, an ultrasonic weld, a glue seal, a solvent seal, a radio frequency weld, or any other type of leak tight seal. A combination of sealing methods may also be used to seal the at least one filter element to the housing.

Referring to FIG. 33 a first fluid flow path is defined between inlet 605 of BFFD 700 and outlet 27 of BFFD 700 with the at least one filter element of the BFFM interposed between inlet 605 and outlet 27, and across the fluid flow path. The first fluid flow path flows from inlet 605, through inlet slot 602, into upstream chamber 613, through the at least one filter element of the BFFM, into vertical channels 22, horizontal channels 23, horizontal collection channel 26, outlet channel 25, into outlet 27.

Referring to FIG. 12 and FIG. 33, when BFFD 700 is used to replace BFFD 200 in biological fluid filtration system 2000, the system will function as follows. The user will purchase the system with all components as shown in FIG. 12, less feed blood bag 98. BFFD 700 will replace BFFD 200, and tubing 85 and vent filtration device 40 will not be used. The user will connect tubing 81 to outlet 92 of feed blood bag 98 in a manner known in the art. Feed blood bag 98 and vent filtration device 30, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 should be open, and tube clamp 97 should be closed.

Referring to FIG. 12, and FIG. 33, BFFD 700 functions as follows. When tube clamp 95 is opened biological fluid (i.e. liquid) will flow from feed blood bag 98, through tubing 81, through inlet 605, through inlet slot 602, into upstream chamber 613 of BFFD 700. Upstream chamber 613 will rapidly fill with biological fluid from the bottom up. The BFFM will wet and air will be purged from BFFD 700 as described for the first embodiment above, because BFFD 700 uses the same filter under drain structure that was used in BFFD 100 of the first embodiment shown in FIG. 2 through FIG. 4.

Referring to FIG. 12, and FIG. 33, once all of the air has been purged from within BFFD 700, biological fluid will continue to flow through the first fluid flow path from the inlet of BFFD 700 to the outlet of BFFD 700, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 700, the pressure downstream of the BFFM and upstream of outlet 27 will be negative as described above in the first embodiment. Once feed blood bag 98 collapses and biological fluid flow through the first fluid flow path stops the differential pressure across the BFFM will become zero, hence the pressure in upstream chamber 613 will become negative. The pressure on upstream surface 666 of flexible diaphragm 660 will be atmospheric because hole 671 of housing inlet half 601 is in fluid flow communication to atmosphere via vent filter element 670, and in fluid flow communication with radial vent channel 603a and circular vent channels 603 of housing inlet half 601. With atmospheric pressure on the outer surface 666 of flexible diaphragm 660, the negative pressure within upstream chamber 613 will cause flexible diaphragm 660 to collapse onto upstream surface 15a of the BFFM, thereby forcing the biological fluid in upstream chamber 613 through the BFFM, into vertical channels 22, horizontal channels 23, horizontal collection channel 26, outlet channel 25, into outlet 27, into tubing 82, and then into receiving blood bag 99.

Referring to FIG. 12, and FIG. 33, when the filtration cycle is complete as just described, the BFFM will remain wetted, vertical channels 22, horizontal channels 23, horizontal collection channel 26, and outlet channel 25, will be filled with biological fluid, and tubing 82 will be filled with biological fluid. Because BFFD 700 does not contain a plenum downstream of the BFFM, the hold up volume of biological fluid within BFFD 700 will be minimized. The user will close tube clamp 96, and then cut and seal tubing 82 above tube clamp 96, and then discard BFFD 700 and feed blood bag 98 in a safe manner. Tube clamp 97 may now be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner.

BFFD 700 can be used to replace BFFD 100 in biological fluid filtration system 1000 shown in FIG. 1. If BFFD 700 is used in this manner, it will purge air and filter biological fluid as described in the first embodiment. Three tube connector 50 and vent filtration device 30 will function as described in the description of the first embodiment above. When the filtration cycle is complete, tubing 83, tubing 81a, and upstream chamber 613 of BFFD 700 will drain as described in the description of the first embodiment above, and flexible diaphragm 660 will remain in the un-collapsed state.

Detailed Description of the Eighth Embodiment

An eighth embodiment of the BFFD constructed in accordance with the principles of the present invention, is shown in FIG. 36 through FIG. 39. BFFD 800 contains a rigid housing that includes housing inlet half 701 and housing outlet half 720. Housing seal surface 729a of housing inlet half 701 is bonded to housing seal surface 729 of housing outlet half 720. The bond is preferably an ultrasonic weld but may be a heat bond, a glue bond, a solvent bond, or any other type of leak tight bond. Housing inlet half 701 is the same as housing inlet half 1 of the first embodiment except that inlet slot 702 is located at the bottom of upstream chamber 713, and housing inlet half 701 does not contain a filter well. The inlet slot 702 could instead be located anywhere above the bottom of upstream chamber 713. Housing outlet half 720 is the same as housing outlet half 20 of the first embodiment, except that housing outlet half 720 contains a first filter well 711 bounded by inner side wall 708 and a plane that goes through first filter seal surface 724, and second filter well 711a bounded by inner side wall 708a and second filter seal surface 724a. First filter well 711 has a larger diameter than second filter well 711a. The first filter well is concentric with the second filter well.

Figure 36:
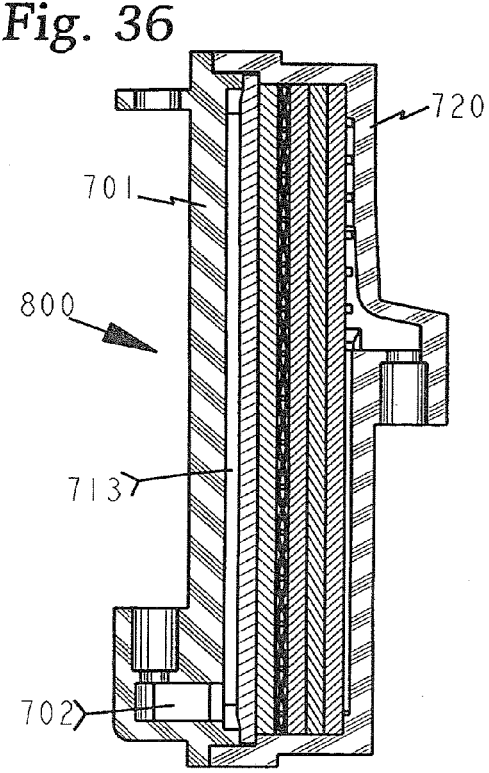
FIG. 36 is a cross-sectional view of an eighth embodiment of a BFFD constructed in accordance with the principles of the present invention, usable for the filtration of biological fluids. The eighth embodiment contains a gel removing filter element, followed by a microaggregate removing filter element, followed by a flow distribution filter element, followed by a leukocyte removing filter element that contains three layers of porous filter material.
Figure 38:
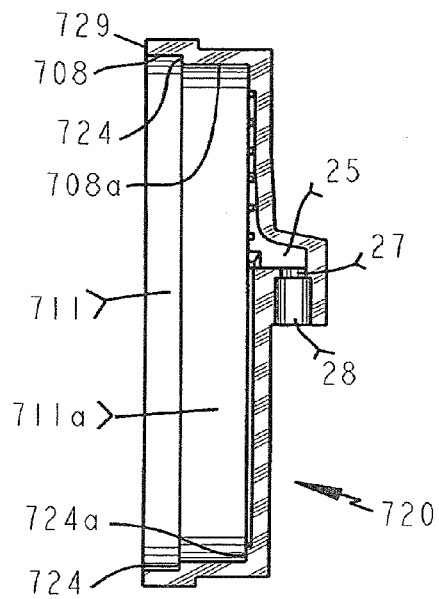
FIG. 38 is a cross-sectional view of the housing outlet half of the BFFD shown in FIG. 36.
Figure 37:
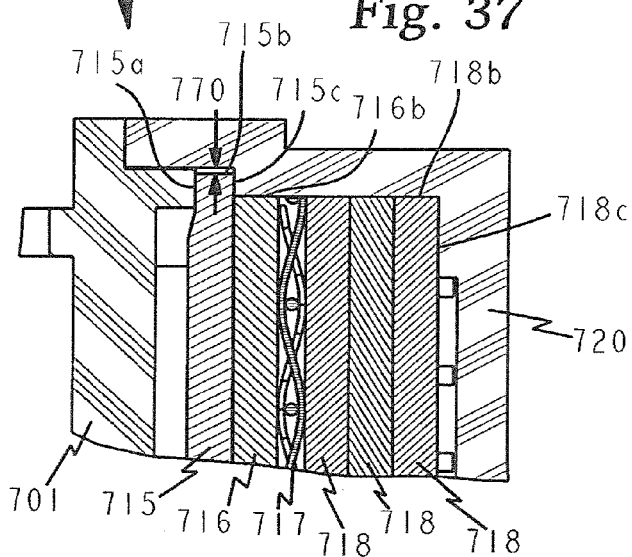
FIG. 37 is a partial cross-sectional view of the BFFD shown in FIG. 36.
Figure 39:
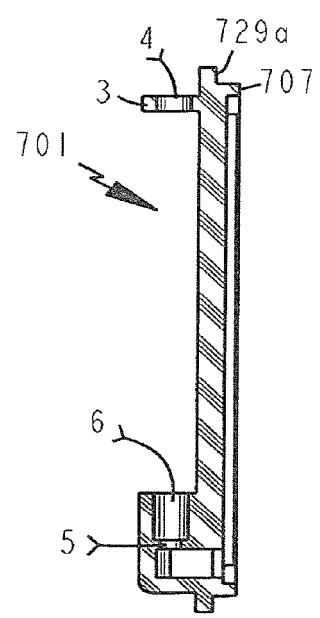
FIG. 39 is a cross-sectional view of the housing inlet half of the BFFD shown in FIG. 36.

Referring to FIG. 36 through FIG. 39, the BFFM contains four filter elements, first filter element 715, second filter element 716, third filter element 717, and fourth filter element 718 comprised of three layers of filter material of the same type. Any of the filter elements may contain one or more layers of the filter material of the same type. The first filter element has a pore size greater than the pore size of the second filter element, the fourth filter element has a pore size smaller than the pore size of the second filter element, while the third filter element has a pore size greater than the pore size of the second filter element. Preferably the pore size of the third filter element is greater than the pore size of the first and second filter elements. When BFFD 800 is used to filter blood or blood product, first filter element 715 may be sized to remove gels from the blood or blood product, second filter element 716 may be sized to remove microaggregates from the blood or blood product, fourth filter element 718 may be sized to remove leukocytes from the blood or blood product, while the third filter element 717 is sized to act as a flow distribution layer. Because gels and microaggregates are large particles they may clump together thereby reducing the flow through the gel-microaggregate filter elements in the region of the clump. The flow distribution filter element will distribute the effluent from the microaggregate filter element evenly over the upstream surface of the leukocyte removing layer, thereby allowing the leukocyte removing layer to be utilized most efficiently. The outside diameter of first filter element 715 is smaller than the inside diameter of inner side wall 708 of housing outlet half 720 (shown by gap 770 in FIG. 37) preventing first filter element 715 from being sealed to BFFD 800 with an interference fit between the perimeter surface 715b of filter element 715 and inner side wall 708 of housing outlet half 720. First filter element 715 is sealed to the housing by compressing the outer periphery of filter element 715 between filter seal surface 707 of housing inlet half 701, and first filter seal surface 724 of housing outlet half 720 as shown in FIG. 36 and FIG. 37. Second filter element 716 and fourth filter element 718 are sealed to the housing an interference fit between the perimeter surface of each filter element and inner side wall 708a of housing outlet half 720. Third filter element 717 is preferably a woven or non-woven screen filter, but could be any type of open pore size depth filter. The main purpose of filter element 717 is flow distribution, therefore it has a large pore size, and is preferably structured to allow flow through it in all directions. Hence the perimeter surface of filter element 717 need not have an interference fit with inner side wall 708. In applications where the blood or blood product is fresh and does not contain gels, the first filter element may be a microaggregate removing filter element, and the second filter element could be eliminated. In this case the third filter element may also be eliminated. As shown in FIG. 36 through FIG. 38, first filter well 711 has a larger inside diameter than second filter well 711a, therefore the filter elements disposed in the first filter well will have a larger outside diameter than the filter elements disposed in the second filter well. Alternately a single filter well as shown in FIG. 13 could be used. Referring to FIG. 13, filter element 15 could be a gel removing filter element, filter element 16 could be a microaggregate removing filter element, filter element 17 could be a flow distribution filter element, and filter element 18 could be a leukocyte removing filter element. As shown in FIG. 13 first filter element 15 has an outside diameter smaller than the inside diameter of the inner side wall of the housing outlet half. Alternately, first filter element 15 could have an outside diameter large enough to seal it to the housing with an interference fit between its outer perimeter and the inner side wall of the housing outlet half, and either the second filter element, or the fourth filter element could have an outside diameter smaller than the inside diameter of the inner side wall of the housing outlet half.

The housing of BFFD 800 is the same as the housing of BFFD 100 of the first embodiment described above with the minor modifications noted above. Therefore BFFD 800 will function exactly as BFFD 100 when used in biological fluid filtration system 1000 of the first embodiment shown in FIG. 1.

If the vent inlet, vent inlet slot, and vent tube socket (shown in FIG. 13) are added to housing inlet half 701, BFFD 800 could be used in biological fluid filtration system 2000 shown in FIG. 12. In this case BFFD 800 would fill and purge air from within BFFD 800 as described in the first embodiment. After the air was purged from BFFD 800, it would function the same as BFFD 200 in biological fluid filtration system 2000.

Housing outlet half 720 could use the filter under drain structure of the second embodiment shown in FIG. 14, in place of the filter under drain structure of the first embodiment. In this case BFFD 800 would fill and purge air from within BFFD 800 as described in the second embodiment.

Detailed Description of the Ninth Embodiment

Figure 40:
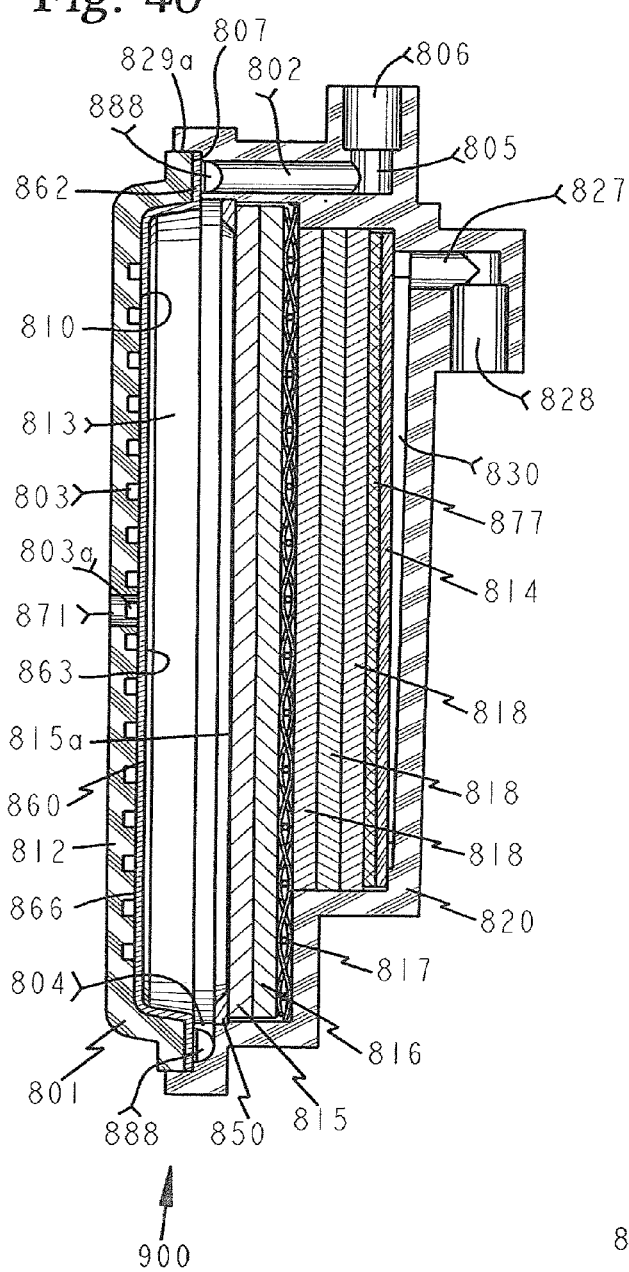
FIG. 40 is a cross-sectional view of a ninth embodiment of a BFFD constructed in accordance with the principles of the present invention, usable for the filtration of biological fluids. The ninth embodiment contains a gel removing filter element, followed by a microaggregate removing filter element, followed by a first flow distribution filter element, followed by a leukocyte removing filter element containing three layers of leukocyte removing porous filter material, followed by a second flow distribution filter element, followed by a particle trapping filter element. The leukocyte removing filter element, and the second flow distribution filter element, and the particle trapping filter element all have a surface area less than the surface area of the gel filter element, the microaggregate filter element, and the first flow distribution filter element. The ninth embodiment also contains a diaphragm.

A ninth embodiment of the BFFD constructed in accordance with the principles of the present invention, is shown in FIG. 40, FIG. 43, and FIG. 44. BFFD 900 may be used in place of BFFD 100 in biological fluid filtration system 1000 shown in FIG. 1, and may also be used in place of BFFD 200 in biological fluid filtration system 2000 shown in FIG. 12.

Referring to FIG. 40, and FIG. 43, BFFD 900 contains a rigid housing that includes housing inlet half 801 and housing outlet half 820. Housing seal surface 829a of housing inlet half 801 is bonded to housing seal surface 829 of housing outlet half 820. The bond is preferably an ultrasonic weld but may be a heat bond, a glue bond, a solvent bond, or any other type of leak tight bond.

Referring to FIG. 40, housing inlet half 801 contains a diaphragm well similar to diaphragm well 509 of housing inlet half 501 shown in FIG. 31. Hole 871 goes through wall 812 and is in fluid flow communication with circular vent channels 803 and radial vent channel 803a. The circular vent channels and the radial vent channel are similar to the circular vent channels and the radial vent channel of housing inlet half 501 shown in FIG. 31. Flexible diaphragm 860 contains inner surface 863, outer surface 866, and flange 862. Flexible diaphragm 860 is similar to flexible diaphragm 560 shown in FIG. 29. The outer surface of flange 862 is sealed to diaphragm seal surface 807 of housing inlet half 801. The seal may be a heat seal, an ultrasonic seal, a glue seal, a solvent seal, or any other type of leak tight seal. Flexible diaphragm 860 may be molded from a flexible rubber material such as silicone rubber, or it may be molded or thermo formed from a material such as PVC, polyethylene, or polypropylene, but is not limited to these materials. Flexible diaphragm 860 is preferably shaped so that in its normal state outer surface 866 conforms to surface 810 of housing inlet half 801. Upstream chamber 813 is bounded by inner surface 863 of flexible diaphragm 860, and by surface 808b of housing outlet half 820, and by upstream surface 815a of filter element 815, and by the inner surface of seal ring 850.

Referring to FIG. 40, FIG. 43, and FIG. 44 housing outlet half 820 contains an open chamber or plenum 830 defined by inner wall 821a, by inner side wall 808b, and by a plane that goes through second filter seal surface 824a. Vertical filter support ribs 822 protrude from inner wall 821a, with the top surface of vertical filter support ribs lying in a plane that goes through second filter seal surface 824a. Plenum 830 may be tapered as shown in FIG. 40, with the depth of the top of the plenum being deeper than the depth of the bottom of the plenum. Outlet 827 is located at the top of plenum 830. Vertical filter support ribs 822 create a filter under drain structure. Housing outlet half 820 contains first filter well 811 bounded by inner side wall 808 and by first filter seal surface 824, and second filter well 811a bounded by inner side wall 808a and by second filter seal surface 824a. First filter well 811 has a larger diameter than second filter well 811a. The horizontal center line of the first filter well is offset below the horizontal center line of the second filter well so that the top of first filter seal surface 824 protrudes above the top of second filter seal surface 824a a sufficient distance to create a compression seal as will be described below, and so that the perimeter of the second filter well is located entirely within the perimeter of the first filter well. Housing outlet half 820 also contains inlet 805, inlet slot 802, circular groove 888, and slot 804. Inlet 805 is in fluid flow communication with upstream chamber 813 via inlet slot 802, circular groove 888, and slot 804. The upper part of first filter well 811 contains a seal ring counter bore bounded by inner side wall 808b, and by surface 824b.

Referring to FIG. 40, FIG. 43, and FIG. 44, the BFFM contains six filter elements, first filter element 815, second filter element 816, third filter element 817, fourth filter element 818 comprised of three layers of filter material of the same type, fifth filter element 877, and sixth filter element 814. Any of the filter elements may contain one or more layers of the filter material of the same type. The first filter element has a pore size greater than the pore size of the second filter element, the fourth filter element has a pore size smaller than the pore size of the second filter element, while the third filter element has a pore size greater than the pore size of the second filter element. Preferably the pore size of the third filter element is greater than the pore size of the first and second filter elements. The fifth filter element has a pore size greater than the fourth filter element, and the sixth filter element has a pore size smaller than the fifth filter element. When BFFD 900 is used to filter blood or blood product, first filter element 815 may be sized to remove gels from the blood or blood product, second filter element 816 may be sized to remove microaggregates from the blood or blood product, fourth filter element 818 may be sized to remove leukocytes from the blood or blood product, while the third filter element 817 is sized to act as a first flow distribution layer. Sixth filter element 814 is used to remove particulates from the filter elements upstream of it, while fifth filter element 877 acts as a second flow distribution layer. Because gels and microaggregates are large particles they may clump together thereby reducing the flow through the gel-microaggregate filter elements in the region of the clump. The first flow distribution filter element will distribute the effluent from the microaggregate filter element evenly over the upstream surface of the leukocyte removing layer, thereby allowing the leukocyte removing layer to be utilized most efficiently. Once the gels and microaggregates have been removed from the blood or blood product, the blood or blood product will be relatively clean and therefore the surface area of the leukocyte removing layer may be made smaller than the surface area of the gel and microaggregate layers, thereby reducing the hold up volume of the BFFD. The gel filter element, and the microaggregate filter element, and the first flow distribution filter element, are inserted into the first filter well of housing outlet half 820. Referring to FIG. 40 and FIG. 44, gel filter element 815, microaggregate filter element 816, and first flow distribution filter element 817, have outside diameters smaller than the inside diameter of inner side wall 808, preventing them from being sealed to BFFD 900 with an interference fit between the perimeter surface of each respective filter element and inner side wall 808 of housing outlet half 820. The outer periphery of the gel filter element, and the outer periphery of the microaggregate filter element, and the outer periphery of the first flow distribution filter element, are sealed to the housing with a compression seal between seal ring 850, and first filter seal surface 824 of housing outlet half 820 as shown in FIG. 40. Seal ring 850 is in the shape of a hollow cylinder with a tapered inner surface as shown in FIG. 40. Alternately, either the gel filter element, or the microaggregate filter element, could have an outside diameter large enough so that it could be sealed to the housing an interference fit between the perimeter surface of the larger diameter filter element and inner side wall 808 of housing outlet half 820. Third filter element 817 is preferably a woven or non-woven screen filter, but could be any type of open pore size depth filter, or could even be an injection molded screen. The main purpose of first flow distribution filter element 817 is flow distribution, therefore it has a large pore size (i.e. the pore size of flow distribution filter element 817 may be larger than the pore size of all of the other filter elements), and is preferably structured to allow flow through it in all directions (i.e. through the flow distribution filter element, and laterally across the flow distribution filter element in both the horizontal and vertical directions). Hence the perimeter surface of filter element 817 need not have an interference fit with inner side wall 808. Housing outlet half 820 also contains a second filter well smaller in diameter than the first filter well into which leukocyte removing filter element 818, second flow distribution filter element 877, and particle trapping filter element 814, are inserted. Leukocyte removing filter element 818 is sealed to the housing an interference fit between the perimeter surface of each layer of the leukocyte removing filter material and inner side wall 808*a* of housing outlet half 820. As shown in FIG. 40, second flow distribution filter element 877 and particle removing filter element 814 have outside diameters smaller than the inside diameter of inner side wall 808*a*, thereby preventing an interference seal between the perimeter surface of each respective filter element and inner side wall 808*a* of housing outlet half 820. The main purpose of second flow distribution filter element 877 is flow distribution, therefore it has a large pore size, and is preferably structured to allow flow through it in all directions. Hence the perimeter surface of filter element 877 need not have an interference fit with inner side wall 808*a*. As shown in FIG. 40, the outer periphery of the downstream surface of particle trapping filter element 814 is sealed to second filter seal surface 824*a* of housing outlet half 820 with a compression seal. Alternately either filter element 877 or filter element 814, or both could have a sufficiently large outside diameter so that they could be sealed to the housing an interference fit between the perimeter surface of each respective filter element and inner side wall 808*a* of housing outlet half 820. Particle trapping filter element 814 could also be sealed to housing outlet half 820 by a heat seal, an ultrasonic seal, a solvent seal, a glue seal, or any other type of leak tight seal. In some applications second flow distribution filter element 877 could be eliminated.

Referring to FIG. 40 and FIG. 43, a first fluid flow path is defined between inlet 805 of BFFD 900 and outlet 827 of BFFD 900 with the BFFM interposed between inlet 805 and outlet 827, and across the fluid flow path. The first fluid flow path flows from inlet 805, through inlet slot 802, through circular groove 888 in both directions (as shown by arrows 885 in FIG. 43), through slot 804, into upstream chamber 813, through the BFFM, into the plenum 830 downstream of the BFFM, and then into outlet 827.

Referring to FIG. 12 and FIG. 40, when BFFD 900 is used to replace BFFD 200 in biological fluid filtration system 2000, the system will function as follows. The user will purchase the system with all components as shown in FIG. 12, less feed blood bag 98. BFFD 900 will replace BFFD 200, tubing 85 and vent filtration device 40 will not be used. The user will connect tubing 81 to outlet 92 of feed blood bag 98 in a manner known in the art. Feed blood bag 98 and vent filtration device 30, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 should be open, and tube clamp 97 should be closed.

Referring to FIG. 12, FIG. 40, and FIG. 43, BFFD 900 functions as follows. When tube clamp 95 is opened biological fluid (i.e. liquid) will flow from feed blood bag 98, through tubing 81, into inlet 805, through inlet slot 802, through circular groove 888 in both directions (as shown by arrows 885 in FIG. 43), through slot 804, into upstream chamber 813. Upstream chamber 813 will rapidly fill with biological fluid from the bottom up. As upstream chamber 813 fills from the bottom up, the initial air in upstream chamber 813 will be displaced by the biological fluid filling upstream chamber 813. The displaced air will be forced through the BFFM, into plenum 830, and then into outlet 827. The biological fluid in upstream chamber 813 will be pressurized, with the pressure at the bottom of upstream chamber 813 being proportional to the distance from the top of the biological fluid in feed blood bag 98 to the bottom of upstream chamber 813, and with the pressure at the top of upstream chamber 813 being proportional to the distance from the top of the biological fluid in feed blood bag 98 to the top of upstream chamber 813. Hence the pressure at the top of upstream chamber 813 will be less than the pressure at the bottom of upstream chamber 813. The positive pressure in upstream chamber 813 will cause the biological fluid to flow through first filter element 815, and second filter element 816 over the entire surface area of the first and second filter elements displacing the air within the pores of the first and second filter elements with biological fluid, thereby wetting the first and second filter elements from the upstream side of first filter element 815 to the downstream side of second filter element 816. The displaced air from upstream chamber 813 and from the first and second filter elements will flow into third filter element 817. Third filter element 817 preferably has an open pore size with a structure that allows flow through it in all directions. Therefore any air or biological fluid that flows from the downstream surface of second filter element 816, will flow into third filter element 817 and then be uniformly distributed over the entire upstream surface of fourth filter element 818, thereby utilizing fourth filter element 818 in the most efficient way. As the first and second filter elements wet, the air that was initially in the pores of the first and second filter elements will be displaced by biological fluid, and flow into the third filter element 817. Because the pressure at the bottom of upstream chamber 813 is greater than the pressure at the top of upstream chamber 813, the flow rate of biological fluid through the first and second filter elements will be greater at the bottom of the first and second filter elements than at the top of the first and second filter elements. Therefore, the first and second filter elements will first become completely wetted from the upstream surface of the first filter element to downstream surface of the second filter element at the bottom of the second filter element. The first and second filter elements will continue to wet with the downstream surface of the second filter element wetting from the bottom to the top. The third filter element will also wet from the bottom to the top. When the liquid level in the third filter element reaches the bottom of fourth filter element 818, the fourth filter element will begin to wet from the bottom up. The first and second filter elements will continue to wet until all of the air in the first and second filter elements has been purged. It is important that the horizontal center line of first filter well 811 is offset the required distance below the horizontal center line of second filter well 811*a* so that the top of first filter seal surface 824 protrudes above the top of second filter seal surface 824*a* no more than the distance required to create a compression seal at the top of the first filter well between seal ring 850 and first filter seal surface 824 of housing outlet half 820, because air will be trapped in the compression seal portion of the first, second, and third filter elements that lie above horizontal line 886 shown in FIG. 43. The fourth, fifth, and sixth filter elements will wet from the bottom up, with the downstream surface of the sixth filter element also wetting from the bottom up, because the pressure at the bottom of the upstream surface of the fourth filter element will be greater than the pressure at the top of the upstream surface of the fourth filter element. Once the bottom of the downstream surface of the sixth filter element has been wetted, the remainder of the downstream surface of the sixth filter element will continue to wet from the bottom up, and biological fluid will start to flow from the bottom of the sixth filter element, into plenum 830. The plenum will fill from the bottom up forcing the air above the liquid level in the plenum into outlet 827, into tubing 82, and then into receiving blood bag 99. The plenum will fill with biological fluid before all of the air has been purged from the upper portion of the fourth, fifth, and sixth filter elements. The remaining air in the upper portion of the fourth, fifth, and sixth filter elements will be displaced by biological fluid and forced into the plenum, where it will bubble to the top of the plenum due to the buoyancy of air in the biological fluid, and then be forced into outlet 827, into tubing 82, and then into receiving blood bag 99 by the flow of biological fluid from plenum 830 into outlet 827. Hence the initial flow of biological fluid through outlet 827, into tubing 82 will be a mixture of air and biological fluid, so that the initial flow into tubing 82 will consist of alternate segments of biological fluid and air.

Referring to FIG. 12, and FIG. 40, once all of the air has been purged from within BFFD 900, biological fluid will continue to flow through the first fluid flow path from the inlet of BFFD 900 to the outlet of BFFD 900, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 900, pressure P3 downstream of the BFFM and upstream of outlet 827 will be negative as described above. Once feed blood bag 98 collapses and biological fluid flow through the first fluid flow path stops the differential pressure across the BFFM will become zero, hence the pressure in upstream chamber 813 will become negative. The pressure on upstream surface 866 of flexible diaphragm 860 will be atmospheric because hole 871 of housing inlet half 801 is open to atmosphere, and hole 871 is in fluid flow communication with radial vent channel 803*a*, and circular vent channels 803. With atmospheric pressure on the outer surface 866 of flexible diaphragm 860, the negative pressure within upstream chamber 813 will cause flexible diaphragm 860 to collapse onto the upstream surface of first filter element 815, thereby forcing the biological fluid in upstream chamber 813 through the BFFM, into plenum 830, into outlet 827, into tubing 82, and then into receiving blood bag 99.

Referring to FIG. 12 and FIG. 40, when the filtration cycle is complete as just described, the BFFM will remain wetted, plenum 830 will be filled with biological fluid, and tubing 82 will be filled with biological fluid. The user will close tube clamp 96, and then cut and seal tubing 82 above tube clamp 96, and then discard BFFD 900 and feed blood bag 98 in a safe manner. Tube clamp 97 may now be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner.

The filter under drain structure of BFFD 900 including plenum 830 and vertical filter support ribs 822 may be replaced with the filter under drain structure of the first embodiment shown in FIG. 3, in which case the filter under drain structure would purge air and fill with biological fluid as described in the description of the first embodiment. If the filter under drain structure of the first embodiment is used to replace plenum 830 and vertical filter support ribs 822, the hold up volume of the BFFD will also be minimized as explained in the description of the first embodiment, because of the lack of a plenum.

The filter under drain structure of BFFD 900 including plenum 830 and vertical filter support ribs 822 may also be replaced with the filter under drain structure of the second embodiment shown in FIG. 14, in which case the filter under drain structure would purge air and fill with biological fluid as described in the second embodiment. If the filter under drain structure of the second embodiment is used to replace plenum 830 and vertical filter support ribs 822, the amount of air that will be purged from the BFFM after biological fluid starts to flow from the outlet will be minimized, and the hold up volume of the BFFD will also be minimized as explained in the description of the second embodiment, because of the lack of a plenum.

Figure 41:
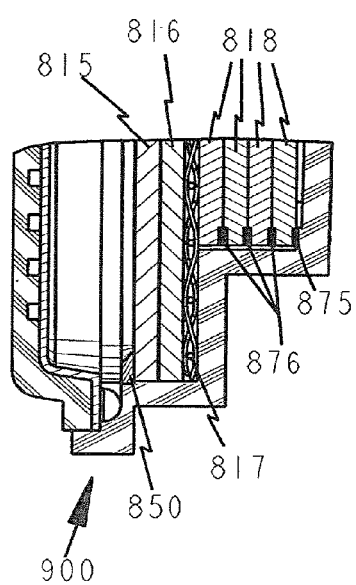
FIG. 41 is a partial cross-sectional view of the BFFD shown in FIG. 40 without the second flow distribution filter element, and without the particle trapping filter element, with a different sealing means being used to seal the filter elements to the housing.

FIG. 41 shows BFFD 900 without fifth filter element 877, and without sixth filter element 814. The first and second filter elements are sealed to the housing with an interference seal between the perimeter surface of the first and second filter elements and inner side wall 808 of housing outlet half 820. The outer periphery of the first filter element is also compression sealed by seal ring 850. The fourth filter element has an outside diameter less than the inside diameter of inner side wall 808*a*. The outer periphery of each layer of filter material of the fourth filter element is bonded to the layer adjacent to it with bond 876, with the outer periphery of the downstream surface of the fourth filter element sealed to second filter seal surface 824*a* with bond 875. The bond could be a heat bond, an ultrasonic bond, a solvent bond, a glue bond, an R.F. bond or any other type of leak tight seal.

Figure 42:
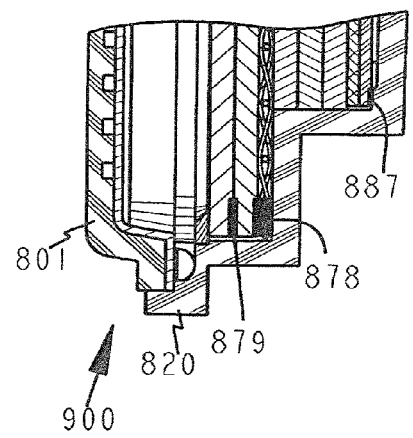
FIG. 42 is a partial cross-sectional view of the BFFD shown in FIG. 40 with a different sealing means being used to seal the filter elements to the housing.

FIG. 42 shows BFFD 900 with the outside diameter of the first and second filter elements less than the inside diameter of inner side wall 808. The outer periphery of the upstream surface of the first filter element is compression sealed by seal ring 850. The outer periphery of the downstream surface of the first filter element is bonded to the outer periphery of the upstream surface of the second filter element with bond 879; the outer periphery of the downstream surface of the second filter element is bonded to the upstream surface of the outer periphery of the third filter element; and the outer periphery of the third filter element is bonded to first filter seal surface 824 with bond 878. The bond could be a heat bond, an ultrasonic bond, a solvent bond, a glue bond, an R.F. bond or any other type of leak tight seal. The fourth filter element is sealed to the housing with an interference seal between the perimeter surface of the fourth filter element and inner side wall 808*a* of housing outlet half 820. The outside diameter of the fifth and sixth filter elements is less than the inside diameter of inner side wall 808*a*. The outer periphery of the downstream surface of the sixth filter element is bonded to second filter seal surface 824*a* with bond 887. The bond could be a heat bond, an ultrasonic bond, a solvent bond, a glue bond, an R.F. bond or any other type of leak tight seal.

FIG. 45 shows BFFD 900 with the perimeter surface of the first, second, and third, filter elements bonded to inner side wall 808 of housing outlet half 820 with bond 874, and with the perimeter surface of the fourth, fifth, and sixth, filter elements bonded to inner side wall 808*a* of housing outlet half 820 with bond 873. The bonds could be a heat bond, an ultrasonic bond, a solvent bond, a glue bond, an R.F. bond or any other type of leak tight seal.

The various filter elements could also be sealed to the housing any combination of seals shown in FIG. 40 through FIG. 42, and FIG. 45.

Detailed Description of the Tenth Embodiment

A tenth embodiment of the BFFD constructed in accordance with the principles of the present invention, is shown in FIG. 46 through FIG. 48. BFFD 1000 contains a rigid housing that includes housing inlet half 901 and housing outlet half 920. Housing seal surface 929*a* of housing inlet half 901 is bonded to housing seal surface 929 of housing outlet half 920. The bond is preferably an ultrasonic weld but may be a heat bond, a glue bond, a solvent bond, or any other type of leak tight bond.

Referring to FIG. 48 housing inlet half 901 contains circular rib 989, and filter support ribs 909. Slot 904*a* extends through the side wall of circular rib 989. Filter seal surface 907 extends 360° around the top of circular rib 989.

Referring to FIG. 46 and FIG. 47 housing outlet half 920 contains an open chamber or plenum 930 defined by inner wall 921*a*, by inner side wall 908*b*, and by a plane that goes through second filter seal surface 924*a*. Vertical filter support ribs 922 protrude from inner wall 921*a*, with the top surface of vertical filter support ribs lying in a plane that goes through second filter seal surface 924*a*. Plenum 930 may be tapered as shown in FIG. 46, with the depth of the top of the plenum being deeper than the depth of the bottom of the plenum. Outlet 927 is located at the top of plenum 930. The vertical filter support ribs create a filter under drain structure that is the same as the filter underdrain structure used in the ninth embodiment. Housing outlet half 920 contains first filter well 911 bounded by inner side wall 908 and by first filter seal surface 924, and second filter well 911*a* bounded by inner side wall 908*a* and by second filter seal surface 924*a*. First filter well 911 has a larger diameter than second filter well 911*a*. The first filter well is concentric with the second filter well. Housing outlet half 920 also contains inlet 905, inlet slot 902, circular groove 988, and slot 904. Inlet 905 is in fluid flow communication with upstream chamber 913 via inlet slot 902, circular groove 988, slot 904, and slot 904*a* of housing inlet half 901.

Referring to FIG. 46, the BFFM contains six filter elements, first filter element 915, second filter element 916, third filter element 917, fourth filter element 918, fifth filter element 977, and sixth filter element 914. Any of the filter elements may contain one or more layers of the filter material of the same type. The first filter element has a pore size greater than the pore size of the second filter element, the fourth filter element has a pore size smaller than the pore size of the second filter element, while the pore size of the third filter element has a pore size greater than the pore size of the second filter element. Preferably the pore size of the third filter element is greater than the pore size of the first and second filter elements. The fifth filter element has a pore size greater than the fourth filter element, and the sixth filter element has a pore size smaller than the fifth filter element. When BFFD 1000 is used to filter blood or blood product, first filter element 915 may be sized to remove gels from the blood or blood product, second filter element 916 may be sized to remove microaggregates from the blood or blood product, fourth filter element 918 may be sized to remove leukocytes from the blood or blood product, while the third filter element 917 is sized to act as a first flow distribution layer. Sixth filter element 914 is used to remove particulates from the filter elements upstream of it, while fifth filter element 977 acts as a second flow distribution layer. Because gels and microaggregates are large particles they may clump together thereby reducing the flow through the gel-microaggregate filter elements in the region of the clump. The first flow distribution filter element will distribute the effluent from the microaggregate filter element evenly over the upstream surface of the leukocyte removing layer, thereby allowing the leukocyte removing layer to be utilized most efficiently. The gel filter element, and the microaggregate filter element are inserted into the first filter well of housing outlet half 820. Gel filter element 915 has outside diameters smaller than the inside diameter of inner side wall 908, preventing it from being sealed to BFFD 1000 with an interference fit between its perimeter surface and inner side wall 908 of housing outlet half 920. The outer periphery of the gel filter element, and the outer periphery of the microaggregate filter element, are sealed to the housing with a compression seal between filter seal surface 907 of housing inlet half 920, and first filter seal surface 924 of housing outlet half 920. In addition the microaggregate filter element has an interference fit between its perimeter surface and inner side wall 908 of housing outlet half 920. Alternately, the gel filter element could have an outside diameter large enough so that it could be sealed to the housing an interference fit between its perimeter surface and inner side wall 908 of housing outlet half 920, and the microaggregate filter element could have an outside diameter smaller than the inside diameter of inner side wall 908 of housing outlet half 920, or both the gel filter element and the microaggregate filter elements could have an outside diameter smaller than the inside diameter of inner side wall 908 of housing outlet half 920. In applications where the blood or blood product does not contain gels, the gel filter element could be eliminated. Housing outlet half 920 also contains second filter well 911a that is smaller in diameter than the first filter well 911 into which first flow distribution filter element 917, leukocyte removing filter element 918, second flow distribution filter element 977, and particle trapping filter element 914, are inserted. First flow distribution filter element 917 is preferably a woven or non-woven screen filter, but could be any type of open pore size depth filter, or it could be a molded screen. The main purpose of first flow distribution filter element 917 is flow distribution, therefore it has a large pore size, and is preferably structured to allow flow through it in all directions. Hence the perimeter surface of third filter element 917 need not have an interference fit with inner side wall 908a of housing outlet half 920. Leukocyte removing filter element 918 is sealed to the housing an interference fit between the perimeter surface of the leukocyte removing filter element and inner side wall 908a of housing outlet half 920. Second flow distribution filter element 977 and particle removing filter element 914 are also sealed to the housing an interference seal between the perimeter surface of each respective filter element and inner side wall 908a of housing outlet half 920. The main purpose of second flow distribution filter element 977 is flow distribution, therefore it has a large pore size, and is preferably structured to allow flow through it in all directions. Hence it is not necessary that the perimeter surface of filter element 977 have an interference fit with inner side wall 908a. In some applications the second flow distribution filter element may be eliminated. As shown in FIG. 46 and FIG. 47, first filter well 911 has a larger inside diameter than second filter well 911a, therefore the filter elements disposed in the first filter well will have a larger outside diameter than the filter elements disposed in the second filter well. Alternately a single filter well as shown in FIG. 13 could be used. Referring to FIG. 13, filter element 15 could be a gel removing filter element, filter element 16 could be a microaggregate removing filter element, filter element 17 could be a first flow distribution filter element, filter element 18 could be a leukocyte removing filter element, and a second flow distribution filter element could be added downstream of filter element 18, with a particle removing filter element added downstream of the second flow distribution filter element. As shown in FIG. 13 first filter element 15 has an outside diameter smaller than the inside diameter of the inner side wall of the housing outlet half. Alternately, first filter element 15 could have an outside diameter large enough to seal it to the housing with an interference fit between its outer perimeter and the inner side wall of the housing outlet half, and either the second filter element, or the fourth filter element could have an outside diameter smaller than the inside diameter of the inner side wall of the housing outlet half, or the first and second filter elements could have an outside diameter smaller than the inside diameter of the inner side wall of the housing outlet half.

Referring to FIG. 46, a first fluid flow path is defined between inlet 905 of BFFD 1000 and outlet 927 of BFFD 1000 with the BFFM interposed between inlet 905 and outlet 927, and across the fluid flow path. The first fluid flow path flows from inlet 905, through inlet slot 902, in both directions through circular groove 988, through slot 904, through slot 904a, into upstream chamber 913, through the BFFM, into the plenum 930 downstream of the BFFM, and then into outlet 927.

Referring to FIG. 1 and FIG. 46, when BFFD 1000 is used to replace BFFD 100 in biological fluid filtration system 1000, the system will function as follows. The user will purchase the system with all components as shown in FIG. 1, less feed blood bag 98. BFFD 1000 will replace BFFD 100. The user will connect tubing 81 to outlet 92 of feed blood bag 98 in a manner known in the art. Feed blood bag 98 and vent filtration device 30, and vent filtration device 40, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 should be open, and tube clamp 97 should be closed.

Referring to FIG. 1 and FIG. 46, BFFD 1000 functions as follows. When tube clamp 95 is opened biological fluid (i.e. liquid) will flow from feed blood bag 98. Three tube connector 50 and vent filtration device 30 will function as described in the description of the first embodiment. Biological fluid will flow into inlet 905, through inlet slot 902, through circular groove 988 in both directions, through slot 904, through slot 904a, into upstream chamber 913, of BFFD 1000. Upstream chamber 913 will rapidly fill with biological fluid from the bottom up. As upstream chamber 913 fills from the bottom up, the initial air in upstream chamber 913 will be displaced by the biological fluid filling upstream chamber 913. The displaced air will be forced through the BFFM, into plenum 930, and then into outlet 927 all of BFFD 1000. The biological fluid in upstream chamber 913 will be pressurized, with the pressure at the bottom of upstream chamber 913 being proportional to the distance from the top of the biological fluid in feed blood bag 98 to the bottom of upstream chamber 913, and with the pressure at the top of upstream chamber 913 being proportional to the distance from the top of the biological fluid in feed blood bag 98 to the top of upstream chamber 913. Hence the pressure at the top of upstream chamber 913 will be less than the pressure at the bottom of upstream chamber 913. The positive pressure in upstream chamber 913 will cause the biological fluid to flow through the BFFM over the entire surface area of the BFFM and to displace the air within the pores of the BFFM with biological fluid, thereby wetting BFFM from the upstream side of first filter element 915 of the BFFM to the downstream side of sixth filter element 914 of the BFFM. As the BFFM wets the air that was initially in the pores of BFFM will be displaced by biological fluid and flow into plenum 930, and then into outlet 927, into tubing 82, into receiving blood bag 99. Because the pressure at the bottom of upstream chamber 913 is greater than the pressure at the top of upstream chamber 913, the flow rate of biological fluid through the BFFM will be greater at the bottom of the BFFM than at the top of the BFFM. Therefore, the BFFM will first become completely wetted from the upstream surface of the BFFM to the downstream surface of the BFFM at the bottom of BFFM. Once the bottom of the downstream surface of the sixth filter element has been wetted, the remainder of the downstream surface of the sixth filter element will continue to wet from the bottom up, and biological fluid will start to flow from the bottom of the sixth filter element, into plenum 930. The plenum will fill from the bottom up forcing the air above the liquid level in the plenum into outlet 927, into tubing 82, and then into receiving blood bag 99. The plenum will fill with biological fluid before all of the air has been purged from the upper portion of the BFFM. The remaining air in the un-wetted upper portion of the BFFM will be displaced by biological fluid and forced into the plenum, where it will bubble to the top of the plenum due to the buoyancy of air in the biological fluid, and then be forced into outlet 927, into tubing 82, and then into receiving blood bag 99 by the flow of biological fluid. Hence the initial flow of biological fluid through outlet 927, into tubing 82 will be a mixture of air and biological fluid, so that the initial flow into tubing 82 will consist of alternate segments of biological fluid and air.

Referring to FIG. 1, and FIG. 46, once all of the air has been purged from within BFFD 1000, biological fluid will continue to flow through the first fluid flow path from the inlet of BFFD 1000 to the outlet of BFFD 1000, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 1000, pressure P4 downstream of the BFFM and upstream of outlet 927 will be negative as described above. Therefore, the biological fluid in tubing 83, tubing 81a, and upstream chamber 913 will be drained as described in the description of the first embodiment above.

If the vent inlet, vent inlet slot, and vent tube socket (shown in FIG. 13) are added to housing inlet half 901, BFFD 1000 could be used in biological fluid filtration system 2000 shown in FIG. 12. In this case BFFD 1000 would fill and purge air from within BFFD 1000 as just described in the description of the tenth embodiment. After the air was purged from BFFD 1000, it would function the same as BFFD 200 in biological fluid filtration system 2000.

The filter under drain structure of BFFD 1000 including plenum 930 and vertical filter support ribs 922 may be replaced with the filter under drain structure of the first embodiment shown in FIG. 3, in which case the filter under drain structure would purge air and fill with biological fluid as described in the description of the first embodiment. If the filter under drain structure of the first embodiment is used to replace plenum 930 and vertical filter support ribs 922, the hold up volume of the BFFD will be minimized as explained in the description of the first embodiment, because of the lack of a plenum.

The filter under drain structure of BFFD 1000 including plenum 930 and vertical filter support ribs 922 may also be replaced with the filter under drain structure of the second embodiment shown in FIG. 14, in which case the filter under drain structure would purge air and fill with biological fluid as described in the description of the second embodiment. If the filter under drain structure of the second embodiment is used to replace plenum 930 and vertical filter support ribs 922, the amount of air that will be purged from the BFFM after biological fluid starts to flow from the outlet will be minimized, and the hold up volume of the BFFD will also be minimized as explained in the description of the second embodiment, because of the lack of a plenum.

Detailed Description of the Eleventh Embodiment

An eleventh embodiment of the BFFD constructed in accordance with the principles of the present invention, is shown in FIG. 49 through FIG. 52. BFFD 1100 may be used in place of BFFD 100 in biological fluid filtration system 1000 shown in FIG. 1, and may also be used in place of BFFD 200 in biological fluid filtration system 2000 shown in FIG. 12.

Figure 49:
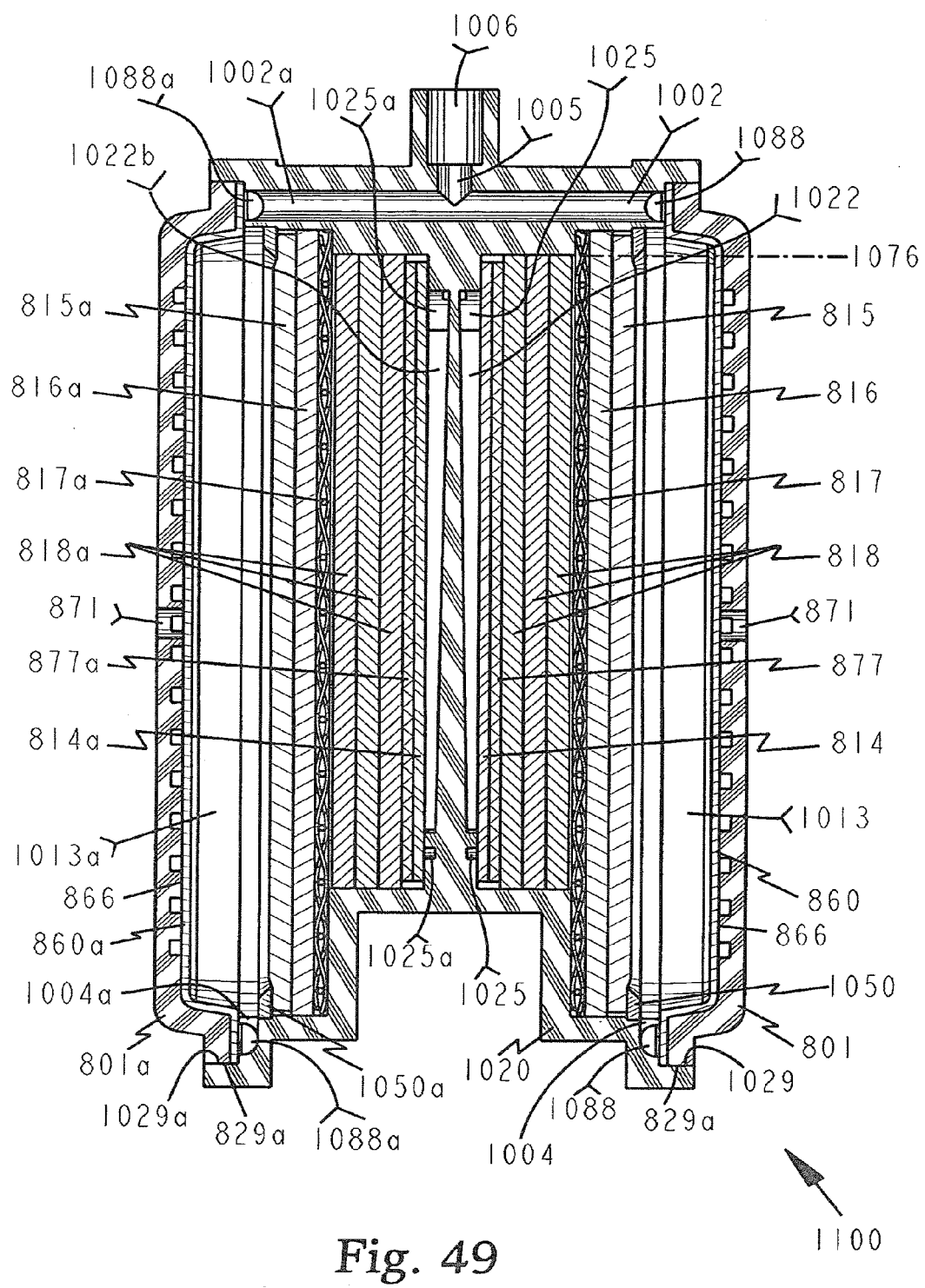
FIG. 49 is a cross-sectional view of an eleventh embodiment of a BFFD constructed in accordance with the principles of the present invention, usable for the filtration of biological fluids. The BFFD shown in FIG. 49 is double sided and uses variable surface area like the BFFD shown in FIG. 40.
Figure 54:
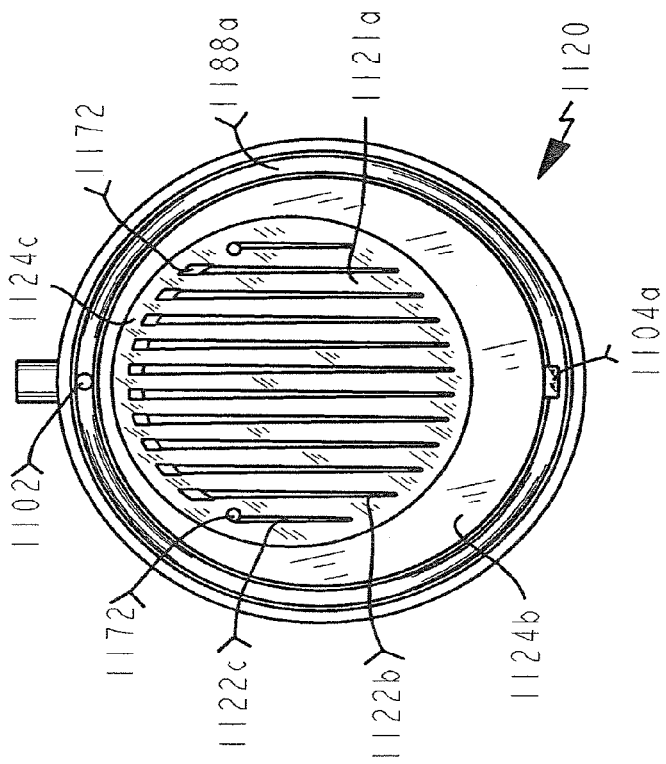
FIG. 54 is a bottom view of the housing outlet half of the BFFD shown in FIG. 55.

Referring to FIG. 49, and FIG. 50, BFFD 1100 contains a rigid housing that includes housing inlet half 801, housing inlet half 801a, and housing outlet half 1020. Housing inlet half 801, and 801a are same as housing inlet half 801 of the ninth embodiment. Housing seal surface 829a of housing inlet half 801, and of housing inlet half 801a, are bonded to housing seal surface 1029 and housing seal surface 1029a respectively, of housing outlet half 1020. The bond is preferably an ultrasonic weld but may be a heat bond, a glue bond, a solvent bond, or any other type of leak tight bond.

Referring to FIG. 49, housing inlet half 801 and housing inlet half 801a are the same as housing inlet half 801 described in the description of the ninth embodiment. Flexible diaphragm 860 and flexible diaphragm 860a are the same as flexible diaphragm 860 described in the description of the ninth embodiment.

Referring to FIG. 49 through FIG. 52 housing outlet half 1020 contains a partition wall 1037 that divides BFFD 1100 into two independent filtration devices having a common inlet, and a common outlet. On the first side of partition wall 1037 housing outlet half 1020 contains first filter well 1011 bounded by inner side wall 1008 and by first filter seal surface 1024, and second filter well 1011a bounded by inner side wall 1008a and by second filter seal surface 1024a. First filter well 1011 has a larger diameter than second filter well 1011a. The horizontal center line of the first filter well is offset below the horizontal center line of the second filter well so that the top of first filter seal surface 1024 protrudes above the top of second filter seal surface 1024a a sufficient distance to create a compression seal as will be described below. First filter well 1011 and second filter well 1011a are the same as first filter well 811 and second filter well 811a respectively of housing outlet half 820 of the ninth embodiment. Housing outlet half 1020 contains a third filter well and a fourth filter well on the opposite side of partition wall 1037 that are mirror images of the first filter well and the second filter well respectively, mirrored about a plane that goes through the center of the partition wall. Housing outlet half 1020 contains first circular outlet channel 1025 and outlet 1027. First circular outlet channel 1025 is in direct fluid flow communication with outlet 1027, and the portion of first circular outlet channel 1025 that adjoins outlet 1027 has a cross-sectional flow area that is greater than the cross-sectional flow area of outlet 1027. Housing outlet half 1020 also contains a plurality of open top closed bottom first vertical channels 1022 and 1022a. The top end of each of the first vertical channels 1022 and 1022a is in fluid flow communication with first circular outlet channel 1025. The first vertical channels may be tapered in width and in depth as shown in FIG. 49 and FIG. 51, or they may be non-tapered like the vertical channels of housing outlet half 120 shown in FIG. 15. The upper part of first circular outlet channel 1025 increases in width to accommodate the flow of biological fluid from first vertical channels 1022 and 1022a. The width of the remainder of first circular outlet channel 1025 (i.e. the lower part of first circular outlet channel 1025) is approximately equal to the width of the first vertical channels. The two outermost first vertical channels designated as first vertical channels 1022a adjoin first circular outlet channel 1025 where the width of first circular outlet channel 1025 is approximately equal to the width of the first vertical channels. Upper side wall 1087 of first circular outlet channel 1025 preferably slopes upward toward outlet 1027 as shown in FIG. 51. The first circular outlet channel and the first vertical channels combined, create a first filter under drain structure, and are cut into first inner wall 1021 of partition wall 1037, so that the inner surface of all of the first channels lies below first inner wall 1021, as shown in FIG. 50. The cross sectional area the first circular outlet channel and of the first vertical channels is defined by the inner surface of each channel and by the downstream surface of the first BFFM. Housing outlet half 1020 contains a second circular outlet channel and a plurality of open top closed bottom second vertical channels on the second side of partition wall 1037, that are in fluid flow communication with the second circular outlet channel, and cut into second inner wall 1021a of partition wall 1037. The second circular outlet channel and second vertical channels create a second filter under drain structure that is a mirror image of the first filter under drain structure, mirrored about a plane that goes through the center of the partition wall. The first circular outlet channel and the second circular outlet channel merge together at through slot 1025b. Outlet 1027 is in direct fluid flow communication with the first circular outlet channel and the second circular outlet channel where the two outlet channels merge. As shown in FIG. 50 and FIG. 51, the distance between first vertical channels 1022 and 1022a is much greater than the width of first vertical channels 1022 and 1022a, and the distance between first vertical channels 1022 and 1022a is also much greater than of the depth of first vertical channels 1022 and 1022a. Because housing outlet half 1020 does not contain an open chamber or plenum downstream of the first BFFM or downstream of the second BFFM, hold up volume is minimized. Housing outlet half 1020 also contains inlet 1005, a cross port labeled first cross port 1002 and second cross port 1002a, first circular groove 1088, second circular groove 1088a, first slot 1004, and second slot 1004a. Inlet 1005 is in fluid flow communication with first upstream chamber 1013 via first cross port 1002, first circular groove 1088, and first slot 1004. Inlet 1005 is also in fluid flow communication with second upstream chamber 1013a via second cross port 1002a, second circular groove 1088a, and second slot 1004a. The upper part of first filter well 1011 contains a first seal ring counter bore bounded by inner side wall 1008b, and by surface 1024b. The upper part of third filter well 1011b contains a second seal ring counter bore that is a mirror image of the first seal ring counter bore, mirrored about a plane that goes through the center of the partition wall.

Referring to FIG. 49 and FIG. 50, BFFD 1100 contains a first BFFM and a second BFFM. The first BFFM is disposed in first filter well 1011 and second filter well 1011a, and the second BFFM is disposed in third filter well 1011b and fourth filter well 1011c. The first BFFM and the second BFFM are the same as the BFFM shown in FIG. 40 of the ninth embodiment, with the exception that there is an interference fit between the perimeter surface of the second filter element of each of the BFFM and the inner side wall of housing outlet half 1020. Any of the BFFM with the seating methods shown in FIG. 37 of the eighth embodiment, or in FIG. 40, 41, 42, or 45, of the ninth embodiment, or in FIG. 46 of the tenth embodiment, or any combination thereof could also be used in place of the BFFM shown in FIG. 49.

Referring to FIG. 49, FIG. 50, and FIG. 51, a first fluid flow path through BFFD 1100 is defined between inlet 1005 of BFFD 1100 and outlet 1027 of BFFD 1100 with the first BFFM interposed between inlet 1005 and outlet 1027, and across the first fluid flow path. The first fluid flow path flows from inlet 1005, through first cross port 1002, in both directions (as shown by arrows 1085 in FIG. 51) through first circular groove 1088, through first slot 1004, into first upstream chamber 1013, through the first BFFM, into the first vertical channels and the first circular outlet channel, and then into outlet 1027. A second fluid flow path through BFFD 1100 is defined between inlet 1005 of BFFD 1100 and outlet 1027 of BFFD 1100 with the second BFFM interposed between inlet 1005 and outlet 1027, and across the second fluid flow path. The second fluid flow path flows from inlet 1005, through second cross port 1002a, in both directions through the second circular groove 1088a, through second slot 1004a, into second upstream chamber 1013a, through the second BFFM, into the second vertical channels and the second circular outlet channel, and then into outlet 1027.

Referring to FIG. 12, FIG. 49, and FIG. 50, when BFFD 1100 is used to replace BFFD 200 in biological fluid filtration system 2000, the system will function as follows. The user will purchase the system with all components as shown in FIG. 12, less feed blood bag 98. BFFD 1100 will replace BFFD 200, and tubing 85 and vent filtration device 40 will not be used. Because outlet tube socket 1028 is located at the top of BFFD 1100, parallel to inlet tube socket 1006, tubing 82 will contain a loop to point downward toward receiving blood bag 99. The user will connect tubing 81 to outlet 92 of feed blood bag 98 in a manner known in the art. Feed blood bag 98 and vent filtration device 30, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 should be open, and tube clamp 97 should be closed.

Referring to FIG. 12, FIG. 49 through FIG. 52, BFFD 1100 functions as follows. When tube clamp 95 is opened biological fluid (i.e. liquid) will flow from feed blood bag 98, through tubing 81, through the first fluid flow path of BFFD 1100 by flowing into inlet 1005, through first cross port 1002, through first circular groove 1088 in both directions (as shown by arrows 1085 in FIG. 51), through slot 1004, into first upstream chamber 1013, of BFFD 1100. First upstream chamber 1013 will rapidly fill with biological fluid from the bottom up. As first upstream chamber 1013 fills from the bottom up, the initial air in first upstream chamber 1013 will be displaced by the biological fluid filling first upstream chamber 1013. The displaced air will be forced through the first BFFM, into first vertical channels 1022 and 1022a and first circular outlet channel 1025, and then into outlet 1027 all of BFFD 1100. The biological fluid in first upstream chamber 1013 will be pressurized, with the pressure at the bottom of first upstream chamber 1013 being proportional to the distance from the top of the biological fluid in feed blood bag 98 to the bottom of first upstream chamber 1013, and with the pressure at the top of first upstream chamber 1013 being proportional to the distance from the top of the biological fluid in feed blood bag 98 to the top of first upstream chamber 1013. Hence the pressure at the top of first upstream chamber 1013 will be less than the pressure at the bottom of first upstream chamber 1013. The positive pressure in first upstream chamber 1013 will cause the biological fluid to flow through first filter element 815, and second filter element 816 over the entire surface area of the first and second filter elements displacing the air within the pores of the first and second filter elements with biological fluid, thereby wetting the first and second filter elements from the upstream side of first filter element 815 to the downstream side of second filter element 816. The displaced air from first upstream chamber 1013 and from the first and second filter elements will flow into third filter element 817. Third filter element 817 preferably has an open pore size and structure that allows flow through it in all directions.

Therefore any air or biological fluid that flows from the downstream surface of second filter element 816, will flow into third filter element 817 and then be uniformly distributed over the entire upstream surface of fourth filter element 818, thereby utilizing fourth filter element 818 in the most efficient way. As the first and second filter elements wet, the air that was initially in the pores of the first and second filter elements will be displaced by biological fluid, and flow into the third filter element 817. Because the pressure at the bottom of first upstream chamber 1013 is greater than the pressure at the top of first upstream chamber 1013, the flow rate of biological fluid through the first and second filter elements will be greater at the bottom of the first and second filter elements than at the top of the first and second filter elements. Therefore, the first and second filter elements will first become completely wetted from the upstream surface of the first filter element to downstream surface of the second filter element at the bottom of the second filter element. The first and second filter elements will continue to wet with the downstream surface of the second filter element wetting from the bottom to the top. The third filter element will also wet from the bottom to the top. When the liquid level in the third filter element reaches the bottom of fourth filter element 818, the fourth filter element will begin to wet from the bottom up. The first and second filter elements will continue to wet until all of the air in the first and second filter elements has been purged. It is important that the horizontal center line of first filter well 1011 is offset the required distance below the horizontal center line of second filter well 1011a so that the top of first filter seal surface 1024 protrudes above the top of second filter seal surface 1024a no more than the distance required to create a compression seal at the top of the first filter well between seal ring 1050 and first filter seal surface 1024 of housing outlet half 1020, because air will be trapped in the compression seal portion of the first, second, and third filter elements that lie above horizontal line 1076 shown in FIG. 49. The fourth, fifth, and sixth filter elements will wet from the bottom up, with the downstream surface of the sixth filter element first becoming wetted at the bottom of the downstream surface of the sixth filter element. If the width of vertical channels 1022 and 1022a is sufficiently small, and the depth of vertical channels 1022 and 1022a is sufficiently shallow, so that the cross-sectional flow area of the vertical channels 1022 and 1022a is sufficiently small, and if the distance between vertical channels 1022 and 1022a is sufficiently large, as described above in the description of the second embodiment, the path of least resistance for continued biological fluid flow through the first BFFM will be through the capillaries of the first BFFM in both the horizontal and vertical directions and not through the first vertical channels, because if the cross-sectional flow area of the first vertical channels is sufficiently small, the displaced air flowing into and through the first vertical channels will create a sufficiently high positive pressure in the first vertical channels to prevent biological fluid from entering the first vertical channels. The downstream surface of the first BFFM (i.e. the downstream surface of the sixth filter element) will therefore wet from the bottom up and the displaced air that was within the first BFFM will continue to flow into the first vertical channels, and into the first circular outlet channel, and then into the outlet. When the downstream surface of the first BFFM has become wetted to the level of the upper part of first circular outlet channel 1025 where first circular outlet channel 1025 begins to taper to a wider width, air flow through the lower part of first circular outlet channel 1025, and air flow through the two outermost first vertical channels 1022a will stop because the downstream surface of the first BFFM adjoining the lower part of the first circular outlet channel and the two outermost first vertical channels will be wetted. Therefore the pressure in the lower part of the first circular outlet channel and the pressure in the two outermost first vertical channels will decrease allowing biological fluid to enter the lower part of the first circular outlet channel and the two outermost first vertical channels from the bottom up, thereby displacing the air that was in the lower part of the first circular outlet channel and the two outermost first vertical channels. At the same time the wetted level of the downstream surface of the first BFFM will continue to wet in the vertical direction, wetting the downstream surface of the first BFFM adjoining the upper part of first circular outlet channel 1025. Because the cross-sectional flow area of the upper part of first circular outlet channel 1025 is not sufficiently small to create a positive pressure in it due to the air flow through it, biological fluid will flow into first circular outlet channel 1025 as first BFFM continues to wet in the vertical direction above the lower part of the first circular outlet channel. The biological fluid flowing into first vertical channels 1022 and 1022a, and into the first circular outlet channel 1025 will flow into outlet 1027 of BFFD 1100 and then into tubing 82 toward receiving blood bag 99. As biological fluid starts to flow into outlet 1027, first BFFM will continue to wet vertically. When tube clamp 95 is opened biological fluid will also flow from feed blood bag 98, through tubing 81, through the second fluid flow path of BFFD 1100 the same way that it flows through the first fluid flow path of BFFD 1100, and the second BFFM will wet, and air will be purged from it as just described for the first fluid flow path of BFFD 1100. Hence the initial flow of biological fluid through the upper part of first circular outlet channel 1025, and through the upper part of second circular outlet channel 1025a, and through outlet 1027, will be a mixture of air and biological fluid so that the initial flow into tubing 82 will consist of alternate segments of biological fluid and air. As described in the description of the second embodiment above, the amount of biological fluid that flows from outlet 1027 will be minimized because of the design of the first and second filter under drain structures, and because of the reduced surface area of the fourth, fifth, and sixth filter elements of the first BFFM and of the second BFFM.

Referring to FIG. 12, and FIG. 49, once all of the air has been purged from within BFFD 1100, biological fluid will continue to flow through the first fluid flow path from the inlet of BFFD 1100 to the outlet of BFFD 1100, and through the second fluid flow path from the inlet of BFFD 1100 to the outlet of BFFD 1100, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 1100, pressure P5 downstream of the first BFFM and downstream of the second BFFM, and upstream of outlet 1027 will be negative as described above in the description of the second embodiment. Once feed blood bag 98 collapses and biological fluid flow through the first fluid flow path and the second fluid flow path of BFFD 1100 stops, the differential pressure across the first BFFM, and the differential pressure across the second BFFM, will become zero, hence the pressure in first upstream chamber 1013 and second upstream chamber 1013a will become negative. The pressure on upstream surface 866 of flexible diaphragm 860 and on upstream surface 866 of flexible diaphragm 860a will be atmospheric because hole 871 of housing inlet half 801 and hole 871 of housing inlet half 801a are open to atmosphere, and hole 871 is in fluid flow communication with radial vent channel 803*a*, and circular vent channels 803 of housing inlet half 801 and housing inlet half 801*a*. With atmospheric pressure on the outer surface 866 of flexible diaphragm 860, the negative pressure within first upstream chamber 1013 will cause flexible diaphragm 860 to collapse onto the upstream surface of first filter element 815, thereby forcing the biological fluid in first upstream chamber 1013 through the first BFFM, into the first vertical channels and into the first circular outlet channel, into outlet 1027, into tubing 82, and then into receiving blood bag 99. Also, with atmospheric pressure on the outer surface 866 of flexible diaphragm 860*a*, the negative pressure within second upstream chamber 1013*a* will cause flexible diaphragm 860*a* to collapse onto the upstream surface of first filter element 815*a*, thereby forcing the biological fluid in second upstream chamber 1013*a* through the second BFFM, into the second vertical channels and into the second circular outlet channel, into outlet 1027, into tubing 82, and then into receiving blood bag 99.

Referring to FIG. 12, and FIG. 49, when the filtration cycle is complete as just described, the first BFFM and the second BFFM will remain wetted, the first vertical channels and first circular outlet channel and the second vertical channels and second circular outlet channel will be filled with biological fluid, and tubing 82 will be filled with biological fluid. Because BFFD 1100 does not contain a plenum downstream of the first BFFM or downstream of the second BFFM, the hold up volume of biological fluid within BFFD 1100 will be minimized. The user will close tube clamp 96, and then cut and seal tubing 82 above tube clamp 96, and then discard BFFD 1100 and feed blood bag 98 in a safe manner. Tube clamp 97 may now be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner.

Detailed Description of the Twelfth Embodiment

A twelfth embodiment of the BFFD constructed in accordance with the principles of the present invention, is shown in FIG. 53 through FIG. 56. BFFD 1200 may be used in place of BFFD 200 in biological fluid filtration system 2000 shown in FIG. 12.

Figure 53:
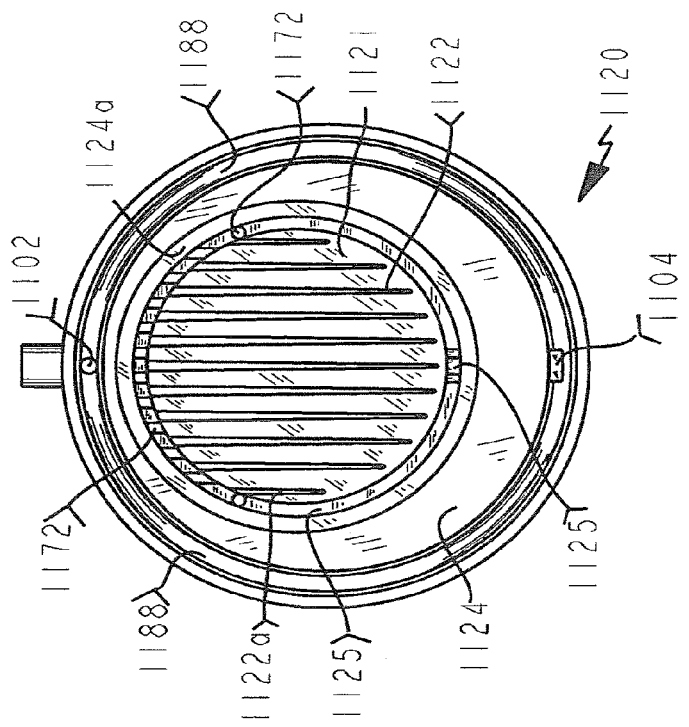
FIG. 53 is a top view of the housing outlet half of the BFFD shown in FIG. 55.

Referring to FIG. 53 through FIG. 56, BFFD 1200 contains a rigid housing that includes housing inlet half 1101, housing inlet half 1101*a*, and housing outlet half 1120. Housing inlet half 1101, and 1101*a* are same as housing inlet half 901 of the tenth embodiment except that housing inlet half 1101 and 1101*a* may or may not contain circular rib 989 shown in FIG. 48. Housing inlet halves 1101 and 1101*a* are bonded to housing outlet half 1120 in the same way that housing inlet half 901 is bonded to housing outlet half 920 as described in the description of the tenth embodiment above. Housing outlet half 1120 is the same as housing outlet half 1020 of the eleventh embodiment with the following exceptions. Vertical channels 1122 and 1122*a* and circular outlet channel 1125 are located on the first side of partition wall 1138, and are cut into first inner wall 1121. Vertical channels 1122 and 1122*a* are the same as vertical channels 1022 and 1022*a*, and may be tapered in width and/or depth as shown, or may be non tapered like vertical channels 122 and 122*a* shown in FIG. 14. Circular outlet channel 1125 has a constant width, with the portion of circular outlet channel 1125 adjoining outlet 1127 increasing in depth, and having a cross sectional flow area greater than the cross sectional flow area of outlet 1127. Vertical channels 1122*b* and 1122*c* are located on the second side of partition wall 1138, and are cut into second inner wall 1121*a*. The vertical center lines of vertical channels 1122*b* and 1122*c* are offset from the vertical centerlines of vertical channels 1122 and 1122*a*, so that the vertical center lines of vertical channels 1122*b* and 1122*c* are located between the vertical center lines of vertical channels 1122 and 1122*a*, as shown in FIG. 53. Ports 1172 place the tops of vertical channels 1122*b* and 1122*c* in fluid flow communication with circular outlet channel 1125. Circular outlet channel 1125 provides a means to place the tops of vertical channels 1122, 1122*a*, 1122*b*, and 1122*c* in fluid flow communication with outlet 1127 located below the bottom of circular outlet channel 1125. Because the second side of partition wall 1138 does not contain a circular outlet channel, and because the vertical channels on the second side of partition wall are offset from the vertical channels on the first side of partition wall 1138, partition wall 1138 may be made thinner than would otherwise be the case, thereby reducing the cost of producing housing outlet half 1120. Housing outlet half 1120 also contains vent inlet 1178 that is in fluid flow communication with first cross port 1102 and with second cross port 1102*a*.

Referring to FIG. 55 and FIG. 56, BFFD 1200 contains a first BFFM and a second BFFM. The first BFFM is disposed in first filter well 1111 and second filter well 1111*a*, and the second BFFM is disposed in third filter well 1111*b* and fourth filter well 1111*c*. The first BFFM and the second BFFM each contain six filter elements. None of the filter elements has an interference fit between the perimeter surface of the filter element and its respective inner side wall of housing outlet half 1120. The outer periphery of the filter elements in first filter well 1111 are bonded to each other and to filter seal surface 1124 by bond 1177, and the outer periphery of the filter elements in second filter well 1111*a* are bonded to each other and to filter seal surface 1124*a* by bond 1176. Likewise, the outer periphery of the filter elements in third filter well 1111*b* are bonded to each other and to filter seal surface 1124*b* by bond 1177*a*, and the outer periphery of the filter elements in third filter well 1111*c* are bonded to each other and to filter seal surface 1124*c* by bond 1176*a*. The bonds may be a glue bond, a heat bond, an ultrasonic bond, a solvent bond, an R.F. bond, or any other type of leak tight bond. Any of the BFFM with the sealing methods shown in FIG. 37 of the eighth embodiment, or in FIG. 40, 41, 42, or 45, of the ninth embodiment, or in FIG. 46 of the tenth embodiment, or in FIG. 49 of the eleventh embodiment, or any combination thereof could also be used in place of the BFFM's shown in FIG. 55.

Referring to FIG. 53 through FIG. 56, a first fluid flow path through BFFD 1200 is defined between inlet 1105 of BFFD 1200 and outlet 1227 of BFFD 1200 with the first BFFM interposed between inlet 1105 and outlet 1127, and across the first fluid flow path. The first fluid flow path flows from inlet 1105, through first cross port 1002, in both directions through first circular groove 1188, through first slot 1104, into first upstream chamber 1113, through the first BFFM, into first vertical channels 1122 and 1122*a*, through circular outlet channel 1125, and then into outlet 1127. A second fluid flow path through BFFD 1200 is defined between inlet 1105 of BFFD 1200 and outlet 1127 of BFFD 1200 with the second BFFM interposed between inlet 1105 and outlet 1127, and across the second fluid flow path. The second fluid flow path flows from inlet 1105, through second cross port 1102*a*, in both directions through the second circular groove 1188*a*, through second slot 1104*a*, into second upstream chamber 1113*a*, through the second BFFM, into the second vertical channels 1122*b* and 1122*c*, through ports 1172, through circular outlet channel 1125, and then into outlet 1127.

Referring to FIG. 12, FIG. 55, and FIG. 56, when BFFD 1200 is used to replace BFFD 200 in biological fluid filtration system 2000, the system will function as follows. The user will purchase the system with all components as shown in FIG. 12, less feed blood bag 98. BFFD 1200 will replace BFFD 200. The BFFD end of tubing 85 will be connected to vent tube socket 1179. The user will connect tubing 81 to outlet 92 of feed blood bag 98 in a manner known in the art. Feed blood bag 98, vent filtration device 40, and vent filtration device 30, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 and tube clamp 94 should be open, and tube clamp 97 should be closed.

Referring to FIG. 12, FIG. 53 through FIG. 56, BFFD 1200 functions as follows. When tube clamp 95 is opened biological fluid will flow from feed blood bag 98, through tubing 81, through the first fluid flow path of BFFD 1200 by flowing into inlet 1105, through first cross port 1102, through first circular groove 1188 in both directions, through slot 1104, into first upstream chamber 1113, of BFFD 1200. First upstream chamber 1113 will fill from the bottom up displacing the air that was in first the upstream chamber, and wetting the first BFFM as described above in the description of the eleventh embodiment. Once the bottom of the downstream surface of the first BFFM has become wetted, the downstream surface of the first BFFM will continue to wet from the bottom up, until the downstream surface of the first BFFM has become wetted to the level of the top of first vertical channels 1122*a*. At this point biological fluid will begin to flow into vertical channels 1122*a* from the bottom up. As the downstream surface of the first BFFM continues to wet vertically, biological fluid will begin to flow into successive vertical channels as the wetted level of the downstream surface of the first BFFM reaches the top of each vertical channel. If circular outlet channel 1125 is sufficiently wide, a small quantity of biological fluid may enter circular outlet channel 1125 before the wetted level of the downstream surface of the first BFFM reaches the top of vertical channels 1122*a*. When tube clamp 95 is opened biological fluid will also flow from feed blood bag 98, through tubing 81, through the second fluid flow path of BFFD 1200 by flowing into inlet 1105, through second cross port 1102*a*, through second circular groove 1188*a* in both directions, through slot 1104*a*, into second upstream chamber 1113*a*, of BFFD 1200. Second upstream chamber 1113*a* will fill from the bottom up displacing the air that was in the second upstream chamber, and wetting the second BFFM as described above in the description of the eleventh embodiment. Once the bottom of the downstream surface of the second BFFM has become wetted, the downstream surface of the second BFFM will continue to wet from the bottom up, until the downstream surface of the second BFFM has become wetted to the level of the top of second vertical channels 1122*c*. At this point biological fluid will begin to flow into second vertical channels 1122*c* from the bottom up. As the downstream surface of the second BFFM continues to wet vertically, biological fluid will begin to flow into successive vertical channels as the wetted level of the downstream surface of the second BFFM reaches the top of the second vertical channels. The air and biological fluid that flows into the second vertical channels will flow through ports 1172, into circular outlet channel 1125, and then into outlet 1127. All of the air will be purged from within BFFD before the pressure P6 downstream of the first BFFM and second BFFM, and upstream of outlet 1127 becomes negative.

Referring to FIG. 10, FIG. 12, and FIG. 55, once all of the air has been purged from within BFFD 1200, biological fluid will continue to flow through the first fluid flow path from the inlet of BFFD 1200 to the outlet of BFFD 1200, and through the second fluid flow path from the inlet of BFFD 1200 to the outlet of BFFD 1200, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 1200, pressure P6 downstream of the first BFFM and downstream of the second BFFM, and upstream of outlet 1127 will be negative as described above in the description of the second embodiment. Vent port 46 of vent filtration device 40 is at atmospheric pressure, therefore, there will be a pressure differential between vent port 46 and the negative pressure P6 downstream of the BFFM. The pressure differential will cause air to flow from vent port 46, through vent filtration media 43, through system port 44, all of vent filtration device 40, through tubing 85, through vent inlet 1178 of BFFD 1200, through first cross port 1102, into first upstream chamber 1133, thereby draining the biological fluid in first upstream chamber 1113 of BFFD 1200. Air will also flow from inlet 1105, through second cross port 1102*a*, into second upstream chamber 1113*a*, thereby draining the biological fluid in second upstream chamber 1113*a* of BFFD 1200.

Referring to FIG. 12, and FIG. 55, when the filtration cycle is complete as just described, the first BFFM and the second BFFM will remain wetted, the first vertical channels and circular outlet channel and the second vertical channels will be filled with biological fluid, and tubing 82 will be filled with biological fluid. Because BFFD 1200 does not contain a plenum downstream of the first BFFM or downstream of the second BFFM, the hold up volume of biological fluid within BFFD 1200 will be minimized. The user will close tube clamp 96, and then cut and seal tubing 82 above tube clamp 96, and then discard BFFD 1200 and the components attached to it in a safe manner. Tube clamp 97 may now be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner.

Detailed Description of the Thirteenth Embodiment

A thirteenth embodiment of the BFFD constructed in accordance with the principles of the present invention, is shown in FIG. 57 and FIG. 58. BFFD 1300 may be used in place of BFFD 200 in biological fluid filtration system 2000 shown in FIG. 12.

Referring to FIG. 57, BFFD 1300 contains a flexible housing that includes flexible housing inlet half 1201 and flexible housing outlet half 1220. Housing seal surface 1229*a* of housing inlet half 1201 is bonded to housing seal surface 1229 of housing outlet half 1220. The bond is preferably an ultrasonic weld but may be a heat bond, a glue bond, a solvent bond, R.F. bond, or any other type of leak tight bond. Housing inlet half contains inlet 1205 and inlet tube socket 1206. Housing outlet half 1220 contains outlet 1227 and outlet tube socket 1228.

Referring to FIG. 57, the BFFM contains four filter elements, first filter element 1215, second filter element 1216, third filter element 1217, and fourth filter element 1218. Any of the filter elements may contain one or more layers of the filter material of the same type. The first filter element has a pore size greater than the pore size of the second filter element, and the fourth filter element has a pore size smaller than the pore size of the second filter element, while the pore size of the third filter element has a pore size greater than the pore size of the second filter element. Preferably the pore size of the third filter element is greater than the pore size of the first and second filter elements. When BFFD 1300 is used to filter blood or blood product, first filter element 1215 may be sized to remove gels from the blood or blood product, second filter element 1216 may be sized to remove microaggregates from the blood or blood product, fourth filter element 1218 may be sized to remove leukocytes from the blood or blood product, while the third filter element 1217 is sized to act as a flow distribution layer. Because gels and microaggregates are large particles they may clump together thereby reducing the flow through the gel-microaggregate filter elements in the region of the clump. The flow distribution filter element will distribute the effluent from the microaggregate filter element evenly over the upstream surface of the leukocyte removing layer, thereby allowing the leukocyte removing layer to be utilized most efficiently. The outside diameter of all of the filter elements as shown in FIG. 57 are smaller than the inside diameter of flexible housing outlet half 1220, preventing the filter elements from being sealed to BFFD 1300 with an interference fit between the perimeter surface of filter elements and inner side wall of flexible housing outlet half 1220. The outer periphery of each filter element is bonded to the outer periphery of the filter element adjacent to it, with the outer periphery of the downstream surface of the BFFM being bonded to flexible housing outlet half 1220 as shown in FIG. 57. The bonds may be a glue bond, a heat bond, an ultrasonic bond, an R.F. bond, a solvent bond, or any other type of leak tight bond. Third filter element 1217 is preferably a woven or non-woven screen filter, but could be any type of open pore size depth filter. The main purpose of filter element 1217 is flow distribution therefore it has a large pore size, and is preferably structured to allow flow through it in all directions. In applications where the blood or blood product is fresh and does not contain gels, the first filter element may be a microaggregate removing filter element, and the second filter element could be eliminated. In this case the third filter element may also be eliminated.

BFFD 1300 also contains filter support screen 1277. Filter support screen 1277 is preferably a woven or non-woven screen that is structured to allow flow through it in all directions, and does not perform any filtration functions. The pore size of filter support screen 1277 is larger than the pore size of the fourth filter element.

Referring to FIG. 57 a first fluid flow path is defined between inlet 1205 of BFFD 1300 and outlet 1227 of BFFD 1300, with the BFFM interposed between inlet 1205 and outlet 1227, and across the fluid flow path. The first fluid flow path flows from inlet 1205, into upstream chamber 1213, through the BFFM, into outlet 127.

Referring to FIG. 12 and FIG. 57, when BFFD 1300 is used to replace BFFD 200 in biological fluid filtration system 2000, the system will function as follows. The user will purchase the system with all components as shown in FIG. 12, less feed blood bag 98. BFFD 1300 will replace BFFD 200, tubing 85 and vent filtration device 40 will not be used. The user will connect tubing 81 to outlet 92 of feed blood bag 98 in a manner known in the art. Feed blood bag 98 and vent filtration device 30, may be hung from a blood bag pole known in the art, and receiving blood bag 99 may be placed on a table top or the like. Tube clamp 95 should be closed before connecting tubing 81 to feed blood bag 98. Before opening tube clamp 95 to start the flow of biological fluid through the system, tube clamp 96 should be open, and tube clamp 97 should be closed.

Referring to FIG. 12, and FIG. 57, BFFD 1300 functions as follows. When tube clamp 95 is opened biological fluid will flow from feed blood bag 98, through tubing 81, into inlet 1205 of BFFD 1300 and then into upstream chamber 1213 of BFFD 1300. Upstream chamber 1213 will rapidly fill with biological fluid from the bottom up. As upstream chamber 1213 fills from the bottom up, the initial air in upstream chamber 213 will be displaced by the biological fluid filling upstream chamber 1213. The displaced air will be forced through the BFFM, into filter support screen 1277. Because the filter support screen 1277 is a woven or non-woven screen with a large pore size that allows flow in all directions, the displaced air will flow through filter support screen filter 1277 into outlet 1227. The biological fluid in upstream chamber 1213 will be pressurized, with the pressure at the bottom of upstream chamber 1213 being proportional to the distance from the top of the biological fluid in feed blood bag 98 to the bottom of upstream chamber 1213, and with the pressure at the top of upstream chamber 1213 being proportional to the distance from the top of the biological fluid in feed blood bag 98 to the top of upstream chamber 1213. Hence the pressure at the top of upstream chamber 1213 will be less than the pressure at the bottom of upstream chamber 1213. The positive pressure in upstream chamber 1213 will cause the biological fluid to flow through the BFFM over the entire surface area of the BFFM and to displace the air within the pores of the BFFM with biological fluid, thereby wetting BFFM from the upstream side of the BFFM to the downstream side of the BFFM. As the BFFM wets the air that was initially in the pores of BFFM will be displaced by biological fluid and flow into the filter support screen, and then into outlet 1227, into tubing 82, and then into receiving blood bag 99. Because the pressure at the bottom of upstream chamber 1213 is greater than the pressure at the top of upstream chamber 1213, the flow rate of biological fluid through the BFFM will be greater at the bottom of the BFFM than at the top of the BFFM. Therefore the BFFM will first become completely wetted from the upstream surface of BFFM to downstream surface of the BFFM at the bottom of the BFFM. The BFFM will continue to wet from the bottom up, with biological fluid flowing from the portions of the BFFM where the downstream surface has been wetted, into the filter support screen, and with air flowing into the filter support screen from the portions of the BFFM where the downstream surface has not been wetted. Therefore, the initial flow of biological fluid into tubing 82 will consist of alternate segments of biological fluid and air.

Referring to FIG. 12, and FIG. 57, once all of the air has been purged from within BFFD 1300, biological fluid will continue to flow through the first fluid flow path from the inlet of BFFD 1300 to the outlet of BFFD 1300, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 1300, pressure P7 downstream of the BFFM and upstream of outlet 1227 will be negative. Once feed blood bag 98 collapses and biological fluid flow through the first fluid flow path stops the differential pressure across the BFFM will become zero, hence the pressure in upstream chamber 1213 will become negative. The pressure on outer surface of flexible housing inlet half 1201 will be atmospheric. With atmospheric pressure on the outer surface of flexible housing inlet half 1201, the negative pressure within upstream chamber 1213 will cause flexible housing inlet half 1201 to collapse onto the upstream surface of the BFFM, thereby forcing the biological fluid in upstream chamber 1213 through the BFFM, into filter support screen 1277, into outlet 1227, into tubing 82, and then into receiving blood bag 99.

Referring to FIG. 12, and FIG. 57, when the filtration cycle is complete as just described, the BFFM will remain wetted, the filter support screen will be filled with biological fluid, and tubing 82 will be filled with biological fluid. The user will close tube clamp 96, and then cut and seal tubing 82 above tube clamp 96, and then discard BFFD 1300 and feed blood bag 98 in a safe manner. Tube clamp 97 may now be opened, and the air in receiving blood bag 99 may be purged from receiving blood bag 99 by squeezing receiving blood bag 99 thereby forcing the air in receiving blood bag 99 through the third fluid flow path from vent port 91 of receiving blood bag 99 to atmosphere. Tubing 84 can then be sealed and cut near receiving blood bag 99, and then tubing 84 and vent filtration device 30 may be discarded in a safe manner.

FIG. 58 shows BFFD 1300 with the perimeter surface of filter elements bonded to one another, and also bonded to the inner side wall of housing outlet half 1220. The bonds may be a glue bond, a heat bond, an ultrasonic bond, an R.F. bond, a solvent bond, or any other type of leak tight bond. BFFD 1300 shown in FIG. 58 functions the same as BFFD 1300 shown in FIG. 57.

Detailed Description of the Fourteenth Embodiment

Figure 59:
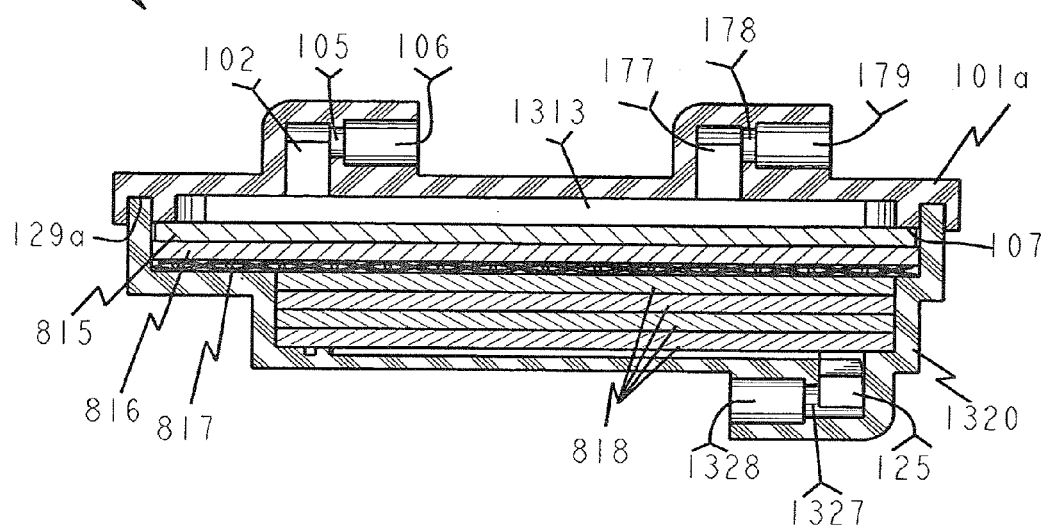
FIG. 59 is a cross-sectional view of a fourteenth embodiment of a BFFD constructed in accordance with the principles of the present invention, usable for the filtration of biological fluids, and containing a gel removing filter element, followed by a microaggregate removing filter element, followed by a first flow distribution filter element, followed by a leukocyte removing filter element containing four layers of leukocyte removing porous filter material.
Figure 60:
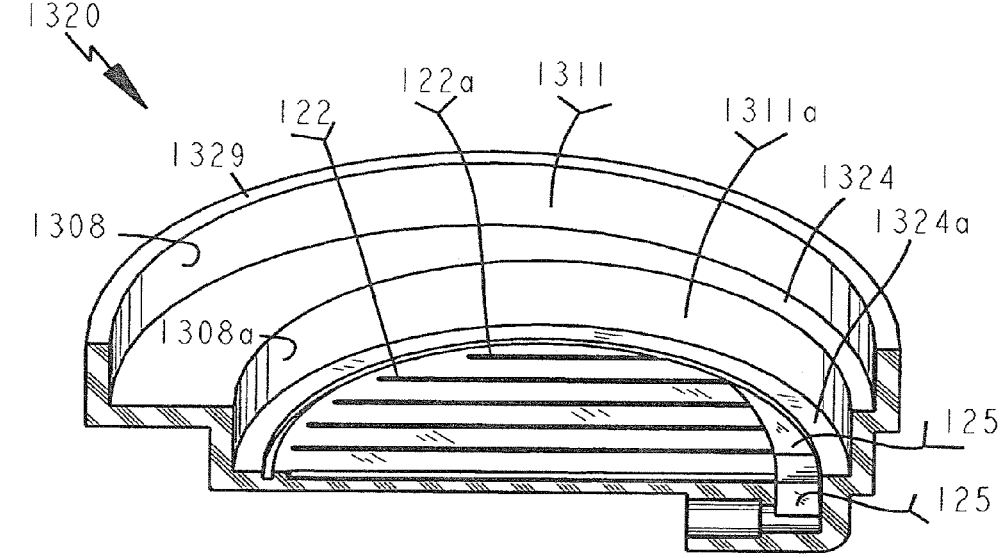
FIG. 60 is an isometric view with portions thereof removed of the housing outlet half of the BFFD shown in FIG. 59.

A fourteenth embodiment of the BFFD constructed in accordance with the principles of the present invention, is shown in FIG. 59 and FIG. 60. BFFD 1400 may be used in place of BFFD 100 in biological fluid filtration system 1000 shown in FIG. 1, or it may be used in place of BFFD 200 in biological fluid filtration system 2000 shown in FIG. 12.

Referring to FIG. 59, and FIG. 60, BFFD 1400 contains a rigid housing that includes housing inlet half 101*a* and housing outlet half 1320. Housing seal surface 129*a* of housing inlet half 101*a* is bonded to housing seal surface 1329 of housing outlet half 1320. The bond is preferably an ultrasonic weld but may be a heat bond, a glue bond, a solvent bond, or any other type of leak tight bond.

Housing inlet half 101*a* is the same as housing inlet half 101 of the second embodiment shown in FIG. 13 with the exception that inlet 105 of housing inlet half 101*a* is located below the center line of housing inlet half 101*a*, and vent inlet of housing inlet half 101*a* is located above the center line of housing inlet half 101*a*.

Referring to FIG. 14, FIG. 44, FIG. 59, and FIG. 60, housing outlet half 1320 contains first filter well 1311 and second filter well 1311*a* that are the same as first filter well 811 and second filter well of housing outlet half 820 shown in FIG. 44. First filter well 1311 has a larger diameter than second filter well 1311*a*. The horizontal center line of the first filter well is offset below the horizontal center line of the second filter well so that the top of first filter seal surface 1324 protrudes above the top of second filter seal surface 1324*a* a sufficient distance to create a compression seal, and so that the perimeter of the second filter well is located entirely within the perimeter of the first filter well. The filter under drain structure of housing outlet half 1320 comprised of vertical channels 122 and 122*a*, and circular outlet channel 125, is the same as the filter underdrain structure of housing outlet half 120 of the second embodiment shown in FIG. 14, with the exception that there are fewer vertical channels in housing outlet half 1320 because of the reduced surface area of the filter elements in the second filter well.

Referring to FIG. 59 and FIG. 60, the BFFM contains four filter elements, first filter element 815, second filter element 816, third filter element 817, and fourth filter element 818 comprised of four layers of filter material of the same type. Any of the filter elements may contain one or more layers of the filter material of the same type. The first filter element has a pore size greater than the pore size of the second filter element, the fourth filter element has a pore size smaller than the pore size of the second filter element, while the third filter element has a pore size greater than the pore size of the second filter element. Preferably the pore size of the third filter element is greater than the pore size of the first and second filter elements. When BFFD 1400 is used to filter blood or blood product, first filter element 815 may be sized to remove gels from the blood or blood product, second filter element 816 may be sized to remove microaggregates from the blood or blood product, fourth filter element 818 may be sized to remove leukocytes from the blood or blood product, while the third filter element 817 is sized to act as a flow distribution layer. Because gels and microaggregates are large particles they may clump together thereby reducing the flow through the gel-microaggregate filter elements in the region of the clump. The flow distribution filter element will distribute the effluent from the microaggregate filter element evenly over the upstream surface of the leukocyte removing layer, thereby allowing the leukocyte removing layer to be utilized most efficiently. Once the gels and microaggregates have been removed from the blood or blood product, the blood or blood product will be relatively clean and therefore the surface area of the leukocyte removing layer may be made smaller than the surface area of the gel and microaggregate layers, thereby reducing the hold up volume of the BFFD. The gel filter element, and the microaggregate filter element, and the first flow distribution filter element, are inserted into the first filter well of housing outlet half 1320. Gel filter element 815, and flow distribution filter element 817, have outside diameters smaller than the inside diameter of inner side wall 808, preventing them from being sealed to BFFD 900 with an interference fit between the perimeter surface of each respective filter element and inner side wall 1308 of housing outlet half 1320. The outer periphery of the gel filter element is sealed to the housing with a compression seal, by compressing the outer periphery of the gel filter element with filter seal surface 107 of housing inlet half 101*a*. Alternately the gel filter element could have an outside diameter large enough so that it could be sealed to the housing an interference fit between the perimeter surface of the gel filter element and inner side wall 1308 of housing outlet half 1320, and the microaggregate filter element could have an outside diameter smaller than the inside diameter of inner side wall 1308, or both the gel filter element and the microaggregate filter element could have outside diameters smaller than the inside diameter of inner side wall 1308. Third filter element 817 is preferably a woven or non-woven screen filter, but could be any type of open pore size depth filter, or any other type of structure that allows flow in all directions. The main purpose of flow distribution filter element 817 is flow distribution, therefore it preferably has a pore size large enough so that it will not retain gels, microaggregates, or leukocytes, and is preferably structured to allow flow through it in all directions. Hence the perimeter surface of filter element 817 need not have an interference fit with inner side wall 1308. Housing outlet half 820 also contains a second filter well smaller in diameter than the first filter well into which leukocyte removing filter element 818 is inserted. Leukocyte removing filter element 818 is sealed to the housing an interference fit between the perimeter surface of each layer of the leukocyte removing filter material and inner side wall 1308*a* of housing outlet half 1320. Alternately, if the blood or blood product is relatively clean, gel filter element 815 may be followed by flow distribution filter element 817, with both filter elements being inserted into the first filter well, and microaggregate filter element 816, could follow flow distribution filter element 817, with the microaggregate filter element having a smaller diameter so that it could be inserted into the second filter well on top of the leukocyte removing filter element. Another alternative would be to make filter element 815 a gel or microaggregate removing filter element, and to make filter element 816 a first leukocyte removing filter element, with filter element 817 being a flow distribution filter element, and with filter element 818 being a second leukocyte filter element. Yet another alternative would to add a fourth filter element to the first filter well in-between filter element 816 and filter element 817, in which case filter element 815 would be a gel removing filter element, filter element 816 would be a microaggregate removing filter element, the fourth filter element in the first filter well would be a first leukocyte removing filter element and filter element 818 would be a second leukocyte removing filter element. Any of the BFFM with the sealing methods shown in FIG. 37 of the eighth embodiment, or in FIG. 40, 41, 42, or 45, of the ninth embodiment, or in FIG. 46 of the tenth embodiment, or in FIG. 49 of the eleventh embodiment, or in FIG. 55 of the twelfth embodiment, or any combination thereof could also be used in place of the BFFM shown in FIG. 59.

Referring to FIG. 59, a first fluid flow path is defined between inlet 105 of BFFD 1400 and outlet 1327 of BFFD 1400 with the BFFM interposed between inlet 105 and outlet 1327, and across the fluid flow path. The first fluid flow path flows from inlet 105, through inlet slot 102, into upstream chamber 1313, through the BFFM, into vertical channels 122 and 122*a*, into circular outlet channel 125, and then into outlet 827.

BFFD 1400 can be used to replace BFFD 100 in biological fluid filtration system 1000 shown in FIG. 1, or it may be used to replace BFFD 200 in biological fluid filtration system 2000 shown in FIG. 12. In either case BFFD 1400 will function as follows. When tube clamp 95 is opened biological fluid will flow from feed blood bag 98 as described in the first and second embodiments above, through the first fluid flow path of BFFD 1400 by flowing into inlet 105, through inlet slot 102, into upstream chamber 1313, of BFFD 1400. Upstream chamber 1313 will rapidly fill with biological fluid from the bottom up. As upstream chamber 1313 fills from the bottom up, the initial air in upstream chamber 1313 will be displaced by the biological fluid filling upstream chamber 1313. The displaced air will be forced through the BFFM, into vertical channels 122 and 122*a* and circular outlet channel 125, and then into outlet 1327 all of BFFD 1400. The biological fluid in upstream chamber 1313 will be pressurized, with the pressure at the bottom of upstream chamber 1313 being proportional to the distance from the top of the biological fluid in feed blood bag 98 to the bottom of upstream chamber 1313, and with the pressure at the top of upstream chamber 1313 being proportional to the distance from the top of the biological fluid in feed blood bag 98 to the top of upstream chamber 1313. Hence the pressure at the top of upstream chamber 1313 will be less than the pressure at the bottom of first upstream chamber 1313. The positive pressure in upstream chamber 1313 will cause the biological fluid to flow through first filter element 815, and second filter element 816 over the entire surface area of the first and second filter elements displacing the air within the pores of the first and second filter elements with biological fluid, thereby wetting the first and second filter elements from the upstream side of first filter element 815 to the downstream side of second filter element 816. The displaced air from upstream chamber 1313 and from the first and second filter elements will flow into third filter element 817. Third filter element 817 preferably has an open pore size and structure that allows flow through it in all directions. Therefore any air or biological fluid that flows from the downstream surface of second filter element 816, will flow into third filter element 817 and then be uniformly distributed over the entire upstream surface of fourth filter element 818, thereby utilizing fourth filter element 818 in the most efficient way. As the first and second filter elements wet, the air that was initially in the pores of the first and second filter elements will be displaced by biological fluid, and flow into the third filter element 817. Because the pressure at the bottom of upstream chamber 1313 is greater than the pressure at the top of upstream chamber 1313, the flow rate of biological fluid through the first and second filter elements will be greater at the bottom of the first and second filter elements than at the top of the first and second filter elements. Therefore, the first and second filter elements will first become completely wetted from the upstream surface of the first filter element to downstream surface of the second filter element at the bottom of the second filter element. The first and second filter elements will continue to wet with the downstream surface of the second filter element wetting from the bottom to the top. The third filter element will also wet from the bottom to the top. When the liquid level in the third filter element reaches the bottom of fourth filter element 818, the fourth filter element will begin to wet from the bottom up. The first and second filter elements will continue to wet until all of the air in the first and second filter elements has been purged. It is important that the horizontal center line of first filter well 1311 is offset the required distance below the horizontal center line of second filter well 1311*a* so that the top of first filter seal surface 1324 protrudes above the top of second filter seal surface 1324*a* no more than the distance required to create a compression seal at the top of the first filter well between filter seal surface 107 of housing inlet half 101*a*, and first filter seal surface 1324 of housing outlet half 1320, because air will be trapped in the compression seal portion of the first, second, and third filter elements that lie above a horizontal line that is tangent to the top of the perimeter of the second filter well. The fourth filter element will wet from the bottom up, with the downstream surface of the fourth filter element first becoming wetted at the bottom of the downstream surface of the fourth filter element. If the width of vertical channels 122 and 122*a* is sufficiently small, and the depth of vertical channels 122 and 122*a* is sufficiently shallow, so that the cross-sectional flow area of the vertical channels 122 and 122*a* is sufficiently small, and if the distance between vertical channels 122 and 122*a* is sufficiently large, as described above in the description of the second embodiment, the path of least resistance for continued biological fluid flow through the BFFM will be through the capillaries of the BFFM in both the horizontal and vertical directions and not through the vertical channels, because if the cross-sectional flow area of the vertical channels is sufficiently small, the displaced air flowing into and through the vertical channels will create a sufficiently high positive pressure in the vertical channels to prevent biological fluid from entering the vertical channels. The downstream surface of the BFFM (i.e. the downstream surface of the fourth filter element) will therefore wet from the bottom up and the displaced air that was within the BFFM will continue to flow into the vertical channels, and into the circular outlet channel, and then into the outlet. When the downstream surface of the BFFM has become wetted to the level of the upper part of circular outlet channel 125 where circular outlet channel 125 begins to taper to a wider width, air flow through the lower part of circular outlet channel 125, and air flow through the two outermost vertical channels 122a will stop because the downstream surface of the BFFM adjoining the lower part of the circular outlet channel and the two outermost vertical channels will be wetted. Therefore the pressure in the lower part of the circular outlet channel and the pressure in the two outermost vertical channels will decrease allowing biological fluid to enter the lower part of the circular outlet channel and the two outermost vertical channels from the bottom up, thereby displacing the air that was in the lower part of the circular outlet channel and the two outermost vertical channels. At the same time the wetted level of the downstream surface of the BFFM will continue to wet in the vertical direction, wetting the downstream surface of the BFFM adjoining the upper part of circular outlet channel 125. Because the cross-sectional flow area of the upper part of circular outlet channel 125 is not sufficiently small to create a positive pressure in it due to the air flow through it, biological fluid will flow into circular outlet channel 125 as the BFFM continues to wet in the vertical direction above the lower part of the circular outlet channel. The biological fluid flowing into vertical channels 122 and 122a, and into the circular outlet channel 125 will flow into outlet 1327 of BFFD 1400 and then into tubing 82 toward receiving blood bag 99. As biological fluid starts to flow into outlet 1327, the BFFM will continue to wet vertically. Hence the initial flow of biological fluid through the upper part of circular outlet channel 125, and through outlet 1327, will be a mixture of air and biological fluid so that the initial flow into tubing 82 will consist of alternate segments of biological fluid and air. As described in the description of the second embodiment above, the amount of biological fluid that flows from outlet 1327 will be minimized because of the design of the filter under drain structure, and because of the reduced surface area of the fourth filter element of the BFFM.

Referring to FIG. 1, FIG. 12, and FIG. 59, once all of the air has been purged from within BFFD 1400, biological fluid will continue to flow through the first fluid flow path from the inlet of BFFD 1400 to the outlet of BFFD 1400, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in tubing 81. If receiving blood bag 99 is positioned at a level that is sufficiently lower than BFFD 1400, the pressure downstream of the BFFM and upstream of outlet 1327 will be negative as described above in the description of the second embodiment. If BFFD 1400 is used in biological fluid filtration system 1000 shown in FIG. 1, vent filtration device 30 and three tube connector 50 will function as described in the description of the first embodiment above, and tubing 83, three tube connector 50, tubing 81a, and upstream chamber 1313 of BFFD 1400 will drain as described above. Vent inlet 178, vent inlet slot 177, and vent tube socket 179 will not be used when BFFD 1400 replaces BFFD 100 in biological fluid filtration system 1000. If BFFD 1400 is used in biological fluid filtration system 2000 shown in FIG. 12, vent filtration device 40 will be connected to vent inlet 178 of housing inlet half 101a via tubing 85, and tubing 85 and upstream chamber 1313 of BFFD 1400 will drain as described above in the description of the second embodiment.

Detailed Description of the Fifteenth Embodiment

A third embodiment of the biological fluid filtration system, and a fifteenth embodiment of the BFFD constructed in accordance with the principles of the present invention, is shown in FIG. 61 through FIG. 74. Biological fluid filtration system 3000 shown in FIG. 61 contains first feed blood 98, second feed blood bag 98a, first receiving blood bag 99, and second receiving blood bag 99a. Interposed between the feed blood bags and receiving blood bags is BFFD 1500. First length of tubing 81 connects the outlet of first feed blood bag 98 to the first inlet tube socket 106 of BFFD 1500. A second length of tubing 81b connects the outlet of second feed blood bag 98a to the second inlet tube socket 106a of BFFD 1500. A third length of tubing 82 connects first outlet tube socket 1428 of BFFD 1500 to the inlet of first receiving blood bag 99. A fourth length of tubing 82a connects second outlet tube socket 1428a of BFFD 1500 to the inlet of second receiving blood bag 99a. A fifth length of tubing 83 connects first vent tube socket 179 of BFFD 1500 to first tube socket 1445 of vent filtration device 1440. A sixth length of tubing 83a connects second vent tube socket 179a of BFFD 1500 to second tube socket 1445a of vent filtration device 1440.

Referring to FIG. 62, BFFD 1500 contains a rigid housing that includes first housing inlet half 101a, second housing inlet half 101aa, and housing outlet half 1420. Preferably the housing inlet halves are bonded to the housing outlet half with an ultrasonic weld, but may be a heat bonded, a glue bonded, a solvent bonded, or bonded by any other type of leak tight bond.

Referring to FIG. 62, first housing inlet half 101a and second housing inlet half 101aa are the same as housing inlet half 101a shown in FIG. 59, and described in the description of the fourteenth embodiment.

Figure 65:
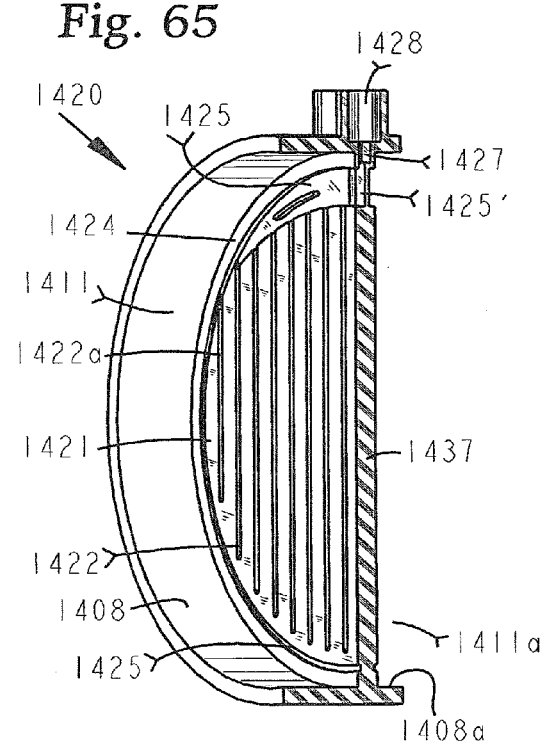
FIG. 65 is an isometric view with portions thereof removed of the housing outlet half of the BFFD shown in FIG. 62.
Figure 68:
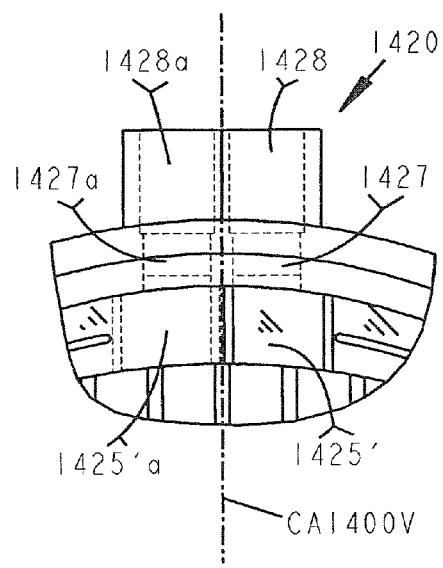
FIG. 68 is a partial top view of the housing outlet half of the BFFD shown in FIG. 62, showing the top outlet and the bottom outlet.
Figure 66:
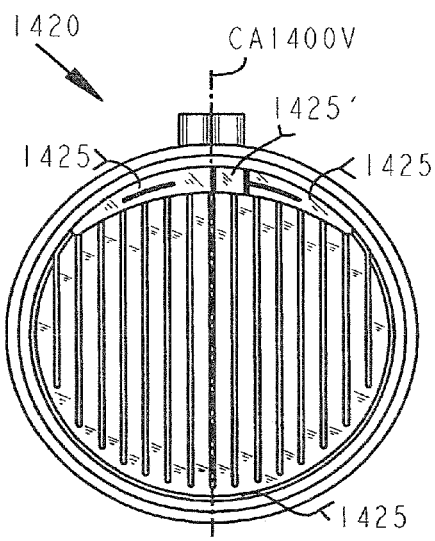
FIG. 66 is a top view of the housing outlet half of the BFFD shown in FIG. 62.
Figure 67:
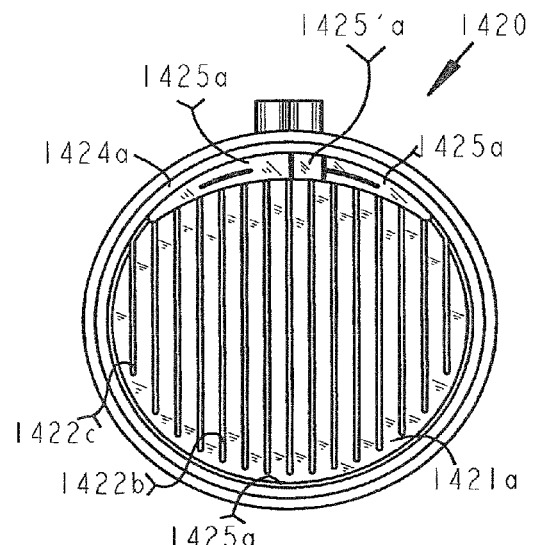
FIG. 67 is a bottom view of the housing outlet half of the BFFD shown in FIG. 62.

Referring to FIG. 62 through FIG. 68 housing outlet half 1420 contains a solid partition wall 1437 that divides BFFD 1500 into a first filtration device with a first inlet and a first outlet on one side of the solid partition wall, and a second filtration device with a second inlet and a second outlet on the other side of the solid partition wall. On the first side of solid partition wall 1437 housing outlet half 1420 contains first filter well 1411 bounded by inner side wall 1408 and by first filter seal surface 1424. Housing outlet half 1420 contains a second filter well 1411a on the opposite side of solid partition wall 1437 bounded by inner side wall 1408a and by second filter seal surface 1424a. Housing outlet half 1420 contains first circular outlet channel 1425 and first outlet 1427 located on the first side of solid partition wall 1437. The portion of first circular outlet channel 1425 that adjoins and is in direct fluid flow communication with first outlet 1427, has a cross-sectional flow area that is greater than the cross-sectional flow area of first outlet 1027 and is designated portion 1425'. Referring to FIG. 68, portion 1425' of first circular outlet channel 1425 is located near the top of first circular outlet channel 1425 an to the right of vertical central axis CA1400V when viewed from first filter well 1411. Housing outlet half 1420 also contains a plurality of open top closed bottom first vertical channels 1422 and 1422a located on the first side of solid partition wall 1437. The top end of each of the first vertical channels 1422 and 1422a is in fluid flow communication with first circular outlet channel 1425. The upper part of first circular outlet channel 1425 increases in width to accommodate the flow of biological fluid from first vertical channels 1422 and 1422a. The width of the remainder of first circular outlet channel 1425 (i.e. the lower part of first circular outlet channel 1425) is approximately equal to the width of the first vertical channels. The two outermost first vertical channels designated as first vertical channels 1422a adjoin first circular outlet channel 1425 where the width of first circular outlet channel 1425 is approximately equal to the width of the first vertical channels. The first circular outlet channel and the first vertical channels combined, create a first filter under drain structure, and are cut into first inner wall 1421 of solid partition wall 1437, so that the inner surface of all of the first channels lies below first inner wall 1421, as shown in FIG. 65. The cross sectional area the first circular outlet channel and of the first vertical channels is defined by the inner surface of each channel and by the downstream surface of the first BFFM. Housing outlet half 1420 also contains second circular outlet channel 1425a and second outlet 1427a located on the second side of solid partition wall 1437. The portion of second circular outlet channel 1425a that adjoins and is in direct fluid flow communication with second outlet 1427a, has a cross-sectional flow area that is greater than the cross-sectional flow area of second outlet 1027a and is designated portion 1425'a. Referring to FIG. 68, portion 1425'a of second circular outlet channel 1425a (shown as dotted lines) is located near the top of second circular outlet channel 1425a an to the left of vertical central axis CA1400V, when viewed from first filter well 1411. Housing outlet half 1420 also contains a plurality of open top closed bottom second vertical channels 1422b and 1422c located on the second side of solid partition wall 1437. The top end of each of the second vertical channels 1422b and 1422c is in fluid flow communication with second circular outlet channel 1425a. The upper part of second circular outlet channel 1425a increases in width to accommodate the flow of biological fluid from second vertical channels 1422b and 1422c. The width of the remainder of second circular outlet channel 1425a (i.e. the lower part of second circular outlet channel 1425a) is approximately equal to the width of the second vertical channels. The two outermost second vertical channels designated as second vertical channels 1422c adjoin second circular outlet channel 1425a where the width of second circular outlet channel 1425a is approximately equal to the width of the second vertical channels. The second circular outlet channel and the second vertical channels combined, create a second filter under drain structure, that are cut into second inner wall 1421a of solid partition wall 1437, so that the inner surface of all of the second channels lies below second inner wall 1421a, as shown in FIG. 67. The cross sectional area the second circular outlet channel and of the second vertical channels is defined by the inner surface of each channel and by the downstream surface of the second BFFM. Solid partition wall 1437 provides a barrier between first circular outlet channel 1425 and second circular outlet channel 1425a, and between first outlet 1427 and second outlet 1427a. As shown in FIG. 65 and FIG. 66, the distance between first vertical channels 1422 and 1422a is much greater than the width of first vertical channels 1422 and 1422a, and the distance between first vertical channels 1422 and 1422a is also much greater than of the depth of first vertical channels 1422 and 1422a. As shown in FIG. 67, the distance between second vertical channels 1422b and 1422c is much greater than the width of second vertical channels 1422b and 1422c, and the distance between second vertical channels 1422b and 1422c is also much greater than of the depth of second vertical channels 1422b and 1422c. Because housing outlet half 1420 does not contain an open chamber or plenum downstream of the first BFFM or downstream of the second BFFM, hold up volume is minimized. FIG. 62 through FIG. 65 show that first filter well 1411 is deeper than second filter well 1411a. However the two filter well could be made to the same depth.

Referring to FIG. 62 through FIG. 65, BFFD 1500 contains a first BFFM and a second BFFM. The first BFFM is disposed in first filter well 1411, and the second BFFM is disposed in second filter well 1411a. Referring to FIG. 62 through FIG. 64, the first BFFM contains four filter elements, first filter element 1415, second filter element 1416, third filter element 1417, and fourth filter element 1418 comprised of three layers of filter material of the same type. Any of the filter elements may contain one or more layers of the filter material of the same type. The first filter element has a pore size greater than the pore size of the second filter element, the fourth filter element has a pore size smaller than the pore size of the second filter element, while the third filter element has a pore size greater than the pore size of the second filter element. Preferably the pore size of the third filter element is greater than the pore size of the first and second filter elements. When BFFD 1500 is used to filter blood or blood product, first filter element 1415 may be sized to remove gels from the blood or blood product, second filter element 1416 may be sized to remove microaggregates from the blood or blood product, fourth filter element 1418 may be sized to remove leukocytes from the blood or blood product, while the third filter element 1417 is sized to act as a flow distribution layer. Because gels and microaggregates are large particles they may clump together thereby reducing the flow through the gel-microaggregate filter elements in the region of the clump. The flow distribution filter element will distribute the effluent from the microaggregate filter element evenly over the upstream surface of the leukocyte removing layer, thereby allowing the leukocyte removing layer to be utilized most efficiently. The outside diameter of first filter element 1415 is smaller than the inside diameter of inner side wall 1408 of housing outlet half 1420 preventing first filter element 1415 from being sealed to BFFD 1500 with an interference fit between the perimeter surface 1415b of first filter element 1415 and inner side wall 1408 of housing outlet half 1420. First filter element 1415 is sealed to the housing by compressing the outer periphery of first filter element 1415 with filter seal surface 1407 of housing inlet half 101a. Second filter element 1416 and fourth filter element 1418 are sealed to the housing an interference fit between the perimeter surface of each filter element and inner side wall 1408 of housing outlet half 1420. Alternately both the first and second filter elements could have outside diameters that are smaller than the inside diameter of inner side wall 1408 of the housing outlet half, thereby preventing both the first filter element and the second filter element from being sealed to BFFD 1500 with an interference fit between the perimeter surface of the filters and inner side wall 1498 of housing outlet half 1429. The outside diameter of third filter element 1417 is smaller than the inside diameter of inner side wall 1408 of housing outlet half 1420 preventing third filter element 1417 from being sealed to BFFD 1500 with an interference fit between the perimeter surface of filter element 1417 and inner side wall 1408 of housing outlet half 1420. Third filter element 1417 is preferably a woven or non-woven screen filter, but could be any type of open pore size depth filter, or any other type of structure that provides for flow in all directions. The main purpose of filter element 1417 is flow distribution therefore it has a large pore size, and is preferably structured to allow flow through it in all directions. In applications where the blood or blood product is fresh and does not contain gels, the first filter element may be a microaggregate removing filter element, and the second filter element could be eliminated. In this case the third filter element may also be eliminated. Referring to FIG. 62 through FIG. 65, the second BFFM contains filter element 1471. The outside diameter of filter element 1471 is smaller than the inside diameter of inner side wall 1408a of housing outlet half 1420 preventing filter element 1471 from being sealed to BFFD 1500 with an interference fit between the perimeter surface 1471b of filter element 1471 and inner side wall 1408a of housing outlet half

1420. Filter element 1471 is sealed to the housing by compressing the outer periphery of filter element 1471 between filter seal surface 1407*a* of housing inlet half 101 and second filter seal surface 1424*a* of housing outlet half 1420. Any of the filter elements in the first filter well could also be bonded to the housing outlet half using a heat bond, an ultrasonic bond, a glue bond, a solvent bond or any other type of leak tight bond, in place of, or in addition to, the use of perimeter seals or compression seals. Likewise the filter element in the second filter well could be bonded to the housing outlet half using a heat bond, an ultrasonic bond, a glue bond, a solvent bond or any other type of leak tight bond, in place of, or in addition to, the use of a perimeter seal or compression seal. Second filter well 1411*a* could be made as deep as first filter well 1411, thereby allowing the second filter well to contain a second BFFM that is the same as the first BFFM contained in the first filter well.

Referring to FIG. 62 through FIG. 68, a first fluid flow path is defined between first inlet 105 of BFFD 1500 and first outlet 1427 of BFFD 1500 with the first BFFM interposed between first inlet 105 and first outlet 1427, and across the first fluid flow path. The first fluid flow path flows from first inlet 105, through first inlet slot 102, into first upstream chamber first 1413, through the first BFFM, into first vertical channels 1422 and 1422*a*, into first circular outlet channel 1425, and then into first outlet 1427. A second fluid flow path is defined between second inlet 105*a* of BFFD 1500 and second outlet 1427*a* of BFFD 1500 with the second BFFM interposed between second inlet 105*a* and second outlet 1427*a*, and across the second fluid flow path. The second fluid flow path flows from second inlet 105*a*, through second inlet slot 102*a*, into second upstream chamber 1413*a*, through the second BFFM, into second vertical channels 1422*b* and 1422*c*, into second circular outlet channel 1425*a*, and then into second outlet 1427*a*. The first fluid flow path is independent of the second fluid flow path, and there is no cross talk between the two. Solid partition wall 1437 is a barrier between the first fluid flow path and the second fluid flow path.

Figure 61:
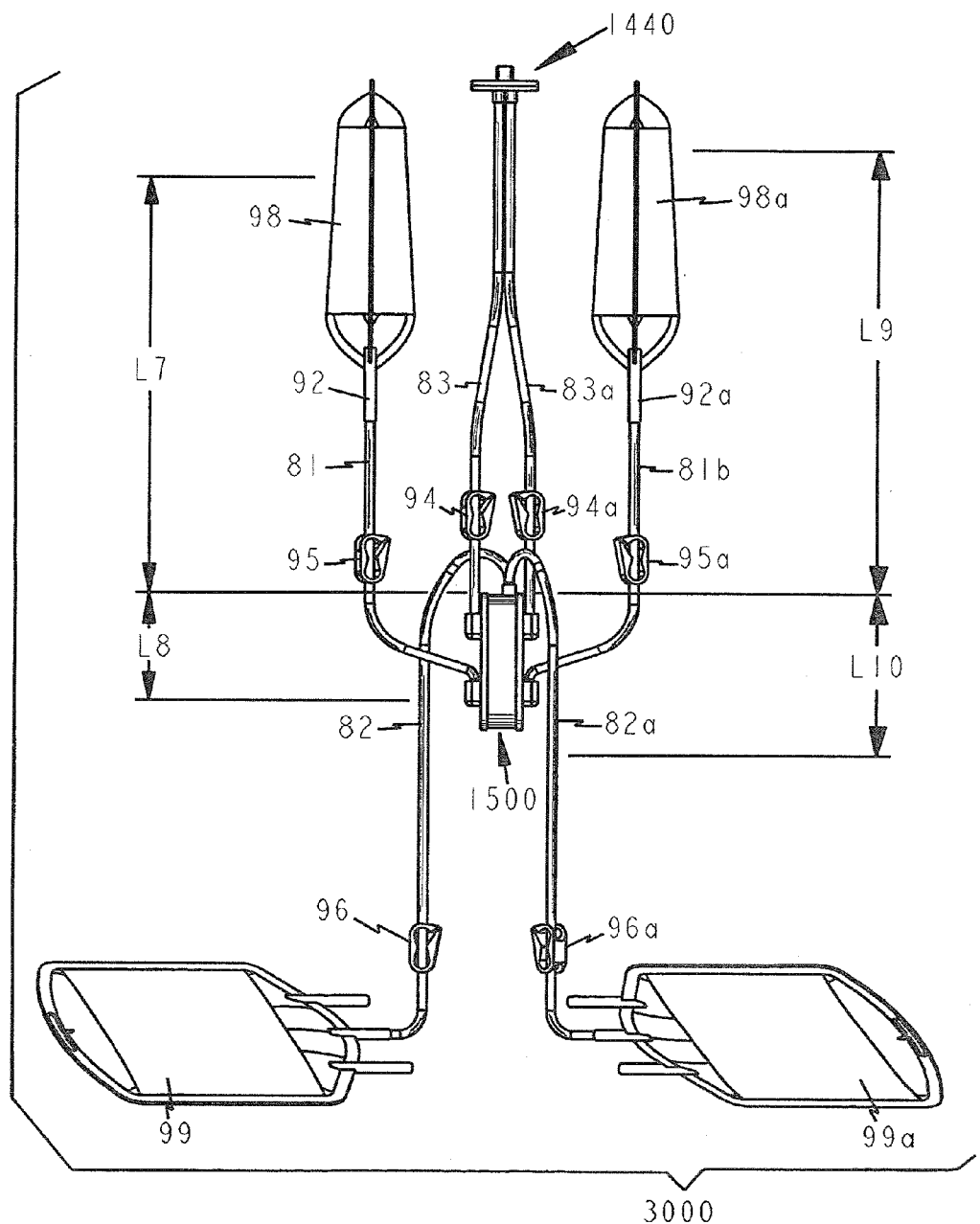
FIG. 61 is an isometric view of a third embodiment of a biological fluid filtration system constructed in accordance with the principles of the present invention, usable for the filtration of biological fluids, containing two feed blood bags, two receiving blood bags, with the fifteenth embodiment of a BFFD interposed between the two feed blood bags and the two receiving blood bags, and with a single vent filtration device connected to the first vent inlet and to the second vent inlet of the biological fluid filtration system via two separate lengths of tubing.

Referring to FIG. 69 through FIG. 71, and FIG. 73, vent filtration device 1440 contains a housing comprised of housing cap 1441 and housing body 1442. The housing contains a vent port 1446, a first system port 1444, a second system port 1444*a*, a first tube socket 1445, and a second tube socket 1445*a*. Housing body 1442 contains two filter support structures separated by solid partition wall 1459. The first filter support structure located on one side of solid partition wall 1459 contains filter support ribs 1447 and is in fluid flow communication with first system port 1444. The second filter support structure located on the other side of solid partition wall 1459 contains filter support ribs 1447*a* and is in fluid flow communication with second system port 1444*a*. Housing body 1442 also contains a filter well 1452 into which vent filtration media 1443 is inserted. Vent filtration media 1443 is sealed to filter seal surface 1450 of housing body 1442 along filter seal area 1449 shown cross-hatched in FIG. 69, thereby isolating the first filter support structure and the first system port from the second filter support structure and the second system port. The seal is preferably a heat seal, but could be an ultrasonic seal, a glue seal, a solvent seal, or any other type of leak tight seal. Alternately vent filtration media 1443 could be made of two separate vent filtration media, with one sealed over the first filter support structure, and with the other sealed over the second filter support structure. Seal surface 1454 of housing cap 1441 is sealed to seal surface 1453 of housing body 1442. A first vent fluid flow path is defined between common vent port 1446 and first system port 1444, with the portion of vent filtration media 1443 that is enclosed by the filter seal around the first filter support structure interposed between common vent port 1446 and first system port 1444 and across the first vent fluid flow path. A second vent fluid flow path is defined between common vent port 1446 and second system port 1444*a*, with the portion of vent filtration media 1443 that is enclosed by the filter seal around the second filter support structure interposed between common vent port 1446 and second system port 1444*a* and across the second vent fluid flow path. The vent filtration media 1443 is shown as a microporous filter media such as a 0.2 μm microporous filter material, but may be any type of depth filter media, such as a non-woven depth filter material, a spun bound filter material, a molded porous filter material or any other type of depth filter material. The vent filtration media may be hydrophobic or hydrophilic. Preferably vent filtration device 1440 is located a sufficient distance above inlet 105 and inlet 105*a* of BFFD 1500 to prevent biological fluid in tubing 83 and tubing 83*a* from contacting vent filtration media 1443 when biological fluid flows through BFFD 1500. Vent filtration device 1440 may be located above the liquid level in first feed blood bag 98 and second feed blood bag 98*a* as shown in FIG. 61. Alternately housing cap 1441' shown in FIG. 72 could replace housing cap 1441 in vent filtration device 1440. Housing cap 1441' is the same as housing body 1442 with the exception that housing cap 1441' does not contain a filter well. When housing cap 1441' is used to replace housing cap 1441, vent filtration media 1443 could be sealed to vent filtration device 1440 by compressing vent filtration media 1443 between seal surface 1451 of housing cap 1441' and filter seal surface 1450 of housing body 1442. When housing cap 1441' is used to replace housing cap 1441, a first vent fluid flow path is defined between first vent port 1446' and first system port 1444, with the portion of vent filtration media 1443 that is enclosed by the filter seal around the first filter support structure interposed between first vent port 1446' and the first system port 1444 and across the first vent fluid flow path. A second vent fluid flow path is defined between second vent port 1446'*a* and second system port 1444*a*, with the portion of vent filtration media 1443 that is enclosed by the filter seal around the second filter support structure interposed between second vent port 1446'*a* and second system port 1444*a* and across the second vent fluid flow path. Because the filter seal in vent filtration device 1440 isolates the first filter support structure and first system port from the second filter support structure and the second system port, the first vent fluid flow path is isolated from the second vent fluid flow path.

Referring to FIG. 74 vent filtration device 1430 could replace vent filtration device 1440. Vent filtration device 1430 contains a housing comprised of housing cap 1431 and housing body 1432. The housing contains a first vent port 1436, a second vent port 1436*a*, a first system port 1434, a second system port 1434*a*, a first vent filtration media 1433, and a second vent filtration media 1433*a*. A first vent fluid flow path is defined between first vent port 1436 and first system port 1434, with first vent filtration media 1433 interposed between the first vent port and the first system port and across the first vent fluid flow path. A second vent fluid flow path is defined between second vent port 1436*a* and second system port 1434*a*, with second vent filtration media 1433*a* interposed between the second vent port and the second system port and across the second vent fluid flow path. The first vent fluid flow path of vent filtration device 1430 is isolated from the second vent fluid flow path of vent filtration device 1430 by solid partition wall 1439. The vent filtration media 1433 and 1433*a* are shown as a depth filter media, such as a wad of cotton, a non-woven depth filter material, a spun bound filter material, a molded porous filter material or any other type of depth filter material. The vent filtration media may be hydrophobic or hydrophilic. Preferably vent filtration device 1430 is located above the liquid level in first feed blood bag 98 and in second feed blood bag 98a as shown in FIG. 61. Referring to FIG. 61 and FIG. 74, when vent filtration device 1430 replaces vent filtration device 1440 in biological fluid filtration system 3000, the top end of tubing 83 would connect to first tube socket 1435 of vent filtration device 1430, and the top end of tubing 83a would connect to second tube socket 1435a of vent filtration device 1430.

Referring to FIG. 61 through FIG. 68, and FIG. 73, biological fluid filtration system 3000 may contain tubing 83, tubing 83a, and vent filtration device 1440. One end of tubing 83 is connected to first tube socket 1445 of vent filtration device 1440 and the other end of tubing 83 is connected to first vent tube socket 179 of BFFD 1500. One end of tubing 83a is connected to second tube socket 1445a of vent filtration device 1440 and the other end of tubing 83a is connected to second vent tube socket 179a of BFFD 1500. A third fluid flow path for biological fluid filtration system 3000 is defined from atmosphere to first vent inlet 178 of BFFD 1500. The third fluid flow path for biological fluid filtration system 3000 flows from common vent port 1446 of vent filtration device 1440, through the portion of vent filtration media 1443 that is enclosed by the filter seal around the first filter support structure of vent filtration device 1440, through first system port 1444 of vent filtration device 1440 through tubing 83, into first vent inlet 178 of BFFD 1500, when tube clamp 94 is open. A fourth fluid flow path for biological fluid filtration system 3000 is defined from atmosphere to second vent inlet 178a of BFFD 1500. The fourth fluid flow path for biological fluid filtration system 3000 flows from common vent port 1446 of vent filtration device 1440, through the portion of vent filtration media 1443 that is enclosed by the filter seal around the second filter support structure of vent filtration device 1440, through second system port 1444a of vent filtration device 1440 through tubing 83a, into second vent inlet 178a of BFFD 1500, when tube clamp 94a is open. Preferably vent filtration device 1440 is located above the liquid level in first feed blood bag 98 and second feed blood bag 98a, as shown in FIG. 61.

Referring to FIG. 61, biological fluid filtration system 3000 functions as follows. The user will purchase the system with all components as shown in FIG. 61, less first feed blood bag 98 and second feed blood bag 98a. The user will connect tubing 81 to outlet 92 of first feed blood bag 98 in a manner known in the art. The user will also connect tubing 81b to outlet 92a of second feed blood bag 98a in a manner known in the art. First feed blood bag 98, second feed blood bag 98a, and vent filtration device 1440 may be hung from a blood bag pole known in the art, with first receiving blood bag 99 and second receiving blood bag 99a placed on a table top or the like, so that the various components of the system will be positioned as shown in FIG. 61. Tube clamps 95 and 95a should be closed before connecting tubing 81 to first feed blood bag 98 and before connecting tubing 81b to second feed blood bag 98a. Before opening tube clamps 95 and 95a to start the flow of biological fluid through the system, tube clamps 94, 94a, 96, and 96a should be open.

Alternately the user will purchase the system with all components as shown in FIG. 61 including the first and second feed blood bags. In this case biological fluid filtration system 3000 may be part of a larger system that contains a unit of fresh blood. The larger system would be placed into a centrifuge where the platelets would be separated from the unit of fresh blood and then transferred into second feed blood bag 98a, and where the packed red blood cells would be separated from the unit of fresh blood and then transferred into first feed blood bag 98, using a process known in the art.

Referring to FIG. 61 through FIG. 68, the first fluid flow path of BFFD 1500 functions as follows. When tube clamp 95 is opened biological fluid (i.e. liquid) will flow from first feed blood bag 98, through tubing 81, into first inlet 105 of BFFD 1500, and then through first inlet slot 102 of BFFD 1500, into first upstream chamber 1413 of BFFD 1500. First upstream chamber 1413 will rapidly fill with biological fluid from the bottom up. As first upstream chamber 1413 fills from the bottom up, the initial air in first upstream chamber 1413 will be displaced by the biological fluid filling first upstream chamber 1413. The displaced air will be forced through the first BFFM, into first vertical channels 1422 and 1422a, into first circular outlet channel 1425, and then into first outlet 1427 all of BFFD 1500. The biological fluid in first upstream chamber 1413 will be pressurized, with the pressure at the bottom of first upstream chamber 1413 being proportional to the distance from the top of the biological fluid in first feed blood bag 98 to the bottom of first upstream chamber 1413, and with the pressure at the top of first upstream chamber 1413 being proportional to the distance from the top of the biological fluid in first feed blood bag 98 to the top of first upstream chamber 1413. Hence the pressure at the top of first upstream chamber 1413 will be less than the pressure at the bottom of first upstream chamber 1413. The positive pressure in first upstream chamber 1413 will cause the biological fluid to flow through the first BFFM over the entire surface area of the first BFFM and to displace the air within the pores of the first BFFM with biological fluid, thereby wetting the first BFFM from the upstream side of the first BFFM to the downstream side of the first BFFM. As the first BFFM wets the air that was initially in the pores of the first BFFM will be displaced by biological fluid and flow into first vertical channels 1422 and 1422a, and into first circular outlet channel 1425, and then into first outlet 1427 all of BFFD 1500, into tubing 82, and then into first receiving blood bag 99. Because the pressure at the bottom of first upstream chamber 1413 is greater than the pressure at the top of first upstream chamber 1413, the flow rate of biological fluid through the first BFFM will be greater at the bottom of the first BFFM than at the top of the first BFFM. Therefore, the first BFFM will first become completely wetted from its upstream surface to its downstream surface, at the bottom of the first BFFM. If the width of first vertical channels 1422 and 1422a is sufficiently small, and the depth of first vertical channels 1422 and 1422a is sufficiently shallow, so that the cross-sectional flow area of first vertical channels 1422 and 1422a is sufficiently small, and if the distance between first vertical channels 1422 is sufficiently large, as described above, the path of least resistance for continued biological fluid flow through the first BFFM will be through the capillaries of the first BFFM in both the horizontal and vertical directions and not through the first vertical channels, because if the cross-sectional flow area of the first vertical channels is sufficiently small, the displaced air flowing into and through the first vertical channels will create a sufficiently high positive pressure in the first vertical channels to prevent biological fluid from entering the first vertical channels. The downstream surface of the first BFFM will therefore wet from the bottom up and the displaced air that was within the first BFFM will continue to flow into the first vertical channels, and into the first circular outlet channel, and then into the first outlet. When the downstream surface of the first BFFM has become wetted to the level of the upper part of first circular outlet channel 1425 where first circular outlet channel 1425 begins to taper to a wider width, air flow through the lower part of first circular outlet channel 1425, and air flow through the two outermost first vertical channels 1422a will stop because the downstream surface of the first BFFM adjoining the lower part of the first circular outlet channel and the two outermost first vertical channels will be wetted. Therefore the pressure in the lower part of the first circular outlet channel and the pressure in the two outermost first vertical channels will decrease allowing biological fluid to enter the lower part of the first circular outlet channel and the two outermost first vertical channels from the bottom up, thereby displacing the air that was in the lower part of the first circular outlet channel and the two outermost first vertical channels. At the same time the wetted level of the downstream surface of the first BFFM will continue to wet in the vertical direction, wetting the downstream surface of the first BFFM adjoining the upper part of first circular outlet channel 1425. Because the cross-sectional flow area of the upper part of first circular outlet channel 1425 is not sufficiently small to create a positive pressure in it due to the air flow through it, biological fluid will flow into first circular outlet channel 1425 as first BFFM continues to wet in the vertical direction above the lower part of the first circular outlet channel. The biological fluid flowing into first vertical channels 1422 and 1422a, and into the first circular outlet channel 1425 will flow into first outlet 1427 of BFFD 1500 and then into tubing 82 toward first receiving blood bag 99. As biological fluid starts to flow into first outlet 1427, first BFFM will continue to wet vertically. Hence the initial flow of biological fluid through the upper part of first circular outlet channel 1425, and through first outlet 1427, will be a mixture of air and biological fluid so that the initial flow into tubing 82 will consist of alternate segments of biological fluid and air.

Referring to FIG. 61 through FIG. 64, when biological fluid starts to flow into tubing 82, the pressure P8 downstream of the first BFFM and upstream of first outlet 1427 (i.e. downstream of the first BFFM, but within BFFD 1500) will be determined by the following formula:

$$P8 = L7 - p - L8$$

Δp is the pressure drop across the first BFFM due to biological fluid flow through the first BFFM.

L7 is the distance between first outlet 1427 of BFFD 1500 and the top of the biological fluid in first feed blood bag 98.

L8 is the height of biological fluid minus any air segments downstream of first outlet 1427, in tubing 82.

Therefore the pressure P8 within BFFD 1500 and downstream of the first BFFM will be greater than or equal to zero until L8=L7−Δp. Because the upper part of first circular outlet channel 1425 is located a sufficient distance above the horizontal center line of BFFD 1500, all of the air will be purged from within the first fluid flow path of BFFD 1500 before the pressure P8 becomes negative. As described above the pressure within first upstream chamber 1413 of BFFD 1500 will be positive as long as biological fluid is flowing into first upstream chamber 1413. The purging of air from within the first fluid flow path BFFD 1500 is totally independent of whether or not the pressure within BFFD 1500 downstream of the first BFFM becomes negative.

Referring to FIG. 61 through FIG. 65 and FIG. 73, once all of the air has been purged from within the first fluid flow path of BFFD 1500, biological fluid will continue to flow through the first fluid flow path from the first inlet of BFFD 1500 to the first outlet of BFFD 1500, and then through tubing 82 into first receiving blood bag 99 until first feed blood bag 98 is emptied of biological fluid. At this point first feed blood bag 98 will be collapsed, effectively sealing the top of tubing 81, thereby preventing the flow of biological fluid in tubing 81. With flow through tubing 81 shut off as just described, air will now flow through the third fluid flow path from common vent port 1446 of vent filtration device 1440, through the portion of vent filtration media 1443 that is enclosed by the filter seal around the first filter support structure of vent filtration device 1440, through first system port 1444 of vent filtration device 1440 through tubing 83, into first vent inlet 178, through first vent inlet slot 177, and then into first upstream chamber 1413, thereby draining the biological fluid in first upstream chamber 1413 of BFFD 1500. To complete the draining of biological fluid as just described, first receiving blood bag 99 must be positioned a sufficient distance below outlet 1427 of BFFD 1500 to create a sufficiently negative pressure downstream of the first BFFM and upstream of outlet 1427 after all of the air has been purged from within BFFD 1500 and tubing 82 is filled with biological fluid, to create a sufficient pressure differential between the upstream surface and the downstream surface of the first BFFM to drain first upstream chamber 1413 to the bottom of first upstream chamber 1413, because as the biological fluid level in first upstream chamber 1413 approaches the bottom of first upstream chamber 1413, the pressure on the bottom of the biological fluid in first upstream 1413 will approach zero.

Referring to FIG. 61 through FIG. 68, when the filtration cycle through the first fluid flow path is complete as just described, the first BFFM will remain wetted, first vertical channels 1422 and 1422a, and first circular outlet channel 1425 will be filled with biological fluid, and tubing 82 will be filled with biological fluid. Because BFFD 1500 does not contain a plenum downstream of the first BFFM, the hold up volume of biological fluid within the first fluid flow path of BFFD 1500 will be minimized.

Referring to FIG. 61 through FIG. 68, the second fluid flow path of BFFD 1500 functions as follows. When tube clamp 95a is opened biological fluid (i.e. liquid) will flow from second feed blood bag 98a, through tubing 81b, into second inlet 105a of BFFD 1500, and then through second inlet slot 102a of BFFD 1500, into second upstream chamber 1413a of BFFD 1500. Second upstream chamber 1413a will rapidly fill with biological fluid from the bottom up. As second upstream chamber 1413a fills from the bottom up, the initial air in second upstream chamber 1413a will be displaced by the biological fluid filling second upstream chamber 1413a. The displaced air will be forced through the second BFFM, into second vertical channels 1422b and 1422c, into second circular outlet channel 1425a, and then into second outlet 1427a all of BFFD 1500. The biological fluid in second upstream chamber 1413a will be pressurized, with the pressure at the bottom of second upstream chamber 1413a being proportional to the distance from the top of the biological fluid in second feed blood bag 98a to the bottom of second upstream chamber 1413a, and with the pressure at the top of second upstream chamber 1413a being proportional to the distance from the top of the biological fluid in second feed blood bag 98a to the top of second upstream chamber 1413a. Hence the pressure at the top of second upstream chamber 1413a will be less than the pressure at the bottom of second upstream chamber 1413a. The positive pressure in second upstream chamber 1413a will cause the biological fluid to flow through the second BFFM over the entire surface area of the second BFFM and to displace the air within the pores of the second BFFM with biological fluid, thereby wetting the second BFFM from the upstream side of the second BFFM to the downstream side of the second BFFM. As the second BFFM wets the air that was initially in the pores of the second BFFM will be displaced by biological fluid and flow into second vertical channels 1422b and 1422c, and into second circular outlet channel 1425a, and then into second outlet 1427a all of BFFD 1500, into tubing 82a, and then into second receiving blood bag 99a. Because the pressure at the bottom of second upstream chamber 1413a is greater than the pressure at the top of second upstream chamber 1413a, the flow rate of biological fluid through the second BFFM will be greater at the bottom of the second BFFM than at the top of the second BFFM. Therefore, the second BFFM will first become completely wetted from its upstream surface to its downstream surface, at the bottom of the second BFFM. If the width of second vertical channels 1422b and 1422c is sufficiently small, and the depth of second vertical channels 1422b and 1422c is sufficiently shallow, so that the cross-sectional flow area of second vertical channels 1422b and 1422c is sufficiently small, and if the distance between second vertical channels 1422b and 1422c is sufficiently large, as described above, the path of least resistance for continued biological fluid flow through the second BFFM will be through the capillaries of the second BFFM in both the horizontal and vertical directions and not through the second vertical channels, because if the cross-sectional flow area of the second vertical channels is sufficiently small, the displaced air flowing into and through the second vertical channels will create a sufficiently high positive pressure in the second vertical channels to prevent biological fluid from entering the second vertical channels. The downstream surface of the second BFFM will therefore wet from the bottom up and the displaced air that was within the second BFFM will continue to flow into the second vertical channels, and into the second circular outlet channel, and then into the second outlet. When the downstream surface of the second BFFM has become wetted to the level of the upper part of second circular outlet channel 1425a where second circular outlet channel 1425a begins to taper to a wider width, air flow through the lower part of second circular outlet channel 1425a, and air flow through the two outermost second vertical channels 1422c will stop because the downstream surface of the second BFFM adjoining the lower part of the second circular outlet channel and the two outermost second vertical channels will be wetted. Therefore the pressure in the lower part of the second circular outlet channel and the pressure in the two outermost second vertical channels will decrease allowing biological fluid to enter the lower part of the second circular outlet channel and the two outermost second vertical channels from the bottom up, thereby displacing the air that was in the lower part of the second circular outlet channel and the two outermost second vertical channels. At the same time the wetted level of the downstream surface of the second BFFM will continue to wet in the vertical direction, wetting the downstream surface of the second BFFM adjoining the upper part of second circular outlet channel 1425a. Because the cross-sectional flow area of the upper part of second circular outlet channel 1425a is not sufficiently small to create a positive pressure in it due to the air flow through it, biological fluid will flow into second circular outlet channel 1425a as the second BFFM continues to wet in the vertical direction above the lower part of the second circular outlet channel. The biological fluid flowing into second vertical channels 1422b and 1422c, and into the second circular outlet channel 1425a will flow into second outlet 1427a of BFFD 1500 and then into tubing 82a toward second receiving blood bag 99a. As biological fluid starts to flow into second outlet 1427a, second BFFM will continue to wet vertically. Hence the initial flow of biological fluid through the upper part of second circular outlet channel 1425a, and through second outlet 1427a, will be a mixture of air and biological fluid so that the initial flow into tubing 82a will consist of alternate segments of biological fluid and air.

Referring to FIG. 61 through FIG. 64, when biological fluid starts to flow into tubing 82a, the pressure P9 downstream of the second BFFM and upstream of second outlet 1427a (i.e. downstream of the second BFFM, but within BFFD 1500) will be determined by the following formula:

$$P9 = L9 - \Delta p - L10$$

$\Delta p$ is the pressure drop across the second BFFM due to biological fluid flow through the second BFFM.

L9 is the distance between second outlet 1427a of BFFD 1500 and the top of the biological fluid in second feed blood bag 98a.

L10 is the height of biological fluid minus any air segments downstream of second outlet 1427a, in tubing 82a.

Therefore the pressure P9 within BFFD 1500 and downstream of the second BFFM will be greater than or equal to zero until $L10 = L9 - \Delta p$. Because the upper part of second circular outlet channel 1425a is located a sufficient distance above the horizontal center line of BFFD 1500, all of the air will be purged from within the second fluid flow path of BFFD 1500 before the pressure P9 becomes negative. As described above the pressure within second upstream chamber 1413a of BFFD 1500 will be positive as long as biological fluid is flowing into second upstream chamber 1413a. The purging of air from within the second fluid flow path of BFFD 1500 is totally independent of whether or not the pressure within BFFD 1500 downstream of the second BFFM becomes negative.

Referring to FIG. 61 through FIG. 65 and FIG. 73, once all of the air has been purged from within the second fluid flow path of BFFD 1500, biological fluid will continue to flow through the second fluid flow path from the second inlet of BFFD 1500 to the second outlet of BFFD 1500, and then through tubing 82a into second receiving blood bag 99a until second feed blood bag 98a is emptied of biological fluid. At this point second feed blood bag 98a will be collapsed, effectively sealing the top of tubing 81b, thereby preventing the flow of biological fluid in tubing 81b. With flow through tubing 81b shut off as just described, air will now flow through the fourth fluid flow path from common vent port 1446 of vent filtration device 1440, through the portion of vent filtration media 1443 that is enclosed by the filter seal around the second filter support structure of vent filtration device 1440, through second system port 1444a of vent filtration device 1440 through tubing 83a, into second vent inlet 178a, through second vent inlet slot 177a, and then into second upstream chamber 1413a, thereby draining the biological fluid in second upstream chamber 1413a of BFFD 1500. To complete the draining of biological fluid as just described, second receiving blood bag 99a must be positioned a sufficient distance below second outlet 1427a of BFFD 1500 to create a sufficiently negative pressure downstream of the second BFFM and upstream of second outlet 1427 after all of the air has been purged from within BFFD 1500 and tubing 82a is filled with biological fluid, to create a sufficient pressure differential between the upstream surface and the downstream surface of the second BFFM to drain second upstream chamber 1413a to the bottom of second upstream chamber 1413a, because as the biological fluid level in second upstream chamber 1413a approaches the bottom of second upstream chamber 1413a, the pressure on the bottom of the biological fluid in second upstream 1413a will approach zero.

Referring to FIG. 61 through FIG. 68, when the filtration cycle through the second fluid flow path is complete as just described, the second BFFM will remain wetted, second vertical channels 1422b and 1422c, and second circular outlet channel 1425a will be filled with biological fluid, and tubing 82a will be filled with biological fluid. Because BFFD 1500 does not contain a plenum downstream of the second BFFM, the hold up volume of biological fluid within the second fluid flow path of BFFD 1500 will be minimized.

Once the filtration cycle through the first and second fluid flow paths of BFFD 1500 is complete as just described, the user will close tube clamp 96 and tube clamp 96a, and then cut and seal tubing 82 above tube clamp 96, and then cut and seal tubing 82a above tube clamp 96a, and then discard BFFD 1500 and the remaining components attached to it in a safe manner.

As can be seen from the above description, the flow of biological fluid through first fluid flow path of BFFD 1500 is completely independent of the flow of biological fluid through second fluid flow path of BFFD 1500, and that solid partition wall 1437 of housing outlet half 1420 isolates the first fluid flow path from the second fluid flow path.

Detailed Description of the Sixteenth Embodiment

A sixteenth embodiment of the BFFD constructed in accordance with the principles of the present invention, is shown in FIG. 75 through FIG. 79. BFFD 1600 may be used in place of BFFD 1500 in biological fluid filtration system 3000 shown in FIG. 61.

Referring to FIG. 75 through FIG. 77, BFFD 1600 contains a rigid housing that includes housing inlet half 201', housing inlet half 201'a, and housing outlet half 1520. Housing inlet half's 201', and 201'a are same as housing inlet half 201 of the third embodiment (shown in FIG. 18) with the exception that inner side wall 208 is shorter. Inner side wall 208 of housing inlet half 201' and inner side wall 208 of housing inlet half 201'a are bonded to outer side wall 1529 of housing outlet half 1520. The bond is preferably an ultrasonic weld but may be a heat bond, a glue bond, a solvent bond, or any other type of leak tight bond.

Referring to FIG. 20, FIG. 21, and FIG. 75 through FIG. 77, BFFD 1600 contains first flexible diaphragm 260 and second flexible diaphragm 260a. First flexible diaphragm 260 and second flexible diaphragm 260a shown in FIG. 75 through FIG. 77 are the same as flexible diaphragm 260 shown in FIG. 20 and FIG. 21 and described in the third embodiment of the present invention.

Referring to FIG. 75 through FIG. 79 housing outlet half 1520 contains a solid partition wall 1537 that divides BFFD 1600 into a first filtration device with a first inlet and a first outlet on one side of the solid partition wall, and a second filtration device with a second inlet and a second outlet on the other side of the solid partition wall. On the first side of solid partition wall 1537 housing outlet half 1520 contains first filter well 1511 bounded by inner side wall 1408 and by first filter seal surface 1424. Housing outlet half 1520 contains a second filter well 1511a on the opposite side of solid partition wall 1537 bounded by inner side wall 1508a and by second filter seal surface 1524a. Circular outlet channel 1425 and vertical channels 1422 and 1422a of housing outlet half 1520 combined, create a first filter under drain structure, cut into first inner wall 1421 of solid partition wall 1537 of housing outlet half 1520, that is the same as the first filter under drain structure of housing outlet half 1420 of the fifteenth embodiment. First outlet 1427 of housing outlet half 1520 is also the same as first outlet 1427 of housing outlet half 1420. The upper part of first filter well 1511 contains seal ring counter bore 1526. The reference numbers that were used to designate features of housing outlet half 1420 of the fifteenth embodiment are used to designate identical features of housing outlet half 1520 of the sixteenth embodiment.

Referring to FIG. 75 through FIG. 79, the second filter well 1511a of housing outlet half 1520 contains an open chamber or plenum 1530 defined by second inner wall 1521a, by inner side wall 1508b, and by a plane that goes through second filter seal surface 1524a. Vertical filter support ribs 1522a protrude from second inner wall 1521a, with the top surface of vertical filter support ribs lying in a plane that goes through second filter seal surface 1524a. Plenum 1530 may be tapered like plenum 830 shown in FIG. 40. Second outlet 1527a is located near the top of plenum 1530. Slot 1525a cut into second inner wall 1521a is in fluid flow communication with second outlet 1527a. Vertical filter support ribs 1522a create a second filter under drain structure.

Referring to FIG. 75 through FIG. 79, BFFD 1600 contains a first BFFM and a second BFFM. The first BFFM is disposed in first filter well 1511, and the second BFFM is disposed in second filter well 1511a. The first BFFM of BFFD 1600 is the same as the first BFFM of BFFD 1500 described in the fifteenth embodiment above. First filter element 1415 of BFFD 1600 is sealed to the housing by compressing the outer periphery of first filter element 1415 with filter seal ring 1560. Like the second BFFM of BFFD 1500, the second BFFM of BFFD 1600 contains one filter element 1571. Filter element 1571 is bonded to second filter seal surface 1524a of housing outlet half 1520 with bond 1573. The bond can be a heat seal, an ultrasonic seal, a glue seal, a solvent seal, or any other type of leak tight seal. Filter element 1571 could be a depth filter, or it could be a microporous filter.

Referring to FIG. 75 through FIG. 79, a first fluid flow path is defined between first inlet 205 of BFFD 1600 and first outlet 1427 of BFFD 1600 with the first BFFM interposed between first inlet 205 and first outlet 1427, and across the first fluid flow path. The first fluid flow path flows from first inlet 205, into first upstream chamber first 1513, through the first BFFM, into vertical channels 1422 and 1422a, into circular outlet channel 1425, and then into first outlet 1427. A second fluid flow path is defined between second inlet 205a of BFFD 1600 and second outlet 1527a of BFFD 1600 with the second BFFM interposed between second inlet 205a and second outlet 1527a, and across the second fluid flow path. The second fluid flow path flows from second inlet 205a, into second upstream chamber 1513a, through the second BFFM, into plenum 1530 downstream of the second BFFM, into slot 1525a, and then into second outlet 1527a. The first fluid flow path is independent of the second fluid flow path, and there is no cross talk between the two. Solid partition wall 1537 is a barrier between the first fluid flow path and the second fluid flow path.

Referring to FIG. 61, BFFD 1600 could replace BFFD 1500 in biological fluid filtration system 3000, in which case biological fluid filtration system 3000 would function as follows. When BFFD 1600 replaces BFFD 1500 vent filtration device 1440, tubing 83, and tubing 83a will be eliminated. The outlet end of tubing 81 will be connected to inlet tube socket 206 of BFFD 1600, and the outlet end of tubing 81b will be connected to inlet tube socket 206a of BFFD 1600. The user will purchase the system with all components as shown in FIG. 61, less vent filtration device 1440, tubing 83, tubing 83a, first feed blood bag 98 and second feed blood bag 98a. The user will connect tubing 81 to outlet 92 of first feed blood bag 98 in a manner known in the art. The user will also connect tubing 81b to outlet 92a of second feed blood bag 98a in a manner known in the art. First feed blood bag 98 and second feed blood bag 98a may be hung from a blood bag pole known in the art, with first receiving blood bag 99 and second receiving blood bag 99a placed on a table top or the like, so that the various components of the system will be positioned as shown in FIG. 61. Tube clamps 95 and 95a should be closed before connecting tubing 81 to first feed blood bag 98 and before connecting tubing 81b to second feed blood bag 98a. Before opening tube clamps 95 and 95a to start the flow of biological fluid through the system, tube clamps 96, and 96a should be open.

Alternately the user will purchase the system with all components as just described in the previous paragraph, including the first and second feed blood bags. In this case biological fluid filtration system 3000 may be part of a larger system that contains a unit of fresh blood. The larger system would be placed into a centrifuge where the platelets would be separated from the unit of fresh blood and then transferred into second feed blood bag 98a, and where the packed red blood cells would be separated from the unit of fresh blood and then transferred into first feed blood bag 98, using a process known in the art.

Referring to FIG. 75 through FIG. 79, the first fluid flow path of BFFD 1600 functions as follows. When tube clamp 95 is opened biological fluid (i.e. liquid) will flow from first feed blood bag 98, through tubing 81, into first inlet 205 of BFFD 1600, and then into first upstream chamber 1513 of BFFD 1600. First upstream chamber 1513 will rapidly fill with biological fluid from the bottom up. Because first circular outlet channel 1425, and first vertical channels 1422 and 1422a, and first outlet 1427 of housing outlet half 1520 of BFFD 1600 are identical to the corresponding features of BFFD 1500, the first fluid flow path of BFFD 1600 will fill and purge air as described in the description of the first fluid flow path for BFFD 1500 in the description of the fifteenth embodiment.

Referring to FIG. 18, FIG. 20, FIG. 21, FIG. 61, and FIG. 75 through FIG. 79, once all of the air has been purged from the first fluid flow path within BFFD 1600, biological fluid will continue to flow through the first fluid flow path from first inlet 205 of BFFD 1600 to first outlet 1427 of BFFD 1600, and then through tubing 82 into first receiving blood bag 99 until first feed blood bag 98 is emptied of biological fluid. At this point first feed blood bag 98 will be collapsed, effectively sealing the top of tubing 81, thereby preventing the flow of biological fluid in tubing 81. If first receiving blood bag 99 is positioned at a level that is sufficiently lower than BFFD 1600, the pressure downstream of the first BFFM and upstream of first outlet 1427 will be negative as described above. Once first feed blood bag 98 collapses and biological fluid flow through the first fluid flow path stops the differential pressure across the first BFFM will become zero, hence the pressure in upstream chamber 1513 will become negative. The pressure on upstream surface 266 of first flexible diaphragm 260 will be atmospheric because hole 271 of housing inlet half 201' is open to atmosphere. With atmospheric pressure on the outer surface 266 of first flexible diaphragm 260, the negative pressure within first upstream chamber 1513 will cause first flexible diaphragm 260 to collapse onto the upstream surface of the first BFFM, thereby forcing the biological fluid in first upstream chamber 1513 through the first BFFM, into the vertical channels and the circular outlet channel, into outlet 1427, into tubing 82, and then into first receiving blood bag 99.

Referring to FIG. 75 through FIG. 78, when the filtration cycle through the first fluid flow path of BFFD 1600 is complete as just described, the first BFFM will remain wetted, vertical channels 1422 and 1422a, and circular outlet channel 1425 will be filled with biological fluid, and tubing 82 will be filled with biological fluid. Because BFFD 1600 does not contain a plenum downstream of the first BFFM, the hold up volume of biological fluid within the first fluid flow path of BFFD 1500 will be minimized.

Referring to FIG. 61 and FIG. 75 through FIG. 77, and FIG. 79, the second fluid flow path of BFFD 1600 functions as follows. When tube clamp 95a is opened biological fluid (i.e. liquid) will flow from second feed blood bag 98a. Biological fluid will flow into inlet 205a, into second upstream chamber 1513a, of BFFD 1600. Second upstream chamber 1513a will rapidly fill with biological fluid from the bottom up. As second upstream chamber 1513a fills from the bottom up, the initial air in second upstream chamber 1513a will be displaced by the biological fluid filling second upstream chamber 1513a. The displaced air will be forced through the second BFFM, into plenum 1530, into slot 1525a, and then into second outlet 1527a all of BFFD 1600. The biological fluid in second upstream chamber 1513a will be pressurized, with the pressure at the bottom of second upstream chamber 1513a being proportional to the distance from the top of the biological fluid in second feed blood bag 98a to the bottom of second upstream chamber 1513a, and with the pressure at the top of second upstream chamber 1513a being proportional to the distance from the top of the biological fluid in second feed blood bag 98a to the top of second upstream chamber 1513a. Hence the pressure at the top of second upstream chamber 1513a will be less than the pressure at the bottom of second upstream chamber 1513a. The positive pressure in second upstream chamber 1513a will cause the biological fluid to flow through the second BFFM over the entire surface area of the second BFFM and to displace the air within the pores of the second BFFM with biological fluid, thereby wetting second BFFM from the upstream side of second BFFM to the downstream side of the second BFFM. As the second BFFM wets the air that was initially in the pores of second BFFM will be displaced by biological fluid and flow into plenum 1530, into slot 1525a, and then into outlet 1527a, into tubing 82a, into second receiving blood bag 99a. Because the pressure at the bottom of second upstream chamber 1513a is greater than the pressure at the top of second upstream chamber 1513a, the flow rate of biological fluid through the second BFFM will be greater at the bottom of the second BFFM than at the top of the second BFFM. Therefore, the second BFFM will first become completely wetted from the upstream surface of the second BFFM to the downstream surface of the second BFFM at the bottom of second BFFM. Once the bottom of the downstream surface of the second BFFM has been wetted, the remainder of the downstream surface of the second BFFM will continue to wet from the bottom up, and biological fluid will start to flow from the bottom of the second BFFM, into plenum 1530. The plenum will fill from the bottom up forcing the air above the liquid level in the plenum into slot 1525a, into second outlet 1527a, into tubing 82a, and then into second receiving blood bag 99a. The plenum will fill with biological fluid before all of the air has been purged from the upper portion of the second BFFM. The remaining air in the un-wetted upper portion of the second BFFM will be displaced by biological fluid and forced into the plenum, where it will bubble to the top of the plenum due to the buoyancy of air in the biological fluid, and then be forced into outlet 1527a, into tubing 82a, and then into second receiving blood bag 99a by the flow of biological fluid. Hence the initial flow of biological fluid through outlet 1527a, into tubing 82a will be a mixture of air and biological fluid, so that the initial flow into tubing 82a will consist of alternate segments of biological fluid and air.

Referring to FIG. 18, FIG. 20, FIG. 21, FIG. 61, FIG. 75 through FIG. 77, and FIG. 79, once all of the air has been purged from the second fluid flow path within BFFD 1600, biological fluid will continue to flow through the second fluid flow path from second inlet 205a of BFFD 1600 to second outlet 1527a of BFFD 1600, and then through tubing 82a into second receiving blood bag 99a until second feed blood bag 98a is emptied of biological fluid. At this point second feed blood bag 98a will be collapsed, effectively sealing the top of tubing 81b, thereby preventing the flow of biological fluid in tubing 81b. If second receiving blood bag 99a is positioned at a level that is sufficiently lower than BFFD 1600, the pressure downstream of the second BFFM and upstream of second outlet 1527a will be negative as described above. Once second feed blood bag 98a collapses and biological fluid flow through the second fluid flow path stops the differential pressure across the second BFFM will become zero, hence the pressure in second upstream chamber 1513a will become negative. The pressure on upstream surface 266 of second flexible diaphragm 260a will be atmospheric because hole 271a of housing inlet half 201'a is open to atmosphere. With atmospheric pressure on the outer surface 266 of second flexible diaphragm 260a, the negative pressure within second upstream chamber 1513a will cause second flexible diaphragm 260a to collapse onto the upstream surface of the second BFFM, thereby forcing the biological fluid in second upstream chamber 1513a through the second BFFM, into plenum 1530, into second outlet 1527a, into tubing 82a, and then into second receiving blood bag 99a.

Once the filtration cycle through the first and second fluid flow paths of BFFD 1600 is complete as just described, the user will close tube clamp 96 and tube clamp 96a, and then cut and seal tubing 82 above tube clamp 96, and then cut and seal tubing 82a above tube clamp 96a, and then discard BFFD 1600 and the remaining components attached to it in a safe manner.

As can be seen from the above description, the flow of biological fluid through first fluid flow path of BFFD 1600 is completely independent of the flow of biological fluid through second fluid flow path of BFFD 1600, and that solid partition wall 1537 of housing outlet half 1520 isolates the first fluid flow path from the second fluid flow path.

Detailed Description of the Seventeenth Embodiment

A seventeenth embodiment of the BFFD constructed in accordance with the principles of the present invention, is shown in FIG. 93 through FIG. 97. BFFD 1900 may be used in place of BFFD 1500 in biological fluid filtration system 3000 shown in FIG. 61.

Figure 94:
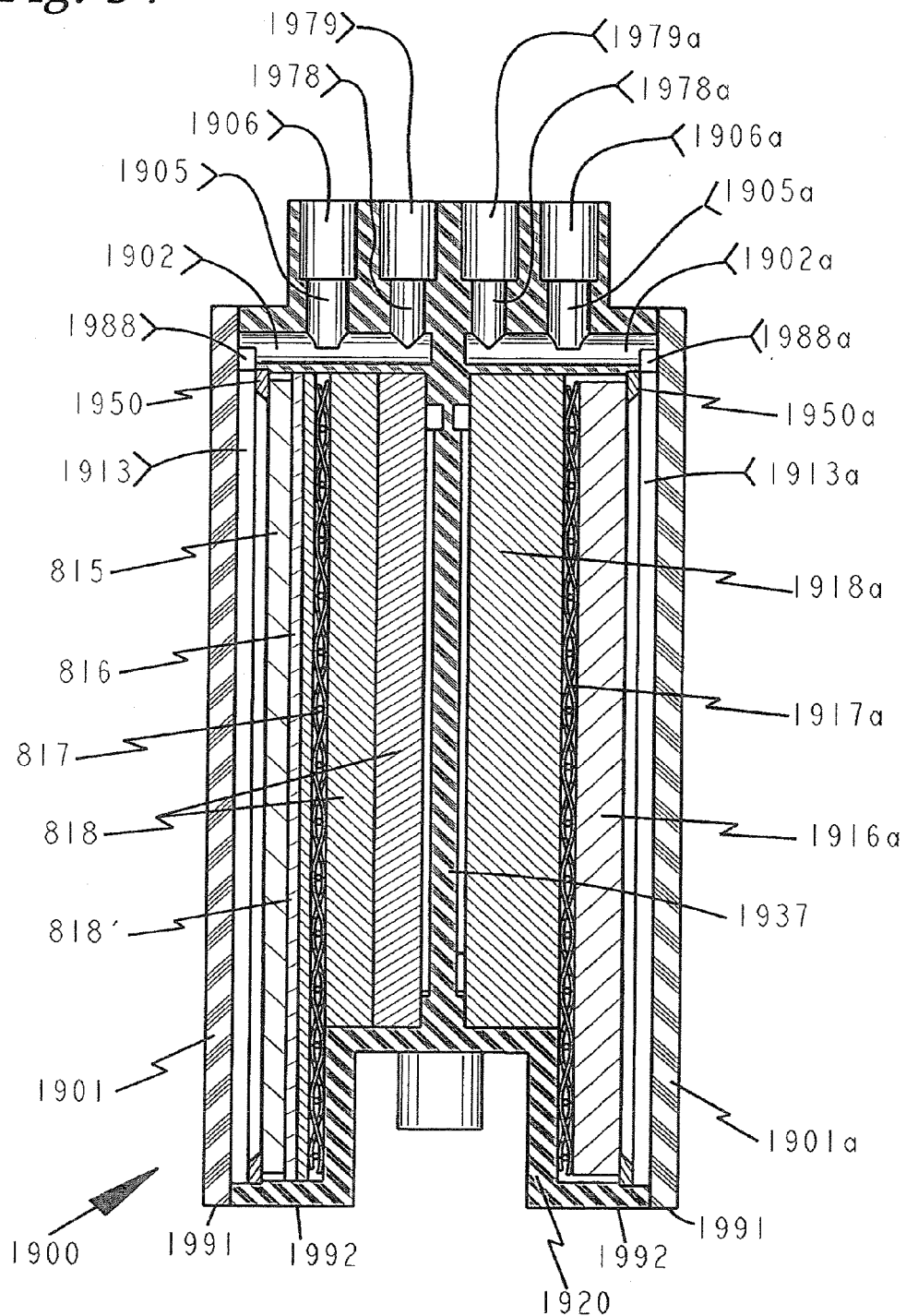
FIG. 94 is a cross-sectional view of the seventeenth embodiment of a BFFD constructed in accordance with the principles of the present invention, usable for the filtration of biological fluids.

Referring to FIG. 94, BFFD 1900 contains a rigid housing that includes first housing inlet half 1901, second housing inlet half 1901a, and housing outlet half 1920. Preferably the housing inlet halves are bonded to the housing outlet half with an ultrasonic weld, but may be a heat bonded, a glue bonded, a solvent bonded, or bonded by any other type of leak tight bond.

Referring to FIGS. 94 through 97, first housing inlet half 1901 and second housing inlet half 1901a are the same as housing inlet half 901 shown in FIG. 48, with the following exceptions. Housing inlet half 1901 and 1901a do not contain circular rib 989 or slot 904a, and the outer boundary of wall 1991 of housing inlet halves 1901 and 1901a is the same as the outer boundary of wall 1992 of housing outlet half 1920 as shown in FIGS. 94 and 95. Alternately housing inlet halves 1901 and 1901a could contain circular rib 989 and slot 904a shown in FIG. 48, and seal rings 1950 and 1950a could be eliminated. Housing inlet half 1901 is bonded to seal surface 1929 of housing outlet half 1920 along weld centerline WCL1971 shown in FIG. 96. Similarly housing inlet half 1901a is bonded to seal surface 1929a of housing outlet half 1920 along a similar weld centerline.

Figure 93:
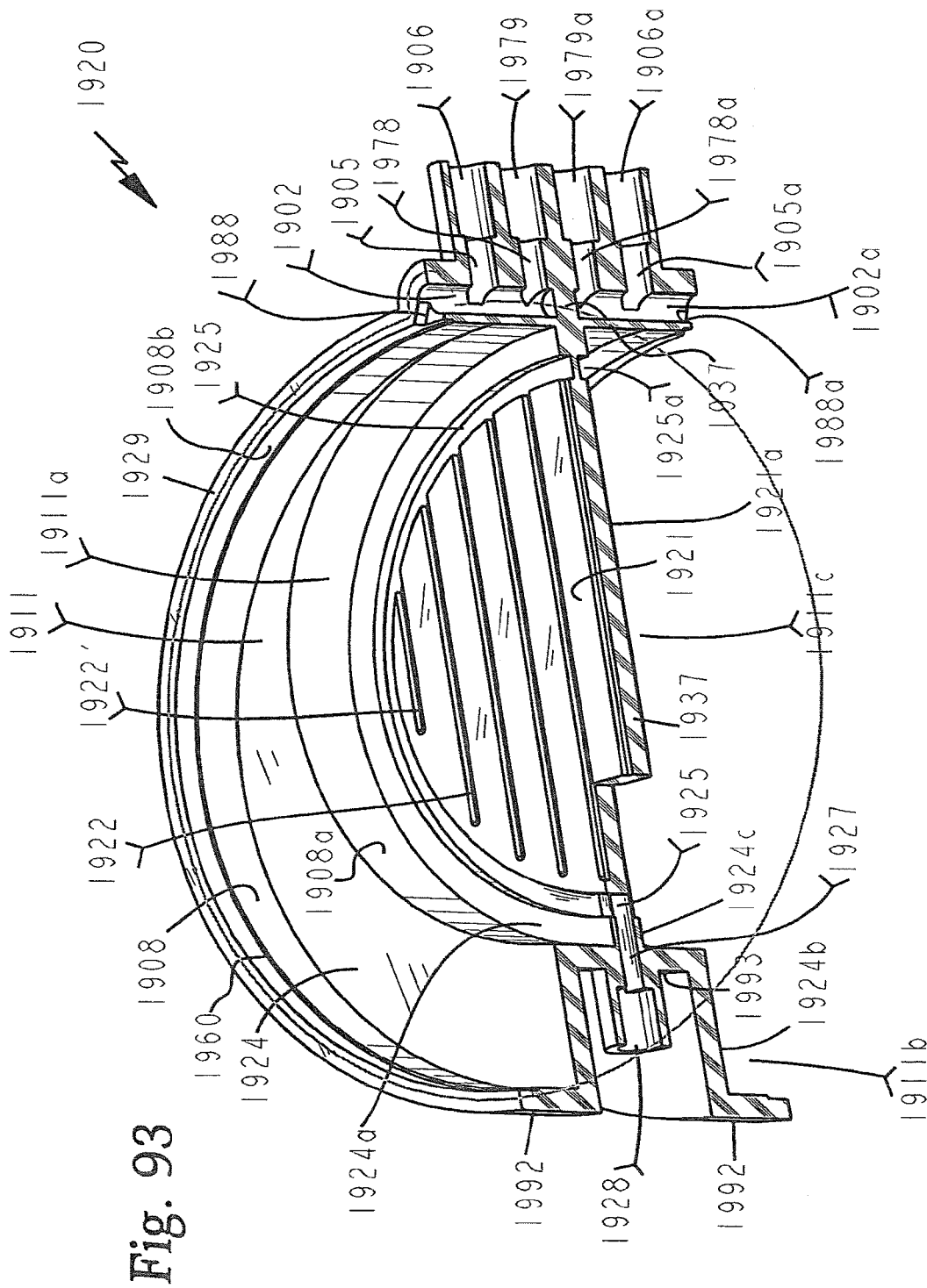
FIG. 93 is an isometric view with portions thereof removed of the housing outlet half of the BFFD shown in FIG. 94.

Referring to FIG. 93 through FIG. 97 housing outlet half 1920 contains a solid partition wall 1937 that divides BFFD 1900 into a first filtration device with a first inlet and a first outlet on one side of the solid partition wall, and a second filtration device with a second inlet and a second outlet on the other side of the solid partition wall. On the first side of solid partition wall 1937 housing outlet half 1920 contains first filter well 1911 bounded by inner side wall 1908 and by first filter seal surface 1924, and second filter well 1911a bounded by inner side wall 1908a and by second filter seal surface 1924a. First filter well 1911 has a larger diameter than second filter well 1911a. The horizontal center line of the first filter well is offset below the horizontal center line of the second filter well so that the top of inner side wall 1908 is tangent to the top of inner side wall 1908a. Housing outlet half 1020 contains a third filter well and a fourth filter well on the opposite side of solid partition wall 1937 that are mirror images of the first filter well and the second filter well respectively, mirrored about a plane that goes through the center of the solid partition wall. Housing outlet half 1920 contains first arc outlet channel 1925 and first outlet 1927. First arc outlet channel 1925 is in direct fluid flow communication with outlet 1927, and the portion of first arc outlet channel 1925 that adjoins outlet 1927 has a cross-sectional flow area that is greater than the cross-sectional flow area of outlet 1927. Housing outlet half 1920 also contains a plurality of open top closed bottom first vertical channels 1922a and 1922. The top end of each of the first vertical channels 1922a and 1922 is in fluid flow communication with first arc outlet channel 1925. The first vertical channels are shown non-tapered, but could be tapered in width and in depth. First arc outlet channel 1925 is sufficiently wide and deep to accommodate the flow of biological fluid from first vertical channels 1922a and 1922. The first arc outlet channel and the first vertical channels combined, create a first filter under drain structure, and are cut into first inner wall 1921 of solid partition wall 1937, so that the inner surface of all of the first channels lies below first inner wall 1921, as shown in FIG. 93. The cross sectional area the first arc outlet channel and of the first vertical channels is defined by the inner surface of each channel and by the downstream surface of the first BFFM. Housing outlet half 1920 contains a second arc outlet channel 1925a and a plurality of open top closed bottom second vertical channels 1922b and 1922c on the second side of solid partition wall 1937. Vertical channels 1922b and 1922c are in fluid flow communication with second arc outlet channel 1925a, and cut into second inner wall 1921a of solid partition wall 1037. The second arc outlet channel and second vertical channels create a second filter under drain structure shown in FIG. 97. FIG. 96 is a front view of housing outlet half 1920 showing the first filter under drain structure. FIG. 97 is a back view of housing outlet half 1920 showing the second filter under drain structure. The back view shown in FIG. 97 is obtained by rotating housing outlet half 1920 shown in FIG. 96, 180° about central axis CL1970. Hence when looking from the front, first arc outlet channel 1925 sweeps counter clockwise from approximately 2 o'clock to approximately 6:30 o'clock, with the arc having an included angle substantially greater than 180° (i.e. substantially greater than a semi-circle), with the outlet portion of first arc outlet channel in direct fluid flow communication with first outlet 1927, which is located to the left of central axis CL1970 when looking at the front of housing outlet half 1920. Similarly when looking from the front, second arc outlet channel 1925a sweeps clockwise from approximately 10 o'clock to approximately 5:30 o'clock, with the arc having an included angle substantially greater than 180° (i.e. substantially greater than a semi-circle), with the outlet portion of second arc outlet channel in direct fluid flow communication with second outlet 1927a (shown as dotted lines in FIG. 97), which is located to the right of central axis CL1970 when looking at the front of housing outlet half 1920. As shown in FIG. 93 and FIG. 96, the distance between first vertical channels 1922a and 1922 is much greater than the width of first vertical channels 1922a and 1922, and the distance between first vertical channels 1922a and 1922 is also much greater than of the depth of first vertical channels 1922a and 1922. Referring to FIG. 96, the first vertical channels to the right of the outlet portion of first arc outlet channel 1925 may be longer than those to the left of the outlet portion of first arc outlet channel 1925 to compensate for the lack of an outlet channel below these vertical channels. Similarly referring to FIG. 97, the second vertical channels to the right of the outlet portion of second arc outlet channel 1925a may be longer than those to the left of the outlet portion of second arc outlet channel 1925a to compensate for the lack of an outlet channel below these vertical channels. Because housing outlet half 1920 does not contain an open chamber or plenum downstream of the first BFFM or downstream of the second BFFM, hold up volume is minimized. Housing outlet half 1920 also contains first inlet 1905, first vent inlet 1978, first cross port 1902, and first inlet slot 1988. Housing outlet half 1920 also contains second inlet 1905a, second vent inlet 1978a, second cross port 1902a, and second inlet slot 1988a. Solid partition wall 1937 isolates the first cross port from the second cross port. First inlet 1905 and first vent inlet 1978 are in fluid flow communication with first upstream chamber 1913 via first cross port 1902, and first inlet slot 1988. Second inlet 1905a and second vent inlet 1978a are in fluid flow communication with second upstream chamber 1913a via second cross port 1902a, and second inlet slot 1988a. The upper part of first filter well 1911 contains a first seal ring counter bore bounded by inner side wall 1908b, and by surface 1960. The upper part of third filter well 1911b contains a second seal ring counter bore that is a mirror image of the first seal ring counter bore, mirrored about a plane that goes through the center of the solid partition wall.

Referring to FIG. 94, BFFD 1900 contains a first BFFM and a second BFFM. The first BFFM is disposed in first filter well 1911 and second filter well 1911a on the first side of solid partition wall 1937, and the second BFFM is disposed in third filter well 1911b and fourth filter well 1911c on the second side of solid partition wall 1937. The BFFM's are asymmetrical in that first BFFM contains five filter elements, and the second BFFM each contains three filter elements. The first BFFM is the same as the BFFM shown in FIG. 59 with the exception that the fourth filter element 818 contains two layers of filter material of the same type instead of four layers, and filter element 818' has been added in-between filter element 816 and filter element 817. Filter element 81' may be a first leukocyte removing filter element and may be made from the same type of filter material as filter element 818, in which case filter element 818 would be a second leukocyte filter element. The first BFFM can be used to filter blood or blood product as described in the fourteenth embodiment, with the additional benefit of having one large diameter leukocyte removing filter element 818', thereby further reducing the leukocyte load on filter element 818. The second BFFM contains three filter elements. When used to filter blood or blood product filter element 1916a could be a gel or microaggregate removing filter element, filter element 1917a could be a flow distribution filter element, and filter element 1918a could be a leukocyte removing filter element. Alternatively filter element 1916a could be a first leukocyte removing filter element, filter element 1917a could be a flow distribution filter element, and filter element 1918a could be a second leukocyte removing filter element.

Any of the BFFM with the sealing methods shown in FIG. 37 of the eighth embodiment, or in FIG. 40, 41, 42, or 45, of the ninth embodiment, or in FIG. 46 of the tenth embodiment, or in FIG. 49 of the eleventh embodiment, or in FIG. 55 of the twelfth embodiment, or in FIG. 62 of the fifteenth embodiment, or in FIG. 75 of the sixteenth embodiment, or any combination thereof could also be used in place of the BFFM's shown in FIG. 94.

Referring to FIG. 94, FIG. 96, and FIG. 97, a first fluid flow path is defined between first inlet 1905 of BFFD 1900 and first outlet 1927 of BFFD 1900 with the first BFFM interposed between first inlet 1905 and first outlet 1927, and across the first fluid flow path. The first fluid flow path flows from first inlet 1905, through first cross port 1902, through first inlet slot 1988, into first upstream chamber first 1913, through the first BFFM, into first vertical channels 1922a and 1922, into first arc outlet channel 1925, and then into first outlet 1927. A second fluid flow path is defined between second inlet 1905a of BFFD 1900 and second outlet 1927a of BFFD 1900 with the second BFFM interposed between second inlet 1905a and second outlet 1927a, and across the second fluid flow path. The second fluid flow path flows from second inlet 1905a, through second cross port 1902a, through second inlet slot 1988a, into second upstream chamber 1913a, through the second BFFM, into second vertical channels 1922b and 1922c, into second arc outlet channel 1925a, and then into second outlet 1927a. The first fluid flow path is independent of the second fluid flow path, and there is no cross talk between the two. Solid partition wall 1937 is a barrier between the first fluid flow path and the second fluid flow path.

Referring to FIG. 61 and FIG. 94, BFFD 1900 may replace BFFD 1500 in biological fluid filtration system 3000. In this case the outlet end of tubing 83 is connected to first vent tube socket 1979 and the outlet end of tubing 83a is connected to second vent tube socket 1979a, the outlet end of tubing 81 is connected to first inlet tube socket 1906, and the outlet end of tubing 81b is connected to second inlet tube socket 1906a.

Referring to FIG. 61, and FIG. 93 through FIG. 97, the first fluid flow path of BFFD 1900 functions as follows. When tube clamp 95 is opened biological fluid will flow from feed blood bag 98, through tubing 81, through the first fluid flow path of BFFD 1900 by flowing into inlet 1905, through first cross port 1902, through first inlet slot 1988, into first upstream chamber 1913, of BFFD 1900. First upstream chamber 1913 will fill from the bottom up displacing the air that was in first the upstream chamber, and wetting the first BFFM as described above in the description of the fifteenth embodiment. Once the bottom of the downstream surface of the first BFFM has become wetted, the downstream surface of the first BFFM will continue to wet from the bottom up, until the downstream surface of the first BFFM has become wetted to the level of the top of the outermost first vertical channels 1922a. At this point biological fluid will begin to flow into vertical channels 1922a from the bottom up, and then into arc outlet channel 1925, and then into outlet 1927, and then into tubing 82. As the downstream surface of the first BFFM continues to wet vertically, biological fluid will begin to flow into successive vertical channels as the wetted level of the downstream surface of the first BFFM reaches the top of each vertical channel, and then flow into arc outlet channel 1925, and then into outlet 1927, and then into tubing 82. If arc outlet channel 1925 is sufficiently wide, a small quantity of biological fluid may enter arc outlet channel 1925 before the wetted level of the downstream surface of the first BFFM reaches the top of vertical channels 1922a. Hence the initial flow of biological fluid into tubing 82 will consist of alternate segments of liquid and air. However, all of the air will be purged from within BFFD before the pressure downstream of the first BFFM and upstream of first outlet 1927 becomes negative.

Referring to FIG. 61 and FIG. 93 through FIG. 96, once all of the air has been purged from within the first fluid flow path of BFFD 1900, biological fluid will continue to flow through the first fluid flow path from the first inlet of BFFD 1900 to the first outlet of BFFD 1900, and then through tubing 82 into first receiving blood bag 99 until first feed blood bag 98 is emptied of biological fluid. At this point first feed blood bag 98 will be collapsed, effectively sealing the top of tubing 81, thereby preventing the flow of biological fluid in tubing 81. With flow through tubing 81 shut off as just described, air will now flow through a third fluid flow path from common vent port 1446 of vent filtration device 1440, through the portion of vent filtration media 1443 that is enclosed by the filter seal around the first filter support structure of vent filtration device 1440, through first system port 1444 of vent filtration device 1440 through tubing 83, into first vent inlet 1978, through first cross port 1902, through first inlet slot 1988, and then into first upstream chamber 1913, thereby draining the biological fluid in first upstream chamber 1913 of BFFD 1900. To complete the draining of biological fluid as just described, first receiving blood bag 99 must be positioned a sufficient distance below first outlet 1927 of BFFD 1900 to create a sufficiently negative pressure downstream of the first BFFM and upstream of first outlet 1927 after all of the air has been purged from within BFFD 1900 and tubing 82 is filled with biological fluid, to create a sufficient pressure differential between the upstream surface and the downstream surface of the first BFFM to drain first upstream chamber 1913 to the bottom of first upstream chamber 1913, because as the biological fluid level in first upstream chamber 1913 approaches the bottom of first upstream chamber 1913, the pressure on the bottom of the biological fluid in first upstream 1913 will approach zero.

Referring to FIG. 61, FIG. 93 and FIG. 94, when the filtration cycle through the first fluid flow path is complete as just described, the first BFFM will remain wetted, first vertical channels 1922a and 1922, and first arc outlet channel 1925 will be filled with biological fluid, and tubing 82 will be filled with biological fluid. Because BFFD 1900 does not contain a plenum downstream of the first BFFM, the hold up volume of biological fluid within the first fluid flow path of BFFD 1900 will be minimized.

The second fluid flow path of BFFD 1900 functions the same as the first fluid flow path of BFFD 1900.

Once the filtration cycle through the first and second fluid flow paths of BFFD 1900 is complete as just described, the user will close tube clamp 96 and tube clamp 96a, and then cut and seal tubing 82 above tube clamp 96, and then cut and seal tubing 82a above tube clamp 96a, and then discard BFFD 1900 and the remaining components attached to it in a safe manner.

The flow of biological fluid through first fluid flow path of BFFD 1900 is completely independent of the flow of biological fluid through second fluid flow path of BFFD 1900, because solid partition wall 1937 of housing outlet half 1920 isolates the first fluid flow path from the second fluid flow path.

Detailed Description of the Eighteenth Embodiment

A fourth embodiment of the biological fluid filtration system, and an eighteenth embodiment of the BFFD constructed in accordance with the principles of the present invention, is shown in FIG. 80 through FIG. 91. Biological fluid filtration system 4000 shown in FIG. 80 contains feed blood 98, and receiving blood bag 99. Interposed between the feed blood bag and receiving blood bag is BFFD 1700. Three tube connector 1650 is interposed between feed blood bag 98 and BFFD 1700. First length of tubing 81 connects the outlet of feed blood bag 98 to first tube socket 1651 of three tube connector 1650. Second length of tubing 81a connects second tube socket 1652 of three tube connector 1650 to the inlet tube socket 1606 of BFFD 1700. Third length of tubing 1683 connects third tube socket 1653 of three tube connector 1650 to tube socket 1828 of diaphragm draining device 1800 (hereinafter referred to as DDD 1800). A fourth length of tubing 82 connects outlet tube socket 1628 of BFFD 1700 to the inlet of receiving blood bag 99. A fifth length of tubing 84 connects a vent port on receiving blood bag 99 to tube socket 1445 of vent filtration device 1440a. A sixth length of tubing 1684 connects outlet vent tube socket 1628a to tube socket 1445a of vent filtration device 1440a. Tubing 81 may contain tube clamp 95, tubing 82 may contain tube clamp 96, tubing 84 may contain tube clamp 97, tubing 1683 may contain tube clamp 1694, and tubing 1684 must contain tube clamp 1697.

Referring to FIGS. 81 through 83, BFFD 1700 contains a rigid housing that includes housing inlet half 101b and housing outlet half 1620. Housing inlet half 101b is the same as housing inlet half 101 shown in FIG. 16 except that housing inlet half 101b does not contain a vent inlet, and flash trap 124" does not contain a break for a hanging tab on the housing outlet half. Housing outlet half 1620 is the same as housing outlet half 120 shown in FIGS. 14 and 15, except that housing outlet half 1620 does not contain a hanging tab, housing outlet half 1620 does contain outlet vent 1627a and outlet vent tube socket 1628a, and the filter under drain structure of housing outlet half 1620 does not contain a circular outlet channel, instead it contains arc outlet channel 1625.

Referring to FIG. 81 and FIG. 82 housing outlet half 1620 contains filter well 1611 bounded by inner side wall 1608 and by a plane that goes through filter seal surface 1624. Housing outlet half 1620 contains arc outlet channel 1625 and outlet 1627. Arc outlet channel 1625 is in direct fluid flow communication with outlet 1627, and the portion of arc outlet channel 1625 that adjoins outlet 1627 has a cross-sectional flow area that is greater than the cross-sectional flow area of outlet 1627. Arc outlet channel 1625 has an included angle substantially less than 180° (i.e. substantially less than a semi-circle). Housing outlet half 1620 also contains a plurality of open top closed bottom vertical channels 1622 and 1622a. The top end of each of the vertical channels 1622 and 1622a is in fluid flow communication with arc outlet channel 1625. The vertical channels are shown non-tapered, but could be tapered in width and in depth. Arc outlet channel 1625 is sufficiently wide and deep to accommodate the flow of biological fluid from vertical channels 1622 and 1622a. The two outermost vertical channels designated as vertical channels 1622a adjoin arc outlet channel 1625 where the width of arc outlet channel 1625 is equal to the width of the vertical channels. The arc outlet channel and the vertical channels combined, create a filter under drain structure, and are cut into inner wall 1621 of wall 1637, so that the inner surface of all of the channels lies below inner wall 1621, as shown in FIG. 82. The cross sectional area of the arc outlet channel and of the vertical channels is defined by the inner surface of each channel and by the downstream surface of the BFFM. As shown in FIG. 82, the distance between vertical channels 1622 and 1622a is much greater than the width of vertical channels 1622 and 1622a; and the distance between vertical channels 1622 and 1622a is also much greater than the depth of vertical channels 1622 and 1622a. Because housing outlet half 1620 does not contain an open chamber or plenum downstream of the BFFM, hold up volume of biological fluid is minimized.

Referring to FIG. 81, BFFD 1700 contains a BFFM that is the same as the first BFFM shown in FIG. 62 of BFFD 1500 and described in the fifteenth embodiment above, except that filter element 1618 of the BFFM shown in FIG. 81 contains two layers of filter material of the same type.

Referring to FIG. 81, a first fluid flow path is defined between inlet 105 of BFFD 1700 and outlet 1627 of BFFD 1700 with the BFFM interposed between inlet 105 and outlet 1627, and across the first fluid flow path. The first fluid flow path flows from inlet 105, through inlet slot 102, into upstream chamber 1613, through the BFFM, into vertical channels 1622 and 1622a, into arc outlet channel 1625, and then into outlet 1627.

Figure 84:
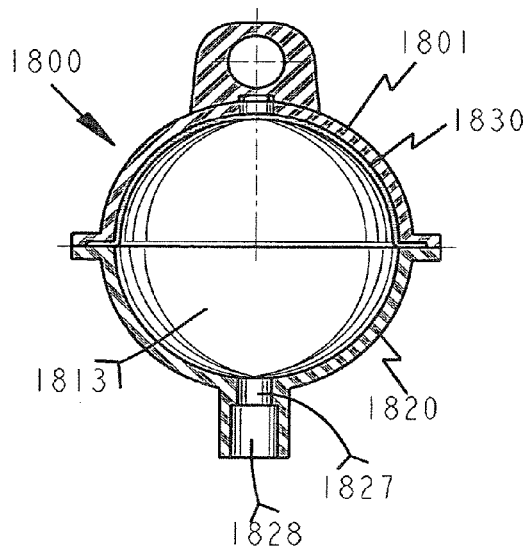
FIG. 84 is a cross-sectional view of the diaphragm draining device shown in FIG. 80 with the diaphragm in its non-deflected state.
Figure 85:
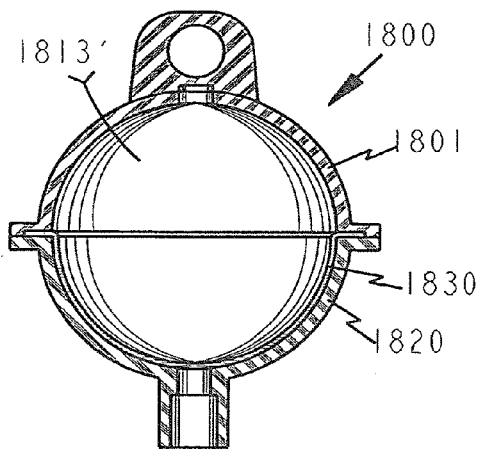
FIG. 85 is a cross-sectional view of the diaphragm draining device shown in FIG. 80 with the diaphragm in its deflected state.
Figure 86:
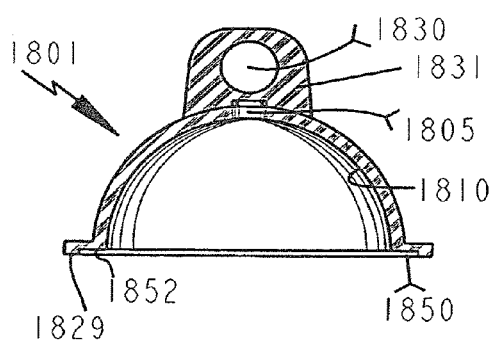
FIG. 86 is a cross-sectional view of the inlet housing of diaphragm draining device shown in FIG. 84 and FIG. 85.
Figure 87:
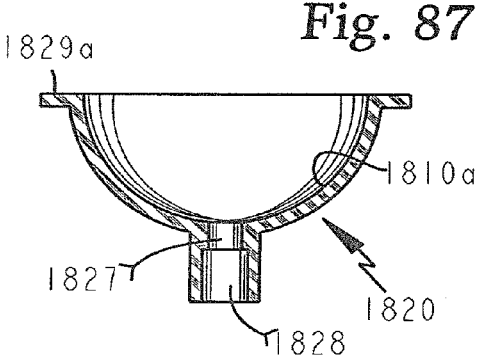
FIG. 87 is a cross-sectional view of the outlet housing of diaphragm draining device shown in FIG. 84 and FIG. 85.
Figure 88:
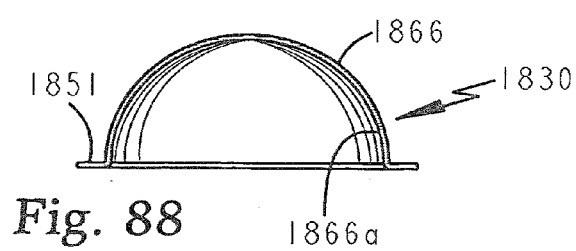
FIG. 88 is a cross-sectional view of the diaphragm of diaphragm draining device shown in FIG. 84 and FIG. 85.

FIGS. 84 through 88 show diaphragm draining device 1800 (hereinafter referred to as DDD 1800). DDD 1800 contains rigid housing inlet half 1801, rigid housing outlet half 1820 and flexible diaphragm 1830. Rigid housing inlet half contains inlet 1805, housing seal surface 1829, diaphragm counterbore 1850, and hanging tab 1831 that contains hanging hole 1830. Housing outlet half 1820 contains outlet 1827, outlet tube socket 1828, and housing seal surface 1829a. FIG. 84 shows DDD 1800 in its normal state with housing seal surface 1829 of housing inlet half 1801 sealed to housing seal surface 1829a of housing outlet half 1820. The seal is preferably an ultrasonic seal, but could be a heat seal, a solvent seal, a glue seal or any other type of leak tight seal. Flexible diaphragm 1830 may be molded from a flexible rubber material such as silicone rubber, or it may be molded or thermo formed from a material such as PVC, polyethylene, or polypropylene, but is not limited to these materials. Flexible diaphragm 1830 is preferably shaped so that in its normal state outer surface 1866 conforms to surface 1810 of housing inlet half 1801. Flexible diaphragm 1830 contains flange 1851 which may be bonded to surface 1852 of housing inlet half 1801. The bond may be a heat bond, an ultrasonic bond, a glue bond, a solvent bond, or any other type of leak tight bond. Alternately, flange 1851 may be compression sealed between surface 1852 of housing inlet half 1801 and housing seal surface 1829a of housing outlet half 1820. FIG. 84 shows DDD 1800 in its normal state with outer surface 1866 in contact with surface 1810 of housing inlet half 1801. In its normal state, DDD 1800 contains chamber 1813 that is in fluid flow communication with outlet 1827. In the normal state chamber 1813 is filled with a gas (normally sterile air) at atmospheric pressure. FIG. 85 shows DDD 1800 with diaphragm 1830 in its completely collapsed state so that inner surface 1866a of diaphragm 1830 contacts inner surface 1810a of housing outlet half 1820.

Referring to FIG. 89 three tube connector 1650 contains first tube socket 1651, second tube socket 1652, and third tube socket 1653. Three tube connector also 1650 contains first channel 1654, second channel 1655, and third channel 1656. Common node 1657 (shown as a dot) places each of the three channels in fluid flow communication with the other two channels. Second channel 1655 contains a flow restriction shown as a channel that is longer and smaller in diameter than the first and second channels. The first channel may be referred to as inlet 1654, the second channel may be referred to as outlet 1655, and the third channel may be referred to as side port 1656. The shape of three tube connector 1650 is not restricted to a tee as shown in FIG. 89, it could be in the form of a Y, for example.

Figure 80:
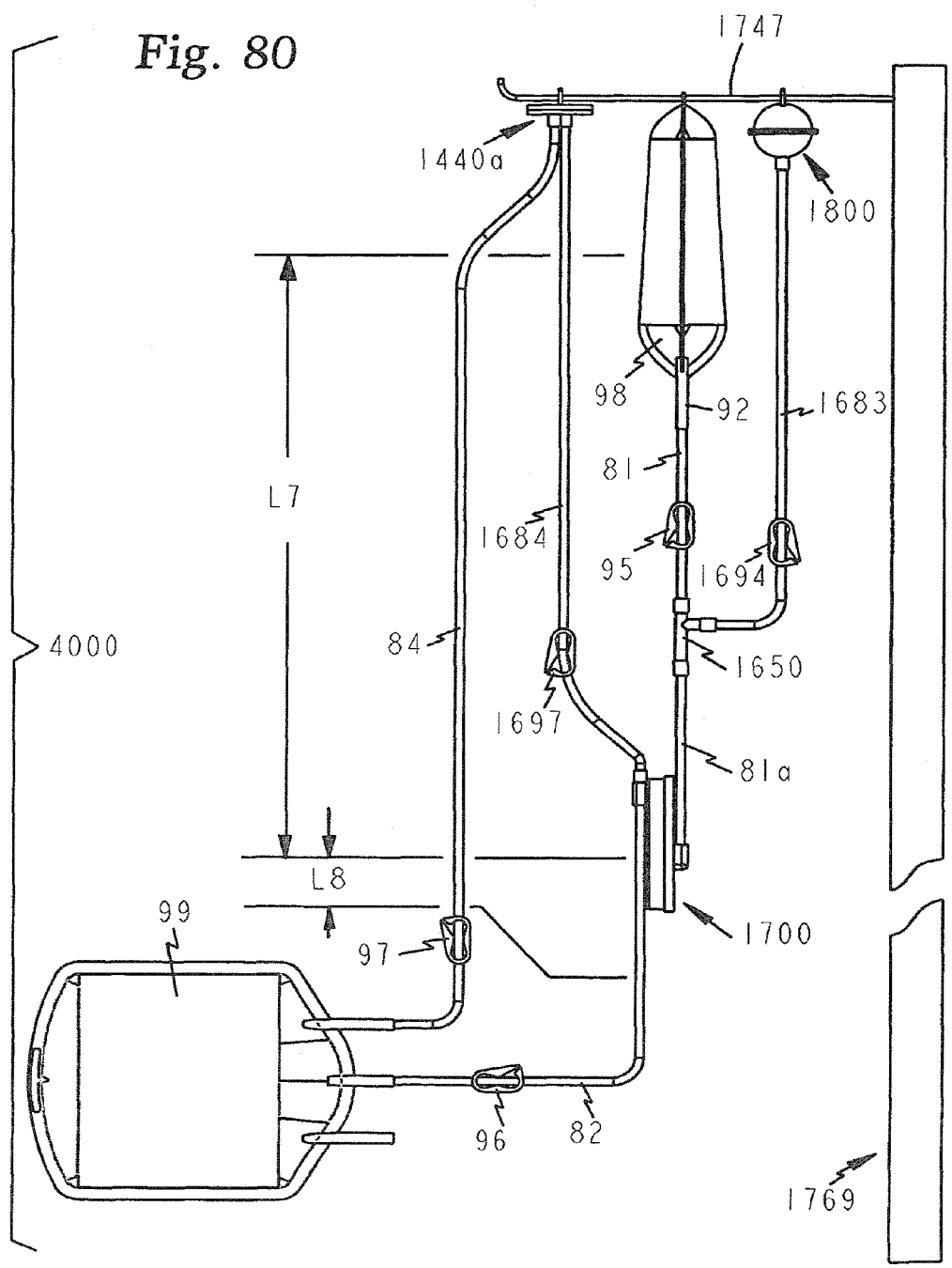
FIG. 80 is an isometric view of a fourth embodiment of a biological fluid filtration system constructed in accordance with the principles of the present invention, usable for the filtration of biological fluids, containing a feed blood bag, a receiving blood bag, with the eighteenth embodiment of a BFFD interposed between the feed blood bag and the receiving blood bag, with a diaphragm draining device connected to a three tube connector containing a restriction, and with a single vent filtration device connected to the vent outlet of the receiving blood bag and to the flow path between the outlet of the BFFD and the receiving blood bag.

Vent filtration device 1440a shown in FIG. 80 is the same as vent filtration device 1440 shown in FIG. 73, except that housing cap 1441a, shown in FIG. 90 and FIG. 91 is used in vent filtration device 1440a. Housing cap 1441a contains one or more vent ports 1446a instead of common vent port 1446 of housing cap 1441. Housing cap 1441a also contains hanging tab 1460 that contains hanging hole 1461. Vent filtration device 1440a could be replaced with two separate vent filtration devices.

Referring to FIG. 80, FIG. 84, and FIG. 89, a second fluid flow path is defined between feed blood bag 98 and common node 1657 of three tube connector 1650, with the flow in the second fluid flow path flowing from feed blood bag 98 through tubing 81, into inlet 1654 of three tube connector 1650, to the common node. A third fluid flow path is defined between common node 1657 of three tube connector 1650 and inlet 105 of BFFD 1700, with the flow in the third fluid flow path flowing from common node 1657, through outlet 1655 (including the flow restriction), through tubing 81a, to inlet 105 of BFFD 1700. A fourth fluid flow path is defined between the common node and chamber 1813 of DDD 1800, with the flow of the fourth fluid flow path flowing from chamber 1813, through outlet 1827 both of DDD 1800, through tubing 1683, through side port 1656 of three tube connector 1650, to the common node of three tube connector 1650. Biological fluid filtration system 4000 contains tubing 84 and vent filtration device 1440a. One end of tubing 84 is connected to tube socket 1445 of vent filtration device 1440a and the other end of tubing 84 is connected to vent port 91 of receiving blood bag 99. A fifth fluid flow path is defined from atmosphere to vent port 91 of receiving blood bag 99. The fifth fluid flow path flows from vent port 1446a of vent filtration device 1440a, through vent filtration media 43 of vent filtration device 1440a, through system port 1444 of vent filtration device 1440a through tubing 84, into vent port 91 of receiving blood bag 99, when tube clamp 97 is open. Preferably vent filtration device 1440a is located above the liquid level in feed blood bag 98 as shown in FIG. 80. A sixth fluid flow path is defined from atmosphere to outlet vent 1627a of BFFD 1700. The sixth fluid flow path flows from vent port 1446a of vent filtration device 1440a, through vent filtration media 43 of vent filtration device 1440a, through system port 1444a of vent filtration device 1440a through tubing 1684, into outlet vent 1627a of BFFD 1700 when tube clamp 1697 is open.

Referring to FIG. 80, FIG. 84, and FIG. 89, biological fluid filtration system 4000 functions as follows. The user will purchase the system with all components as shown in FIG. 80, less feed blood bag 98. The user will connect tubing 81 to outlet 92 of feed blood bag 98 in a manner known in the art. Feed blood bag 98, DDD 1800, and vent filtration device 1440a may be hung from hook 1747 of blood bag pole 1769, and receiving blood bag 99 may be placed on a table top or the like, so that the various components of the system will be positioned as shown in FIG. 80. However, it is not necessary to position DDD 1800 above the common node of three tube connector 1650, nor is it necessary to position vent filtration device 1440a above outlet vent 1627a as long as tube clamps 97 and 1697 are closed during the filtration cycle. Tube clamp 95 should be closed before connecting tubing 81 to feed blood bag 98. Before opening tube clamp 95 to start the flow of biological fluid (i.e. liquid) through the system, tube clamps 1694 and 96 should be open, and tube clamp 97 and 1697 should be closed. When tube clamp 95 is opened biological fluid (i.e. liquid) will flow from feed blood bag 98, through tubing 81, into inlet 1654 of three tube connector 1650, through outlet 1655 of three tube connector 1650, through tubing 81a, into inlet 105 of BFFD 1700, and then through inlet slot 102 of BFFD 1700, into upstream chamber 1613 of BFFD 1700. Because outlet 1655 of three tube connector 1650 contains a flow restriction, the flow downstream of the inlet and downstream of the side port of the three tube connector will be automatically restricted, and a positive pressure will be created at common node 1657 of three tube connector 1650. Also because flexible diaphragm 1830 is sealed to DDD 1800 with a liquid/air tight seal, air can not escape through inlet 1805 of DDD 1800. Therefore the air in tubing 1683 and in chamber 1813 of DDD 1800 will be pressurized so that only a very small quantity of biological fluid if any will enter tubing 1683. Upstream chamber 1613 will rapidly fill with biological fluid from the bottom up. As upstream chamber 1613 fills from the bottom up, the initial air in upstream chamber 1613 will be displaced by the biological fluid filling upstream chamber 1613. The displaced air will be forced through the BFFM, into vertical channels 1622 and 1622a, into arc outlet channel 1625, and then into outlet 1627 all of BFFD 1700. The biological fluid in upstream chamber 1613 will be pressurized, with the pressure at the bottom of upstream chamber 1613 being proportional to the distance from the top of the biological fluid in feed blood bag 98 to the bottom of upstream chamber 1613, and with the pressure at the top of upstream chamber 1613 being proportional to the distance from the top of the biological fluid in feed blood bag 98 to the top of upstream chamber 1613. Hence the pressure at the top of upstream chamber 1613 will be less than the pressure at the bottom of upstream chamber 1613. The positive pressure in upstream chamber 1613 will cause the biological fluid to flow through the BFFM over the entire surface area of the BFFM and to displace the air within the pores of the BFFM with biological fluid, thereby wetting BFFM from the upstream side of the BFFM to the downstream side of the BFFM. As the BFFM wets the air that was initially in the pores of BFFM will be displaced by biological fluid and flow into vertical channels 1622 and 1622e, and into arc outlet channel 1625, and then into outlet 1627 all of BFFD 1700, into tubing 82, and then into receiving blood bag 99. Because the pressure at the bottom of upstream chamber 1613 is greater than the pressure at the top of upstream chamber 1613, the flow rate of biological fluid through the BFFM will be greater at the bottom of the BFFM than at the top of the BFFM. Therefore, the BFFM will first become completely wetted from the upstream surface of the BFFM to downstream surface of the BFFM at the bottom of the BFFM. If the width of vertical channels 1622 and 1622a is sufficiently small, and the depth of vertical channels 1622 and 1622a is sufficiently shallow, so that the cross-sectional flow area of vertical channels 1622 and 1622a is sufficiently small, and if the distance between vertical channels 1622 is sufficiently large, the path of least resistance for continued biological fluid flow through the BFFM will be through the capillaries of the BFFM in both the horizontal and vertical directions and not through the vertical channels, because if the cross-sectional flow area of the vertical channels is sufficiently small, the displaced air flowing into and through the vertical channels will create a sufficiently high positive pressure in the vertical channels to prevent biological fluid from entering the vertical channels. The downstream surface of the BFFM will therefore wet from the bottom up and the displaced air that was within the BFFM will continue to flow into the vertical channels, and into the arc outlet channel, and then into the outlet. When the downstream surface of the BFFM has become wetted to the level of the top of vertical channels 1622a, air flow through the two outermost vertical channels 1622a will stop because the downstream surface of the BFFM below the top of the two outermost vertical channels will be wetted. Therefore the pressure in the two outermost vertical channels will decrease allowing biological fluid to enter the two outermost vertical channels from the bottom up, thereby displacing the air that was in the two outermost vertical channels. At the same time the wetted level of the downstream surface of the BFFM will continue to wet in the vertical direction, wetting the downstream surface of the BFFM adjoining arc outlet channel 1625. Because the cross-sectional flow area of arc outlet channel 1625 is not sufficiently small to create a positive pressure in it due to the air flow through it, biological fluid will begin to flow into vertical channels 1622 and into arc outlet channel 1625 as BFFM continues to wet in the vertical direction. The biological fluid flowing into vertical channels 1622 and 1622a, and into arc outlet channel 1625 will flow into outlet 1627 of BFFD 1700 and then into tubing 82 toward receiving blood bag 99. As biological fluid starts to flow into outlet 1627, the BFFM will continue to wet vertically. Hence the initial flow of biological fluid through arc outlet channel 1625, and through outlet 1627, will be a mixture of air and biological fluid so that the initial flow into tubing 82 will consist of alternate segments of biological fluid and air. As was be seen in the experimental data of the second embodiment, a BFFD constructed in accordance with the principles of the present invention, as shown in FIG. 81 through FIG. 83, will purge approximately 98% of the initial air in BFFD 1700 before biological fluid begins to flow into outlet 1627.

Referring to FIG. 81 and FIG. 82, when biological fluid starts to flow into tubing 82, the pressure P10 downstream of the BFFM and upstream of outlet 1627 (i.e. downstream of the BFFM, but within BFFD 1700) will be determined by the following formula:

$$P10 = L7 - \Delta p - L8$$

Δp is the pressure drop across the BFFM due to biological fluid flow through the BFFM.

L7 is the distance between outlet 1627 of BFFD 1700 and the top of the biological fluid in feed blood bag 98.

L8 is the height of biological fluid minus any air segments downstream of outlet 1627, in tubing 82.

Therefore the pressure P10 within BFFD 1700 and downstream of the BFFM will be greater than or equal to zero until L8=L7−Δp. Because the upper part of arc outlet channel 1625 is located a sufficient distance above the horizontal center line of BFFD 1700, all of the air will be purged from within BFFD 1700 before the pressure P10 becomes negative. As described above the pressure within upstream chamber 1613 of BFFD 1700 will be positive as long as biological fluid is flowing into upstream chamber 1613. The purging of air from within BFFD 1700 is only dependent upon the positive pressure upstream of the BFFM and is totally independent of whether or not the pressure within BFFD 1700 downstream of the BFFM becomes negative.

Referring to FIG. 80, FIG. 81, FIG. 84 through FIG. 89, once all of the air has been purged from within BFFD 1700, biological fluid will continue to flow through the first fluid flow path from the inlet of BFFD 1700 to the outlet of BFFD 1700, and then through tubing 82 into receiving blood bag 99 until feed blood bag 98 is emptied of biological fluid. At this point feed blood bag 98 will be collapsed, effectively sealing the top of tubing 81, thereby preventing the flow of biological fluid in the second fluid flow path between the outlet of feed blood bag 98 and common node 1657 of three tube connector 1650. If receiving blood bag 99 is positioned a sufficient distance below BFFD 1700 to create a sufficiently negative pressure downstream of the BFFM and upstream of outlet 1627 after all of the air has been purged from within BFFD 1700 and tubing 82 is filled with biological fluid. The negative pressure downstream of the BFFD will cause a suction force on the biological fluid in BFFD 1700 and in the biological fluid in tubing 81a. Because the outer surface 1866 of flexible diaphragm 1830 is at atmospheric pressure via inlet 1805 of DDD 1800, the suction force will automatically drain the biological fluid from tubing 1683, and from the side port 1656, and from outlet 1655 of DOD 1800, and from tubing 81a, and from upstream chamber 1613, through the BFFM, through outlet 1627 of BFFD 1700 through tubing 82, into receiving blood bag 99. The suction force will automatically cause flexible diaphragm 1830 to collapse so that the air that was in chamber 1813 of DDD 1800 will displace the biological fluid being drained from upstream of the BFFM. As long as the volume of chamber 1813 of DOD 1800 is greater than or equal to the volume of biological fluid being drained, all of the biological fluid will be automatically drained as just described. FIG. 85 shows DDD 1800 with diaphragm 1866 completely collapsed. If the volume of chamber 1813 of DDD 1800 is greater than the volume of biological fluid being drained, then diaphragm 1866 will only partially collapse. When the filtration cycle is complete, biological fluid will remain within the BFFM, and in the filter under drain structure of housing outlet half 1620, and in tubing 82. DDD 1800 could replace vent filtration device 30 shown in FIG. 1, or vent filtration device 40 shown in FIG. 12. Two DDD 1800 could replace vent filtration device 1440 shown in FIG. 61. The advantage of replacing vent filtration devices with DDD's is that the DDD does not have a port that is open to atmosphere, therefore the system becomes a closed system.

Referring to FIG. 80, when the filtration cycle is complete as just described, the user can open tube clamp 1697. If receiving blood bag 99 is positioned a sufficient distance below outlet 1627 of BFFD 1700 so that all of tubing 82 is positioned above receiving blood bag 99, air will flow through the sixth fluid flow path from vent port 1446a of vent filtration device 1440a, through vent filtration media 1443 of vent filtration device 1440a, through system port 1444a of vent filtration device 1440a, through tubing 1684, into outlet vent 1627a of BFFD 1700, and then into outlet 1627 of BFFD 1700, and then into tubing 82, thereby draining the biological fluid in tubing 82 into receiving blood bag 99. After mixing the biological fluid in receiving blood bag 99, a quantity of mixed biological fluid can be squeezed from receiving blood bag 99 back into tubing 82. Tube clamp 1697 may now be closed thereby preventing the biological fluid that was just squeezed into tubing 82 from draining. Tubing 82 may contain marks to divide it into segments. In this case tubing 82 will now be sealed at each segment so that the mixed biological fluid remaining in each segment could be used for cross matching and/or testing purposes. Tubing 82 can now be cut above the top segment in tubing 82. Tube clamp 97 may now be opened, and the air in receiving blood bag 99 may be purged from receiving blood bag 99 by squeezing receiving blood bag 99 thereby forcing the air in receiving blood bag 99 through the fifth fluid flow path from vent port 91 of receiving blood bag 99 to atmosphere. Tubing 84 can then be sealed and cut near receiving blood bag 99, and then tubing 84, vent filtration device 1440a, BFFD 1700 with all of the components attached to it may be discarded in a safe manner. Alternately a quantity of biological fluid from receiving blood bag 99 may be squeezed into tubing 84 to be used for testing and/or cross matching purposes, after the air is purged from the receiving blood bag. In this case tubing 84 may contain marks to divide it into segments. Tubing 84 would be sealed above the level of biological fluid in it, and at each segment mark, and then the portion of tubing 84 above the uppermost seal along with vent filtration device 40 would be cut away and discarded in a safe manner.

Any of the BFFD's of previous embodiments could also contain an outlet vent and an outlet vent tube socket, and be used in biological fluid filtration system 4000.

Detailed Description of the Nineteenth Embodiment

Figure 92:
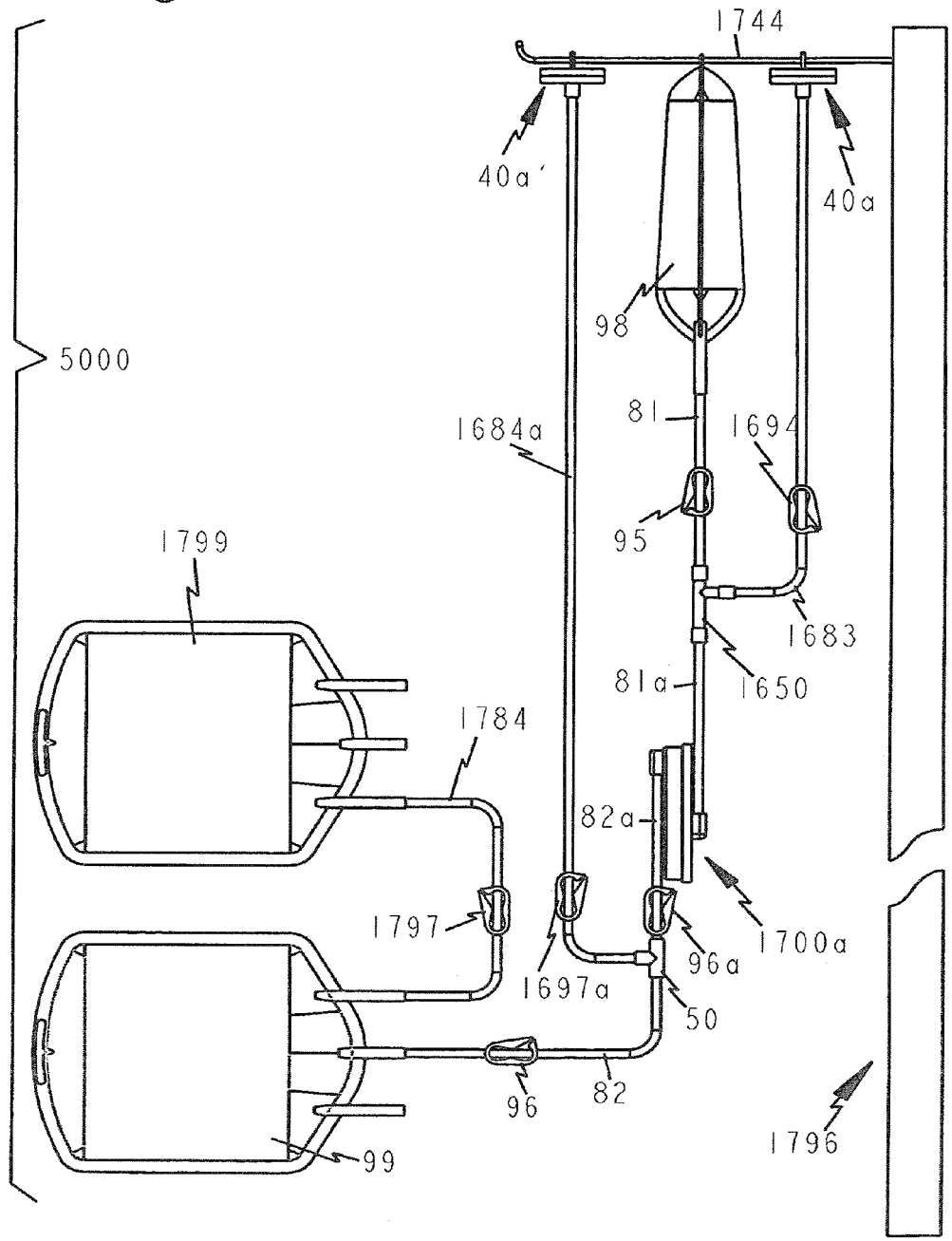
FIG. 92 is an isometric view of a fifth embodiment of a biological fluid filtration system constructed in accordance with the principles of the present invention, usable for the filtration of biological fluids, containing a feed blood bag, a receiving blood bag, with the nineteenth embodiment of a BFFD interposed between the feed blood bag and the receiving blood bag, with a vent filtration device connected to a three tube connector containing a restriction, and with a vent filtration device connected to a tee below the outlet of the BFFD, and with a burp bag connected to the vent outlet of the receiving blood bag.

A fifth embodiment of the biological fluid filtration system, and an nineteenth embodiment of the BFFD constructed in accordance with the principles of the present invention, is shown in FIG. 92. Biological fluid filtration system 5000 shown in FIG. 92 contains feed blood 98, and receiving blood bag 99. Interposed between the feed blood bag and receiving blood bag is BFFD 1700a. BFFD 1700a is the same as BFFD 1700 shown in FIG. 81, except that BFFD 1700a does not contain outlet vent 1627a and outlet vent tube socket 1628a. Three tube connector 1650 shown in FIG. 89 is interposed between feed blood bag 98 and BFFD 1700a. First length of tubing 81 connects outlet 92 of feed blood bag 98 to first tube socket 1651 of three tube connector 1650. Second length of tubing 81a connects second tube socket 1652 of three tube connector 1650 to the inlet tube socket 1606 of BFFD 1700a. Third length of tubing 1683 connects third tube socket 1653 of three tube connector 1650 to tube socket 45 of vent filtration device 40a. Vent filtration device 40a is the same as vent filtration device 40 shown in FIG. 10, except that housing cap 41 is replaced with a housing cap 1441a shown in FIGS. 90 and 91. Vent filtration device 40a' is the same as vent filtration device 40a. A fourth length of tubing 82a connects outlet tube socket 1628 of BFFD 1700a to tube socket 51 of three tube connector 50 shown in FIG. 6. A fifth length of tubing 82 connects tube socket 52 of three tube connector 50 to receiving blood bag 99. A sixth length of tubing 1684a connects tube socket 53 of three tube connector 50 to tube socket 45 of vent filtration device 40a. A seventh length of tubing 1797 connects the vent port of receiving blood bag 99 to the inlet port of air bag 1799. Tubing 81 may contain tube clamp 95, tubing 82 may contain tube clamp 96, tubing 82a may contain tube clamp 96a, tubing 1784 may contain tube clamp 1797, tubing 1683 may contain tube clamp 1694, and tubing 1684a must contain tube clamp 1697a.

Referring to FIG. 89, and FIG. 92, biological fluid filtration system 5000 functions as follows. The user will purchase the system with all components as shown in FIG. 92, less feed blood bag 98. The user will connect tubing 81 to outlet 92 of feed blood bag 98 in a manner known in the art. Feed blood bag 98, and vent filtration devices 40a may be hung from hook 1747 of blood bag pole 1769, with receiving blood bag 99 and air bag 1799 placed on a table top or the like, so that the various components of the system will be positioned as shown in FIG. 92. However, it is not necessary to position vent filtration device 40a' above three tube connector 50 as long as tube clamp 1697a is closed during the filtration cycle. Tube clamp 95 should be closed before connecting tubing 81 to feed blood bag 98. Before opening tube clamp 95 to start the flow of biological fluid (i.e. liquid) through the system, tube clamps 1694, 96 and 96a should be open, and tube clamp 1697a and 1797 should be closed. When tube clamp 95 is opened biological fluid (i.e. liquid) will flow from feed blood bag 98, through tubing 81, into inlet 1654 of three tube connector 1650, through outlet 1655 of three tube connector 1650, through tubing 81a, into inlet 105 of BFFD 1700a, and then through inlet slot 102 of BFFD 1700a, into upstream chamber 1613 of BFFD 1700a. Because outlet 1655 of three tube connector 1650 contains a flow restriction the flow of biological fluid downstream of the inlet and of the side port of the three tube connector will be automatically restricted, and a positive pressure will be created at common node 1657 of three tube connector 1650. The positive pressure at common node 1657 will force a quantity of biological fluid into tubing 1683 with the displaced air in tubing 1683 being expelled through the vent ports 1446a of vent filtration device 40a. The positive pressure at common node 1657 will prevent air from entering tubing 81a while biological fluid flows through tubing 81 and 81a. Upstream chamber 1613 will rapidly fill with biological fluid from the bottom up. BFFD 1700a will wet, purge air, and filter the same as BFFD 1700 of the eighteenth embodiment. When feed blood bag 98 is emptied, it will be collapsed, effectively sealing the top of tubing 81, thereby preventing the flow of biological fluid in the fluid flow path between the outlet of feed blood bag 98 and common node 1657 of three tube connector 1650. If receiving blood bag 99 is positioned a sufficient distance below BFFD 1700a to create a sufficiently negative pressure downstream of the BFFM and upstream of outlet 1627 after all of the air has been purged from within BFFD 1700a and tubing 82 is filled with biological fluid, the negative pressure downstream of the BFFD will cause a suction force on the biological fluid in BFFD 1700a and in the biological fluid in tubing 81a. Because vent ports 1446a of vent filtration device 40a are open to atmosphere, the suction force will automatically drain the biological fluid from tubing 1683, the side port and outlet of three tube connector 1650, from tubing 81a, and from upstream chamber 1613 of BFFD 1700a, with the drained biological fluid being displaced with air entering tubing 1683 through vent filtration device 40a.

Referring to FIG. 92, when the filtration cycle is complete as just described, the user can close tube clamp 96a and open tube clamp 1697a. If receiving blood bag 99 is positioned a sufficient distance below outlet 1627 of BFFD 1700a so that all of tubing 82 is positioned above receiving blood bag 99, air will flow from vent ports 1446a, through vent filtration media 43, through system port 44 all of vent filtration device 40a', through tubing 1684a, through the side port and outlet of three tube connector 50, and then into tubing 82, thereby draining the biological fluid from tubing 82 into receiving blood bag 99. After mixing the biological fluid in receiving blood bag 99, a quantity of mixed biological fluid can be squeezed from receiving blood bag 99 back into tubing 82. Tube clamp 1697a may now be closed thereby preventing the biological fluid that was just squeezed into tubing 82 from draining. Tubing 82 may contain marks to divide it into segments. In this case tubing 82 will now be sealed at each segment so that the mixed biological fluid remaining in each segment could be used for cross matching and/or testing purposes. Tubing 82 can now be cut above the top segment in tubing 82 and BFFD 1700a and the components attached to it can be discarded in a safe manner. Tube clamp 1797 may now be opened, and the air in receiving blood bag 99 may be purged from receiving blood bag 99 by squeezing receiving blood bag 99 thereby forcing the air in receiving blood bag 99 through tubing 1784 into air bag 1799. Tubing 1784 could then be sealed near receiving blood bag 99, and then cut above the seal so that air bag 1799 could be discarded in a safe manner. Alternately a quantity of biological fluid from receiving blood bag 99 may be squeezed into tubing 1784 to be used for testing and/or cross matching purposes, after the air is purged from the receiving blood bag. In this case tubing 1784 may contain marks to divide it into segments. Tubing 1784 would be sealed above the level of biological fluid in it, and at each segment mark, and then the portion of tubing 84 above the uppermost seal along with air bag 1799 would be cut away and discarded in a safe manner. Vent filtration device 40 of FIG. 1 could be replaced with air bag 1799 so that the air in receiving blood bag 99 of FIG. 1 could be expressed into air bag 1799. Likewise, vent filtration device 30 of FIG. 12 could be replaced with air bag 1799 so that the air in receiving blood bag 99 of FIG. 12 could be expressed into air bag 1799.

What is claimed is:
1. A method of processing biological fluid comprising:
 a) providing a biological fluid filtration device having a first inlet, wherein the first inlet including an inlet end and an outlet end, and a first outlet and at least one first filter element interposed between the first inlet and the first outlet, and defining a first fluid flow path, that is completely independent of and isolated from a second fluid flow path, and that flows from the first inlet through the first filter element into the first outlet;
 said biological fluid filtration device further having a second inlet, wherein the second inlet includes an inlet end and an outlet end, wherein the outlet end of the second inlet is completely isolated from the outlet end of the first inlet within the device, and a second outlet and at least one second filter element interposed between the second inlet and the second outlet, and defining a second fluid flow path, that is completely independent of and isolated from the first fluid flow path, and that flows from the second inlet through the second filter element into the second outlet;
 said biological fluid filtration device further including a solid partition wall interposed between the first fluid flow path and the second fluid flow path, with said solid partition wall isolating the entire first fluid flow path, from the first inlet to the first outlet, from the entire second fluid flow path, from the second inlet to the second outlet;
 wherein, flow into said first outlet stops when flow into said first inlet stops, and wherein, flow into said second outlet stops when flow into said second inlet stops.
2. A method of processing biological fluid comprising:
 a) providing a biological fluid filtration device having a first inlet and a first outlet and at least one first filter element interposed between the first inlet and the first outlet, and defining a first fluid flow path, that is completely independent of and isolated from a second fluid flow path, and that flows from the first inlet through the first filter element into the first outlet;
 said biological fluid filtration device further having a second inlet and a second outlet and at least one second filter element interposed between the second inlet and the second outlet, and defining a second fluid flow path, that is completely independent of and isolated from the first fluid flow path, and that flows from the second inlet through the second filter element into the second outlet;
 said biological fluid filtration device further including a solid partition wall interposed between the first fluid flow path and the second fluid flow path, with said solid partition wall isolating the entire first fluid flow path, from the first inlet to the first outlet, from the entire second fluid flow path, from the second inlet to the second outlet;

wherein, flow into said first inlet continues after flow into said first outlet starts, with flow into said first inlet stopping when the filtration of the biological fluid through said first fluid flow path is complete; and wherein, flow into said second inlet continues after flow into said second outlet starts, with flow into said second inlet stopping when the filtration of the biological fluid through said second fluid flow path is complete.

3. A method of processing biological fluid comprising:
a) providing a biological fluid filtration apparatus comprising:
  a biological fluid filtration device having a first inlet and a first outlet, and defining a first fluid flow path, that is completely independent of and isolated from a second fluid flow path, between the first inlet and the first outlet, and having at least one first filter element interposed between the first inlet and the first outlet and across the first fluid flow path,
  said biological fluid filtration device further having a second inlet and a second outlet, and defining a second fluid flow path, that is completely independent of and isolated from the first fluid flow path, between the second inlet and the second outlet, and having at least one second filter element interposed between the second inlet and the second outlet and across the second fluid flow path,
  said biological fluid filtration device further including a solid partition wall interposed between the entire first fluid flow path and the entire second fluid flow path, with said solid partition wall isolating the entire first fluid flow path, from the first inlet to the first outlet, from the entire second fluid flow path, from the second inlet to the second outlet,
  with said apparatus further including a first collapsible blood bag with the interior of said first collapsible blood bag in fluid flow communication with said first inlet,
  with said apparatus also including a second collapsible blood bag with the interior of said second collapsible blood bag in fluid flow communication with said first outlet and
b) flowing biological fluid from said first collapsible blood bag, through said first inlet, through said at least one first filter element, through said first outlet, into said second collapsible blood bag.

4. The method of processing biological fluid comprising:
a) providing a biological fluid filtration apparatus comprising:
  a biological fluid filtration device having a first inlet and a first outlet, and defining a first fluid flow path, that is completely independent of and isolated from a second fluid flow path, between the first inlet and the first outlet, and having at least one first filter element interposed between the first inlet and the first outlet and across the first fluid flow path,
  said biological fluid filtration device further having a second inlet and a second outlet, and defining a second fluid flow path, that is completely independent of and isolated from the first fluid flow path, between the second inlet and the second outlet, and having at least one second filter element interposed between the second inlet and the second outlet and across the second fluid flow path,
  said biological fluid filtration device further including a solid partition wall interposed between the entire first fluid flow path and the entire second fluid flow path, with said solid partition wall isolating the entire first fluid flow path, from the first inlet to the first outlet, from the entire second fluid flow path, from the second inlet to the second outlet,
  with said apparatus further including a first collapsible blood bag with the interior of said first collapsible blood bag in fluid flow communication with said first inlet,
  with said apparatus further including a second collapsible blood bag with the interior of said second collapsible blood bag in fluid flow communication with said first outlet,
  with said apparatus further including a third collapsible blood bag with the interior of said third collapsible blood bag in fluid flow communication with said second inlet,
  with said apparatus further including a fourth collapsible blood bag with the interior of said fourth collapsible blood bag in fluid flow communication with said second outlet, and
b) flowing biological fluid from said first collapsible blood bag, through said first inlet, through said at least one first filter element, through said first outlet, into said second collapsible blood bag, and
c) flowing biological fluid from said third collapsible blood bag, through said second inlet, through said at least one second filter element, through said second outlet, into said fourth collapsible blood bag.

5. The method of processing biological fluid of claim 4 wherein said biological fluid is blood or blood product.

6. The method of processing biological fluid of claim 5 wherein said at least one first filter element is pore sized to remove leukocytes from the blood or blood product.

7. The method of processing biological fluid of claim 6 wherein said at least one first filter element is used to filter blood or blood products, and wherein said at least one first filter element includes:
  a) a first filter element pore sized to remove gels from the blood or blood product,
  b) a second filter element pore sized to remove microaggregates from the blood or blood product,
  c) a third filter element pore sized to act as a flow distribution layer, and
  d) a fourth filter element pore sized to remove leukocytes from the blood or blood product.

8. The method of processing biological fluid of claim 7 wherein said at least one second filter element is used to filter blood or blood products, and wherein said at least one second filter element includes:
  a) a first filter element pore sized to remove microaggregates from the blood or blood product,
  b) a second filter element pore sized to remove leukocytes from the blood or blood product,
  c) a third filter element pore sized to act as a flow distribution layer, and
  d) a fourth filter element pore sized to remove particulates from the blood or blood product.

9. A method of processing biological fluid comprising:
a) providing a biological fluid filtration device having a first inlet and a first outlet, and defining a first fluid flow path, that is completely independent of, and isolated from, a second fluid flow path, between the first inlet and the first outlet, and having at least one first filter element interposed between the first inlet and the first outlet and across the first fluid flow path,
  said biological fluid filtration device further having a second inlet and a second outlet, and defining a second fluid flow path, that is completely independent of and isolated from the first fluid flow path, between the second inlet and the second outlet, and having at least one second filter element interposed between the second inlet and the second outlet and across the second fluid flow path, said biological fluid filtration device further containing a solid partition wall interposed between the entire first fluid flow path and the entire second fluid flow path, with said solid partition wall isolating the entire first fluid flow path, from the first inlet to the first outlet, from the entire second fluid flow path, from the second inlet to the second outlet, b) passing a first quantity of biological fluid through said first fluid flow path, with the at least one first filter element removing the un-desired components of the first quantity of biological fluid from the first quantity of biological fluid, with the filtered first quantity of biological fluid containing the desired components of the first quantity of biological fluid flowing through said first outlet and c) passing a second quantity of biological fluid through said second fluid flow path, with the at least one second filter element removing the un-desired components of the second quantity of biological fluid from the second quantity of biological fluid, with the filtered second quantity of biological fluid containing the desired components of the second quantity of biological fluid flowing through said second outlet.

10. A method of processing biological fluid comprising:
providing a biological fluid filtration device having a first inlet and a first outlet, and defining a first fluid flow path between the first inlet and the first outlet, and having at least one first filter element interposed between the first inlet and the first outlet and thereby causing a first quantity of biological fluid being filtered to flow through the at least one first filter element and out the first outlet, said biological fluid filtration device further having a second inlet and a second outlet, and defining a second fluid flow path between the second inlet and the second outlet, and having at least one second filter element interposed between the second inlet and the second outlet and thereby causing a second quantity of biological fluid being filtered to flow through the at least one second filter element and out the second outlet, with said biological fluid filtration device containing a solid partition wall interposed between the entire first fluid flow path and the entire second fluid flow path, with said solid partition wall isolating the entire first fluid flow path, from the first inlet to the first outlet, from the entire second fluid flow path, from the second inlet to the second outlet, wherein the filtered biological fluid flowing out of the first outlet does not contain any components of the biological fluid flowing through the second fluid flow path, and wherein the filtered biological fluid flowing out of the second outlet does not contain any components of the biological fluid flowing through the first fluid flow path.

11. A method of processing biological fluid comprising:
providing a biological fluid filtration device having a first inlet and a first outlet, and defining a first fluid flow path between the first inlet and the first outlet, and having at least one first filter element interposed between the first inlet and the first outlet and thereby causing a first quantity of biological fluid being filtered to flow through the at least one first filter element and out the first outlet, said biological fluid filtration device further having a second inlet and a second outlet, and defining a second fluid flow path between the second inlet and the second outlet, and having at least one second filter element interposed between the second inlet and the second outlet and thereby causing a second quantity of biological fluid being filtered to flow through the at least one second filter element and out the second outlet, with said biological fluid filtration device containing a solid partition wall interposed between the entire first fluid flow path, from the first inlet to the first outlet, and the entire second fluid flow path, from the second inlet to the second outlet, wherein the filtered biological fluid flowing out of the first outlet is completely isolated from the filtered biological fluid flowing out of the second outlet by said solid partition wall.

12. A method of processing biological fluid comprising:
providing a biological fluid filtration device having a first inlet and a first outlet, and defining a first fluid flow path between the first inlet and the first outlet, and having at least one first filter element interposed between the first inlet and the first outlet and thereby causing a first quantity of biological fluid being filtered to flow through the at least one first filter element and out the first outlet, said biological fluid filtration device further having a second inlet and a second outlet, and defining a second fluid flow path between the second inlet and the second outlet, and having at least one second filter element interposed between the second inlet and the second outlet and thereby causing a second quantity of biological fluid being filtered to flow through the at least one second filter element and out the second outlet with said biological fluid filtration device containing a solid partition wall interposed between the entire first fluid flow path and the entire second fluid flow path, with said solid partition wall isolating the entire first fluid flow path, from the first inlet to the first outlet, from the entire second fluid flow path, from the second inlet to the second outlet, thereby allowing a first type of biological fluid to be filtered through the first fluid flow path, and a second completely different type of biological fluid to be filtered through the second fluid flow path.

13. A method of processing biological fluid comprising:
a) providing a biological fluid filtration device having a first inlet and a first outlet, and defining a first fluid flow path between the first inlet and the first outlet, and having at least one first filter element interposed between the first inlet and the first outlet and thereby causing a first quantity of biological fluid, completely separate and distinct from a second quantity of biological fluid, being filtered to flow through the at least one first filter element and out the first outlet, said biological fluid filtration device further having a second inlet and a second outlet, and defining a second fluid flow path between the second inlet and the second outlet, and having at least one second filter element interposed between the second inlet and the second outlet and thereby causing a second quantity of biological fluid, completely separate and distinct from the first quantity of biological fluid, being filtered to flow through the at least one second filter element and out the second outlet with said biological fluid filtration device containing a solid partition wall interposed between the first fluid flow path and the second fluid flow path, with said solid partition wall isolating the entire first fluid flow path, from the first inlet to the first outlet, from the entire second fluid flow path, from the second inlet to the second outlet, b) passing a first quantity of biological fluid through said first fluid flow path and c) passing a second quantity of biological fluid through said second fluid flow path.

14. A biological fluid filtration device comprising:
a) a housing containing a first filter well on the first side of a solid partition wall, and a second filter well on the second side of the solid partition wall,
b) a first biological fluid filtration media disposed in said first filter well, and a second biological fluid filtration media disposed in said second filter well,
c) said housing also containing a first inlet and a first outlet and defining a first fluid flow path between the first inlet and the first outlet, thereby causing a first quantity of biological fluid, completely separate and distinct from a second quantity of biological fluid, being filtered to flow through the first biological fluid filter media and out the first outlet,
d) said housing further containing a second inlet and a second outlet, and defining a second fluid flow path between the second inlet and the second outlet thereby causing a second quantity of biological fluid, completely separate and distinct from the first quantity of biological fluid, being filtered to flow through the second biological fluid filter media and out the second outlet,
e) with said first biological fluid filtration media capable of removing un-desired components of biological fluid, while allowing the desired components of biological fluid to pass through said first biological fluid filtration media,
f) with said second biological fluid filtration media capable of removing un-desired components of biological fluid, while allowing the desired components of biological fluid to pass through said second biological fluid filtration media and
g) with said solid partition wall completely isolating the entire first fluid flow path, from the first inlet to the first outlet, from the entire second fluid flow path, from the second inlet to the second outlet.

15. A method of processing a biological fluid comprising:
passing the biological fluid through a biological fluid filtration device having a first inlet and a first outlet, and defining a first fluid flow path between the first inlet and the first outlet, and having at least one first filter element interposed between the first inlet and the first outlet and across the first fluid flow path,
said biological fluid filtration device further having a second inlet and a second outlet, and defining a second fluid flow path between the second inlet and the second outlet, and having at least one second filter element interposed between the second inlet and the second outlet and across the second fluid flow path,
said biological fluid filtration device further containing a solid partition wall interposed between the first fluid flow path and the second fluid flow path,
said solid partition wall completely isolating the entire first fluid flow path, from the first inlet to the first outlet, from the entire second fluid flow path, from the second inlet to the second outlet, with the first filter element located on one side of said solid partition wall, with the second filter element located on the other side of said solid partition wall,
thereby allowing a first type of biological fluid to be filtered through the first fluid flow path, and a second completely different type of biological fluid to be filtered through the second fluid flow path.

16. The method of processing the biological fluid of claim 15 wherein the first filter element is composed of a different type of filter material than the second filter element.

17. The method of processing the biological fluid of claim 15 wherein said first filter element includes an upstream side and a downstream side, and wherein said biological fluid filtration device further includes a vent port in fluid flow communication with the upstream side of said first filter element.

18. The method of processing a biological fluid of claim 17 wherein a venting means is connected to said vent port, with the venting means allowing filtered air to enter said vent port after biological fluid filtration through said first fluid flow path is complete, thereby draining the upstream side of said first filter element.

19. A method of processing a biological fluid comprising:
passing the biological fluid through a biological fluid filtration device having a first inlet and a first outlet, and defining a first fluid flow path between the first inlet and the first outlet, and having at least one first filter element interposed between the first inlet and the first outlet and across the first fluid flow path,
said biological fluid filtration device further having a second inlet and a second outlet, and defining a second fluid flow path between the second inlet and the second outlet, and having at least one second filter element interposed between the second inlet and the second outlet and across the second fluid flow path,
said biological fluid filtration device further containing a solid partition wall interposed between the first fluid flow path and the second fluid flow path,
said solid partition wall completely isolating the entire first fluid flow path, from the first inlet to the first outlet, from the entire second fluid flow path, from the second inlet to the second outlet, with the first filter element located on one side of said solid partition wall, with the second filter element located on the other side of said solid partition wall,
wherein the filtered biological fluid flowing out of the first outlet does not contain any components of the biological fluid flowing through the second fluid flow path, and wherein the filtered biological fluid flowing out of the second outlet does not contain any components of the biological fluid flowing through the first fluid flow path.

20. A method of processing a biological fluid comprising:
passing the biological fluid through a biological fluid filtration device having a first inlet and a first outlet, and defining a first fluid flow path between the first inlet and the first outlet, and having at least one first filter element interposed between the first inlet and the first outlet and across the first fluid flow path,
said biological fluid filtration device further having a second inlet and a second outlet, and defining a second fluid flow path between the second inlet and the second outlet, and having at least one second filter element interposed between the second inlet and the second outlet and across the second fluid flow path,
said biological fluid filtration device further containing a solid partition wall interposed between the first fluid flow path and the second fluid flow path so that the entire first fluid flow path, from the first inlet to the first outlet, is completely isolated from the entire second fluid flow path, from the second inlet to the second outlet, by said solid partition wall, with the first filter element disposed on one side of said solid partition wall, with the second filter element disposed on the opposite side of said solid partition wall, wherein the filtered biological fluid flowing out of the first outlet is completely isolated from the filtered biological fluid flowing out of the second outlet by said solid partition wall.

21. A method of processing a biological fluid comprising:
a) providing a biological fluid filtration device having a first inlet and a first outlet, and defining a first fluid flow path between the first inlet and the first outlet, and having at least one first filter element interposed between the first inlet and the first outlet and across the first fluid flow path, said biological fluid filtration device further having a second inlet and a second outlet, and defining a second fluid flow path between the second inlet and the second outlet, and having at least one second filter element interposed between the second inlet and the second outlet and across the second fluid flow path, said biological fluid filtration device further containing a solid partition wall interposed between the first fluid flow path and the second fluid flow path, with said partition wall completely isolating the entire first fluid path, from the first inlet to the first outlet, from the entire second fluid flow path, from the second inlet to the second outlet, with the at least one first filter element disposed on one side of said solid partition wall, and with the at least one second filter element disposed on the other side of said solid partition wall, b) flowing a first quantity of biological fluid through said first fluid flow path, c) flowing a second quantity of biological fluid through said second fluid flow path.

22. A method of processing a biological fluid comprising:
a) providing a biological fluid filtration device comprising:
   a self contained housing that includes a solid partition wall, with a first filter well on the first side of said solid partition wall, and with a second filter well on the second side of said solid partition wall,
   a first filter element including a first side and a second side, disposed inside of and sealed to said first filter well to prevent bypass around said first filter element,
   a second filter element including a first side and a second side, disposed inside of and sealed to said second filter well to prevent bypass around said second filter element,
   a first chamber located between the first side of said solid partition wall and the first side of said first filter element,
   a second chamber located between the second side of said first filter element and said housing,
   a third chamber located between the second side of said solid partition wall and the first side of said second filter element,
   a fourth chamber located between the second side of said second filter element and said housing,
   a first port in fluid flow communication with said first chamber, a second port in fluid flow communication with said second chamber,
   a third port in fluid flow communication with said third chamber,
   a fourth port in fluid flow communication with said fourth chamber,
   a first fluid flow path flowing between said first and second ports, with said first fluid flow path flowing through said first chamber, said first filter element and said second chamber,
   a second fluid flow path flowing between said third and fourth ports, with said second fluid flow path flowing through said third chamber, said second filter element and said fourth chamber,
with the first and second fluid flow paths being completely independent of each other, and with said solid partition wall isolating the entire first fluid flow path, from a first inlet to a first outlet, from the entire second fluid flow path, from a second inlet to a second outlet, b) flowing a first quantity of biological fluid through said first fluid flow path, thereby filtering said first quantity of biological fluid through said first filter element;

c) flowing a second quantity of biological fluid through said second fluid flow path, thereby filtering said second quantity of biological fluid through said second filter element.

23. A biological fluid filtration device comprising:
a self contained housing that includes a solid partition wall, with a first filter well on the first side of said solid partition wall, and with a second filter well on the second side of said solid partition wall;
a first filter element including a first side and a second side, disposed inside of and sealed to said first filter well to prevent bypass around said first filter element;
a second filter element including a first side and a second side, disposed inside of and sealed to said second filter well to prevent bypass around said second filter element,
a first chamber located between the first side of said solid partition wall and the first side of said first filter element,
a second chamber located between the second side of said first filter element and said housing,
a third chamber located between the second side of said solid partition wall and the first side of said second filter element,
a fourth chamber located between the second side of said second filter element and said housing,
a first port in fluid flow communication with said first chamber,
a second port in fluid flow communication with said second chamber,
a third port in fluid flow communication with said third chamber;
a fourth port in fluid flow communication with said fourth chamber,
a first fluid flow path flowing between said first and second ports with said first fluid flow path flowing through said first chamber, said first filter element and said second chamber;
a second fluid flow path flowing between said third and fourth ports, with said second fluid flow path flowing through said third chamber, said second filter element and said fourth chamber, with said partition wall completely isolating the entire first fluid flow path, from a first inlet to a first outlet, from the entire second fluid flow path, from a second inlet to a second outlet.

24. The biological fluid filtration device of claim 23 wherein said housing further includes a vent port in fluid flow communication with said second chamber.

* * * * *